(12) United States Patent
Zhong et al.

(10) Patent No.: US 10,947,206 B2
(45) Date of Patent: Mar. 16, 2021

(54) CGAS ANTAGONIST COMPOUNDS

(71) Applicants: ImmuneSensor Therapeutics, Inc., Dallas, TX (US); The Board of Regents of the University of Texas System, Austin, TX (US)

(72) Inventors: Boyu Zhong, Irving, TX (US); Lijun Sun, Dallas, TX (US); Heping Shi, Dallas, TX (US); Jing Li, Beijing (CN); Chuo Chen, Dallas, TX (US); Zhijian Chen, Dallas, TX (US)

(73) Assignees: ImmuneSensor Therapeutics, Inc., Dallas, TX (US); The Board of Regents of the University of Texas System, Austin, TX (US)

( * ) Notice: Subject to any disclaimer, the term of this patent is extended or adjusted under 35 U.S.C. 154(b) by 0 days.

(21) Appl. No.: 15/953,494

(22) Filed: Apr. 15, 2018

(65) Prior Publication Data

US 2018/0230115 A1    Aug. 16, 2018

Related U.S. Application Data

(63) Continuation of application No. PCT/US2017/026019, filed on Apr. 4, 2017.

(60) Provisional application No. 62/355,403, filed on Jun. 28, 2016, provisional application No. 62/318,435, filed on Apr. 5, 2016.

(51) Int. Cl.

| | |
|---|---|
| *C07D 277/34* | (2006.01) |
| *C07D 417/14* | (2006.01) |
| *A61K 31/429* | (2006.01) |
| *A61K 31/4365* | (2006.01) |
| *A61K 31/4439* | (2006.01) |
| *A61K 31/506* | (2006.01) |
| *A61K 31/519* | (2006.01) |
| *A61K 31/427* | (2006.01) |
| *C07D 277/40* | (2006.01) |
| *A61K 31/437* | (2006.01) |
| *A61K 31/426* | (2006.01) |
| *A61K 31/381* | (2006.01) |
| *A61K 31/433* | (2006.01) |
| *A61K 31/4709* | (2006.01) |
| *A61K 39/39* | (2006.01) |
| *A61K 45/06* | (2006.01) |
| *A61K 31/454* | (2006.01) |
| *A61K 31/4725* | (2006.01) |
| *A61K 31/497* | (2006.01) |
| *A61K 31/4985* | (2006.01) |
| *A61K 31/501* | (2006.01) |
| *C07D 277/36* | (2006.01) |
| *C07D 403/06* | (2006.01) |
| *C07D 417/04* | (2006.01) |
| *C07D 417/06* | (2006.01) |
| *C07D 417/10* | (2006.01) |
| *C07D 417/12* | (2006.01) |
| *C07D 471/04* | (2006.01) |
| *C07D 495/04* | (2006.01) |
| *C07D 513/04* | (2006.01) |

(52) U.S. Cl.
CPC .......... *C07D 277/34* (2013.01); *A61K 31/381* (2013.01); *A61K 31/426* (2013.01); *A61K 31/427* (2013.01); *A61K 31/429* (2013.01); *A61K 31/433* (2013.01); *A61K 31/437* (2013.01); *A61K 31/4365* (2013.01); *A61K 31/4439* (2013.01); *A61K 31/454* (2013.01); *A61K 31/4709* (2013.01); *A61K 31/4725* (2013.01); *A61K 31/497* (2013.01); *A61K 31/4985* (2013.01); *A61K 31/501* (2013.01); *A61K 31/506* (2013.01); *A61K 31/519* (2013.01); *A61K 39/39* (2013.01); *A61K 45/06* (2013.01); *C07D 277/36* (2013.01); *C07D 277/40* (2013.01); *C07D 403/06* (2013.01); *C07D 417/04* (2013.01); *C07D 417/06* (2013.01); *C07D 417/10* (2013.01); *C07D 417/12* (2013.01); *C07D 417/14* (2013.01); *C07D 471/04* (2013.01); *C07D 495/04* (2013.01); *C07D 513/04* (2013.01)

(58) Field of Classification Search
CPC ........................... A61K 31/381; C07D 277/34
See application file for complete search history.

(56) References Cited

U.S. PATENT DOCUMENTS

| | | | |
|---|---|---|---|
| 9,174,951 B2 * | 11/2015 | Chen | .................... C07D 277/34 |
| 10,138,278 B2 * | 11/2018 | Gautier | ............... C07D 277/36 |
| 2006/0258561 A1 | 11/2006 | Balschmidt et al. | |

(Continued)

FOREIGN PATENT DOCUMENTS

| | | |
|---|---|---|
| CN | 1882560 A | 12/2006 |
| CN | 102170864 A | 8/2011 |
| EP | 0343643 A2 | 11/1989 |

(Continued)

OTHER PUBLICATIONS

Swathi et al (2015), STN International (Columbus, Ohio) HCAPLUS database, Accession No. 2015: 764486.*

(Continued)

*Primary Examiner* — Golam M Shameem
(74) *Attorney, Agent, or Firm* — Carl A. Morales; Seth E. Snyder; Dechert LLP

(57) ABSTRACT

Disclosed are novel compounds of Formula I that are cGAS antagonists, methods of preparation of the compounds, pharmaceutical compositions comprising the compounds, and their use in medical therapy.

46 Claims, No Drawings

(56) References Cited

U.S. PATENT DOCUMENTS

2011/0218182 A1 9/2011 Dakin et al.
2016/0068560 A1 3/2016 Patel et al.

FOREIGN PATENT DOCUMENTS

| WO | 1993/13077 A1 | 7/1993 |
| WO | 2004/024061 A2 | 3/2004 |
| WO | 2004/054515 A2 | 7/2004 |
| WO | 2005/040163 A1 | 5/2005 |
| WO | 2005/042712 A2 | 5/2005 |
| WO | 2007/014838 A1 | 2/2007 |
| WO | 2010/015818 A1 | 2/2010 |

OTHER PUBLICATIONS

Zelisko et al (2015), STN International (Columbus, Ohio), HCAPLUS database, Accession No. 2015: 1783199.*
Carroll et al (2011), STN International (Columbus, Ohio) HCAPLUS database, Accession No. 2011: 960503.*
Blagg et al (2010), STN International (Columbus, Ohio) HCAPLUS database, Accession No. 2010: 1071135.*
Shibnath Ghatak et al. "Novel di-tertiary-butyl phenylhydrazones as dual cyclooxygenase-2/5-lipoxygenase inhibitors: Synthesis, COX/LOX inhibition, molecular modeling, and insights into their cytotoxicities," Bioorganic & Medicinal Chemistry Letters, vol. 24, No. 1, Jan. 1, 2014, pp. 317-324, XP055445955.
Wang Fang et al. "Design, synthesis and anti-inflammatory evaluation of novel 5-benzylidene-3,4-dihalo-furan-2-one derivatives," European Journal of Medicinal Chemistry, Elsevier, Amsterdam, NL, vol. 72, Nov. 20, 2013, pp. 35-45, XP028829442.
Extended European Search Report dated Sep. 26, 2019 corresponding to European Patent Application No. 17779694.3.
Pubchem. CID 97857. Mar. 26, 2005, pp. 1-15. Retrieved from the Internet <URL: https://pubchem.ncbi.nlm.nih.gov/compound/97857>; p. 3, formula.
International Search Report corresponding to International Application No. PCT/US17/26019 dated Aug. 29, 2017.
International Written Opinion corresponding to international Application No. PCT/US17/26019 dated Aug. 29, 2017.
Pardasani et al., "Synthetic and antibacterial studies of rhodanine derivatives with indol-2,3-diones," indian Journal of Chem., vol. 40B, 2001, pp. 1275-1278.
Zervosen et al., "Interactions between Penicillin-Binding Proteins (PBPs) and Two Novel Classes of PBP Inhibitors, Arylalkylidene Rhodanines and Arylalkylidene Iminothiazolidin-4-ones," Antimicrobial Agents and Chemotherapy, Mar. 2004, p. 961-969.
Habib et al., "Synthesis and antimicrobial activity of rhodanine derivatives," Eur. J. Med Chem (1997) 32, 759-762.
Dayam et al., b-Diketo Acid Pharmacophore Hypothesis. 1. Discovery of a Novel Class of HIV-1 Integrase Inhibitors, J. Med. Chem. (2005), 48, 111-120.
Terashima et al., "Effects of a New Aldose Reductase Inhibitor on Various Tissues in Vitro," the Journal of Pharmacology and Experimental Therapeutics, vol. 229, No. 1 (1984).
Ravi et al., "5-isopropylidene-3-ethyl rhodanine induce growth inhibition followed by apoptosis in leukemia cells," European Journal of Medicinal Chemistry 45 (2010) 2748-2752.
Powers et al., "SAR and Mode of Action of Novel Non-Nucleoside Inhibitors of Hepatitis C NS5b RNA Polymerase," J Med. Chem. 2006, 49, 1034-1046.
Sudo et al., "Novel Hepatitis C Virus Protease Inhibitors: Thiazolidine Derivatives," Biochemical and Biophysical Research Communications, 238, 643-647 (1997).
Fresneau et al., "Synthesis, Activity, and Molecular Modeling of New 2,4-Dioxo-5-(naphthylmethylene)-3-thiazolidineacetic Acids and 2-Thioxo Analogues as Potent Aldose Reductase Inhibitors," J. Med. Chem. 1998, 41, 4706-4715.
Grant et al., "The Synthesis and SAR of Rhodanines as Novel Class C beta-Lactamase Inhibitors," Bioorganic & Medicinal Chemistry Letters 10 (2000) 2179-2182.
Soltero-Higgin et al., "Identification of Inhibitors for UDP-Galactopyranose Mutase," J. Am. Chem. Soc. 2004, 126, 10532-10533.
Orchard et al., "Rhodanine-3-acetic acid derivatives as inhibitors of fungal protein mannosyl transferase 1 (PMT1)," Bioorganic & Medicinal Chemistry Letters 14 (2004) 3975-3978.
Whitesitt et al., "Synthesis and Structure-Activity Relationships of Benzophenones as Inhibitors of Cathepsin D," Bioorganic & Medicinal Chemistry Letters vol. 6, No. 18, 2157-2162 (1996).
Forino et al., "Efficient synthetic inhibitors of anthrax lethal factor," PNAS (2005), vol. 102, No. 27, 9499-9504.
Free et al., "Mechanism of Inhibition of Histidine Decarboxylase by Rhodanines," Biochemical Pharmacology (1971), vol. 20, pp. 1421-1428.
Cutshall et al., "Rhodanine derivatives as inhibitors of JSP-1," Bioorganic & Medicinal Chemistry Letters 15 (2005) 3374-3379.
Irvine et al., "Rhodanine derivatives as novel inhibitors of PDE4," Bioorganic & Medicinal Chemistry Letters 18 (2008) 2032-2037.
Azizmohammadi et al., "2H-chromene derivatives bearing thiazolidine-2,4-dione, rhodanine or hydantoin moieties a potential anticancer agents," European Journal of Medicinal Chemistry 59 (2013) 15-22.
Knight et al., "Discovery of GSK2126458, a Highly Potent Inhibitor of PI3K and the Mammalian Target of Rapamycin," ACS Med. Chem. Lett. (2010), 1, 39-43.

* cited by examiner

CGAS ANTAGONIST COMPOUNDS

CROSS-REFERENCE TO RELATED APPLICATIONS

This application is a continuation of International Application No. PCT/US17/026019, filed on Apr. 4, 2017, which claims the benefit of U.S. Provisional Application No. 62/318,435, filed Apr. 5, 2016, and U.S. Provisional Application No. 62/355,403, filed Jun. 28, 2016, the entire contents of each of which is hereby incorporated by reference herein.

TECHNICAL FIELD

The present invention provides novel cGAS antagonist compounds, pharmaceutical compositions thereof, and their use in medical therapy. In particular, the compounds of the invention are useful for treating inflammatory, allergic, autoimmune, and infectious diseases. The compounds can also be used for the treatment of senescence- or age-related diseases, such as neurodegenerative diseases, cardiovascular diseases, liver and renal diseases, cancer and premature aging.

BACKGROUND

Cytosolic DNA induces type-I interferons and other cytokines that are important for immune defense against microbial infections and malignant cells but can also result in autoimmunity. This DNA signaling pathway requires the adaptor protein STING (Stimulator of Interferon Genes) and the transcription factors NF-κB and IRF3, but the mechanism of DNA sensing was unclear until recently. WO 2014099824 to The University of Texas disclosed that mammalian cytosolic extracts synthesized cyclic-GMP-AMP (cGAMP) in vitro from ATP and GTP in the presence of DNA but not RNA. DNA transfection or DNA virus infection of mammalian cells also triggered cGAMP production. cGAMP bound to STING, leading to the activation of IRF3 and induction of type-I interferons including interferon-β (IFN-β). Thus, cGAMP represents the first cyclic di-nucleotide in metazoa and it functions as an endogenous second messenger that triggers interferon production in response to cytosolic DNA.

Through biochemical fractionation and quantitative mass spectrometry, the inventors on WO 2014099824 also identified a cGAMP synthase (cGAS), which belongs to the nucleotidyltransferase family. Overexpression of cGAS activated the transcription factor IRF3 and induced IFN in a STING-dependent manner. Knockdown of cGAS inhibited IRF3 activation and IFN induction by DNA transfection or DNA virus infection. cGAS bound to DNA in the cytoplasm and catalyzed cGAMP synthesis. These results indicate that cGAS is a cytosolic DNA sensor that induces interferons by producing the second messenger cGAMP.

Several additional patents applications in this field have henceforth published:

US20140205653 and US 20140341976 to Aduro Biotech disclose cyclic-di-nucleotide (CDN) compounds that activate and inhibit STING, respectively. In particular, the CDNs of the invention are provided in the form of a composition comprising one or more cyclic purine dinucleotides which activate or inhibit STING-dependent TBK1 activation and the resulting production of type I interferon.

WO 2015077354 A1 to The University of Chicago discloses Methods and compositions for treating cancer by intratumorally administering a stimulator of interferon genes (STING) agonist are disclosed herein. In some embodiments, there are provided compositions and methods concerning methods for treating cancer in a subject comprising administering to the subject an effective amount of a stimulator of interferon genes (STING) agonist, wherein the STING agonist is administered intratumorally.

WO 2015161762 to Fudan University discloses the use of cyclic dinucleotide cGAMP for preparing antitumor drugs, wherein the tumor is gastric cancer, lung cancer, colon cancer, liver cancer, prostate cancer or pancreatic cancer. cGAMP was shown to inhibit the growth of human tumor cell lines in immune compromised mice.

WO 2015185565 to GlaxoSmithKline discloses a cyclic dinucleotide analog or a pharmaceutically acceptable salt and tautomers thereof, compositions, combinations and medicaments containing said compounds and processes for their preparation. The invention also relates to the use of said compounds, combinations, compositions and medicaments, in the treatment of diseases and conditions in which modulation of STING (Stimulator of Interferon Genes) is beneficial, for example inflammation, allergic and autoimmune diseases, infectious diseases, cancer and as vaccine adjuvants.

WO 2014179335 to Memorial Sloan Kettering Cancer Center discloses compositions, methods, kits, and assays related to the use and/or exploitation of isomers of cGAMP as well as the structure of the enzyme cGAS.

To our knowledge, no specific antagonist of cGAS has been reported or patented. Genetic experiments have demonstrated that deletion of cGAS rescues lethal autoimmune diseases in mouse models (Gao et al., 2015, PNAS 112, E5699), suggesting that cGAS inhibitors may be used for the treatment of human autoimmune and autoinflammatory diseases, including systemic lupus erythematosus (SLE), scleroderma, psoriasis, Aicardi Goutieres syndrome, Sjogren's syndrome, rheumatoid arthritis, inflammataory bowel diseases, multiple sclerosis, diabetes, cardiovascular, and neurodegenerative diseases. In addition, because DNA damage causes senescence and induces proinflammatory cytokines, cGAS inhibitors may be used to treat senescence- or age-related diseases. There is an urgent need to develop first-in-class, potent and specific chemical inhibitors of cGAS for the treatment of these debilitating human diseases.

SUMMARY OF THE INVENTION

Formula I Encompasses Formula Ia-Id.

In one aspect, the invention provides a compound of Formula Ia, or a pharmaceutically acceptable salt thereof,

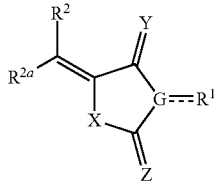

Formula Ia wherein:
X is NH or S;
Y is O or S;
Z is O, S, $CHR^{1a}$ or $NR^{1a}$;

$R^{1a}$ is hydrogen, $C_{1-6}$alkyl, or $C_{1-6}$alkyl selectively functionalized with one or more halogen, thiol, hydroxyl, carbonyl, carboxyl, carbonyloxyl, $C_{1-6}$alkoxy, $C_{1-6}$hydroxyalkoxy, amino, $C_{1-6}$alkylamino, di($C_{1-6}$alkyl)amino, or azido groups; G is N or C;

if G is N, $R^1$ is hydrogen $C_{1-6}$alkyl, or $C_{1-6}$alkyl selectively functionalized with one or more halogen, thiol, hydroxyl, carbonyl, carboxyl, carbonyloxyl, $C_{1-6}$alkoxy, $C_{1-6}$hydroxyalkoxy, amino, $C_{1-6}$alkylamino, di($C_{1-6}$alkyl)amino, or azido groups, if G is N and if Z includes $R^{1a}$, $R^1$-$R^{1a}$ is connected as a —CH$_2$CH$_2$—, —CH$_2$CH$_2$CH$_2$—, —CH=CH—, —C(CH$_3$)=CH—, or —CH=C(CH$_3$)— group; and if G is C and if Z includes $R^{1a}$, $R^1$-$R^{1a}$ is connected as a =CH—CH=CH—, =N—CH=CH—, or =CH—N=CH— group;

$R^1$ is hydrogen or $C_{1-6}$alkyl, or $R^1$-$R^{1a}$ are connected form a —CH$_2$CH$_2$—, —CH$_2$CH$_2$CH$_2$—, —CH=CH—, —C(CH$_3$)=CH—, or —CH=C(CH$_3$)— group or together with carbon or nitrogen atoms to which they are attached form a pyridine, pyrimidine or pyrazine ring;

$R^2$ is hydrogen, halo, $C_{1-6}$alkyl, or $C_{1-6}$alkyl selectively functionalized with one or more halogen, thiol, hydroxyl, carbonyl, carboxyl, carbonyloxyl, $C_{1-6}$alkoxy, $C_{1-6}$hydroxyalkoxy, amino, $C_{1-6}$alkylamino, di($C_{1-6}$alkyl)amino, or azido groups;

$R^{2a}$ is phenyl or a heteroaryl group selected from the group consisting of imidazolyl, pyridyl, pyridizinyl, pyrimidinyl, and pyrazinyl, wherein the phenyl or heterocyclic group is optionally substituted with 1-4 substituents independently selected from the group consisting of halogen, —SR$^{3a}$, —S(O)R$^{3a}$, —OR$^{3a}$, —OCH$_2$R$^{3b}$, —OCH(CH$_3$)R$^{3b}$, —OC(O)NHR$^{3a}$, —NR$^{3a}$R$^4$, —NHSO$_2$R$^{3a}$, azido, —CHO, —CO$_2$R$^{3a}$, cyano, $C_{1-6}$alkyl or —CR$^{5a}$R$^{6a}$R$^{7a}$, $C_{2-6}$alkenyl, —C(R$^{5a}$)=C(R$^{8a}$)(R$^{9a}$), $C_{2-6}$alkynyl, and —C≡CR$^{8a}$;

$R^{3a}$, $R^{3b}$, and $R^{4a}$ are independently hydrogen, phenyl, naphthyl, pyridyl, pyrimidinyl, imidazolyl, 1,2,3-triazolyl, quinolinyl, isoquinolinyl, thiazolyl, tetrazolyl groups, $C_{1-6}$alkyl, cyclic —($C_{1-8}$alkyl)-, cyclic —($C_{1-6}$oxaalkyl)-, cyclic —($C_{1-6}$azaalkyl)-, $C_{2-6}$alkenyl, or $C_{2-6}$alkynyl;

wherein the phenyl, naphthyl, pyridyl, pyrimidinyl, imidazolyl, 1,2,3-triazolyl, quinolinyl, isoquinolinyl, and thiazolyl, tetrazolyl groups are optionally substituted with 1-3 substituents independently selected from the group consisting of halogen, thiol, $C_{1-6}$alkyl thioether, $C_{1-6}$alkyl sulfoxide, $C_{1-6}$alkyl, $C_{1-6}$alkoxyl, amino, $C_{1-6}$alkylamino, $C_{1-6}$dialkylamino, $C_{1-6}$alkyl sulfonamide, azido, —CHO, —CO$_2$H, $C_{1-6}$alkyl carboxylate, cyano, $C_{2-6}$alkenyl, and $C_{2-6}$alkynyl group; and the $C_{1-6}$alkyl, cyclic —($C_{1-8}$alkyl)-, cyclic —($C_{1-6}$oxaalkyl)-, cyclic —($C_{1-6}$azaalkyl)-, $C_{2-6}$alkenyl, and $C_{2-6}$alkynyl groups are selectively functionalized with one or more halogen, thiol, hydroxyl, carbonyl, carboxyl, carbonyloxyl, $C_{1-6}$alkoxy, $C_{1-6}$hydroxyalkoxy, amino, $C_{1-6}$alkylamino, di($C_{1-6}$alkyl)amino, azido, piperidinyl, phenyl, naphthyl, pyridyl, pyrimidinyl, imidazolyl, 1,2,3-triazolyl, quinolinyl, isoquinolinyl, thiazolyl, or tetrazolyl groups; and $R^{5a}$, $R^{6a}$, $R^{7a}$, $R^{8a}$ and $R^{9a}$ are independently hydrogen, phenyl, naphthyl, pyridyl, pyrimidinyl, imidazolyl, 1,2,3-triazolyl, quinolinyl, isoquinolinyl, thiazolyl, tetrazolyl groups, $C_{1-6}$alkyl, cyclic —($C_{1-8}$alkyl)-, cyclic —($C_{1-6}$oxaalkyl)-, cyclic —($C_{1-6}$azaalkyl)-, $C_{2-6}$alkenyl, $C_{2-6}$alkynyl, $C_{1-6}$alkoxyl, cyclic —($C_{1-8}$alkoxyl)-, cyclic —($C_{1-6}$oxaalkoxyl)-, cyclic —($C_{1-6}$azaalkoxyl)-;

wherein the phenyl, naphthyl, pyridyl, pyrimidinyl, imidazolyl, 1,2,3-triazolyl, quinolinyl, isoquinolinyl, and thiazolyl, tetrazolyl groups are optionally substituted with 1-3 substituents independently selected from the group consisting of halogen, thiol, $C_{1-6}$alkyl thioether, $C_{1-6}$alkyl sulfoxide, $C_{1-6}$alkyl, $C_{1-6}$alkoxyl, amino, $C_{1-6}$alkylamino, $C_{1-6}$dialkylamino, $C_{1-6}$alkyl sulfonamide, azido, —CHO, —CO$_2$H, $C_{1-6}$alkyl carboxylate, cyano, $C_{2-6}$alkenyl, and $C_{2-6}$alkynyl group, and the $C_{1-6}$alkyl, cyclic —($C_{1-8}$alkyl)-, cyclic —($C_{1-6}$oxaalkyl)-, cyclic —($C_{1-4}$azaalkyl)-, $C_{2-6}$alkenyl, and $C_{2-6}$alkynyl groups are selectively functionalized with one or more halogen, thiol, hydroxyl, carbonyl, carboxyl, carbonyloxyl, $C_{1-6}$alkoxy, $C_{1-6}$hydroxyalkoxy, amino, $C_{1-6}$alkylamino, di($C_{1-6}$alkyl)amino, azido, piperidinyl, phenyl, naphthyl, pyridyl, pyrimidinyl, imidazolyl, 1,2,3-triazolyl, quinolinyl, isoquinolinyl, thiazolyl, or tetrazolyl groups.

In one embodiment, X is S, Y is O or S, and $R^{2a}$ is a imidazolyl, pyridyl, pyridizinyl, pyrimidinyl, or pyrazinyl group with 0-3 substituents independently selected from the group consisting of halogen, —SR$^{3a}$, —S(O)R$^{3a}$, —OR$^{3a}$, —OCH$_2$R$^{3b}$, —OCH(CH$_3$)R$^{3b}$, —OC(O)NHR$^{3a}$, —NR$^{3a}$R$^{4a}$, —NHSO$_2$R$^{3a}$, azido, carbonyl, —CHO, CO$_2$R$^{3a}$, cyano, $C_{1-6}$alkyl or —CR$^{5a}$R$^{6a}$R$^{7a}$, $C_{2-6}$alkeny, —C(R$^{5a}$)=C(R$^{8a}$)(R$^{9a}$), $C_{2-6}$alkynyl, and —C≡CR$^{8a}$.

In another embodiment, X is S, Y is O or S, and $R^{2a}$ is imidazolyl group with 0-3 substituents independently selected from the group consisting of halogen, —SR$^{3a}$, —S(O)R$^{3a}$, —OR$^{3a}$, —OCH$_2$R$^{3b}$, —OCH(CH$_3$)R$^{3b}$, —OC(O)NHR$^{3a}$, —NR$^{3a}$R$^{4a}$, —NHSO$_2$R$^{3a}$, azido, —CHO, CO$_2$R$^{3a}$, cyano, $C_{1-6}$alkyl or —CR$^{5a}$R$^{6a}$R$^{7a}$, $C_{2-6}$alkeny, —C(R$^{5a}$)=C(R$^{8a}$)(R$^{9a}$), $C_{2-6}$alkynyl, and —C≡CR$^{8a}$ In another embodiment, X is S, Y is O or S, and $R^{2a}$ is pyridyl group with 0-3 substituents independently selected from the group consisting of halogen, —SR$^{3a}$, —S(O)R$^{3a}$, —OR$^{3a}$, —OCH$_2$R$^{3b}$, —OCH(CH$_3$)R$^{3b}$, —OC(O)NHR$^{3a}$, —NR$^{3a}$R$^{4a}$, —NHSO$_2$R$^{3a}$, azido, —CHO, CO$_2$R$^{3a}$, cyano, $C_{1-6}$alkyl or —CR$^{5a}$R$^{6a}$R$^{7a}$, $C_{2-6}$alkeny, —C(R$^{5a}$)=C(R$^{8a}$)(R$^{9a}$), $C_{2-6}$alkynyl, and —C≡CR$^{8a}$.

In another embodiment, X is S, Y is O or S, and $R^{2a}$ is pyridizinyl group with 0-3 substituents independently selected from the group consisting of halogen, —SR$^{3a}$, —S(O)R$^{3a}$, —OR$^{3a}$, —OCH$_2$R$^{3b}$, —OCH(CH$_3$)R$^{3b}$, —OC(O)NHR$^{3a}$, —NR$^{3a}$R$^{4a}$, —NHSO$_2$R$^{3a}$, azido, —CHO, CO$_2$R$^{3a}$, cyano, $C_{1-6}$alkyl or —CR$^{5a}$R$^{6a}$R$^{7a}$, $C_{2-6}$alkeny, —C(R$^{5a}$)=C(R$^{8a}$)(R$^{9a}$), $C_{2-6}$alkynyl, and —C≡CR$^{8a}$.

In another embodiment, X is S, Y is O or S, and $R^{2a}$ is pyrimidinyl group with 0-3 substituents independently selected from the group consisting of halogen, —SR$^{3a}$, —S(O)R$^{3a}$, —OR$^{3a}$, —OCH$_2$R$^{3b}$, —OCH(CH$_3$)R$^{3b}$, —OC(O)NHR$^{3a}$, —NR$^{3a}$R$^{4a}$, —NHSO$_2$R$^{3a}$, azido, —CHO, CO$_2$R$^{3a}$, cyano, $C_{1-6}$alkyl or —CR$^{5a}$R$^{6a}$R$^{7a}$, $C_{2-6}$alkeny, —C(R$^{5a}$)=C(R$^{8a}$)(R$^{9a}$), $C_{2-6}$alkynyl, and —C≡CR$^{8a}$.

In another embodiment, X is S, Y is O or S, and $R^{2a}$ is pyrazinyl group with 0-3 substituents independently selected from the group consisting of halogen, —SR$^{3a}$, —S(O)R$^{3a}$, —OR$^{3a}$, —OCH$_2$R$^{3b}$, —OCH(CH$_3$)R$^{3b}$, —OC(O)NHR$^{3a}$, —NR$^{3a}$R$^{4a}$, —NHSO$_2$R$^{3a}$, azido, —CHO, CO$_2$R$^{3a}$, cyano, $C_{1-6}$alkyl or —CR$^{5a}$R$^{6a}$R$^{7a}$, $C_{2-6}$alkeny, —C(R$^{5a}$)=C(R$^{8a}$)(R$^{9a}$), $C_{2-6}$alkynyl, and —C≡CR$^{8a}$.

In another embodiment, X is S, Y is O or S, and $R^{2a}$ is phenyl group with 0-4 substituents independently selected from the group consisting of halogen, —SR$^{3a}$, —S(O)R$^{3a}$, —OR$^{3a}$, —OCH$_2$R$^{3b}$, —OCH(CH$_3$)R$^{3b}$, —OC(O)NHR$^{3a}$, —NR$^{3a}$R$^{4a}$, —NHSO$_2$R$^{3a}$, azido, —CHO, CO$_2$R$^{3a}$, cyano, C$_{1-6}$alkyl or —CR$^{5a}$R$^{6a}$R$^{7a}$, C$_{2-6}$alkeny, —C(R$^{5a}$)=C(R$^{8a}$)(R$^{9a}$), C$_{2-6}$alkynyl, and —C≡CR$^{8a}$.

In another embodiment, X is S, Y is O or S, G is N, and R$^1$ is hydrogen C$_{1-6}$alkyl, or C$_{1-6}$alkyl selectively functionalized with one or more halogen, thiol, hydroxyl, carbonyl, carboxyl, carbonyloxyl, C$_{1-6}$alkoxy, C$_{1-6}$hydroxyalkoxy, amino, C$_{1-6}$alkylamino, di(C$_{1-6}$alkyl)amino, or azido groups.

In another embodiment, X is S, Y is O or S, G is N, and R$^1$-R$^{1a}$ is connected as a —CH$_2$CH$_2$—, —CH$_2$CH$_2$CH$_2$—, —CH=CH—, —C(CH$_3$)=CH—, or —CH=C(CH$_3$)— group.

In another embodiment, The compound of claim 1, or a pharmaceutically acceptable salt thereof, wherein X is S, Y is O or S, G is C, Z is NR$^{1a}$, and R$^1$-R$^{1a}$ is connected as a =CH—CH=CH—, =N—CH=CH—, or =CH—N=CH— group.

In another embodiment, X is S, Y is O or S, and R$^2$ is hydrogen, halogen, C$_{1-6}$alkyl, or C$_{1-6}$alkyl selectively functionalized with one or more halogen, thiol, hydroxyl, carbonyl, carboxyl, carbonyloxyl, C$_{1-6}$alkoxy, C$_{1-6}$hydroxyalkoxy, amino, C$_{1-6}$alkylamino, di(C$_{1-6}$alkyl)amino, or azido groups.

In another embodiment, R$^2$ is hydrogen, Cl, Br, or methyl

In another embodiment, the invention provides a compound of Formula Ib, or a pharmaceutically acceptable salt thereof,

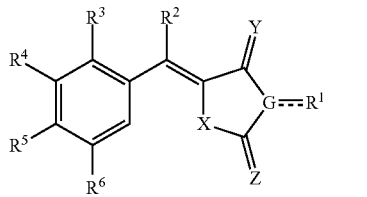

Formula Ib wherein:
X is NH or S;
Y is O or S;
Z is O, S, CHR$^{8a}$ or NR;
R$^{1a}$ is hydrogen, C$_{1-6}$alkyl, or C$_{1-6}$alkyl selectively functionalized with one or more halogen, thiol, hydroxyl, carbonyl, carboxyl, carbonyloxyl, C$_{1-6}$alkoxy, C$_{1-6}$hydroxyalkoxy, amino, C$_{1-6}$alkylamino, di(C$_{1-6}$alkyl) amino, or azido groups; G is N or C;
if G is N, R$^1$ is hydrogen C$_{1-6}$alkyl, or C$_{1-6}$alkyl selectively functionalized with one or more halogen, thiol, hydroxyl, carbonyl, carboxyl, carbonyloxyl, C$_{1-6}$alkoxy, C$_{1-6}$hydroxyalkoxy, amino, C$_{1-6}$alkylamino, di(C$_{1-6}$alkyl)amino, or azido groups, or R$^1$-R$^{1a}$ is connected as a —CH$_2$CH$_2$—, —CH$_2$CH$_2$CH$_2$—, —CH=CH—, —C(CH$_3$)—CH—, or —CH=C(CH$_3$)— group; and if G is C, R$^1$-R$^{1a}$ is connected as a =CH—CH=CH—, =N—CH=CH—, or =CH—N=CH— group;
R$^1$ is hydrogen or C$_{1-6}$alkyl, or R$^1$-R$^{1a}$ are connected form a —CH$_2$CH$_2$—, —CH$_2$CH$_2$CH$_2$—, —CH=CH—, —C(CH$_3$)=CH—, or —CH=C(CH$_3$)— group or together with carbon or nitrogen atoms to which they are attached form a pyridine, pyrimidine or pyrazine ring;

R$^2$ is hydrogen, halo, C$_{1-6}$alkyl, or C$_{1-6}$alkyl selectively functionalized with one or more halogen, thiol, hydroxyl, carbonyl, carboxyl, carbonyloxyl, C$_{1-6}$alkoxy, C$_{1-6}$hydroxyalkoxy, amino, C$_{1-6}$alkylamino, di(C$_{1-6}$alkyl)amino, or azido groups;

R$^3$, R$^5$, and R$^6$ are independently hydrogen, halogen, —SR$^{3a}$, —S(O)R$^{3a}$, —OR$^{3a}$, —OCH$_2$R$^{3b}$, —OCH(CH$_3$)R$^{3b}$, —OC(O)NHR$^{3a}$, —NR$^{3a}$R$^{4a}$, —NHSO$_2$R$^{3a}$, azido, —CHO, CO$_2$R$^{3a}$, cyano, C$_{1-6}$alkyl or —CR$^{5a}$R$^{6a}$R$^{7a}$, C$_{2-6}$alkeny, —C(R$^{5a}$)=C(R$^{8a}$)(R$^{9a}$), C$_{2-6}$alkynyl, —C≡CR$^{8a}$, or R$^2$-R$^3$ is connected as a —CH$_2$CH$_2$— or —CH$_2$CH$_2$CH$_2$— group;

R$^{3a}$, R$^{3b}$, and R$^{48}$ are independently hydrogen, phenyl, naphthyl, pyridyl, pyrimidinyl, imidazolyl, 1,2,3-triazolyl, quinolinyl, isoquinolinyl, thiazolyl, tetrazolyl groups, C$_{1-6}$alkyl, cyclic —(C$_{1-8}$alkyl)-, cyclic —(C$_{1-6}$oxaalkyl)-, cyclic —(C$_{1-6}$azaalkyl)-, C$_{2-6}$alkenyl, C$_{2-6}$alkynyl;

wherein the phenyl, naphthyl, pyridyl, pyrimidinyl, imidazolyl, 1,2,3-triazolyl, quinolinyl, isoquinolinyl, and thiazolyl, tetrazolyl groups are optionally substituted with 1-3 substituents independently selected from the group consisting of halogen, thiol, C$_{1-6}$alkyl thioether, C$_{1-6}$alkyl sulfoxide, C$_{1-6}$alkyl, C$_{1-6}$alkoxyl, amino, C$_{1-6}$alkylamino, C$_{1-6}$dialkylamino, C$_{1-6}$alkyl sulfonamide, azido, —CHO, —CO$_2$H, C$_{1-6}$alkyl carboxylate, cyano, C$_{2-6}$alkeny, and C$_{2-6}$alkynyl group; and the C$_{1-6}$alkyl, cyclic —(C$_{1-6}$alkyl)-, cyclic —(C$_{1-6}$oxaalkyl)-, cyclic —(C$_{1-6}$azaalkyl)-, C$_{2-6}$alkenyl, and C$_{2-6}$alkynyl groups are selectively functionalized with one or more halogen, thiol, hydroxyl, carbonyl, carboxyl, carbonyloxyl, C$_{1-6}$alkoxy, C$_{1-6}$hydroxyalkoxy, amino, C$_{1-6}$alkylamino, di(C$_{1-6}$alkyl)amino, azido, piperidinyl, phenyl, naphthyl, pyridyl, pyrimidinyl, imidazolyl, 1,2,3-triazolyl, quinolinyl, isoquinolinyl, thiazolyl, or tetrazolyl groups;

R$^4$ is hydrogen or halogen.

In another embodiment, X is S, Y is O or S, G is N, and R$^1$ is hydrogen C$_{1-6}$alkyl, or C$_{1-6}$alkyl selectively functionalized with one or more halogen, thiol, hydroxyl, carbonyl, carboxyl, carbonyloxyl, C$_{1-6}$alkoxy, C$_{1-6}$hydroxyalkoxy, amino, C$_{1-6}$alkylamino, di(C$_{1-6}$alkyl)amino, or azido groups.

In another embodiment, X is S, Y is O or S, G is N, and R$^1$-R$^{1a}$ is connected as a —CH$_2$CH$_2$—, —CH$_2$CH$_2$CH$_2$—, —CH=CH—, —C(CH$_3$)=CH—, or —CH=C(CH$_3$)— group.

In another embodiment, X is S, Y is O or S, G is C, Z is NR$^{1a}$, and R$^1$-R$^{1a}$ is connected as a =CH—CH=CH—, =N—CH=CH—, or =CH—N=CH— group.

In another embodiment, R$^2$ is hydrogen, Cl, Br, or methyl.

In another embodiment, X is S, Y is O or S, G is N, and R$^1$ is hydrogen C$_{1-6}$alkyl, or C$_{1-6}$alkyl selectively functionalized with one or more halogen, thiol, hydroxyl, carbonyl, carboxyl, carbonyloxyl, C$_{1-6}$alkoxy, C$_{1-6}$hydroxyalkoxy, amino, C$_{1-6}$alkylamino, di(C$_{1-6}$alkyl)amino, or azido groups.

In another embodiment, X is S, Y is O or S, G is C, Z is NR$^{1a}$, and R$^1$-R$^{1a}$ is connected as a =CH—CH=CH—, =N—CH=CH—, or =CH—N=CH— group.

In another embodiment, the invention provides a compound of Formula Ic, or a pharmaceutically acceptable salt thereof,

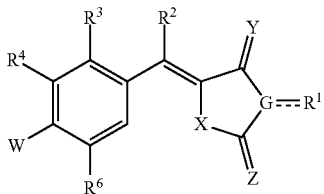

Formula Ic wherein:
X is NH or S;
Y is O or S;
Z is O, S, CHR$^{1a}$ or NR$^{1a}$;
R$^{1a}$ is hydrogen, C$_{1-6}$alkyl, or C$_{1-6}$alkyl selectively functionalized with one or more halogen, thiol, hydroxyl, carbonyl, carboxyl, carbonyloxyl, C$_{1-6}$alkoxy, C$_{1-6}$hydroxyalkoxy, amino, C$_{1-6}$alkylamino, di(C$_{1-6}$alkyl)amino, or azido groups;
G is N or C;
if G is N, R$^1$ is hydrogen C$_{1-6}$alkyl, or C$_{1-6}$alkyl selectively functionalized with one or more halogen, thiol, hydroxyl, carbonyl, carboxyl, carbonyloxyl, C$_{1-6}$alkoxy, C$_{1-6}$hydroxyalkoxy, amino, C$_{1-6}$alkylamino, di(C$_{1-6}$alkyl)amino, or azido groups, or R$^1$-R$^{1a}$ is connected as a —CH$_2$CH$_2$—, —CH$_2$CH$_2$CH$_2$—, —CH═CH—, —C(CH$_3$)═CH— or —CH═C(CH$_3$)— group; and if G is C, R$^1$-R$^{1a}$ is connected as a ═CH—CH═CH—, ═N—CH═CH—, or ═CH—N═CH— group;
W is OR$^{10a}$ or NHR$^{10a}$;
wherein R$^{10a}$ is hydrogen, C$_{1-6}$alkyl, C$_{1-6}$alkyl selectively functionalized with one or more halogen, thiol, hydroxyl, carbonyl, carboxyl, carbonyloxyl, C$_{1-6}$alkoxy, C$_{1-6}$hydroxyalkoxy, amino, C$_{1-6}$alkylamino, di(C$_{1-6}$alkyl)amino, or azido groups, or R$^{10a}$-R$^6$ is connected as a —CH$_2$—CH$_2$—, —CH═CH—, —N═CH—, or —CH═N— group;
R$^2$ is hydrogen, halo, C$_{1-6}$alkyl, or C$_{1-6}$alkyl selectively functionalized with one or more halogen, thiol, hydroxyl, carbonyl, carboxyl, carbonyloxyl, C$_{1-6}$alkoxy, C$_{1-6}$hydroxyalkoxy, amino, C$_{1-6}$alkylamino, di(C$_{1-6}$alkyl)amino, or azido groups;
R$^3$ and R$^6$ are independently hydrogen, halogen, —SR$^{3a}$, —S(O)R$^{3a}$, —OR$^{3a}$, —OCH$_2$R$^{3b}$, —OCH(CH$_3$)R$^{3b}$, —OC(O)NHR$^{3a}$, —NR$^{3a}$R$^{4a}$, —NHSO$_2$R$^{3a}$, azido, —CHO, CO$_2$R$^{3a}$, cyano, C$_{1-6}$alkyl or —CR$^{5a}$R$^{6a}$R$^{7a}$, C$_{2-6}$alkeny, —C(R$^{5a}$)═C(R$^{8a}$)(R$^{9a}$), C$_{2-6}$alkynyl, —C≡CR$^{8a}$, or R$^2$-R$^3$ are connected as a —CH$_2$CH$_2$— or —CH$_2$CH$_2$CH$_2$— group;
R$^{3a}$, R$^{3b}$, and R$^{4a}$ are independently hydrogen, phenyl, naphthyl, pyridyl, pyrimidinyl, imidazolyl, 1,2,3-triazolyl, quinolinyl, isoquinolinyl, thiazolyl, tetrazolyl groups, C$_{1-6}$alkyl, cyclic —(C$_{1-8}$alkyl)-, cyclic —(C$_{1-6}$oxaalkyl)-, cyclic —(C$_{1-6}$azaalkyl)-, C$_{2-6}$alkenyl, C$_{2-6}$alkynyl;
wherein the phenyl, naphthyl, pyridyl, pyrimidinyl, imidazolyl, 1,2,3-triazolyl, quinolinyl, isoquinolinyl, thiazolyl, or tetrazolyl groups are optionally substituted with 1-3 substituents independently selected from the group consisting of halogen, thiol, C$_{1-6}$alkyl thioether, C$_{1-6}$alkyl sulfoxide, C$_{1-6}$ alkyl, C$_{1-6}$alkoxyl, amino, C$_{1-6}$alkylamino, C$_{1-6}$dialkylamino, C$_{1-6}$alkyl sulfonamide, azido, —CHO, —CO$_2$H, C$_{1-6}$alkyl carboxylate, cyano, C$_{2-6}$alkeny, and C$_{2-6}$alkynyl group; and the C$_{1-6}$alkyl, cyclic —(C$_{1-6}$alkyl)-, cyclic —(C$_{1-6}$oxaalkyl)-, cyclic —(C$_{1-6}$azaalkyl)-, C$_{2-6}$alkenyl, or C$_{2-6}$alkynyl groups are selectively functionalized with one or more halogen, thiol, hydroxyl, carbonyl, carboxyl, carbonyloxyl, C$_{1-6}$alkoxy, C$_{1-6}$hydroxyalkoxy, amino, C$_{1-6}$alkylamino, di(C$_{1-6}$alkyl)amino, azido, piperidinyl, phenyl, naphthyl, pyridyl, pyrimidinyl, imidazolyl, 1,2,3-triazolyl, quinolinyl, isoquinolinyl, thiazolyl, or tetrazolyl groups;
R$^4$ is hydrogen or halogen In another embodiment, X is S, Y is O or S, Z is O or S, G is N, and R$^1$ is hydrogen C$_{1-6}$alkyl, or C$_{1-6}$alkyl selectively functionalized with one or more halogen, thiol, hydroxyl, carbonyl, carboxyl, carbonyloxyl, C$_{1-6}$alkoxy, C$_{1-6}$hydroxyalkoxy, amino, C$_{1-6}$alkylamino, di(C$_{1-6}$alkyl)amino, or azido groups.

In another embodiment, X is S, Y is O or S, G is N, Z is NR$^{1a}$, and R$^1$-R$^{1a}$ is connected as a —CH$_2$CH$_2$—, —CH$_2$CH$_2$CH$_2$—, —CH═CH—, —C(CH$_3$)═CH—, or —CH═C(CH$_3$)— group.

In another embodiment, X is S, Y is O or S, G is C, Z is NR$^{1a}$, and R$^1$-R$^{1a}$ is connected as a ═CH—CH═CH—, ═N—CH═CH—, or ═CH—N═CH— group.

In another embodiment, R$^2$ is hydrogen, Cl, Br, or methyl.

In another embodiment, the invention provides a compound of Formula Id, or a pharmaceutically acceptable salt thereof,

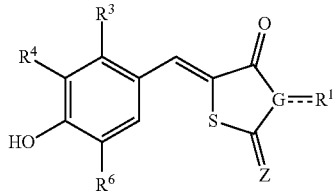

Formula Id wherein:
Z is O, S, CHR$^{1a}$ or NR$^{1a}$;
R$^{1a}$ is hydrogen, C$_{1-6}$alkyl, or C$_{1-6}$alkyl selectively functionalized with one or more halogen, thiol, hydroxyl, carbonyl, carboxyl, carbonyloxyl, C$_{1-6}$alkoxy, C$_{1-6}$hydroxyalkoxy, amino, C$_{1-6}$alkylamino, di(C$_{1-6}$alkyl)amino, or azido groups;
G is N or C;
if G is N, R$^1$ is hydrogen C$_{1-6}$alkyl, or C$_{1-6}$alkyl selectively functionalized with one or more halogen, thiol, hydroxyl, carbonyl, carboxyl, carbonyloxyl, C$_{1-6}$alkoxy, C$_{1-6}$hydroxyalkoxy, amino, C$_{1-6}$alkylamino, di(C$_{1-6}$alkyl)amino, or azido groups, or R$^1$-R$^{1a}$ is connected as a —CH$_2$CH$_2$—, —CH$_2$CH$_2$CH$_2$—, —CH═CH—, —C(CH$_3$)═CH— or —CH═C(CH$_3$)— group; and if G is C, R$^1$-R$^{1a}$ is connected as a ═CH—CH═CH—, ═N—CH═CH—, or ═CH—N═CH— group;
R$^3$ and R$^4$ are independently hydrogen or halogen;
R$^6$ is hydrogen, halogen, —SR$^{3a}$, —S(O)R$^{3a}$, —OR$^{3a}$, —OCH$_2$R$^{3b}$, —OCH(CH$_3$)R$^{3b}$, —OC(O)NHR$^{3a}$, —NR$^{3a}$R$^{4a}$, —NHSO$_2$R$^{3a}$, azido, —CHO, CO$_2$R$^{3a}$, cyano, C$_{1-6}$alkyl or —CR$^{5a}$R$^{6a}$R$^{7a}$, C$_{2-6}$alkeny, —C(R$^{5a}$)═C(R$^{8a}$)(R$^{9a}$), C$_{2-6}$alkynyl, —C≡CR$^{8a}$, or R$^2$-R$^3$ are connected as a —CH$_2$CH$_2$— or —CH$_2$CH$_2$CH$_2$— group;
R$^{3a}$, R$^{3b}$, and R$^{4a}$ are independently hydrogen, phenyl, naphthyl, pyridyl, pyrimidinyl, imidazolyl, 1,2,3-triazolyl, quinolinyl, isoquinolinyl, thiazolyl, tetrazolyl groups, $C_{1-6}$alkyl, cyclic —($C_{1-8}$alkyl)-, cyclic —($C_{1-6}$oxaalkyl)-, cyclic —($C_{1-6}$azaalkyl)-, $C_{2-6}$alkenyl, $C_{2-6}$alkynyl;
wherein the phenyl, naphthyl, pyridyl, pyrimidinyl, imidazolyl, 1,2,3-triazolyl, quinolinyl, isoquinolinyl, thiazolyl, or tetrazolyl groups are optionally substituted with 1-3 substituents independently selected from the group consisting of halogen, thiol, $C_{1-6}$alkyl thioether, $C_{1-6}$alkyl sulfoxide, $C_{1-6}$alkyl, $C_{1-6}$alkoxyl, amino, $C_{1-6}$alkylamino, $C_{1-6}$dialkylamino, $C_{1-6}$alkyl sulfonamide, azido, —CHO, —CO$_2$H, $C_{1-6}$alkyl carboxylate, cyano, $C_{2-6}$alkeny, and $C_{2-6}$alkynyl group; and the $C_{1-6}$alkyl, cyclic —($C_{1-8}$alkyl)-, cyclic —($C_{1-6}$oxaalkyl)-, cyclic —($C_{1-6}$azaalkyl)-, $C_{2-6}$alkenyl, or $C_{2-6}$alkynyl groups are selectively functionalized with one or more halogen, thiol, hydroxyl, carbonyl, carboxyl, carbonyloxyl, $C_{1-6}$alkoxy, $C_{1-6}$hydroxyalkoxy, amino, $C_{1-6}$alkylamino, di($C_{1-6}$alkyl)amino, azido, piperidinyl, phenyl, naphthyl, pyridyl, pyrimidinyl, imidazolyl, 1,2,3-triazolyl, quinolinyl, isoquinolinyl, thiazolyl, or tetrazolyl groups In another embodiment, Z is O or S, G is N, and $R^1$ is hydrogen $C_{1-6}$alkyl, or $C_{1-6}$alkyl selectively functionalized with one or more halogen, thiol, hydroxyl, carbonyl, carboxyl, carbonyloxyl, $C_{1-6}$alkoxy, $C_{1-6}$hydroxyalkoxy, amino, $C_{1-6}$alkylamino, di($C_{1-6}$alkyl)amino, or azido groups.

In another embodiment, G is N, Z is $NR^{1a}$, and $R^1$-$R^{1a}$ is connected as a —CH$_2$CH$_2$—, —CH$_2$CH$_2$CH$_2$—, —CH═CH—, —C(CH$_3$)═CH—, or —CH═C(CH$_3$)— group.

In another embodiment, G is C, Z is $NR^{1a}$, and $R^1$-$R^{1a}$ is connected as a ═CH—CH═CH—, ═N—CH═CH—, or ═CH—N═CH— group.

In another embodiment, G is N, $R^1$ is methyl, Z is O, $R^3$ and $R^4$ are independently hydrogen or halogen, and $R^6$ is —$OR^{3a}$, —OCH$_2R^{3b}$, or —OCH(CH$_3$)$R^{3b}$; wherein
$R^{3a}$ and $R^{3b}$ are independently hydrogen, phenyl, naphthyl, pyridyl, pyrimidinyl, imidazolyl, 1,2,3-triazolyl, quinolinyl, isoquinolinyl, thiazolyl, tetrazolyl groups, $C_{1-6}$alkyl, cyclic —($C_{1-8}$alkyl)-, cyclic —($C_{1-6}$oxaalkyl)-, cyclic —($C_{1-6}$azaalkyl)-, $C_{2-6}$alkenyl, $C_{2-6}$alkynyl;
wherein the phenyl, naphthyl, pyridyl, pyrimidinyl, imidazolyl, 1,2,3-triazolyl, quinolinyl, isoquinolinyl, thiazolyl, or tetrazolyl groups are optionally substituted with 1-3 substituents independently selected from the group consisting of halogen, thiol, $C_{1-6}$alkyl thioether, $C_{1-6}$alkyl sulfoxide, $C_{1-6}$alkyl, $C_{1-6}$alkoxyl, amino, $C_{1-6}$alkylamino, $C_{1-6}$dialkylamino, $C_{1-6}$alkyl sulfonamide, azido, —CHO, —CO$_2$H, $C_{1-6}$alkyl carboxylate, cyano, $C_{2-6}$alkeny, and $C_{2-6}$alkynyl group; and the $C_{1-6}$alkyl, cyclic —($C_{1-8}$alkyl)-, cyclic —($C_{1-6}$oxaalkyl)-, cyclic —($C_{1-6}$azaalkyl)-, $C_{2-6}$alkenyl, or $C_{2-6}$alkynyl groups are selectively functionalized with one or more halogen, thiol, hydroxyl, carbonyl, carboxyl, carbonyloxyl, $C_{1-6}$alkoxy, $C_{1-6}$hydroxyalkoxy, amino, $C_1$-6alkylamino, di($C_{1-6}$alkyl)amino, azido, piperidinyl, phenyl, naphthyl, pyridyl, pyrimidinyl, imidazolyl, 1,2,3-triazolyl, quinolinyl, isoquinolinyl, thiazolyl, or tetrazolyl groups.

In another embodiment, the compound of Formula I comprising the structure:

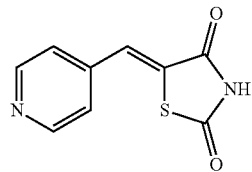 [SMILES: O=C1NC(=O)/C(=C/c2ccncc2)S1]

or a pharmaceutically acceptable salt thereof.

In another embodiment, the compound of Formula I comprising the structure:

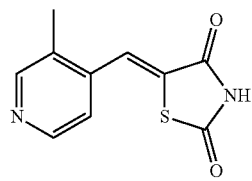

or a pharmaceutically acceptable salt thereof.

In another embodiment, the compound of Formula I comprising the structure:

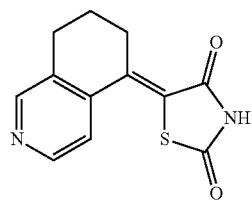 [SMILES: O=C1NC(=O)/C(=C2\CCCc3cnccc32)S1]

or a pharmaceutically acceptable salt thereof.

In another embodiment, the compound of Formula I comprising the structure:

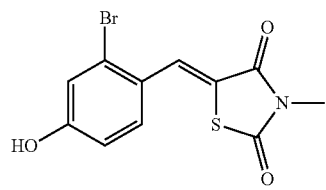 [SMILES: CN1C(=O)S/C(=C\c2ccc(O)cc2Br)C1=O]

or a pharmaceutically acceptable salt thereof.

In another embodiment, the compound of Formula I comprising the structure:

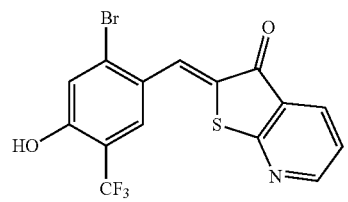

or a pharmaceutically acceptable salt thereof.

In another embodiment, the compound of Formula I comprising the structure:

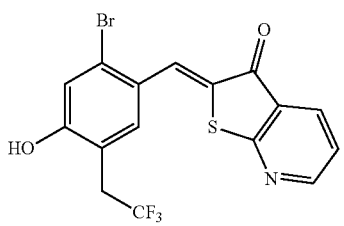

or a pharmaceutically acceptable salt thereof.

In another embodiment, the compound of Formula I comprising the structure:

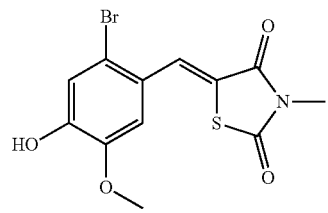 [SMILES: COc1cc(/C=C2\SC(=O)N(C)C2=O)c(Br)cc1O]

or a pharmaceutically acceptable salt thereof.

In another embodiment, the compound of Formula I comprising the structure:

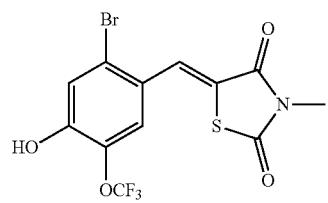

or a pharmaceutically acceptable salt thereof.

In another embodiment, the compound of Formula I comprising the structure:

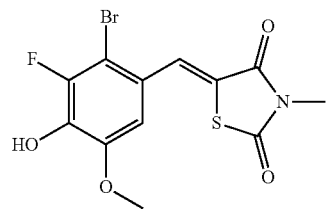 [SMILES: COc1cc(/C=C2\SC(=O)N(C)C2=O)c(Br)c(F)c1O]

or a pharmaceutically acceptable salt thereof.

In another embodiment, the compound of Formula I comprising the structure:

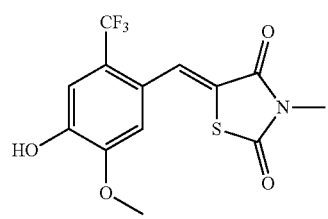

or a pharmaceutically acceptable salt thereof.

In another embodiment, the compound of Formula I comprising the structure:

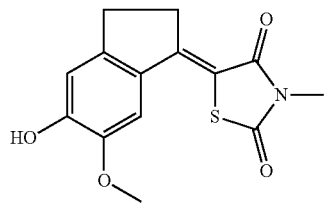 [SMILES: COc1cc2c(cc1O)CC/C2=C1/SC(=O)N(C)C1=O]

or a pharmaceutically acceptable salt thereof.

In another embodiment, the compound of Formula I comprising the structure:

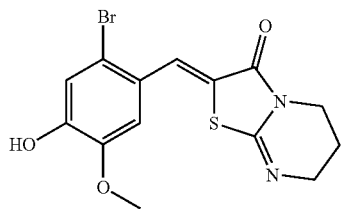 [SMILES: COc1cc(/C=c2\sc3n(c2=O)CCCN=3)c(Br)cc1O]

or a pharmaceutically acceptable salt thereof.

In another embodiment, the compound of Formula I comprising the structure:

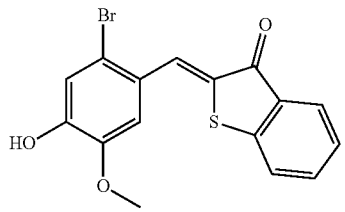

or a pharmaceutically acceptable salt thereof.

In another embodiment, the compound of Formula I comprising the structure:

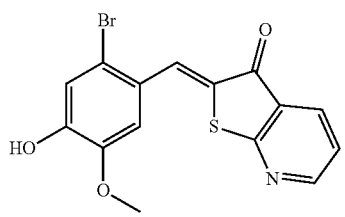

or a pharmaceutically acceptable salt thereof.

In another embodimet, the compound of Formual I comprising the structure:

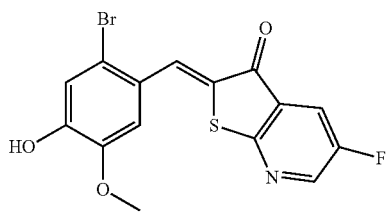 [SMILES: COc1cc(/C=C2\Sc3ncc(F)cc3C2=O)c(Br)cc1O]

or a pharmaceutically acceptable salt thereof.

In another embodiment, the compound of Formula I comprising the structure:

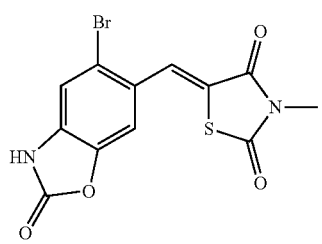 [SMILES: CN1C(=O)S/C(=C\c2cc3oc(=O)[nH]c3cc2Br)C1=O]

or a pharmaceutically acceptable salt thereof.

In another embodiment, the compound of Formula I comprising the structure:

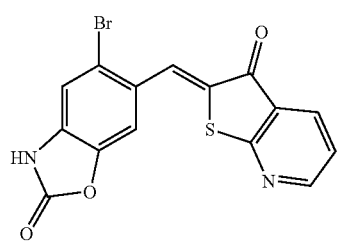 [SMILES: O=C1/C(=C/c2cc3oc(=O)[nH]c3cc2Br)Sc2ncccc21]

or a pharmaceutically acceptable salt thereof.

In another embodiment, the compound of Formula I comprising the structure:

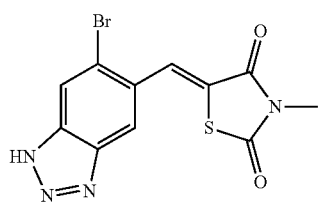 [SMILES: CN1C(=O)S/C(=C\c2cc3nn[nH]c3cc2Br)C1=O]

or a pharmaceutically acceptable salt thereof.

In another embodiment, the compound of Formula I comprising the structure:

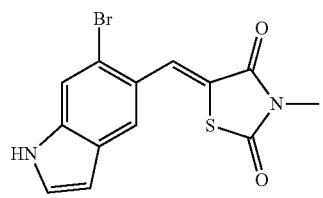

or a pharmaceutically acceptable salt thereof.

In another embodiment, the compound of Formula I comprising the structure:

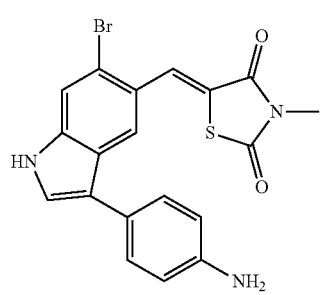 [SMILES: CN1C(=O)S/C(=C\c2cc3c(-c4ccc(N)cc4)c[nH]c3cc2Br)C1=O]

or a pharmaceutically acceptable salt thereof.

In another embodiment, the compound of Formula I comprising the structure:

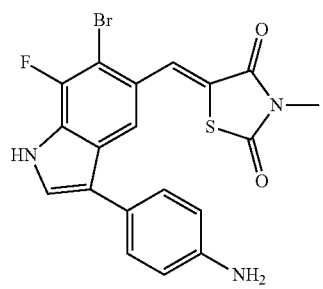 [SMILES: CN1C(=O)S/C(=C\c2cc3c(-c4ccc(N)cc4)c[nH]c3c(F)c2Br)C1=O]

or a pharmaceutically acceptable salt thereof.

In another embodiment, the compound of Formula I comprising the structure:

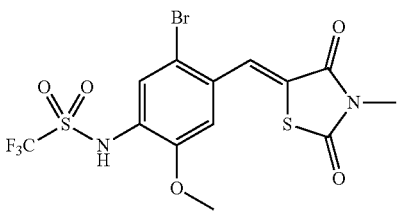 [SMILES: COc1cc(/C=C2\SC(=O)N(C)C2=O)c(Br)cc1NS(=O)(=O)C(F)(F)F]

or a pharmaceutically acceptable salt thereof.

In another embodiment, the compound of Formula I comprising the structure:

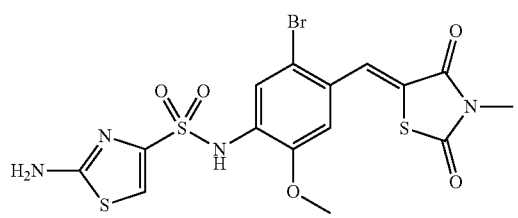 [SMILES: COc1cc(/C=C2\SC(=O)N(C)C2=O)c(Br)cc1NS(=O)(=O)c1csc(N)n1]

or a pharmaceutically acceptable salt thereof.

In another embodiment, the compound of Formula I comprising the structure:

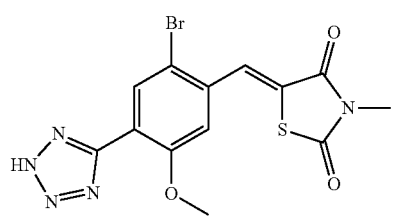 [SMILES: COc1cc(/C=C2\SC(=O)N(C)C2=O)c(Br)cc1-c1nn[nH]n1]

or a pharmaceutically acceptable salt thereof.

In another embodiment, the compound of Formula I comprising the structure:

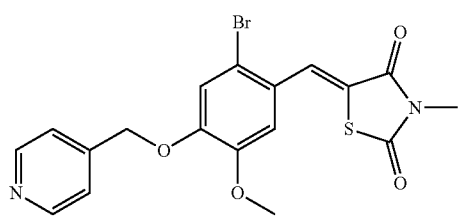 [SMILES: COc1cc(/C=C2\SC(=O)N(C)C2=O)c(Br)cc1OCc1ccncc1]

or a pharmaceutically acceptable salt thereof.

In another embodiment, the compound of Formula I comprising the structure:

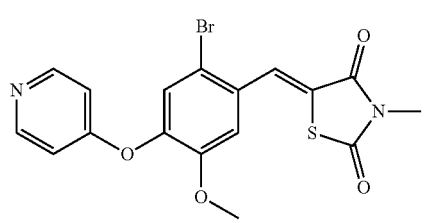 [SMILES: COc1cc(/C=C2\SC(=O)N(C)C2=O)c(Br)cc1Oc1ccncc1]

or a pharmaceutically acceptable salt thereof.

In another embodiment, the compound of Formula I comprising the structure:

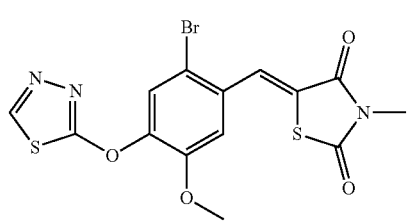 [SMILES: COc1cc(/C=C2\SC(=O)N(C)C2=O)c(Br)cc1Oc1nncs1]

or a pharmaceutically acceptable salt thereof.

In another embodiment, the compound of Formula I comprising the structure:

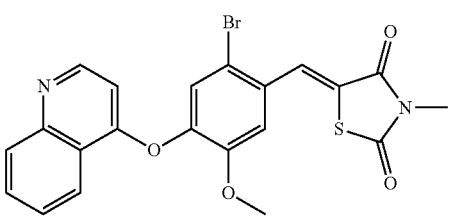 [SMILES: COc1cc(/C=C2\SC(=O)N(C)C2=O)c(Br)cc1Oc1ccnc2ccccc12]

or a pharmaceutically acceptable salt thereof.

In another embodiment, the compound of Formula I comprising the structure:

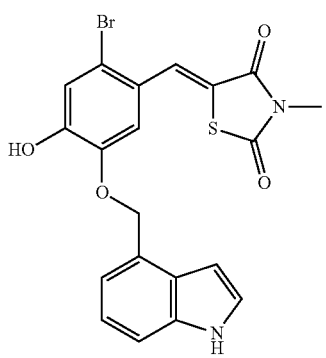 [SMILES: CN1C(=O)S/C(=C\c2cc(OCc3cccc4[nH]ccc34)c(O)cc2Br)C1=O]

or a pharmaceutically acceptable salt thereof.

In another embodiment, the compound of Formula I comprising the structure:

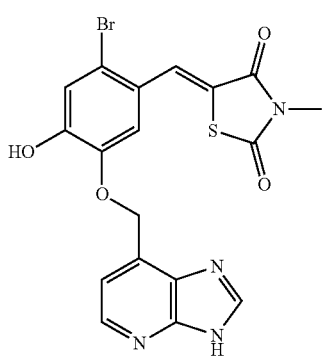 [SMILES: CN1C(=O)S/C(=C\c2cc(OCc3ccnc4[nH]cnc34)c(O)cc2Br)C1=O]

or a pharmaceutically acceptable salt thereof.

In another embodiment, the compound of Formula I comprising the structure:

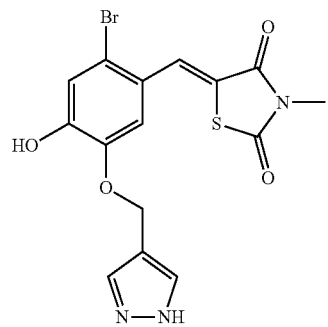 [SMILES: CN1C(=O)S/C(=C\c2cc(OCc3cn[nH]c3)c(O)cc2Br)C1=O]

or a pharmaceutically acceptable salt thereof.

In another embodiment, the compound of Formula I comprising the structure:

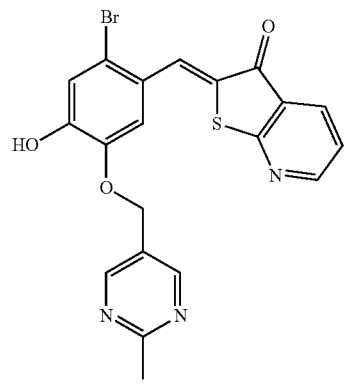

or a pharmaceutically acceptable salt thereof.

In another embodiment, the compound of Formula I comprising the structure:

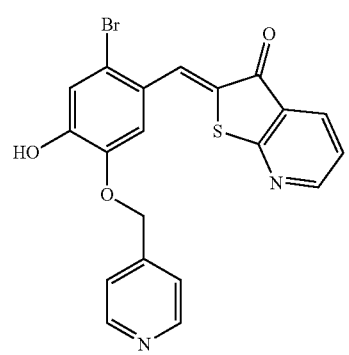 [SMILES: O=C1/C(=C/c2cc(OCc3ccncc3)c(O)cc2Br)Sc2ncccc21]

or a pharmaceutically acceptable salt thereof.

In another embodiment, the compound of Formula I comprising the structure:

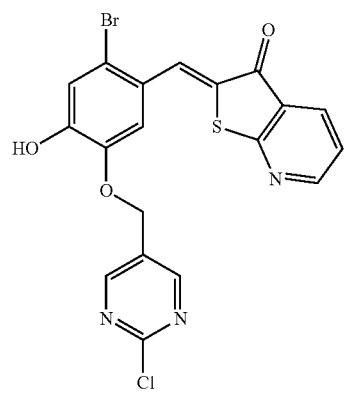

or a pharmaceutically acceptable salt thereof.

In another embodiment, the compound of Formula I comprising the structure:

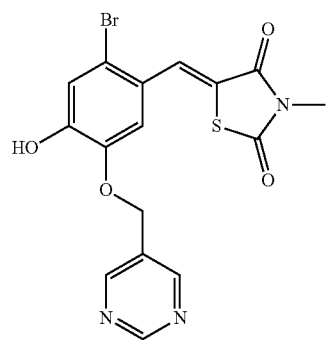 [SMILES: CN1C(=O)S/C(=C\c2cc(OCc3cncnc3)c(O)cc2Br)C1=O]

or a pharmaceutically acceptable salt thereof.

In another embodiment, the compound of Formula I comprising the structure:

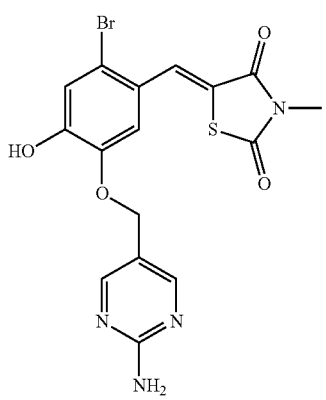 [SMILES: CN1C(=O)S/C(=C\c2cc(OCc3cnc(N)nc3)c(O)cc2Br)C1=O]

or a pharmaceutically acceptable salt thereof.

In another embodiment, the compound of Formula I comprising the structure:

19

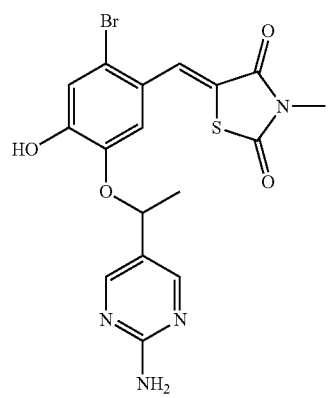 [SMILES: CC(Oc1cc(/C=C2\SC(=O)N(C)C2=O)c(Br)cc1O)c1cnc(N)nc1]

or a pharmaceutically acceptable salt thereof.

In another embodiment, the compound of Formula I comprising the structure:

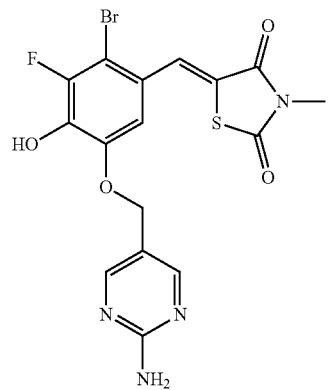

or a pharmaceutically acceptable salt thereof.

In another embodiment, the compound of Formula I comprising the structure:

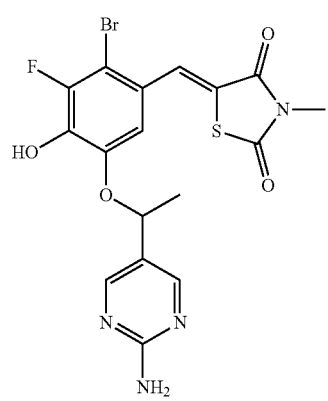

or a pharmaceutically acceptable salt thereof.

In another embodiment, the compound of Formula I comprising the structure:

20

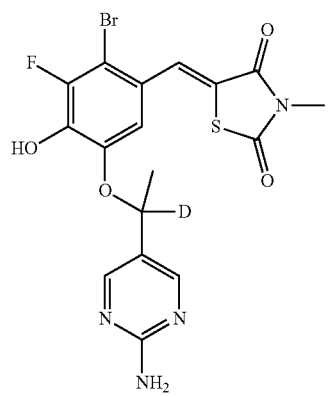

or a pharmaceutically acceptable salt thereof.

In another embodiment, the compound of Formula I comprising the structure:

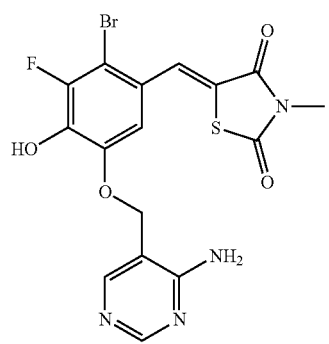 [SMILES: CN1C(=O)S/C(=C\c2cc(OCc3cncnc3N)c(O)c(F)c2Br)C1=O]

or a pharmaceutically acceptable salt thereof.

In another embodiment, the compound of Formula I comprising the structure:

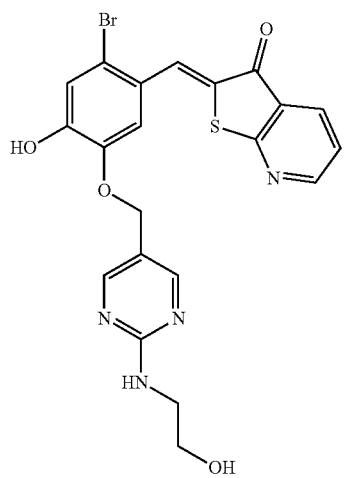 [SMILES: O=C1/C(=C/c2cc(OCc3cnc(NCCO)nc3)c(O)cc2Br)Sc2ncccc21]

or a pharmaceutically salt thereof.

In another embodiment, the compound of Formula I comprising the structure:

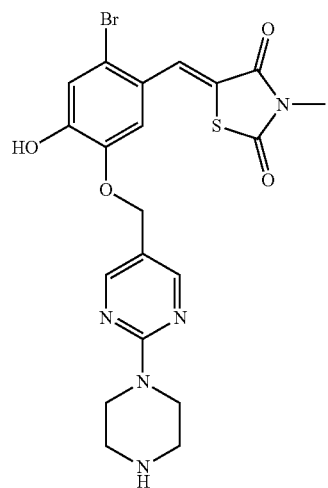

or a pharmaceutically acceptable salt thereof.

In another embodiment, the compound of Formula I comprising the structure:

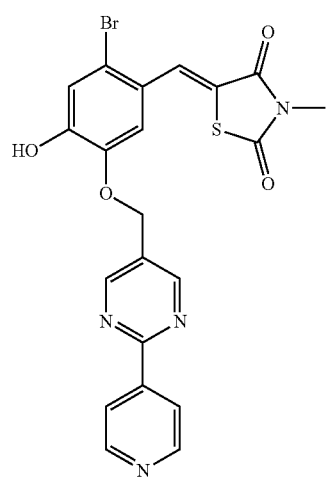

or a pharmaceutically acceptable salt thereof.

In another embodiment, the compound of Formula I comprising the structure:

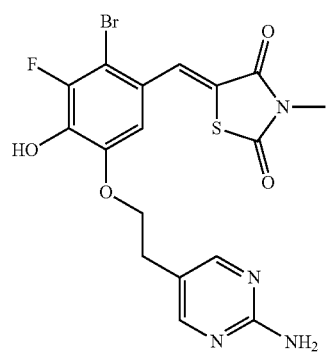 [SMILES: CN1C(=O)S/C(=C\c2cc(OCCc3cnc(N)nc3)c(O)c(F)c2Br)C1=O]

or a pharmaceutically acceptable salt thereof.

In another embodiment, the compound of Formula I comprising the structure:

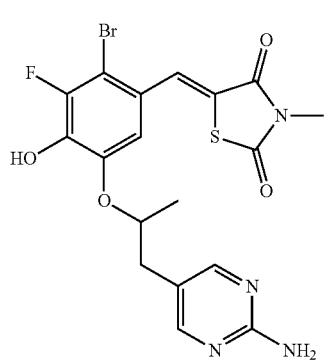

or a pharmaceutically acceptable salt thereof.

In another embodiment, the compound of Formula I comprising the structure:

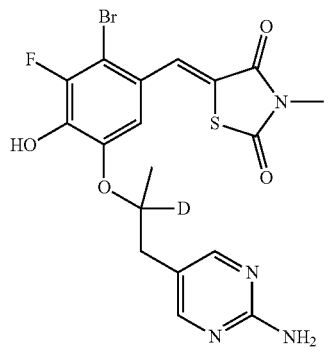 [SMILES: [2H]C(C)(Cc1cnc(N)nc1)Oc1cc(/C=C2\SC(=O)N(C)C2=O)c(Br)c(F)c1O]

or a pharmaceutically acceptable salt thereof.

In another embodiment, the compound of Formula I comprising the structure:

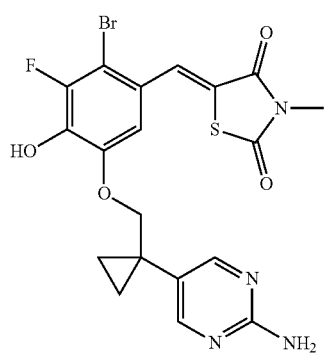 [SMILES: CN1C(=O)S/C(=C\c2cc(OCC3(c4cnc(N)nc4)CC3)c(O)c(F)c2Br)C1=O]

or a pharmaceutically acceptable salt thereof.

In another embodiment, the compound of Formula I comprising the structure:

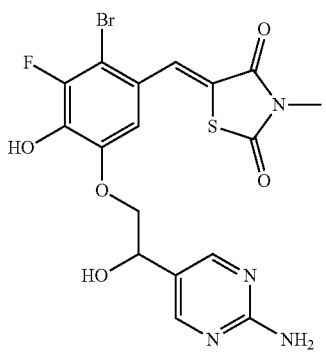 [SMILES: CN1C(=O)S/C(=C\c2cc(OCC(O)c3cnc(N)nc3)c(O)c(F)c2Br)C1=O]

or a pharmaceutically acceptable salt thereof.

In another embodiment, the compound of Formula I comprising the structure:

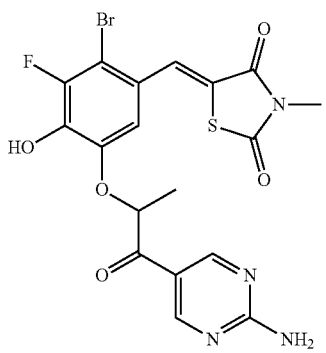

or a pharmaceutically acceptable salt thereof.

In another aspect, the present invention provides a pharmaceutical composition comprising a compound of Formula I, or a pharmaceutically acceptable salt thereof, and one or more of pharmaceutically acceptable excipients.

In another aspect, the present invention provides a compound of Formula I, or a pharmaceutically acceptable salt thereof, for use in therapy.

In another aspect, the present invention provides a compound of Formula I, or a pharmaceutically acceptable salt thereof, for use in the treatment of a disease or condition in which modulation of cGAS activity is beneficial.

In another aspect, the present invention provides a compound of Formula I, or a pharmaceutically acceptable salt thereof, for use in the treatment of an inflammatory, allergic, autoimmune, or infectious disease.

In another aspect, the present invention provides a compound of Formula I, or a pharmaceutically acceptable salt thereof, for use in the treatment of a senescence- or age-related disease.

In another aspect, the present invention provides a method for treating a disease or condition for which modulation of cGAS activity is beneficial comprising: administering to a patient in need thereof, a therapeutically effective amount of a compound of Formula I, or a pharmaceutically acceptable salt thereof.

In another aspect, the present invention provides a method of treating an inflammatory, allergic, autoimmune, or infectious disease comprising: administering to a patient in need thereof, a therapeutically effective amount of a compound of Formula I, or a pharmaceutically acceptable salt thereof.

In another aspect, the present invention provides a method of treating a senescence- or age-related disease comprising: administering to a patient in need thereof, a therapeutically effective amount of a compound of Formula I, or a pharmaceutically acceptable salt thereof.

In another aspect, the present invention provides the use of a compound of Formula I, or a pharmaceutically acceptable salt thereof, in the manufacture of a medicament for use the treatment of a disease or condition for which modulation of cGAS is beneficial.

In another aspect, the present invention provides the use of a compound of Formula I, or a pharmaceutically acceptable salt thereof, in the manufacture of a medicament for use the treatment of an inflammatory, allergic, autoimmune or infectious disease.

In another aspect, the present invention provides the use of a compound of Formula I, or a pharmaceutically acceptable salt thereof, in the manufacture of a medicament for use the treatment of a senescence- or age-related disease.

In another aspect, the present invention provides pharmaceutical composition comprising: a compound of Formula I, or a pharmaceutically acceptable salt thereof, and at least one further therapeutic agent.

In another aspect, the present invention provides a pharmaceutical composition comprising: a compound of Formula I, or a pharmaceutically acceptable salt thereof, at least one further therapeutic agent, and one or more of pharmaceutically acceptable excipients.

In another aspect, the present invention provides a pharmaceutical composition comprising: a compound of Formula I, or a pharmaceutically acceptable salt thereof, and at least one further therapeutic agent for use in therapy.

In another aspect, the present invention provides a pharmaceutical composition comprising: a compound of Formula I, or a pharmaceutically acceptable salt thereof, and at least one further therapeutic agent for use in the treatment of a disease or condition for which modulation of cGAS is beneficial.

In another aspect, the present invention provides a pharmaceutical composition comprising: a compound of Formula I, or a pharmaceutically acceptable salt thereof, and at least one further therapeutic agent for use in the treatment of an inflammatory, allergic, autoimmune, or infectious diseases.

In another aspect, the present invention provides a pharmaceutical composition comprising: a compound of Formula I, or a pharmaceutically acceptable salt thereof, and at least one further therapeutic agent for use in the treatment of a senescence- or age-related disease.

In another aspect, the present invention provides a method for treating a disease or condition for which modulation of cGAS is beneficial comprising: administering to a patient in need thereof, a therapeutically effective amount of a combination comprising a compound of Formula I, or a pharmaceutically acceptable salt thereof, and at least one further therapeutic agent.

In another aspect, the present invention provides a method of treating an inflammatory, allergic, autoimmune or infectious disease comprising: administering to a patient in need thereof, a therapeutically effective amount of a pharmaceutical composition comprising: a compound of Formula I, or a pharmaceutically acceptable salt thereof, and at least one further therapeutic agent.

In another aspect, the present invention provides a method of treating a senescence- or age-related disease comprising: administering to a patient in need thereof, a therapeutically effective amount of a pharmaceutical composition comprising: a compound of Formula I, or a pharmaceutically acceptable salt thereof, and at least one further therapeutic agent.

While aspects for each variable have generally been listed above separately for each variable this invention includes those compounds in which several or each aspect in formula I is selected from each of the aspects listed above. Therefore, this invention is intended to include all combinations of aspects for each variable.

DETAILED DESCRIPTION OF THE INVENTION

As used herein:

The term "a compound of the invention" includes all solvates, complexes, polymorphs, radiolabeled derivatives, tautomers, stereoisomers, and optical isomers of the compounds of Formula I, and salts thereof, unless otherwise specified.

The term "effective amount" means that amount of a drug or pharmaceutical agent that will elicit the biological or medical response of a tissue, system, animal or human that is being sought, for instance, by a researcher or clinician.

The term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

The term "prophylaxis" includes prevention and refers to a measure or procedure which is to prevent rather than cure or treat a disease. Preventing refers to a reduction in risk of acquiring or developing a disease causing at least one clinical symptom of the disease not to developing a subject that may be exposed to a disease-causing agent or a subject predisposed to the disease in advance of disease outset.

The term "pharmaceutically acceptable" refers to those compounds, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

The term "pharmaceutically acceptable excipients" includes all diluents, carriers, binders, glidants, and other components of pharmaceutical formulations with which the compound of the invention is administered.

The compounds of the invention may exist in solid or liquid form. In solid form, compound of the invention may exist in a continuum of solid states ranging from fully amorphous to fully crystalline.

The term 'amorphous' refers to a state in which the material lacks long range order at the molecular level and, depending upon the temperature, may exhibit the physical properties of a solid or a liquid. Typically, such materials do not give distinctive X-ray diffraction patterns and, while exhibiting the properties of a solid, are more formally described as a liquid. Upon heating, a change from solid to liquid properties occurs which is characterized by a change of state, typically second order ('glass transition').

The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterized by a phase change, typically first order ('melting point').

The compounds of the invention may have the ability to crystallize in more than one form, a characteristic, which is known as polymorphism, and it is understood that such polymorphic forms ("polymorphs") are within the scope of the invention. Polymorphism generally can occur as a response to changes in temperature or pressure or both and can also result from variations in the crystallization process. Polymorphs can be distinguished by various physical characteristics known in the art such as x-ray diffraction patterns, solubility and melting point.

The compound of Formula I may exist in solvated and unsolvated forms. As used herein, the term "solvate" refers to a complex of variable stoichiometry formed by a solute (in this invention, a compound of formula I or a salt) and a solvent. Such solvents for the purpose of the invention may not interfere with the biological activity of the solute. The skilled artisan will appreciate that pharmaceutically acceptable solvates may be formed for crystalline compounds wherein solvent molecules are incorporated into the crystalline lattice during crystallization. The incorporated solvent molecules may be water molecules or non-aqueous such as ethanol, isopropanol, DMSO, acetic acid, ethanolamine, and ethyl acetate molecules. Crystalline lattice incorporated with water molecules are typically referred to as "hydrates". Hydrates include stoichiometric hydrates as well as compositions containing variable amounts of water. The present invention includes all such solvates.

It is also noted that some compounds may form tautomers. 'Tautomers' refer to compounds that are interchangeable forms of a particular compound structure, and that vary in the displacement of hydrogen atoms and electrons. Thus, two structures may be in equilibrium through the movement of electrons and an atom (usually H). For example, enols and ketones are tautomers because they are rapidly interconverted by treatment with either acid or base. It is understood that all tautomers and mixtures of tautomers of the compounds of the present invention are included within the scope of the compounds of the present invention. For absolute clarity, in the compounds of formula I when $R^1$ or $R^3$ represent OH, the compounds will form the keto tautomer (=O).

The compounds of Formula I may be in the form of a salt. Typically, the salts of the present invention are pharmaceutically acceptable salts. Salts encompassed within the term "pharmaceutically acceptable salts" refer to non-toxic salts of the compounds of this invention. For a review on suitable salts, see e.g., Berge et al, J. Pharm. Sci. 1977, 66, 1-19. Suitable pharmaceutically acceptable salts can include acid addition salts. A pharmaceutically acceptable acid addition salt can be formed by reaction of a compound of Formula I with a suitable inorganic or organic acid (such as hydrobromic, hydrochloric, sulfuric, nitric, phosphoric, p-toluenesulfonic, benzenesulfonic, methanesulfonic, ethanesulfonic, naphthalenesulfonic such as 2-naphthalenesulfonic), optionally in a suitable solvent such as an organic solvent, to give the salt which is usually isolated for example by crystallisation and filtration. A pharmaceutically acceptable acid addition salt of a compound of Formula I can be, for example, a hydrobromide, hydrochloride, sulfate, nitrate, phosphate, p-toluenesulfonate, benzenesulfonate, methanesulfonate, ethanesulfonate, or naphthalenesulfonate (e.g. 2-naphthalenesulfonate) salt. Other non-pharmaceutically acceptable salts, e.g. trifluoroacetates, may be used, for example in the isolation of compounds of the invention, and are included within the scope of this invention.

The invention includes within its scope all possible stoichiometric and non-stoichiometric forms of the compounds of Formula I.

While it is possible that, for use in therapy, the compound of the invention may be administered as the raw chemical, it is possible to present the compound of the invention as the active ingredient in a pharmaceutical composition. Such compositions can be prepared in a manner well known in the pharmaceutical art and comprise at least one active compound. Accordingly, the invention further provides pharmaceutical compositions comprising a compound of the invention and one or more pharmaceutically acceptable excipients. The excipient(s) must be acceptable in the sense of being compatible with the other ingredients of the composition and not deleterious to the recipient thereof. In accordance with another aspect of the invention there is also provided a process for the preparation of a pharmaceutical composition including the agent, or pharmaceutically acceptable salts thereof, with one or more pharmaceutically acceptable excipients. The pharmaceutical composition can be for use in the treatment and/or prophylaxis of any of the conditions described herein.

Generally, the compound of the invention is administered in a pharmaceutically effective amount. The amount of the compound actually administered will typically be determined by a physician, in the light of the relevant circumstances, including the condition to be treated, the chosen route of administration, the actual compound-administered, the age, weight, and response of the individual patient, the severity of the patient's symptoms, and the like. Pharmaceutical compositions may be presented in unit dose forms containing a predetermined amount of active ingredient per unit dose. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient, vehicle or carrier. Typical unit dosage forms include prefilled, premeasured ampules or syringes of the liquid compositions or pills, tablets, capsules or the like in the case of solid compositions.

Preferred unit dosage compositions are those containing a daily dose or sub-dose, or an appropriate fraction thereof, of an active ingredient. Such unit doses may therefore be administered once or more than once a day. Such pharmaceutical compositions may be prepared by any of the methods well known in the pharmacy art.

Pharmaceutical compositions may be adapted for administration by any appropriate route, for example by the oral (including buccal or sublingual), rectal, inhaled, intranasal, topical (including buccal, sublingual or transdermal), vaginal or parenteral (including subcutaneous, intramuscular, intravenous or intradermal) route. Such compositions may be prepared by any method known in the art of pharmacy, for example by bringing into association the active ingredient with the carrier(s) or excipient(s).

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert excipient such as ethanol, glycerol, water and the like. Powders are prepared by reducing the compound to a suitable fine size and mixing with a similarly prepared pharmaceutical excipient such as an edible carbohydrate, as, for example, starch or mannitol. Flavoring, preservative, dispersing and coloring agent can also be present.

Capsules are made by preparing a powder mixture, as described above, and filling formed gelatin sheaths. Excipients including glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, excipients including suitable binders, glidants, lubricants, sweetening agents, flavors, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate. magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, suspensions, syrups and elixirs can be prepared in dosage unit form so that a given quantity contains a predetermined amount of the compound. Syrups can be prepared by dissolving the compound in a suitably flavoured aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit compositions for oral administration can be microencapsulated. The composition can also be prepared to prolong or sustain the release as for example by coating or embedding particulate material in polymers, wax or the like.

The compounds of the invention may also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines. Pharmaceutical compositions adapted for transdermal administration may be presented as discrete patches intended to remain in intimate contact with the epidermis of the recipient for a prolonged period of time.

Pharmaceutical compositions adapted for topical administration may be formulated as ointments, creams, suspensions, lotions, powders, solutions, pastes, gels, sprays, aerosols or oils.

For treatments of the eye or other external tissues, for example mouth and skin, the compositions are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical compositions adapted for topical administrations to the eye include eye drops wherein the active ingredient is dissolved or suspended in a suitable carrier, especially an aqueous solvent.

Pharmaceutical compositions adapted for topical administration in the mouth include lozenges, pastilles and mouth washes.

Pharmaceutical compositions adapted for rectal administration may be presented as suppositories or as enemas.

Dosage forms for nasal or inhaled administration may conveniently be formulated as aerosols, solutions, suspension drops, gels or dry powders.

Compositions for intranasal administration include aqueous compositions administered to the nose by drops or by pressurised pump. Suitable compositions contain water as the diluent or carrier for this purpose. Compositions for administration to the lung or nose may contain one or more excipients, for example one or more suspending agents, one or more preservatives, one or more surfactants, one or more tonicity adjusting agents, one or more co-solvents, and may include components to control the pH of the composition, for example a buffer system. Further, the compositions may contain other excipients such as antioxidants, for example sodium metabisulphite, and taste-masking agents. Compositions may also be administered to the nose or other regions of the respiratory tract by nebulisation. Intranasal compositions may permit the compound(s) of Formula I or (a) pharmaceutically acceptable salt(s) thereof to be delivered to all areas of the nasal cavities (the target tissue) and further, may permit the compound(s) of Formula I or (a) pharmaceutically acceptable salt(s) thereof to remain in contact with the target tissue for longer periods of time. A suitable dosing regime for intranasal compositions would be for the patient to inhale slowly through the nose subsequent to the nasal cavity being cleared. During inhalation, the composition would be administered to one nostril while the other is manually compressed. This procedure would then be repeated for the other nostril. Typically, one or two sprays per nostril would be administered by the above procedure one, two, or three times each day, ideally once daily. Of particular interest are intranasal compositions suitable for once-daily administration.

The suspending agent(s), if included, will typically be present in an amount of from 0.1 to 5% (w/w), such as from 1.5% to 2.4% (w/w), based on the total weight of the composition. Examples of pharmaceutically acceptable suspending agents include, but are not limited to, Avicef (microcrystalline cellulose and carboxymethylcellulose sodium), carboxymethylcellulose sodium, veegum, tragacanth, bentonite, methylcellulose, xantha n gum, carbopol and polyethylene glycols.

Compositions for administration to the lung or nose may contain one or more excipients may be protected from microbial or fungal contamination and growth by inclusion of one or more preservatives. Examples of pharmaceutically acceptable anti-microbial agents or preservatives include, but are not limited to, quaternary ammonium compounds (for example benzalkonium chloride, benzethonium chloride, cetrimide, cetylpyridinium chloride, lauralkonium chloride and myristyl picolinium chloride), mercurial agents (for example phenylmercuric nitrate, phenylmercuric acetate and thimerosal), alcoholic agents (for example chlorobutanol, phenylethyl alcohol and benzyl alcohol), antibacterial esters (for example esters ofp-hydroxybenzoic acid), chelating agents such as disodium edetate (EDTA) and other anti-microbial agents such as chlorhexidine, chlorocresol, sorbic acid and its salts (such as potassium sorbate) and polymyxin. Examples of pharmaceutically acceptable antifungal agents or preservatives include, but are not limited to, sodium benzoate, sorbic acid, sodium propionate, methylparaben, ethylparaben, propylparaben and butylparaben. The preservative(s), if included, may be present in an amount of from 0.001 to 1% (w/w), such as from 0.015% to 0.5% (w/w) based on the total weight of the composition. Compositions (for example wherein at least one compound is in suspension) may include one or more surfactants which functions to facilitate dissolution of the medicament particles in the aqueous phase of the composition. For example, the amount of surfactant used is an amount which will not cause foaming during mixing. Examples of pharmaceutically acceptable surfactants include fatty alcohols, esters and ethers, such as polyoxyethylene (20) sorbitan monooleate (Polysorbate 80), macrogol ethers, and poloxamers. The surfactant may be present in an amount of between about 0.01 to 10% (w/w), such as from 0.01 to 0.75% (w/w), for example about 0.5% (w/w), based on the total weight of the composition.

One or more tonicity-adjusting agent(s) may be included to achieve tonicity with body fluids e.g. fluids of the nasal cavity, resulting in reduced levels of irritancy. Examples of pharmaceutically acceptable tonicity-adjusting agents include, but are not limited to, sodium chloride, dextrose, xylitol, calcium chloride, glucose, glycerine and sorbitol. A tonicity-adjusting agent, if present, may be included in an amount of from 0.1 to 10% (w/w), such as from 4.5 to 5.5% (w/w), for example about 5.0% (w/w), based on the total weight of the composition.

The compositions of the invention may be buffered by the addition of suitable buffering agents such as sodium citrate, citric acid, trometamol, phosphates such as disodium phosphate (for example the dodecahydrate, heptahydrate, dihydrate and anhydrous forms), or sodium phosphate and mixtures thereof.

A buffering agent, if present, may be included in an amount of from 0.1 to 5% (w/w), for example 1 to 3% (w/w) based on the total weight of the composition.

Examples of taste-masking agents include sucralose, sucrose, saccharin or a salt thereof, fructose, dextrose, glycerol, corn syrup, aspartame, acesulfame-K, xylitol, sorbitol, erythritol, ammonium glycyrrhizinate, thaumatin, neotame, mannitol, menthol, *eucalyptus* oil, camphor, a natural flavouring agent, an artificial flavouring agent, and combinations thereof.

One or more co-solvent(s) may be included to aid solubility of the medicament compound(s) and/or other excipients. Examples of pharmaceutically acceptable co-solvents include, but are not limited to, propylene glycol, dipropylene glycol, ethylene glycol, glycerol, ethanol, polyethylene glycols (for example PEG300 or PEG400), and methanol. In one embodiment, the co-solvent is propylene glycol.

Co-solvent(s), if present, may be included in an amount of from 0.05 to 30% (w/w), such as from 1 to 25% (w/w), for example from 1 to 10% (w/w) based on the total weight of the composition.

Compositions for inhaled administration include aqueous, organic or aqueous/organic mixtures, dry powder or crystalline compositions administered to the respiratory tract by pressurised pump or inhaler, for example, reservoir dry powder inhalers, unit-dose dry powder inhalers, pre-metered multi-dose dry powder inhalers, nasal inhalers or pressurised aerosol inhalers, nebulisers or insufflators. Suitable compositions contain water as the diluent or carrier for this purpose and may be provided with conventional excipients such as buffering agents, tonicity modifying agents and the like. Aqueous compositions may also be administered to the nose and other regions of the respiratory tract by nebulisation. Such compositions may be aqueous solutions or suspensions or aerosols delivered from pressurised packs, such as a metered dose inhaler, with the use of a suitable liquefied propellant.

Compositions for administration topically to the nose (for example, for the treatment of rhinitis) or to the lung, include pressurised aerosol compositions and aqueous compositions delivered to the nasal cavities by pressurised pump. Compositions which are non-pressurised and are suitable for administration topically to the nasal cavity are of particular interest. Suitable compositions contain water as the diluent or carrier for this purpose. Aqueous compositions for administration to the lung or nose may be provided with conventional excipients such as buffering agents, tonicity-modifying agents and the like. Aqueous compositions may also be administered to the nose by nebulisation.

A fluid dispenser may typically be used to deliver a fluid composition to the nasal cavities. The fluid composition may be aqueous or non-aqueous, but typically aqueous. Such a fluid dispenser may have a dispensing nozzle or dispensing orifice through which a metered dose of the fluid composition is dispensed upon the application of a user-applied force to a pump mechanism of the fluid dispenser. Such fluid dispensers are generally provided with a reservoir of multiple metered doses of the fluid composition, the doses being dispensable upon sequential pump actuations. The dispensing nozzle or orifice may be configured for insertion into the nostrils of the user for spray dispensing of the fluid composition into the nasal cavity.

Dry powder compositions for topical delivery to the lung by inhalation may, for example, be presented in capsules and cartridges of for example gelatine, or blisters of for example laminated aluminium foil, for use in an inhaler or insufflator. Powder blend compositions generally contain a powder mix for inhalation of the compound of formula I or a pharmaceutically acceptable salt thereof and a suitable powder base (carrier/diluent/excipient substance) such as mono-, di-, or polysaccharides (for example lactose or starch). Dry powder compositions may also include, in addition to the drug and carrier, a further excipient (for example a ternary agent such as a sugar ester for example cellobiose octaacetate, calcium stearate, or magnesium stearate.

Pharmaceutical compositions adapted for parental administration include aqueous and nonaqueous sterile injection solutions which may contain anti-oxidants, buffers, bacteriostats and solutes which render the composition isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

It should be understood that in addition to the ingredients particularly mentioned above, the compositions may include other agents conventional in the art having regard to the type of formulation in question, for example, those suitable for oral administration may include flavouring agents.

A therapeutically effective amount of the agent will depend upon a number of factors including, for example, the age and weight of the subject, the precise condition requiring treatment and its severity, the nature of the formulation, and the route of administration, and will ultimately be at the discretion of the attendant physician or veterinarian. In particular, the subject to be treated is a mammal, particularly a human.

The agent may be administered in a daily dose. This amount may be given in a single dose per day or more usually in a number (such as two, three, four, five or six) of sub-doses per day such that the total daily dose is the same.

Suitably, the amount of the compound of the invention administered according to the present invention will be an amount selected from 0.01 mg to 10 g per day (calculated as the free or unsalted compound).

The compounds of Formula I and pharmaceutically acceptable salts thereof may be employed alone or in combination with other therapeutic agents. The compounds of Formula I and pharmaceutically acceptable salts thereof and the other pharmaceutically active agent(s) may be administered together or separately and, when administered separately, administration may occur simultaneously or sequentially, in any order, by any convenient route in separate or combined pharmaceutical compositions. The amounts of the compound(s) of Formula I or pharmaceutically acceptable salt(s) thereof and the other pharmaceutically active agent(s) and the relative timings of administration will be selected in order to achieve the desired combined therapeutic effect. The compound(s) of Formula I or pharmaceutically acceptable salt(s) thereof and further therapeutic agent(s) may be employed in combination by administration simultaneously in a unitary pharmaceutical composition including both compounds. Alternatively, the combination may be administered separately in separate pharmaceutical compositions, each including one of the compounds in a sequential manner wherein, for example, the compound of the invention is administered first and the other second and visa versa. Such sequential administration may be close in time (e.g. simultaneously) or remote in time. Furthermore, it does not matter if the compounds are administered in the same dosage form, e.g. one compound may be administered topically and the other compound may be administered orally. Suitably, both compounds are administered orally.

The combinations may be presented as a combination kit. By the term "combination kit" "or kit of parts" as used herein is meant the pharmaceutical composition or compositions that are used to administer the combination according to the invention. When both compounds are administered simultaneously, the combination kit can contain both compounds in a single pharmaceutical composition, such as a tablet, or in separate pharmaceutical compositions. When the compounds are not administered simultaneously, the combination kit will contain each compound in separate pharmaceutical compositions either in a single package or in separate pharmaceutical compositions in separate packages. The combination kit can also be provided by instruction, such as dosage and administration instructions. Such dosage and administration instructions can be of the kind that are provided to a doctor, for example by a drug product label, or they can be of the kind that are provided by a doctor, such as instructions to a patient.

When the combination is administered separately in a sequential manner wherein one is administered first and the other second or vice versa, such sequential administration may be close in time or remote in time. For example, administration of the other agent several minutes to several dozen minutes after the administration of the first agent, and administration of the other agent several hours to several days after the administration of the first agent are included, wherein the lapse of time is not limited. For example, one agent may be administered once a day, and the other agent may be administered 2 or 3 times a day, or one agent may be administered once a week, and the other agent may be administered once a day and the like. It will be clear to a person skilled in the art that, where appropriate, the other therapeutic ingredients(s) may be used in the form of salts, for example as alkali metal or amine salts or as acid addition salts, or prodrugs, or as esters, for example lower alkyl esters, or as solvates, for example hydrates, to optimize the activity and/or stability and/or physical characteristics, such as solubility, of the therapeutic ingredient. It will be clear also that, where appropriate, the therapeutic ingredients may be used in optically pure form.

When combined in the same composition it will be appreciated that the two compounds must be stable and compatible with each other and the other components of the composition and may be formulated for administration. When formulated separately they may be provided in any convenient composition, conveniently, in such a manner as known for such compounds in the art.

When the compound of Formula I is used in combination with a second therapeutic agent active against the same disease, condition or disorder, the dose of each compound may differ from that when the compound is used alone. Appropriate doses will be readily appreciated by those skilled in the art.

In one embodiment, the mammal in the methods and uses of the present invention is a human. The compounds of the invention are useful in the treatment of diseases and conditions in which modulation of cGAS is beneficial. As modulators of the immune response, the compounds of Formula I and pharmaceutically acceptable salts thereof may also be useful, as stand-alone, in combination or as adjuvants, in the treatment of diseases and conditions in which modulation of cGAS is beneficial.

In one aspect, the disease or condition is an inflammatory, allergic or autoimmune diseases such as systemic lupus erythematosus, psoriasis, insulin-dependent diabetes mellitus (IDDM), scleroderma, Aicardi Gourtiers syndrome, dermatomyositis, inflammatory bowel diseases, multiple sclerosis, rheumatoid arthritis and Sjogren's syndrome (SS).

In another aspect, the disease or condition is an infectious disease such as bacterial, viral or parasitic disease in which modulation of cGAS activity is beneficial.

In another aspect, the disease or condition is a senescence- or age-related disease, including a neurodegenerative disease such as Alzheimer's or Parkinson disease, cardiovascular diseases such as atherosclerosis or myocardial infaction, liver or renal diseases, cancer or premature aging.

Inflammation represents a group of vascular, cellular, and neurological responses to trauma. Inflammation can be characterized as the movement of inflammatory cells such as monocytes, neutrophils and granulocytes into the tissues. This is usually associated with reduced endothelial barrier function and edema into the tissues. Inflammation can be classified as either acute or chronic. Acute inflammation is the initial response of the body to harmful stimuli and is achieved by the increased movement of plasma and leukocytes from the blood into the injured tissues. A cascade of biochemical event propagates and matures the inflammatory response, involving the local vascular system, the immune system, and various cells within the injured tissue. Prolonged inflammation, known as chronic inflammation, leads to a progressive shift in the type of cells which are present at the site of inflammation and is characterized by simultaneous destruction and healing of the tissue from the inflammatory process.

When occurring as part of an immune response to infection or as an acute response to trauma, inflammation can be beneficial and is normally self-limiting. However, inflammation can be detrimental under various conditions. This includes the production of excessive inflammation in response to infectious agents, which can lead to significant organ damage and death (for example, in the setting of sepsis). Moreover, chronic inflammation is generally deleterious and is at the root of numerous chronic diseases, causing severe and irreversible damage to tissues. In such settings, the immune response is often directed against self-tissues (autoimmunity), although chronic responses to foreign entities can also lead to bystander damage to self-tissues. The aim of anti-inflammatory therapy is therefore to reduce this inflammation, to inhibit autoimmunity when present and to allow for the physiological process or healing and tissue repair to progress.

The compounds of the invention may be used to treat inflammation of any tissue and organs of the body, including musculoskeletal inflammation, vascular inflammation, neural inflammation, digestive system inflammation, ocular inflammation, inflammation of the reproductive system, and other inflammation, as exemplified below.

Musculoskeletal inflammation refers to any inflammatory condition of the musculoskeletal system, particularly those conditions affecting skeletal joints, including joints of the hand, wrist, elbow, shoulder, jaw, spine, neck, hip, knew, ankle, and foot, and conditions affecting tissues connecting muscles to bones such as tendons. Examples of musculoskeletal inflammation which may be treated with compounds of the invention include arthritis (including, for example, osteoarthritis, rheumatoid arthritis, psoriatic arthritis, ankylosing spondylitis, acute and chronic infectious arthritis, arthritis associated with gout and pseudogout, and juvenile idiopathic arthritis), tendonitis, synovitis, tenosynovitis, bursitis, fibrositis (fibromyalgia), epicondylitis, myositis, and osteitis (including, for example, Paget's disease, osteitis pubis, and osteitis fibrosa cystic). Ocular inflammation refers to inflammation of any structure of the eye, including the eye lids. Examples of ocular inflammation which may be treated with the compounds of the invention include blepharitis, blepharochalasis, conjunctivitis, dacryoadenitis, keratitis, keratoconjunctivitis sicca (dry eye), scleritis, trichiasis, and uveitis. Examples of inflammation of the nervous system which may be treated with the compounds of the invention include encephalitis, Guillain-Barre syndrome, meningitis, neuromyotonia, narcolepsy, multiple sclerosis, myelitis and schizophrenia.

Examples of inflammation of the vasculature or lymphatic system which may be treated with the compounds of the invention include arthrosclerosis, arthritis, phlebitis, vasculitis, and lymphangitis.

Examples of inflammatory conditions of the digestive system which may be treated with the compounds of the invention include cholangitis, cholecystitis, enteritis, enterocolitis. gastritis, gastroenteritis, inflammatory bowel disease (such as Crohn's disease and ulcerative colitis), ileitis, and proctitis.

Examples of inflammatory conditions of the reproductive system which may be treated with the compounds of the invention include cervicitis, chorioamnionitis, endometritis, epididymitis, omphalitis, oophoritis, orchitis, salpingitis, tubo-ovarian abscess, urethritis, vaginitis, vulvitis, and vulvodynia.

The agents may be used to treat autoimmune conditions having an inflammatory component. Such conditions include systemic lupus erythematosus, acute disseminated alopecia universalise, Behcet's disease, Chagas' disease, chronic fatigue syndrome, dysautonomia, encephalomyelitis, ankylosing spondylitis, aplastic anemia, hidradenitis suppurativa, autoimmune hepatitis, autoimmune oophoritis, celiac disease, Crohn's disease, diabetes mellitus type 1, giant cell arteritis, goodpasture's syndrome. Grave's disease, Guillain-Barre syndrome, Hashimoto's disease, Henoch-Schonlein purpura, Kawasaki's disease, microscopic colitis, microscopic polyarteritis, mixed connective tissue disease, multiple sclerosis, myasthenia gravis, opsoclonus myoclonus syndrome, optic neuritis, ord's thyroiditis, pemphigus, polyarteritis nodosa, polymyalgia, rheumatoid arthritis, Reiter's syndrome, Sjogren's syndrome, Aicardi Gourtiers syndrome, temporal arteritis, Wegener's granulomatosis, warm autoimmune haemolytic anemia, interstitial cystitis, lyme disease, morphea, psoriasis, sarcoidosis, scleroderma, ulcerative colitis, and vitiligo.

The compounds of the invention may be used to treat T-cell mediated hypersensitivity diseases having an inflammatory component. Such conditions include contact hypersensitivity, contact dermatitis (including that due to poison ivy), uticaria, skin allergies, respiratory allergies (hayfever, allergic rhinitis) and gluten-sensitive enteropathy (Celiac disease).

Other inflammatory conditions which may be treated with the agents include, for example, appendicitis, dermatitis, dermatomyositis, endocarditis, fibrositis, gingivitis, glossitis, hepatitis, hidradenitis suppurativa, iritis, laryngitis, mastitis, myocarditis, nephritis, otitis, pancreatitis, parotitis, percarditis, peritonoitis, pharyngitis, pleuritis, pneumonitis, prostatistis, pyelonephritis, and stomatisi, transplant rejection (involving organs such as kidney, liver, heart, lung, pancreas (e.g., islet cells), bone marrow, cornea, small bowel, skin allografts, skin homografts, and heart valve xengrafts, sewrum sickness, and graft vs host disease), acute pancreatitis, chronic pancreatitis, acute respiratory distress syndrome. Sexary's syndrome, congenital adrenal hyperplasis, nonsuppurative thyroiditis, hypercalcemia associated with cancer, pemphigus, bullous dermatitis herpetiformis, severe erythema multiforme, exfoliative dermatitis, seborrheic dermatitis, seasonal or perennial allergic rhinitis, bronchial asthma, contact dermatitis, astopic dermatitis, drug hypersensistivity reactions, allergic conjunctivitis, keratitis, herpes zoster ophthalmicus, iritis and oiridocyclitis, chorioretinitis, optic neuritis, symptomatic sarcoidosis, fulminating or disseminated pulmonary tuberculosis chemotherapy, idiopathic thrombocytopenic purpura in adults, secondary thrombocytopenia in adults, acquired (autroimmine) haemolytic anemia, leukaemia and lymphomas in adults, acute leukaemia of childhood, regional enteritis, autoimmune vasculitis, multiple sclerosis, chronic obstructive pulmonary disease, solid organ transplant rejection, sepsis. Preferred treatments include treatment of transplant rejection, rheumatoid arthritis, psoriatic arthritis, multiple sclerosis. Type 1 diabetes, asthma, inflammatory bowel disease, systemic lupus erythematosis, psoriasis, chronic pulmonary disease, and inflammation accompanying infectious conditions (e.g., sepsis).

In a further aspect, the invention provides a compound of Formula I or a pharmaceutically acceptable salt thereof for use in the treatment of an inflammatory, allergic or autoimmune disease.

In a further aspect, the invention provides a method of treating an inflammatory, allergic or autoimmune disease comprising: administering to a patient in need thereof a therapeutically effective amount of a compound of Formula I or a pharmaceutically acceptable salt thereof.

In a further aspect, the invention provides the use of a compound of Formula I or a pharmaceutically acceptable salt thereof in the manufacture of a medicament for the treatment of an inflammatory, allergic or autoimmune disease.

The Compounds of Formula I and pharmaceutically acceptable salts thereof may be used in combination with one or more other agents in the prevention or treatment of an allergic inflammatory autoimmune disease, wherein such other agents can include: antigen immunotherapy agents; anti-histamines; steroids, NSAIDs; bronchodilators (e.g. beta 2 agonists, adrenergic agonists, anticholinergic agents, theophylline); methotrexate; leukotriene modulators; monoclonal antibody agents such as anti-lgE, anti-TNF, anti-IL-5, anti-IL-6, anti-IL-12, anti-IL-1 and similar agents; receptor therapies agents such as entanercept; and antigen non-specific immunotherapeutic agents such interferon or other cytokines/chemokines, cytokine/chemokine receptor modulators, cytokine agonists or antagonists, and TLR antagonist.

In a further aspect, the present invention provides a pharmaceutical composition comprising a compound of Formula I, or a pharmaceutically acceptable salt thereof, and at least one further therapeutic agent useful in the treatment of an allergic, inflammatory, or autoimmune disease.

In a further aspect, the present invention provides a pharmaceutical composition comprising a compound of Formula I, or a pharmaceutically acceptable salt thereof, and at least one further therapeutic agent useful in the treatment of an allergic, inflammatory or autoimmune disease for use in therapy.

In a further aspect, the present invention provides a pharmaceutical composition comprising a compound of Formula I, or pharmaceutically acceptable salt thereof, and at least one further therapeutic agent useful in the treatment of an allergic inflammatory or autoimmune disease, for use in the treatment of allergic, inflammatory or autoimmune disease.

In a further aspect, the present invention provides the use of a pharmaceutical composition comprising a compound of Formula I, or a pharmaceutically acceptable salt thereof, and at least one further therapeutic agent useful in the treatment of an allergic, inflammatory or autoimmune disease in the manufacture of a medicament for the treatment of an allergic, inflammatory or autoimmune disease.

In a further aspect, the present invention provides a method of treating an allergic, inflammatory or autoimmune disease comprising: administering to a patient in need thereof a therapeutically effective amount of a pharmaceutical composition comprising a compound of Formula I, or a pharmaceutically acceptable salt thereof, and at least one further therapeutic agent useful in the treatment of an allergic, inflammatory, or autoimmune disease.

In a further aspect, the present invention provides a pharmaceutical composition comprising a compound of Formula I, or a pharmaceutically acceptable salt thereof, at least one further therapeutic agent useful in the treatment of an allergic, inflammatory or autoimmune disease, and one or more of pharmaceutically acceptable excipients.

In a further aspect, the present invention provides a compound of Formula I, or a pharmaceutically acceptable salt thereof, for use in the treatment of an infectious disease.

In a further aspect, the present invention provides a method of treating an infectious disease comprising administering to a patient in need thereof a therapeutically effective amount of a compound of Formula I, or a pharmaceutically acceptable salt thereof.

In a further aspect, the present invention provides the use of a compound of Formula I, or a pharmaceutically acceptable salt thereof, in the manufacture of a medicament for the treatment of an infectious disease. In one embodiment, the compound of the invention may be employed with other therapeutic methods of treating infectious disease. In particular, bacterial and parasite infections, such as *Mycobacterium tuberculosis* and malaria, respectively, which exploit the type-I interferon pathway for their advantage, may be treated with a cGAS inhibitor.

The compounds of Formula I, and pharmaceutically acceptable salts thereof, may be used in combination with one or more agents useful in the prevention or treatment of bacterial and viral infections. Examples of such agents include: polymerase inhibitors; replication inhibitors such as acyclovir, famciclovir, ganciclovir, cidofovir and lamivudine; protease inhibitors such as the HIV protease inhibitors saquinavir, ritonavir, indinavir, nelfinavir, amprenavir, fosamprenavir, brecanavir, atazanavir, tipranavir, palinavir, lasinavir, and the HCV protease inhibitors BILN2061, VX-950, SCH503034; nucleoside and nucleotide reverse transcriptase inhibitors such as zidovudine, didanosine, lamivudine, zalcitabine, abacavir, stavidine, adefovir, adefovir dipivoxil, fozivudine, todoxil, emtricitabine, alovudine, amdoxovir, and elvucitabine; non-nucleoside reverse transcriptase inhibitors (including an agent having anti-oxidation activity such as immunocal or oltipraz) such as nevirapine, delavirdine, efavirenz, loviride, immunocal, oltipraz, capravirine, TMC-278, TMC-125, and etravirine; entry inhibitors such as enfuvirtide (T-20), T-1249, PRO-542, PRO-140, TNX-355, BMS-806, 5-Helix and similar agents; integrase inhibitors such as L-870 and 180; budding inhibitors such as PA-344 and PA-457; chemokine receptor inhibitors such as vicriviroc (Sch-C), Sch-D, TAK779, maraviroc (UK-427,857), and TAK449; neuraminidase inhibitors such as CS-8958, zanamivir, oseltamivir, and peramivir; ion channel blockers such as amantadine or rimantadine; interfering RNA and antisense oligonucleotides and such as ISIS-14803; and antiviral agents of undetermined mechanism of action, such as ribavirin.

The compounds of Formula I and pharmaceutically acceptable salts thereof, may also be used in combination with one or more other agents which may be useful in the prevention or treatment of viral infections such as immune therapies (e.g. interferon or other cytokines/chemokines, cytokine/chemokine receptor modulators, cytokine agonists or antagonists and similar agents); therapeutic vaccines; antifibrotic agents; and anti-inflammatory agents such as corticosteroids or NSAIDs (non-steroidal anti-inflammatory agents).

In a further aspect, the present invention provides a pharmaceutical composition comprising a compound of Formula I, or a pharmaceutically acceptable salt thereof, and at least one further therapeutic agent useful in the treatment of an infectious disease.

In a further aspect, the present invention provides a pharmaceutical composition comprising a compound of Formula I, or a pharmaceutically acceptable salt thereof, and at least one further therapeutic agent useful in the treatment of an infectious disease for use in therapy.

In a further aspect, the present invention provides a pharmaceutical composition comprising a compound of Formula I, or pharmaceutically acceptable salt thereof, and at least one further therapeutic agent useful in the treatment of an infectious disease, for use in the treatment of an infectious disease.

In a further aspect, the present invention provides the use of a pharmaceutical composition comprising a compound of Formula I, or a pharmaceutically acceptable salt thereof, and at least one further therapeutic agent useful in the treatment of an infectious disease in the manufacture of a medicament for the treatment of an infectious disease.

In a further aspect, the present invention provides a method of treating an infectious disease comprising administering to a patient in need thereof, a therapeutically effective amount of a pharmaceutical composition comprising a compound of Formula I, or a pharmaceutically acceptable salt thereof, and at least one further therapeutic agent useful in the treatment of an infectious disease.

In a further aspect, the present invention provides a pharmaceutical composition comprising a compound of Formula I or a pharmaceutically acceptable salt thereof, at least one further therapeutic agent useful in the treatment of infectious disease, and one or more of pharmaceutically acceptable excipients.

In another aspect, the invention provides a compound of Formula I or a pharmaceutically acceptable salt thereof for use in the treatment of a senescence- or age-related disease.

In a further aspect, the invention provides a method of treating a senescence- or age-related disease comprising: administering to a patient in need thereof a therapeutically effective amount of a compound of Formula I or a pharmaceutically acceptable salt thereof.

In a further aspect, the invention provides the use of a compound of Formula I or a pharmaceutically acceptable salt thereof in the manufacture of a medicament for the treatment of a senescence- or age-related disease.

In a further aspect, the present invention provides a pharmaceutical composition comprising a compound of Formula I, or a pharmaceutically acceptable salt thereof, and at least one further therapeutic agent useful in the treatment of a senescence- or age-related disease.

In a further aspect, the present invention provides a pharmaceutical composition comprising a compound of Formula I, or a pharmaceutically acceptable salt thereof, and at least one further therapeutic agent useful in the treatment of a senescence- or age-related disease for use in therapy.

In a further aspect, the present invention provides a pharmaceutical composition comprising a compound of Formula I, or pharmaceutically acceptable salt thereof, and at least one further therapeutic agent useful in the treatment of a senescence- or age-related disease, for use in the treatment of a senescence- or age-related disease.

In a further aspect, the present invention provides the use of a pharmaceutical composition comprising a compound of Formula I, or a pharmaceutically acceptable salt thereof, and at least one further therapeutic agent useful in the treatment of a senescence- or age-related disease in the manufacture of a medicament for the treatment of a senescence- or age-related disease.

In a further aspect, the present invention provides a method of treating a senescence- or age-related disease comprising administering to a patient in need thereof, a therapeutically effective amount of a pharmaceutical composition comprising a compound of Formula I, or a pharmaceutically acceptable salt thereof, and at least one further therapeutic agent useful in the treatment of a senescence- or age-related disease.

In a further aspect, the present invention provides a pharmaceutical composition comprising a compound of Formula I or a pharmaceutically acceptable salt thereof, at least one further therapeutic agent useful in the treatment of a senescence- or age-related disease, and one or more of pharmaceutically acceptable excipients.

Compounds of Formula I may be prepared by methods known in the art of organic synthesis as set forth in the schemes below and/or the specific Examples described below. In all of the methods, it is well understood that protecting groups for sensitive or reactive groups may be employed where necessary in accordance with general principles of chemistry. Protecting groups are manipulated according to standard methods of organic synthesis (T. W. Green and P. G. M. Wuts (1999) Protective Groups in Organic Synthesis, $3^{rd}$ edition, John Wiley & Sons). These groups are removed at a convenient stage of the compound synthesis using methods that are readily apparent to those skilled in the art. The selection of processes as well as the reaction conditions and order of their execution shall be consistent with the preparation of compounds of Formula I.

The following list provides definitions of certain abbreviations as used herein. It will be appreciated that the list is not exhaustive, but the meaning of those abbreviations not herein below defined will be readily apparent to those skilled in the art: AIBN is 2,2'-azobisisobutyronitrile; ATP is adenosine 5'-triphosphate; BPO is benzoyl peroxide; n-BuLi is n-butyllithium; BzCl is benzoyl chloride; CDI is 1,1'-carbonyldiimidazole; cGAS is cyclic GMP-AMP synthase; CO is carbon monooxide; Cu(OAc)$_2$ is copper(II) acetate; CuCN is copper(I) cynide; CuI is copper(I) iodide; DAST is (diethylamino)sulfur trifluoride; DBU is 1,8-diazabicyclo[5.4.0]undec-7-ene; DCE is dichloroethane; DCM is dichloromethane; DDQ is 2,3-dichloro-5,6-dicyano-p-benzoquinone; DHP is 3,4-dihydro-2H-pyran; DIAD is diisopropyl azodicarboxylate; DIBAL-H is diisobutylaluminum hydride; DIPA is diisopropylamine; DIPEA is N,N-diisopropylethylamine; DMAP is 4-(dimethylamino)pyridine; DMB is 2,4-dimethoxybenzyl; DMF is N,N-dimethylformamide; DMP is Dess-Martin periodinane; DMSO is dimethyl sulfoxide; EA is ethyl acetate; EtMgBr is ethylmagnesium bromide; Et$_2$O is diethyl ether; EtOH is ethanol; GTP is guanosine triphosphate; HCl is hydrochloric acid; HMTA is hexamethylenetetramine; HOAc is acetic acid; HPLC is high performance liquid chromatography; LAH is lithium aluminum hydride; mCPBA is 3-chloroperbenzoic acid; MeCN is acetonitrile; MeI is iodomethane; MeOH is methanol; MeMgBr is methylmagnesium bromide; MOMCl is chloromethyl methyl ether; MOM is methoxymethoxy; MS is mass spectrometer or mass spectrum; MsCl is methanesulfonyl chloride; MTBE is methyl tert-butyl ether; NaH is sodium hydride; NaOH is sodium hydroxide; NBS is N-bromosuccinimide; NMM is N-methylmorpholine; NMR is nuclear magnetic resonance; Pd(dba)$_2$ is bis(dibenzylideneacetone)palladium(0); Pd(dppf)Cl$_2$ is [1,1'-bis(diphenylphosphino)ferrocene]dichloropalladium(II); Pd(OAc)$_2$ is palladium(II) acetate; Pd(PPh$_3$)$_2$Cl$_2$ is bis(triphenylphosphine)palladium(II) dichloride; Pd(PPh$_3$)$_4$ is tetrakis(triphenylphosphine) palladium(0); Pd/C is palladium on carbon; PDC is pridinium dichromate; PE is petroleum ether; PMB is 4-methoxybenzyl; PPh$_3$ is triphenylphosphine; prep-HPLC is preparative high performance liquid chromatography; prep-TLC is preparative thin-layer chromatography; Py is pyridine; TBAF is tetra-n-butylammonium fluoride; TBSCl is tert-butyldimethylsilyl chloride; TEA is triethylamine; TFA is trifluoroacetic acid; THF is tetrahydrofuran; THP is tetrahydropyranyl; TLC is thin-layer chromatography; TSA is p-toluenesulfonic acid monohydrate, and TsCl is p-toluenesulfonyl chloride.

Intermediate Preparations

General Procedures

Procedure A (Amide Coupling)

To a solution of amine and TEA in the indicated solvent is added acyl chloride dropwise at room temperature. After stirring for 16 hours, the mixture is concentrated.

Procedure B (Suzuki Coupling)

To a solution of aryl halide in the indicated solvent is added boronic acid or ester, carbonate base, and palladium catalyst at room temperature. After stirring at 100° C. overnight, the mixture is cooled and concentrated.

Procedure C (Sodium Borohydride Reduction)

To a solution of aldehyde in the indicated solvent is added sodium borohydride at 0° C. After stirring at room temperature for 2 hours, water is added and the mixture is concentrated.

Procedure D (DIBAL-H Reduction)

To a solution of ester in THF is added DIBAL-H dropwise at 0° C. After stirring at room temperature for 2 hours, water, 15% NaOH solution, water, and anhydrous sodium sulfate are added sequentiallly at 0° C. The resulting slurry is stirred at room temperature for 1 hour and then filtered. The filter cake is washed with EA and the filtrate is concentrated.

Procedure E (LAH Reduction)

To a solution of ester in THF is added LAH at 0° C. After stirring at room temperature for 3 hours, water, 15% NaOH solution and water are added sequentially. The mixture is then stirred at room temperature for 15 minutes, filtered, and concentrated.

Procedure F (Alcohol Chlorination)

To a solution of alcohol in the indicated solvent is added thionyl chloride dropwise at 0° C. After stirring at room temperature for 20 minutes, the mixture is concentrated.

Procedure G (DMP Oxidation)

To a solution of alcohol in DCM is added DMP. Water is optionally added to facilitate the reaction. After stirring for 1 hour, the mixture is concentrated and EA and 10% sodium thiosulfate are added. The layers are separated and the organic layer is washed with brine, dried over anhydrous sodium sulfate, and concentrated.

Preparation of A

Preparation of A1

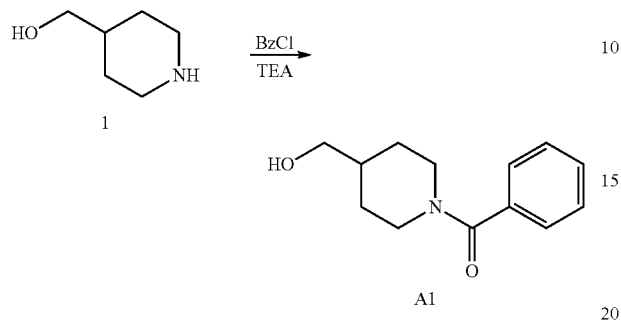

Following Procedure A using 1 (1.0 g, 8.7 mmol), TEA (1.35 mL, 10.4 mmol), DCM (10 mL), and BzCl (1.1 mL, 9.5 mmol), then purify with silica gel column chromatography (EA:PE=1:4) to give A1 as an oil (900 mg, 43% yield). (MS: [M+H]$^+$220.1)

The following compounds are prepared by essentially the same method as for A1.

| Intermediate | Structure | MS |
|---|---|---|
| A2 | 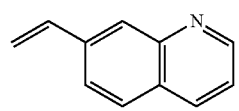 | [M + H]$^+$ 221.1 |
| A3 | 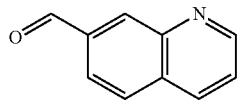 [SMILES: O=Cc1ccc2cccnc2c1] | [M + H]$^+$ 221.1 |
| A4 | 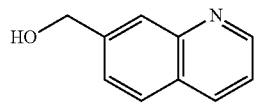 [SMILES: OCc1ccc2cccnc2c1] | [M + H]$^+$ 221.1 |

Preparation of A5

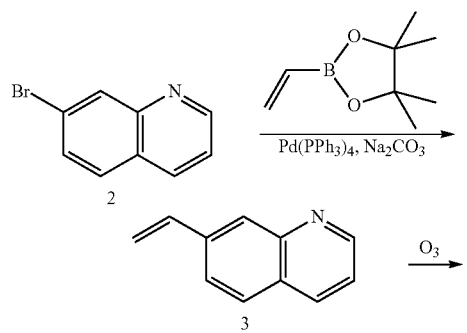

Step 1: Alkene 3

Following Procedure B using 2 (1 g, 4.81 mmol), dioxane (9 mL), water (1 mL), vinylboronic acid pinacol ester (888 mg, 5.77 mmol), sodium carbonate (1.27 g 12.02 mmol), and Pd(PPh$_3$)$_4$, then purify with silica gel column chromatography to give 3 as an oil (680 mg, 91% yield). (MS: [M+H]$^+$ 156.1) Step 2: aldehyde 4

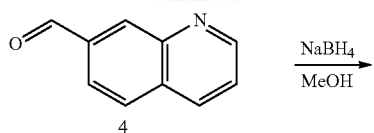

To a solution 3 (680 mg, 4.38 mmol) in MeOH/DCM (15 mL/15 mL) at −78° C. is bubbled with ozone slowly until a blue color persists. The solution is then purged with nitrogen for 15 minutes before treated with sodium bicarbonate (200 mg) and dimethyl sulfide (1.5 mL). After stirring at room temperature overnight, the mixture is diluted with water (30 mL) and extracted with DCM (30 mL×3). The combined organic layers are dried over anhydrous sodium sulfate, filtered, and concentrated to give curde 4 as a yellow oil (500 mg, 73% yield). (MS: [M+H]$^+$ 158.1)

Step 3: A5

Following Procedure C using crude 4 (1.0 g, 6.35 mmol), MeOH, and sodium borohydride (360 mg, 9.55 mmol), then quench with water (1 mL) and purify with silica gel column chromatography (MeOH:DCM=1:50) to give A5 as a solid (650 mg, 65% yield). (MS: [M+H]$^+$ 160.1)

The following compounds are prepared by essentially the same method as for A5.

| Intermediate | Structure | MS |
|---|---|---|
| A6 | 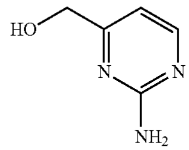 | [M + H]⁺ 126.1 |
| A7 | 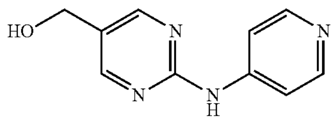 [SMILES: OCc1cnc(Nc2ccncc2)nc1] | [M + H]⁺ 203.1 |

Preparation of A8

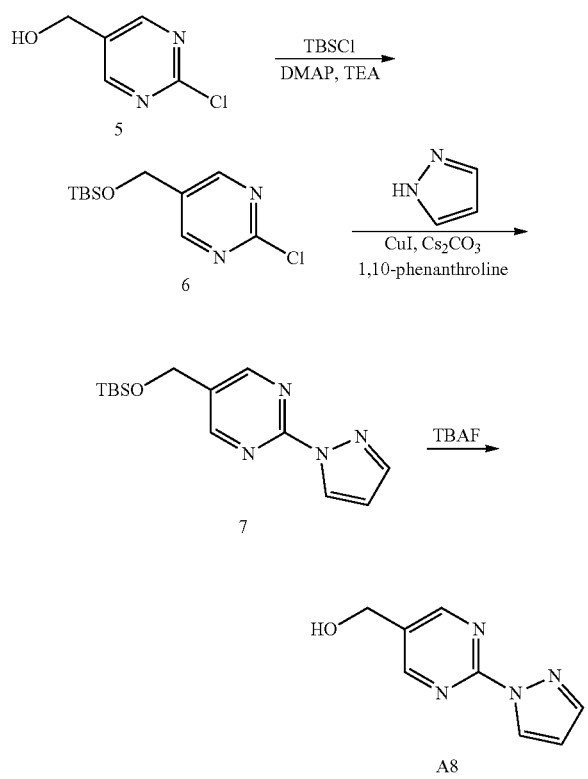

Step 1: Silyl Ether 6

To a solution of 5 (288 mg, 2.0 mmol) in THF is added DMAP (244 mg, 2.0 mmol), TEA (0.25 mL, 2.0 mmol), and TBSCl (600 mg, 4.0 mmol). After stirring at room temperature for 16 hours, the mixture is concentrated and purified by silica gel column chromatography (MeOH:DCM=1:100) to give 6 as a white solid (400 mg, 78% yield). (MS: [M+H]⁺ 259.1)

Step 2: Pyrazole 7

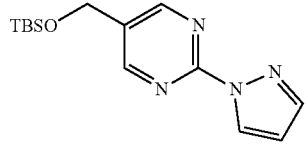 [SMILES: CC(C)(C)[Si](C)(C)OCc1cnc(-n2cccn2)nc1]

A mixture of 6 (258 mg, 1.0 mmol), pyrazole, cesium carbonate (656 mg, 2.0 mmol), CuI (19 mg, 0.1 mmol), and 1,10-phenanthroline (18 mg, 0.1 mmol), in DMSO (5 mL) is react at 130° C. under microwave irradiation for 45 minutes. After cooling to room temperature, the mixture is diluted with EA (20 mL), washed with water (50 mL×3), dried over anhydrous sodium sulfate, filtered, concentrated, and purify by silica gel column chromatography (MeOH:DCM=1:100) to give 7 as a white solid (80 mg, 27% yield). (MS: [M+H]⁺ 291.2)

Step 3: A8

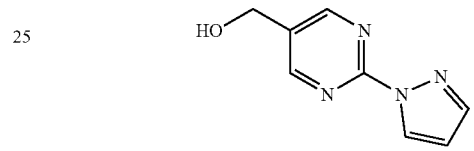

To a solution of 7 (80 mg 0.276 mmol) in THF (2 mL) is added TBAF (86 mg, 0.331 mmol) at room temperature. After stirring at room temperature for 1 hour, the mixture is concentrated and purified by silica gel column chromatography (MeOH:DCM=1:30) to give A5 as a white solid (48 mg, 100% yield). (MS: [M+H]⁺ 177.1)

The following compounds are prepared by essentially the same method as for A8.

| Intermediate | Structure | MS |
|---|---|---|
| A9 | 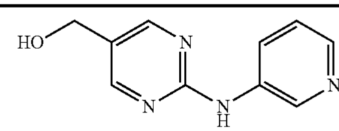 | [M + H]⁺ 203.1 |
| A10 | 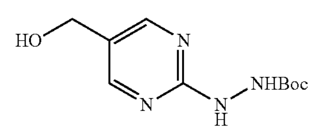 [SMILES: CC(C)(C)OC(=O)NNc1ncc(CO)cn1] | — |

Preparation of A11

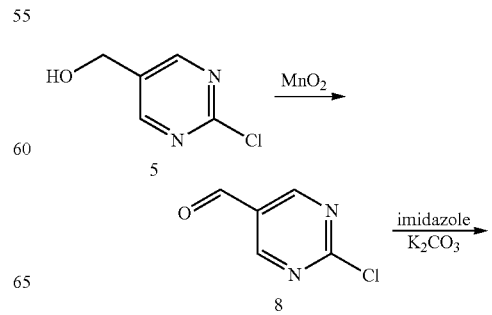

-continued

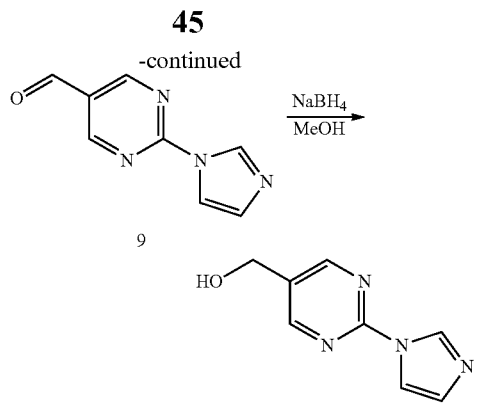

Step 1: Aldehyde 8

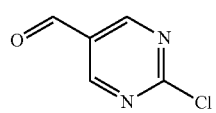

To a solution of 5 (500 mg, 3.47 mmol) in DCM is added activated manganese(IV) oxide (1.5 g, 17.4 mmol) at room temperature. After stirring at 40° C. for 4 hours, the mixture is filtered and concentrated to give crude 8 as a solid (400 mg, 80%). (MS: [M+H]+ 143.0)

Step 2: Imidazole 9

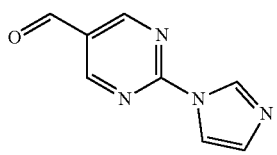 [SMILES: O=Cc1cnc(-n2ccnc2)nc1]

A mixture of 8 (50 mg, 0.35 mmol), imidazole (47 mg, 0.7 mmol), and potassium carbonate (138 mg, 1.05 mmol) in DMF (2 mL) is stirred at 50° C. for 16 hours. The mixture is then diluted with EA (20 mL), washed with aqueous lithium chloride solution (20 mL×3), dried over anhydrous sodium sulfate, filtered, concentrated, and purified by silica gel column chromatography (MeOH:DCM=1:50) to give 9 as a white solid (70 mg, 100% yield). (MS: [M+H]+ 175.1)

Step 3: A11

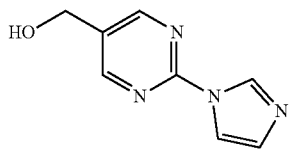 [SMILES: OCc1cnc(-n2ccnc2)nc1]

Following Procedure C using 9 (70 mg, 0.4 mmol), MeOH, and sodium borohydride (15.2 mg, 0.4 mmol), then quench with water (0.25 mL) and purify with prep-TLC (MeOH:DCM=1:30) to give A11 as a white solid (50 mg, 71% yield). (MS: [M+H]+177.1)

The following compound is prepared by essentially the same method as for A11.

| Intermediate | Structure | MS |
|---|---|---|
| A12 | 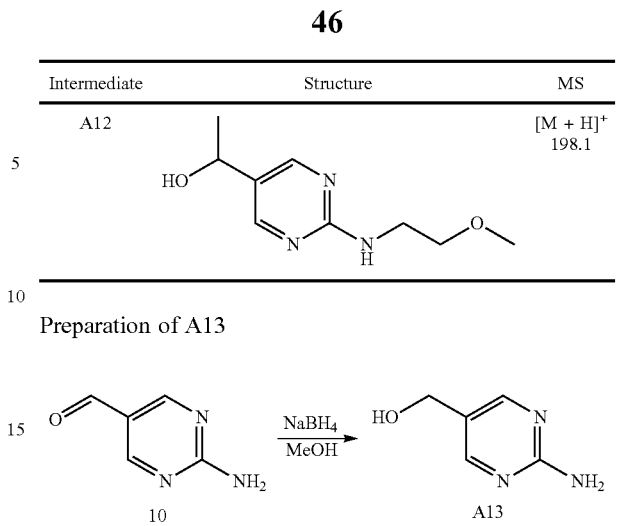 | [M + H]+ 198.1 |

Preparation of A13

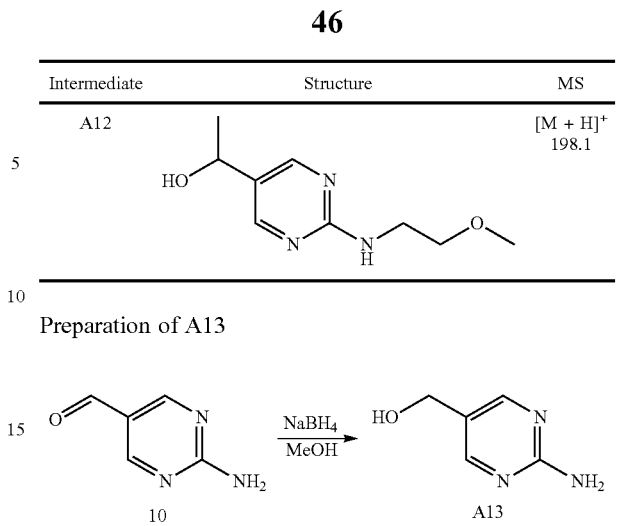

Following Procedure C using 10 (1.0 g, 8.12 mmol), MeOH (10 mL), and sodium borohydride (615 mg, 16.25 mmol), then purify with silica gel column chromatography (MeOH:DCM=1:20) to give A13 as a white solid. (300 mg, 30% yield). (MS: [M+H]+ 126.1)

The following compounds are prepared by essentially the same method as for A13.

| Intermediate | Structure | MS |
|---|---|---|
| A14 | 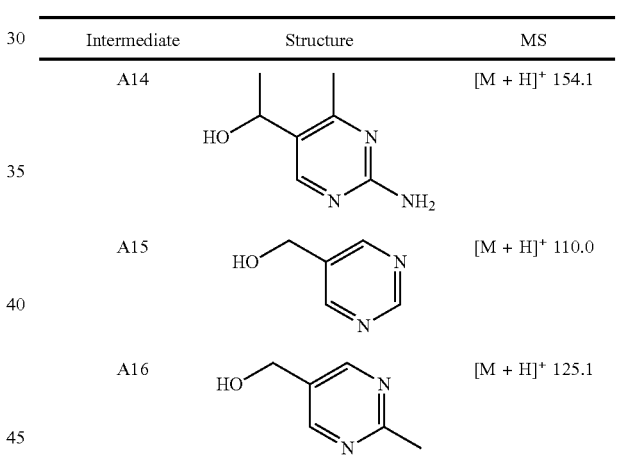 | [M + H]+ 154.1 |
| A15 | 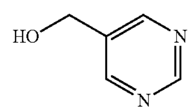 | [M + H]+ 110.0 |
| A16 | 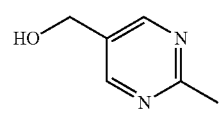 | [M + H]+ 125.1 |

Preparation of A17

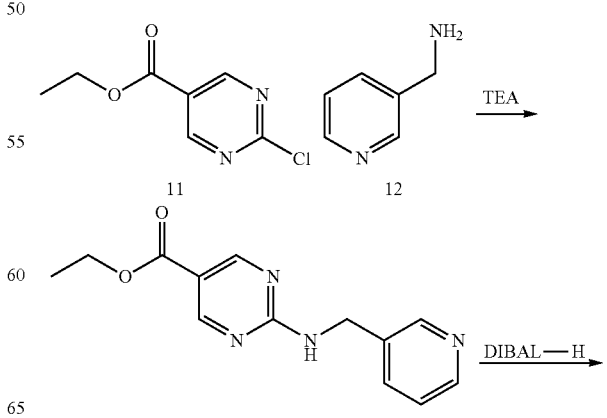

-continued

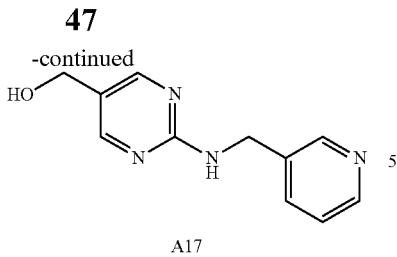

A17

Step 1: Pyridine 13

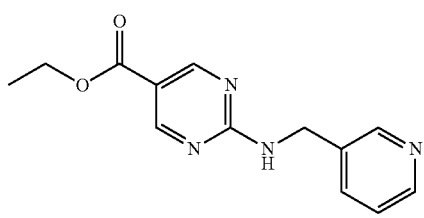 [SMILES: CCOC(=O)c1cnc(NCc2cccnc2)nc1]

To a solution of 11 (600 mg, 3.32 mmol) in THF (15 mL) is added 12 (696 mg, 6.40 mmol) and TEA (1.34 mL, 9.60 mmol) at room temperature. After stirring at 25° C. for 2 hours, the mixture is concentrated and purified by silica gel column chromatography (EA:PE=1:10 to 1:5) to give 13 (819 mg, 98% yield) as a white solid. (MS: [M+H]$^+$ 259.0)

Step 2: A17

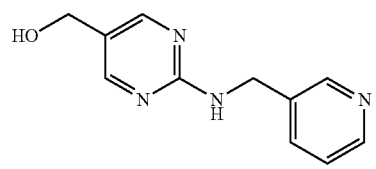 [SMILES: OCc1cnc(NCc2cccnc2)nc1]

Following Procedure D using 13 (819 mg, 3.17 mmol), THF (5 mL), DIBAL-H (1.5 M in toluene, 8.4 mL, 12.6 mmol), then quench with water (0.50 mL), 15% NaOH solution (0.50 mL), water (1.26 mL), and anhydrous sodium sulfate (5 g), and purify with silica gel column chromatography (EA:PE=1:1) to give A17 as a white solid (610 mg, 89% yield). (MS: [M+H]$^+$ 217.0).

The following compounds are prepared by essentially the same method as for A17.

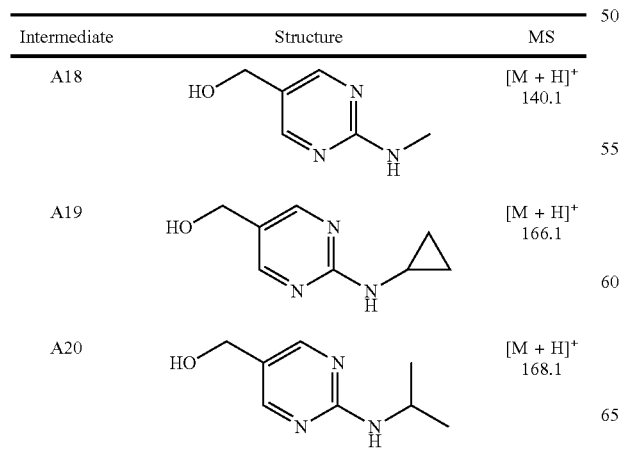

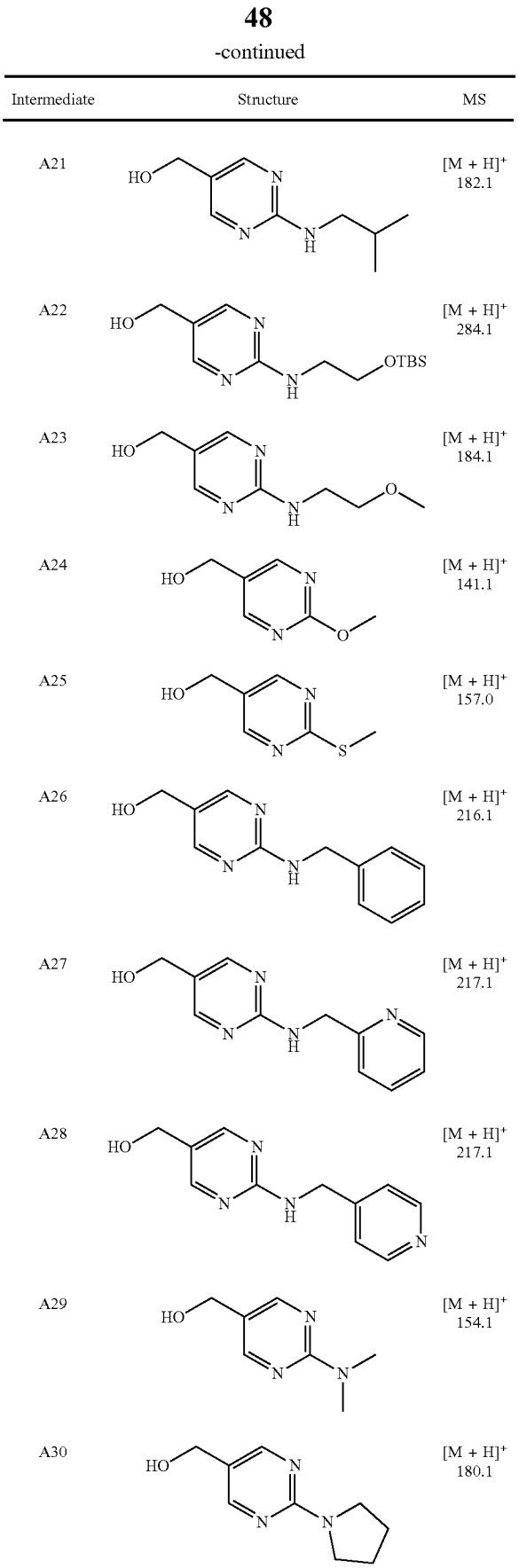

| Intermediate | Structure | MS |
|---|---|---|
| A31 | HO—[pyrimidine]-N(piperidine) | [M + H]+ 194.1 |
| A32 | HO—[pyrimidine]-N(piperazine-NBoc) | [M + H]+ 295.2 |
| A33 | HO—[pyrimidine]-N(morpholine) | [M + H]+ 196.1 |
| A34 | HO—[pyrimidine]-N(N-methylpiperazine) | [M + H]+ 209.1 |

Preparation of A35

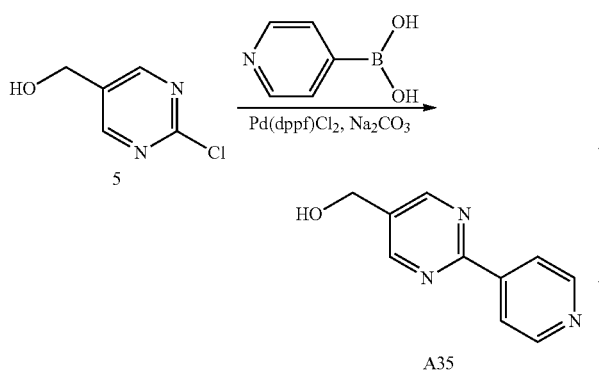

Following Procedure B using 5 (150 mg, 1.04 mmol), 4-pyridinylboronic acid (191 mg, 1.56 mmol), sodium carbonate (220 mg, 2.1 mmol), dioxane (5 mL), water (0.5 mL), and Pd(dppf)Cl₂ (50 mg, 0.07 mmol), react at 90° C. for 4 hours and then purify with silica gel column chromatography (EA:PE=1:2) to give A35 as a solid (100 mg, 78% yield). (MS: [M+H]⁺ 188.1)

Preparation of A36:

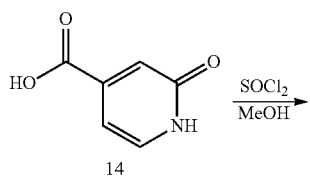

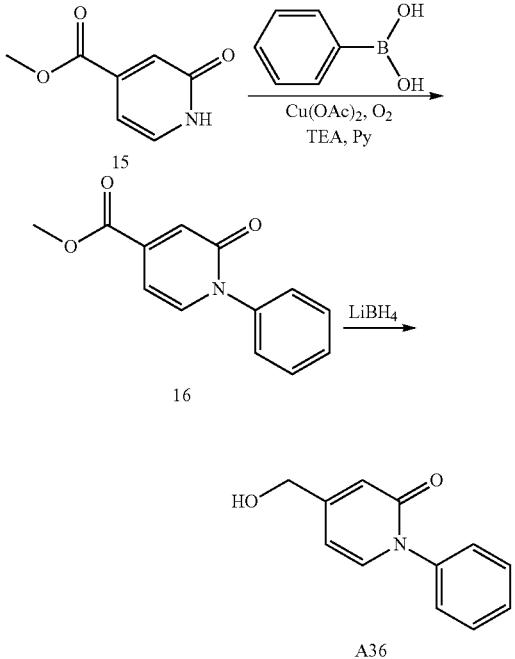

Step 1: Ester 15

To a solution of 14 (20 g, 144 mmol) in MeOH (250 mL) is added thionyl chloride (34.2 g, 288 mmol) at 0° C. After stirring at room temperature for 12 hour, the mixture is concentrated and then partitioned between saturated aqueous sodium bicarbonate (100 mL) and Et₂O (100 mL). The aqueous layer is extracted with Et₂O (50 mL×3). The combined organic layers are dried over anhydrous sodium sulfate, filtered, and concentrated to give crude 15 (10 g 45% yield) as a white solid. (MS: [M+H]⁺ 154.1)

Step 2: Ester 16

To a mixture of crude 15 (2 g 13.1 mmol), phenylboronic acid (1.93 g, 15.7 mmol), TEA (2.64 g, 26.1 mmol), Py (2.07 g, 26.1 mmol) in DCM (20 mL) is added Cu(OAc)₂ (3.56 g, 19.6 mmol). After reacting at room temperature overnight under oxygen, the mixture is filtered, concentrated, and purify by silica gel column chromatography (MeOH: DCM=1:50) to give 16 as a yellow solid (2.3 g, 77% yield). (MS: [M+H]⁺ 230.1)

Step 3: A36

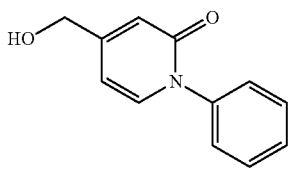 [SMILES: O=c1cc(CO)ccn1-c1ccccc1]

To a solution of 16 (500 mg, 2.18 mmol) in THF (10 mL) is added lithium borohydride (2 M in THF, 1.64 mL, 3.28 mmol) dropwise at 0° C. After stirring at room temperature for 30 minutes, MeOH (15 mL) and water (3 mL) are added at 0° C. The mixture is then stirred at room temperature for 30 minutes before concentrated and purified by silica gel column chromatography (MeOH:DCM=1:50) to give A36 as a yellow solid (400 mg, 91% yield). (MS: $[M+H]^+$ 202.1)

Preparation of A37

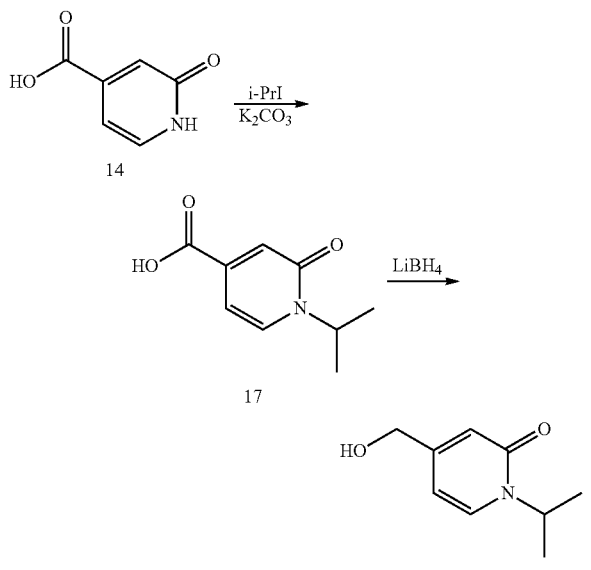

Step 1: Ester 17

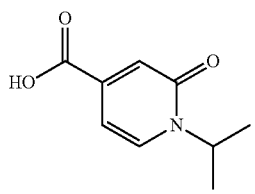

A mixture of 14 (500 mg, 3.27 mmol), potassium carbonate (901 mg, 6.54 mmol) and 2-iodopropane (555 mg, 3.27 mmol) in DMF (3 mL) is stirred at room temperature overnight. The mixture is then diluted with water (5 mL) and extracted with EA (10 mL×3). The combined organic layers are dried over anhydrous sodium sulfate, filtered, and concentrated to give crude 17 as a yellow oil (446 mg, 70% yield). (MS: $[M+H]^+$ 196.1)

Step 2: A37

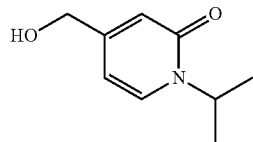

Following the procedure for A36 using crude 17 (400 mg, 2.05 mmol), THF (10 mL), and lithium borohydride (2 M in THF solution, 1.55 mL, 3.1 mmol), then purify with silica gel column chromatography (MeOH:DCM=1:50) to give A37 as a yellow solid (200 mg, 58% yield). (MS: $[M+H]^+$ 168.1)

Preparation of A38

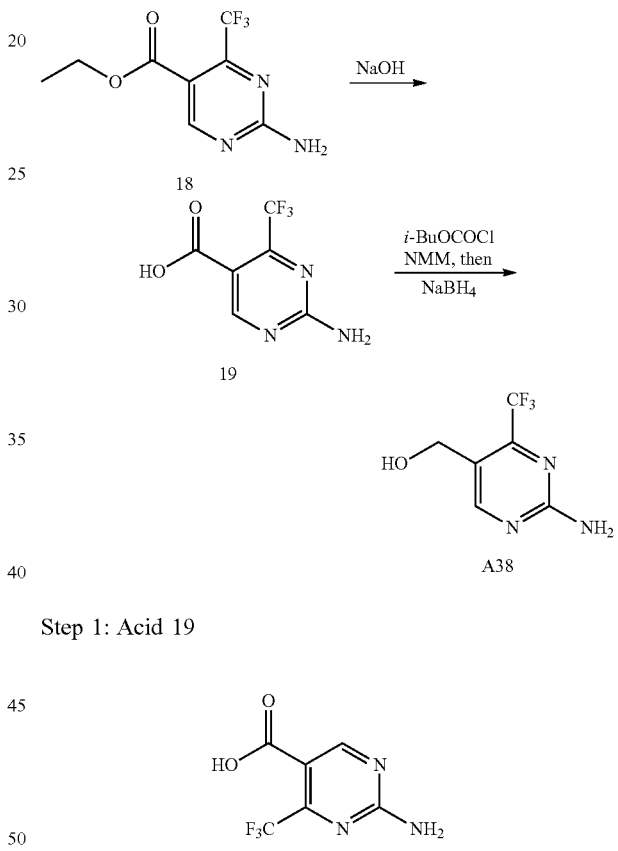

Step 1: Acid 19

To a solution of 18 (800 mg, 3.40 mmol) in MeOH (20 mL) and water (20 mL) is added NaOH (408 mg, 10.2 mmol). After stirring at room temperature overnight, the mixture is concentrated and the residue is dissolved in water (10 mL) followed by acidified to pH 1 by addition of concentrated aqueous HCl. The precipitate is collected by filtration and dried to give crude 19 (600 mg, 91% yield). (MS: $[M+H]^+$ 236.0)

Step 2: A38

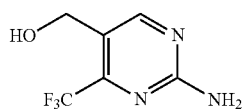

To a solution of crude 19 (100 mg, 0.48 mmol) in THF (5 mL) is added isobutyl chloroformate (0.05 mL, 0.58 mmol) followed by NMM (0.06 mL, 0.58 mmol) at −10° C. After stirring for 10 minutes, the mixture is filtered and sodium borohydride (37 mg, 0.96 mmol) in water (0.2 mL) is added dropwise at 0° C. After stirring at room temperature for 20 minutes, the mixture is concentrated and the residue is partitioned between EA (20 mL) and water (10 mL). The organic layer is washed with brine (10 mL), dried over anhydrous sodium sulfate, concentrated, and purified by silica gel column chromatography (MeOH:DCM=1:100) to give A38 as a colorless oil (50 mg, 74% yield). (MS: [M+H]⁺ 194.1)

Preparation of A39:

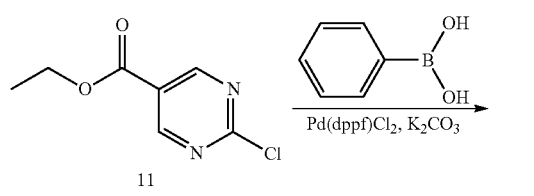

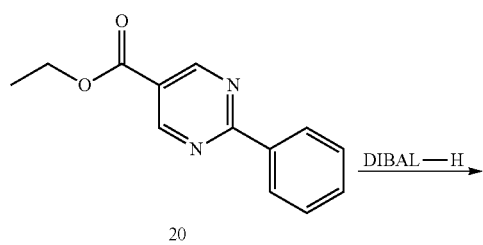

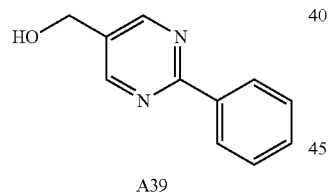

A39

Step 1: Ester 20

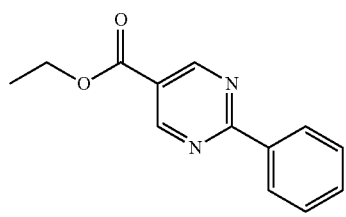 [SMILES: CCOC(=O)c1cnc(-c2ccccc2)nc1]

Following Procedure B using 11 (500 mg, 2.67 mmol), dioxane (10 mL), phenylboronic acid (650 mg, 5.36 mmol), potassium carbonate (1.85 g, 13.4 mmol), and Pd(dppf)Cl₂ (50 mg), then purified by silica gel column chromatography (EA:PE=1:100 to 1:50) to give 20 as a white solid (400 mg, 65% yield). (MS: [M+H]⁺ 229.1)

Step 2: A39

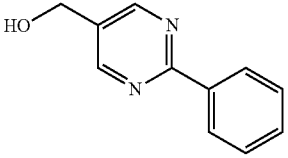 [SMILES: OCc1cnc(-c2ccccc2)nc1]

Following Procedure D using 20 (400 mg, 1.75 mmol), THF (20 mL), and DIBAL-H (1.5 M in toluene, 4.1 mL, 6.13 mmol), then purify with silica gel column chromatography (EA:PE=1:1) to give A39 as a white solid (240 mg, 74% yield). (MS: [M+H]⁺ 187.1)

Preparation of A40

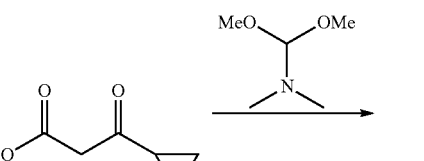

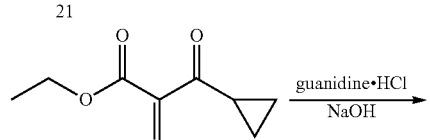

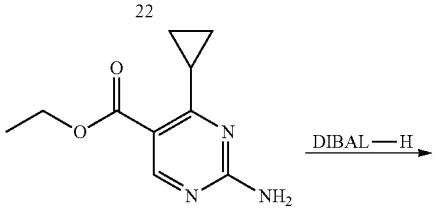

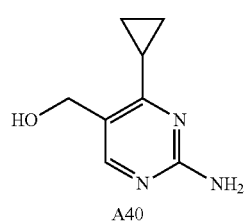

A40

Step 1: Ester 22

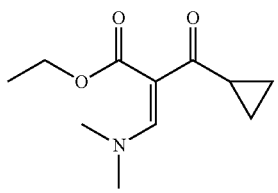

A solution of 21 (1.53 g, 9.8 mmol) and N,N-dimethylformamide dimethyl acetal (2 g, 16.8 mmol) in dioxane (20 mL) is heated at 100° C. for 4 hours. The mixture is then cooled, concentrated, co-evaporated with toluene to give crude 22 as a yellow oil (2.1 g, 78% yield). (MS: [M+H]+ 214.1)

Step 2: Pyrimidine 23

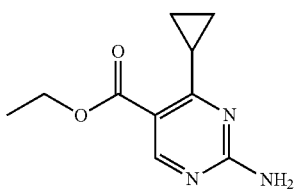

To a solution of 22 (1 g, 4.73 mmol) and guanidine hydrochloride (452 mg, 4.73 mmol) in n-butanol (40 mL) is added NaOH (189 mg, 4.73 mmol). After stirring at 120° C. for 2 hours, the mixture is concentrated and the residue is dissolved EA (100 mL), washed with brine (30 mL×3), dried over anhydrous sodium sulfate, filtered, concentrated, and triturated with n-hexane (30 mL). The solid is collected by filtration, washed with hexane (3 mL×3), and dried to give 23 as a pale yellow solid (400 mg, 40% yield). (MS: [M+H]+ 208.1)

Step 3: A40

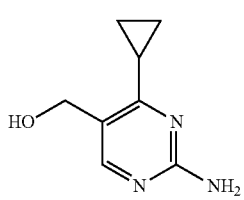 [SMILES: Nc1ncc(CO)c(C2CC2)n1]

Following Procedure D using 23 (100 mg, 0.48 mmol), THF (5 mL), and DIBAL-H (1.5 M in toluene, 1.3 ml, 1.93 mmol), but quench with 15% aqueous NaOH solution (0.5 mL) to give crude A40 as a white solid (60 mg, 40% yield). (MS: [M+H]+166.1)

Preparation of A41

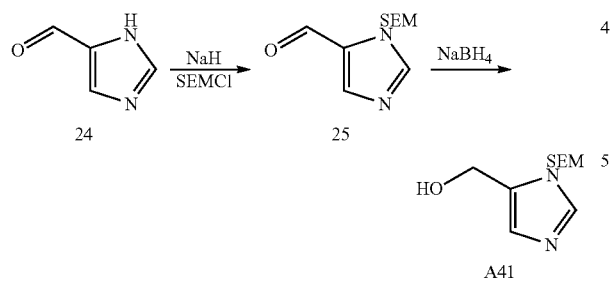

Step 1: Aldehyde 25

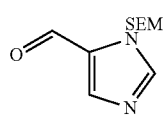

To a solution of 24 (1.0 g, 10.4 mmol) in DMF (10 mL) is added NaH (625 mg, 15.6 mmol) at 0° C. After stirring at room temperature for 1 hour, 2-(trimethylsilyl)ethoxymethyl chloride (2.0 g, 12.5 mmol) is added dropwise at 0° C. The mixture is then stirred for 16 hours before diluted with EA (50 mL), washed with aqueous lithium chloride solution (20 mL×4), dried over anhydrous sodium sulfate, filtered, concentrated, and purified by silica gel column chromatography (MeOH:DCM=1:10) to give 25 as a brown oil (1.0 g, 43% yield). (MS: [M+H]+ 227.1)

Step 2: A41

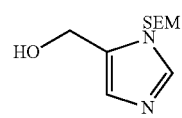

Following Procedure C using 25 (1.0 g, 4.4 mmol), THF (10 mL), and sodium borohydride (152 mg, 6.6 mmol), then quench with water (0.1 mL) and purify with silica gel column chromatography (MeOH:DCM=1:10) to give A41 as a brown oil (450 mg, 45% yield). (MS: [M+H]+ 229.1)

Preparation of A42

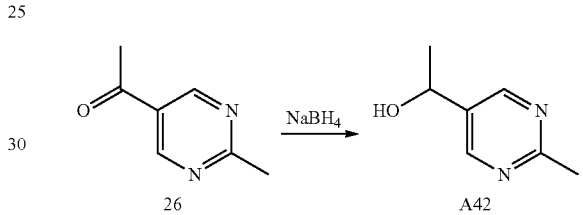

Following Procedure C using 26 (408 mg, 3.0 mmol), THF (5 mL), MeOH (1 mL), and sodium borohydride (230 mg, 6.0 mmol), then quench with water (0.1 mL) and purify with silica gel column chromatography (MeOH:DCM=1:30) to give A42 as an oil (220 mg, 53% yield). (MS: [M+H]+ 139.1)

Preparation of A43

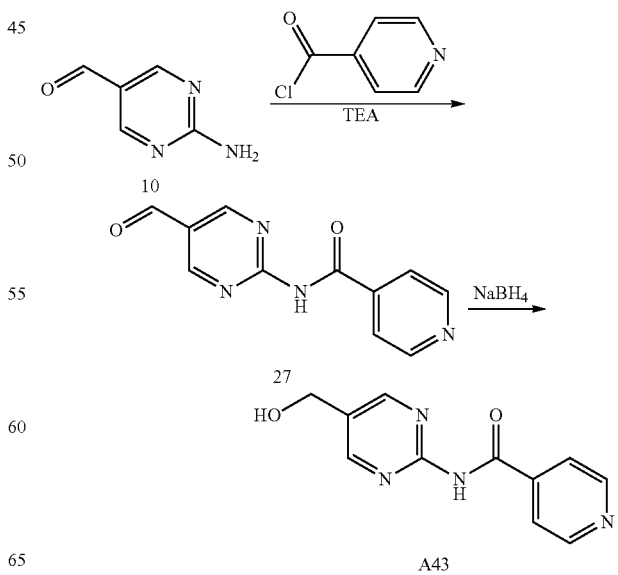

Step 1: Aldehyde 27

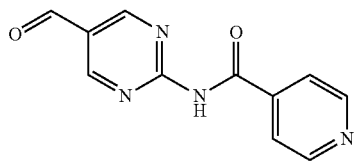 [SMILES: O=Cc1cnc(NC(=O)c2ccncc2)nc1]

Following Procedure A using isonicotinoyl chloride (2.76 g, 19.5 mmol), dioxane (20 mL), 10 (800 mg, 6.5 mmol), and TEA (5.42 mL, 39 mmol), react at 100° C. and then dilute the mixture with EA (20 mL), wash with water (30 mL) and brine (50 mL), concentrate, and purify with silica gel column chromatography (MeOH:DCM=1:50) to give 27 as a white solid (400 mg, 27% yield). (MS: [M+H]$^+$ 229.1)

Step 2: A43

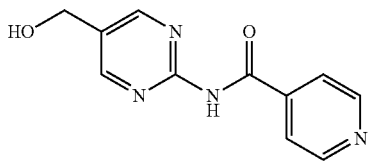 [SMILES: O=C(Nc1ncc(CO)cn1)c1ccncc1]

Following Procedure C using 27 (300 mg, 1.31 mmol), MeOH (5 mL), and sodium borohydride (75 mg, 1.97 mmol), then purify with silica gel column chromatography (MeOH:DCM=1:20) to give A43 as a white solid (180 mg, 60% yield). (MS: [M+H]$^+$ 231.1)

Preparation of A44

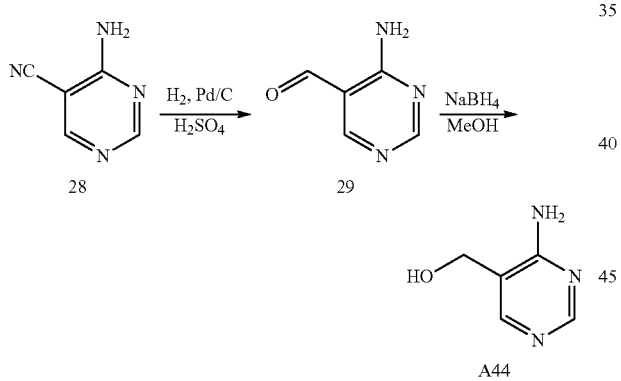

Step 1: Aldehyde 29

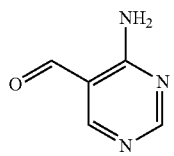

To a mixture of 28 (150 mg, 1.25 mmol) in 50% aqueous H$_2$SO$_4$ solution (2 mL) is added Pd/C (5 wt. %, 15 mg). After stirring at room temperature under hydrogen for 8 hours, the mixture is neutralized with solid sodium bicarbonate at 0° C. and extracted with EA (30 mL×5). The combined organic layers are dried over anhydrous sodium sulfate, filtered, and concentrated to give crude 29 as a white solid (100 mg, 65% yield). (MS: [M+H]$^+$ 124.0)

Step 2: A44

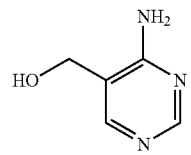

Following Procedure C using 29 (100 mg, 0.8 mmol), MeOH (0.5 mL), THF (1.5 mL), and sodium borohydride (34 mg, 0.9 mmol), then purify with silica gel column chromatography (MeOH:DCM=1:50) to give A44 as a white solid (90 mg, 88% yield). (MS: [M+H]$^+$ 126.1)

Preparation of A45

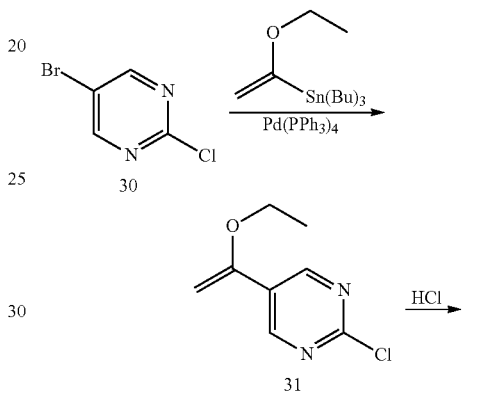

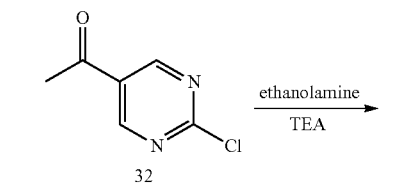

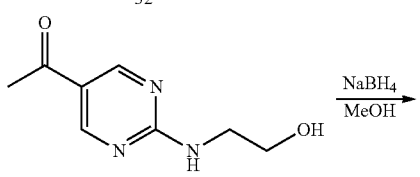

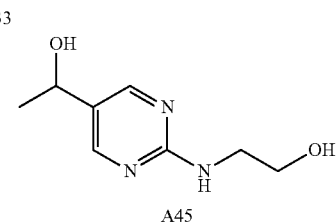

Step 1: Enol Ether 31

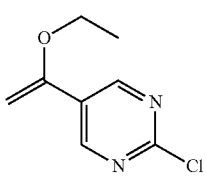

A mixture of 30 (1.0 g 5.17 mmol) in DMF (20 mL) is added tributyl(1-ethoxyvinyl)tin (1.8 g 5.17 mmol) and Pd(PPh₃)₄ (150 mg 0.13 mmol). After stirring at 100° C. for 2 hours, saturated aqueous potassium fluoride solution (20 mL) is added and the mixture is stirred for 30 minutes. The mixture is then diluted with EA (50 mL), washed with brine (30 mL×3), dried over anhydrous sodium sulfate, filtered, and concentrated to give crude 31 as a white solid (560 mg, 66% yield). (MS: [M+H]⁺ 185.0)

Step 2: Ketone 32

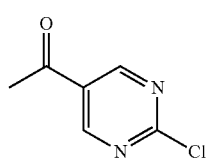

To a solution of crude 31 (560 mg 3.0 mmole) in THF (20 mL) is added aqueous HCl solution (1 M, 5 mL) at room temperature. After stirring at room temperature for 5 hours, the mixture is concentrated and the residue is partitioned between saturated aqueous sodium bicarbonate (20 mL) and EA (100 mL). The organic layer is washed with brine (20 mL×3), dried over anhydrous sodium sulfate, filtered, concentrated, and purified by silica gel column chromatography (DCM:PE=1:1) to give 32 as a white solid (450 mg, 95% yield). (MS: [M+H]⁺ 157.0)

Step 3: Alcohol 33

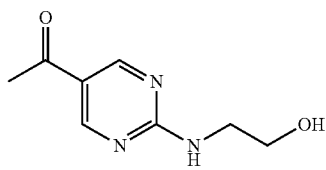

To a solution of 32 (130 mg, 0.67 mmol) in EtOH (5 mL) is added ethanolamine (50 mg, 0.67 mmol) at room temperature. After stirring at 80° C. for 30 minutes, the mixture is cooled and concentrated to give 33 as a colorless oil (162 mg, 100% yield). (MS: [M+H]⁺ 182.1)

Step 4: A45

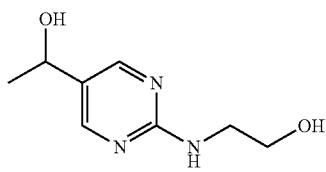

Following Procedure C using 33 (160 mg, 0.87 mmole), MeOH (5 mL), and sodium borohydride (15.5 mg, 0.41 mmol), then purify with silica gel column chromatography (DCM) to give A45 as a colorless oil (150 mg, 99% yield). (MS: [M+H]⁺ 184.1)

Preparation of A46

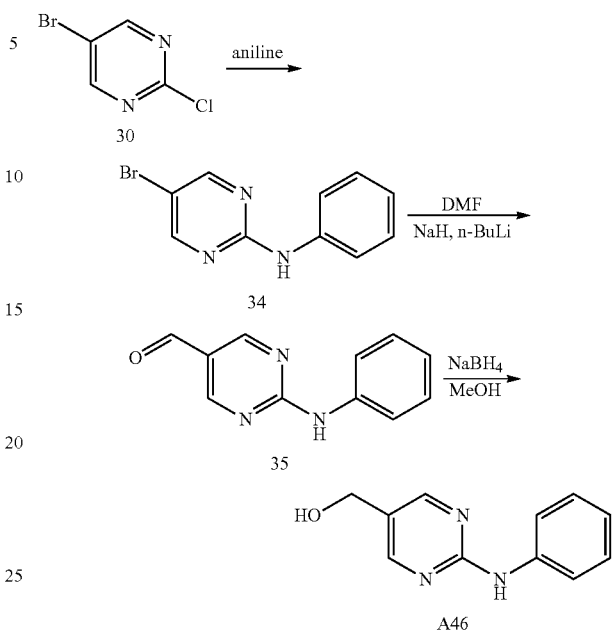

Step 1: Pyrimidine 34

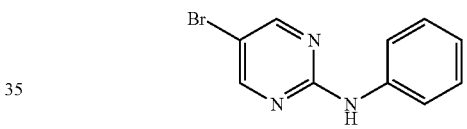

To a solution of 30 (580 mg, 3.0 mmol) in n-butanol (6 mL) is added aniline (335 mg, 3.6 mmol). After stirring at 110° C. for 4 hours, the mixture is concentrated and purified by silica gel column flash chromatography (EA:PE=1:10) to give 34 as an off-white solid (500 mg, 66% yield). (MS: [M+H]⁺ 250.0)

Step 2: Aldehyde 35

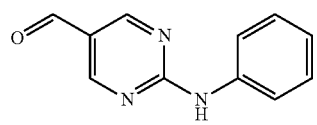 [SMILES: O=Cc1cnc(Nc2ccccc2)nc1]

A solution of 34 (500 mg, 2.0 mmol) and NaH (72 mg, 3.0 mmol) in THF (5 mL) is stirred at −70° C. for 15 minutes before n-BuLi (2.5 M, 1.2 mL, 3.0 mmol) is added dropwise. After stirring for 1 hour, DMF (1 mL) is added dropwise and the mixture is stirred at room temperature for 1 hour before pouring into saturated ammonium chloride solution (20 mL). The mixture is then extracted with EA (30 mL×3). The combined organic layers are dried over anhydrous sodium sulfate, filtered, concentrated, and purified by silica gel column chromatography (EA:PE=1:10) to give 35 as a white solid (150 mg, 37% yield). (MS: [M+H]⁺ 200.0)

Step 3: A46

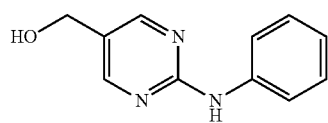 [SMILES: OCc1cnc(Nc2ccccc2)nc1]

Following Procedure C using 35 (150 mg, 0.7 mmol), MeOH (2 mL), and sodium borohydride (42 mg, 1.1 mmol), then purify with silica gel column chromatography (EA: PE=1:2) to give A46 as a white solid (115 mg, 76% yield). (MS: [M+H]$^+$ 202.0)

Preparation of A47

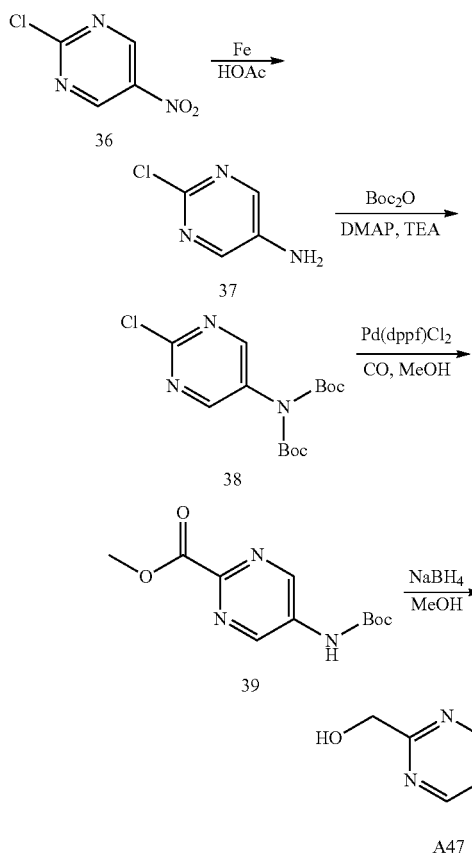

Step 1: Pyrimidine 37

To a solution of 36 (400 mg, 2.5 mmol) in HOAc (5 mL) is added Fe (700 mg, 12.5 mmol). After stirring at 75° C. for 2 hours, the mixture is cooled to room temperature, filtered, concentrated, and purified by silica gel column chromatography (EA:PE=1:5) to give 37 as as an oil (320 mg, 98% yield). (MS: [M+H]$^+$ 130.0)

Step 2: Pyrimidine 38

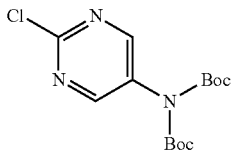 [SMILES: CC(C)(C)OC(=O)N(C(=O)OC(C)(C)C)c1cnc(Cl)nc1]

To a solution of 37 (300 mg, 2.3 mmol) in MeCN (1.5 mL) and THF (1.5 mL) are added TEA (468 mg, 4.6 mmol), DMAP (284 mg, 2.3 mmol), and di-tert-butyl dicarbonate (2.5 g, 11.6 mmol). After stirring at room temperature for 2 hours, the mixture is concentrated and purified by silica gel column chromatography (EA:PE=1:100) to give 38 as a white solid (380 mg, 49% yield). (MS: [M+H]$^+$ 330.1)

Step 3: Ester 39

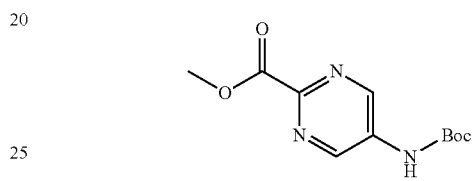

To a solution of 38 (380 mg, 1.1 mmol) and TEA (348 mg, 3.4 mmol) in MeOH (5 mL) is added Pd(dppf)Cl$_2$ (169 mg, 0.2 mmol). After stirring at 100° C. under CO (60 psi) for 16 hours, the mixture is cooled to room temperature, filtered, concentrated, and purified by silica gel column chromatography (MeOH:DCM=1:50) to give 39 as a light pink solid (260 mg, 89% yield). (MS: [M+H]$^+$ 254.1)

Step 4: A47

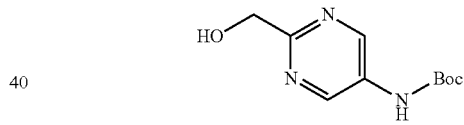

Following Procedure C using 39 (200 mg, 0.8 mmol), MeOH (3 mL), and sodium borohydride (45 mg, 1.2 mmol), and quench with saturated ammonium chloride solution (1 mL), extract with EA (20 mL), dry over anhydrous sodium sulfate, filter, concentrate, and purify with silica gel column chromatography (MeOH:DCM=1:20) to give A47 as an off-white solid (150 mg, 84% yield). (MS: [M+H]$^+$ 226.1)

Preparation of A48

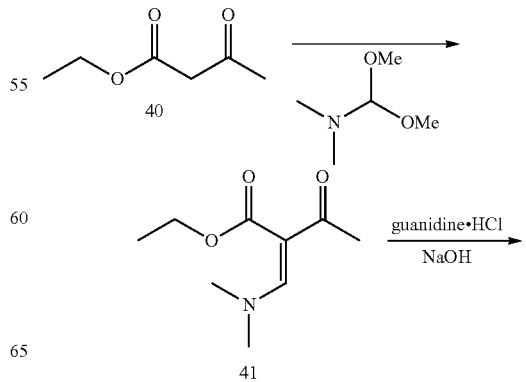

Step 3: Acid 43

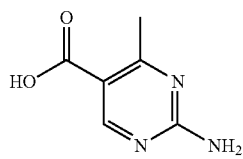

To a solution of 42 (500 mg, 2.8 mmol) in MeOH (20 mL) and water (20 mL) is added NaOH (331 mg, 8.3 mmol). After stirring at room temperature overnight, the mixture is concentrated and the residue is dissolved in water (10 mL) and acidified to pH 1 with concentrated aqueous HCl. The precipitate is collected by filtration and dried to give 43 (330 mg, 85% yield). (MS: $[M+H]^+$ 154.1)

Step 4: A48

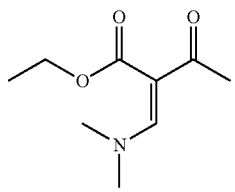

To a solution of 43 (100 mg, 0.65 mmol) in THF (5 mL) is added isobutyl chloroformate (89 mg, 0.65 mmol) followed by NMM (66 mg, 0.65 mmol) at −10° C. After stirring for 10 minutes, the precipitate is removed by filtration. To the filtrate is added a solution of sodium borohydride (37 mg, 0.96 mmol) in water (0.2 mL) at 0° C. After stirring at room temperature for 20 minutes, the mixture is concentrated and the residue is partitioned between EA (20 mL) and water (10 mL). The organic layer is washed with brine (10 mL), dried over anhydrous sodium sulfate, filtered, concentrated, and purified by silica gel column chromatography (MeOH:DCM=1:100) to give A48 as a colorless oil (60 mg, 67% yield). (MS: $[M+H]^+$ 140.1)

Preparation of A49

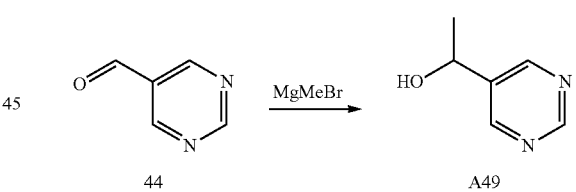

To a solution of 44 (100 mg, 0.9 mmol) in THF (2 mL) is added MgMeBr (1 M, 1.1 mL, 1.1 mmol) dropwise at −70° C. After stirring for 1 hour, EtOH (1 mL) is added at 0° C. and then the mixture is acidified with 2 M HCl to pH 6. The mixture is then extracted with EA (10 mL×2). The combined organic layers are dried over anhydrous sodium sulfate, filtered, concentrated, and purified by silica gel column chromatography (MeOH:DCM=1:50) to give A49 as a colorless oil (80 mg, 70% yield). (MS: $[M+H]^+$ 125.1)

Preparation of A50

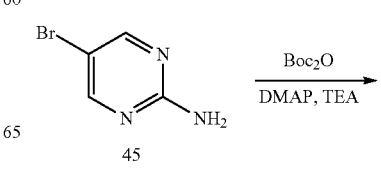

-continued

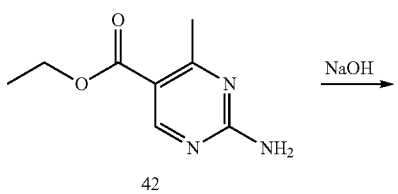

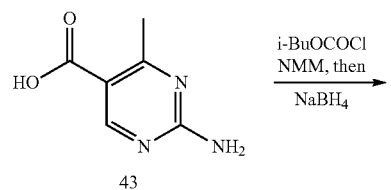

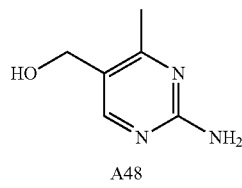

Step 1: Ester 41

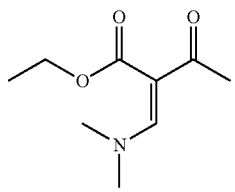

A mixture of 40 (10 g 26.8 mole) and N,N-dimethylformamide dimethyl acetal (10 g, 84.5 mmol) is stirred at room temperature overnight. The mixture is then concentrated, co-evaporated with toluene (10 mL×3) to give crude 41 as a yellow oil (14 g, 100% yield). (MS: $[M+H]^+$ 186.1)

Step 2: Pyrimidine 42

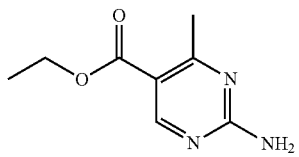

To a solution of 41 (3 g, 16.2 mmol) and guanidine hydrochloride (1.55 g, 16.2 mmol) in n-butanol (50 mL) is added NaOH (648 mg, 16.2 mmol). After stirring at 120° C. for 2 hours, the mixture is concentrated and the residue is dissolved in EA (100 mL), washed with water (50 mL) and brine (50 mL), dried over anhydrous sodium sulfate, filtered, concentrated, and triturated with n-hexane (50 mL). The solid is collected by filtration, washed with hexane (5 mL×3), and dried to give 42 as a white solid (800 mg, 28% yield). (MS: $[M+H]^+$ 182.1)

-continued

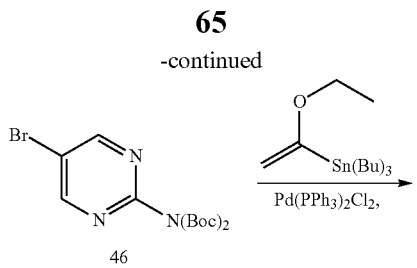

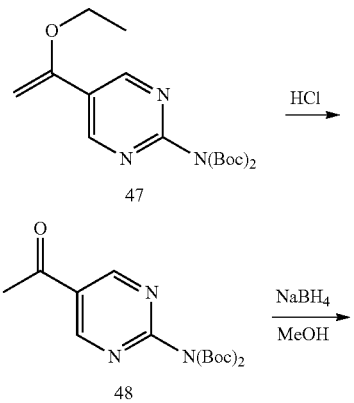

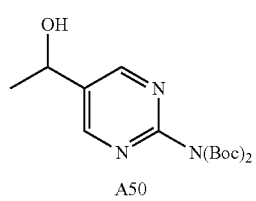

Step 1: Pyrimidine 46

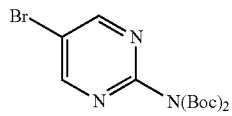

To a solution of 45 (5.0 g, 28.7 mmol) in THF (50 mL) are added di-tert-butyl dicarbonate (13.8 g, 63.2 mmol), TEA (12.0 mL, 86 mmol), and DMAP (360 mg, 2.87 mmol). After stirring at 60° C. for 16 hour, the mixture is concentrated and purified by silica gel column chromatography (EA:PE=1:5) to give 46 as a white solid (9.0 g, 84% yield). (MS: [M+H]$^+$ 374.1)

Step 2: Enol Ether 47

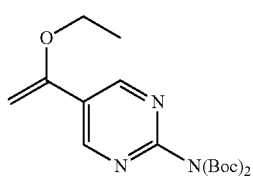

Following the procedure for 31 using 46 (3.0 g, 8.0 mmol), DMF (30 mL), tributyl(1-ethoxyvinyl)stannane (4.3 g, 12.0 mmol), and Pd(PPh$_3$)$_2$Cl$_2$ (281 mg, 0.4 mmol), react at 80° C. for 16 hours and then purify with silica gel column chromatography (EA:PE=1:8) to give 47 as an oil (2.49 g, 85% yield). (MS: [M+H]$^+$ 366.2)

Step 3: Ketone 48

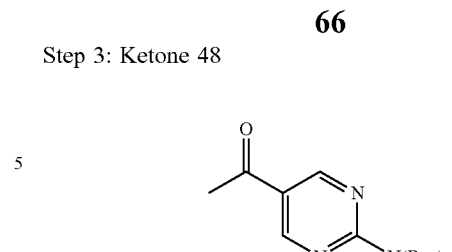

To a solution of 47 (2.49 g, 6.82 mmol) in THF (5 mL) is added aqueous HCl solution (1 M, 2 mL, 2.0 mmol) at room temperature. After stirring for 3 hours, the mixture is concentrated and purified by silica gel column chromatography (EA:PE=1:5) to give 48 as a white solid (2.1 g, 91% yield). (MS: [M+H]$^+$ 338.2)

Step 4: A50

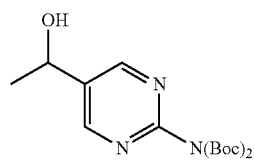

Following Procedure C using 48 (1.0 g, 2.97 mmol), THF (8 mL), MeOH (1 mL), and sodium borohydride (26 mg, 0.68 mmol), then purify with silica gel column chromatography (EA:PE=1:1) to give A50 as a white solid (819 mg, 82% yield). (MS: [M+H]$^+$ 340.2)

Preparation of AA1

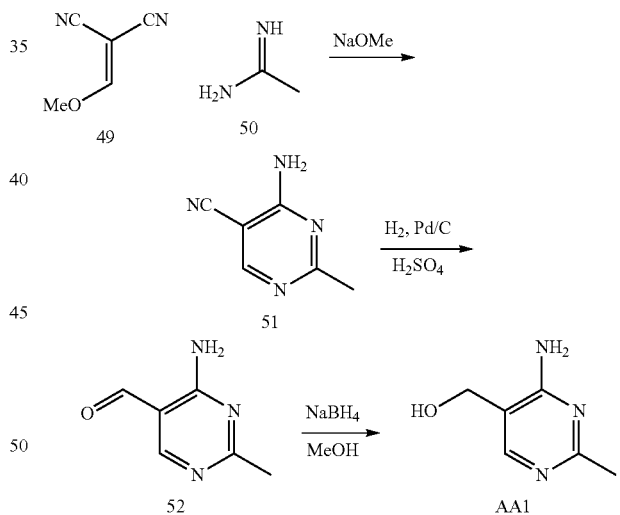

Step 1: Pyrimidine 51

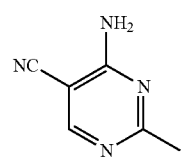

To a suspension of 50 (3.87 g, 40.9 mmol) in EtOH (10 mL) is added a solution of sodium methoxide (2.2 g, 40.9 mmol) in EtOH (10 mL). After stirring at room temperature for 40 minutes, the mixture is filtered and the solid is washed with EtOH (1 mL). The filtrate is then treated with 49 (2.5 g, 20.5 mmol) and the resulting solid is collected by filtration and dried to give 51 (700 mg, 26%). (MS: [M+H]⁺ 109.0)

Step 2: Aldehyde 52

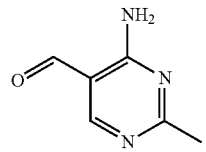

To a solution of 51 (700 mg, 5.2 mmol) in water and $H_2SO_4$ is added Pd/C (10 wt. %, 543 mg). After stirring at room temperature under hydrogen for 16 hours, the mixture is filtered through a pad of Celite and washed with water. The filtrate is treated with ammonium hydroxide, and the solid is collected by filtration and dried to give 52 (500 mg, 70%). (MS: [M+H]⁺ 138.1)

Step 3: AA1

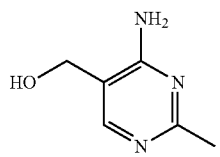

Following Procedure C using 52 (500 mg, 3.6 mmol), MeOH (2 mL), THF (2 mL), and sodium borohydride (138 mg, 3.6 mmol), then purify with silica gel column chromatography (DCM) to give AA1 as a white solid (250 mg, 50%). (MS: [M+H]⁺ 140.0)

Preparation of AA2

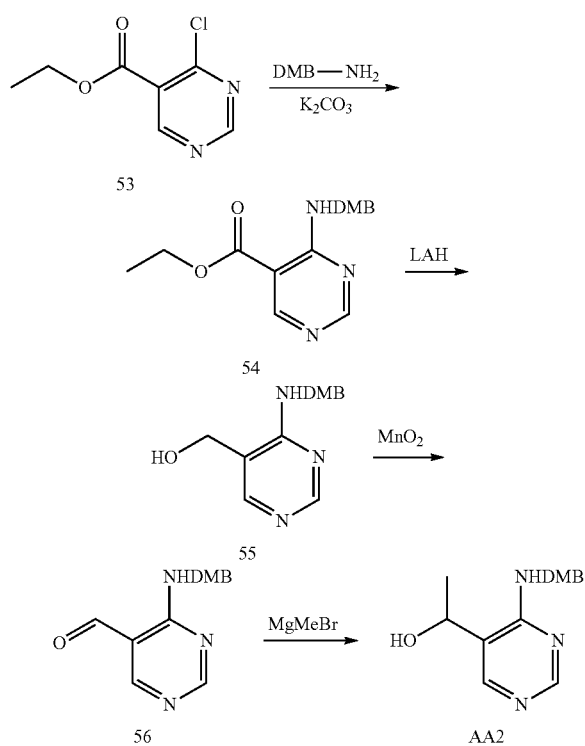

Step 1: Pyrimidine 54

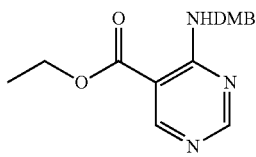

To a solution of 53 (500 mg, 2.68 mmol) in DMF is added potassium carbonate (555 mg, 4.02 mmol) and 2,4-dimethoxybenzylamine (500 mg, 2.99 mmol). After stirring at 50° C. for 3 hours, the mixture is cooled, diluted with EA, and washed with saturated aqueous lithium chloride solution (20 mL×3). The organic layer is dried over anhydrous sodium sulfate, concentrated, and purified by silica gel column chromatography to give 54 as a solid. (617 mg, 73%). (MS: [M+H]⁺ 318.1)

Step 2: Alcohol 55

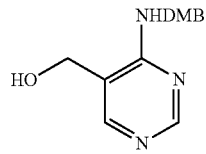

Following Procedure E using 54 (617 mg, 1.95 mmol), THF, LAH (555 mg, 4.02 mmol), and quenching with water (0.2 mL), 15% NaOH solution (0.2 mL) and water (0.6 mL), then purify with silica gel column chromatography to give 55 as an oil. (200 mg, 37%). (MS: [M+H]⁺ 276.1)

Step 3: Aldehyde 56

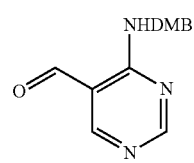

To a solution of 55 (200 mg, 0.73 mmol) in DCM (5 mL) is added activated manganese(IV) oxide (632 mg, 7.3 mmol). After stirring at room temperature for 3 hours, the mixture is filtered, concentrated, and purified by silica gel column chromatography to give 56 as a white solid (180 mg, 90%). (MS: [M+H]⁺ 274.1)

Step 4: AA2

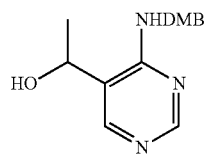

To a solution of 56 (180 mg, 0.66 mmol) in THF (3 mL) is added MeMgBr (3 M in THF, 0.33 mL) at −78° C. After stirring for 2 hours, saturated aqueous ammonium chloride solution is added and the mixture is extracted with EA (10 mL×3). The combined organic layers are dried over anhydrous sodium sulfate, filtered, concentrated, and purified by silica gel column chromatography to give AA2 as a white solid (88 mg, 46%). (MS: [M+H]+290.1)

Preparation of AA3

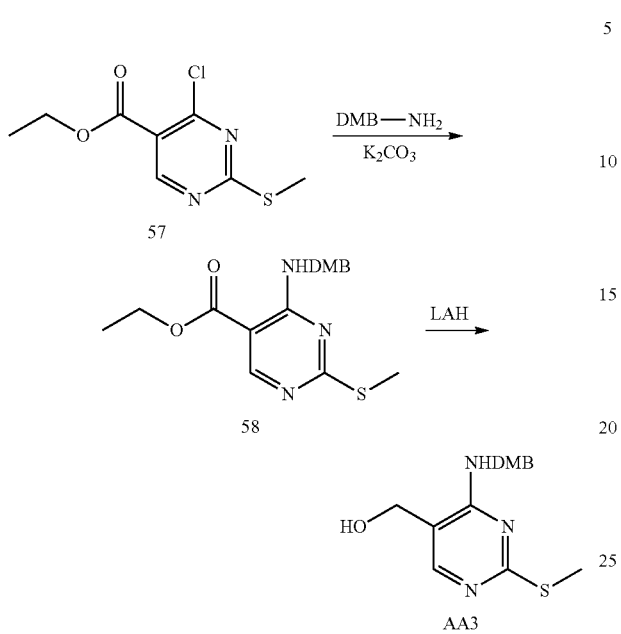

Step 1: Pyrimidine 58

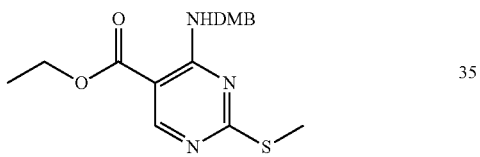

To a solution of 57 (2.0 g, 8.62 mmol) in MeCN (20 mL) is added 2,4-dimethoxybenzylamine (1.43 g, 8.62 mmol) and potassium carbonate (2.37 g, 17.2 mmol). After stirring at 50° C. for 3 hours, the mixture is cooled and concentrated. Ethanol (20 mL) is then added and the resulting suspension is stirred at room temperature for 1 hour. The solid is collected by filtration and washed with EtOH (1 mL) to give 58 as a yellow solid (2.3 g, 72% yield). (MS: [M+H]+ 364.0)

Step 2: AA3

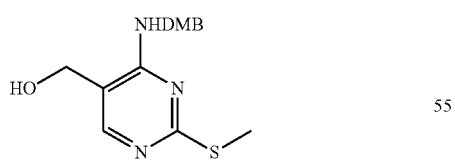

Following Procedure E using 58 (500 mg, 1.37 mmol), THF (50 mL), and LAH (104 mg, 2.74 moml), then quench with saturated aqueous ammonium chloride solution (10 mL), extract with EA (50 mL×3), dry over anhydrous sodium sulfate, filter, concentrate, and purify with silica gel column chromatography (EA:PE=1:1) to give AA3 as an white solid (309 mg, 70%). (MS: [M+H]+ 322.2)

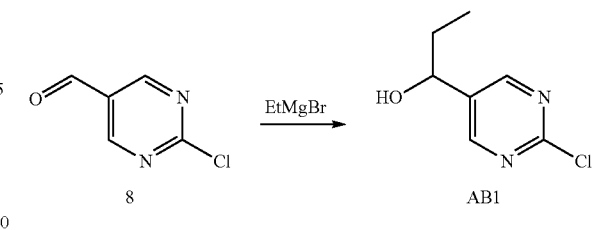

Prepared by essentially the same method as for AA2. (MS: [M+H]+ 173.6).

Preparation of AB2

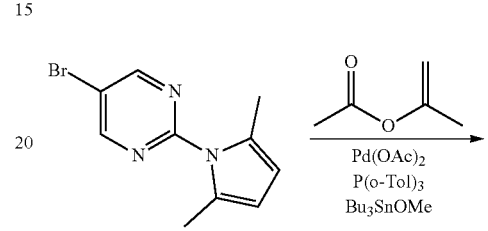

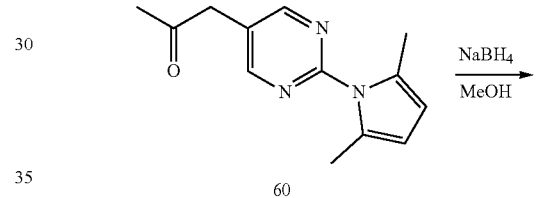

Step 1: Ketone 60

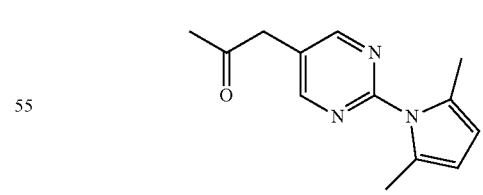

A mixture of 59 (300 mg, 1.19 mmol), isopropenyl acetate (143 mg, 1.43 mmol), tributyltin methoxide (458.5 mg, 1.43 mmol) and Pd(OAc)$_2$ in toluene (20 mL) is stirred at 100° C. for 16 hours. After cooling to room temperature, the mixture is concentrated and purified by silica gel column chromatography (EA:PE=1:10) to give 60 as a white solid (110 mg, 40.3%). (MS: [M+H]+ 230.1)

Step 2: AB2

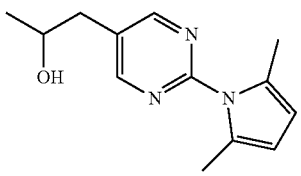 [SMILES: Cc1ccc(C)n1-c1ncc(CC(C)O)cn1]

Prepared by essentially the same method as for A42. (MS: [M+H]⁺ 232.1)

Preparation of B

Preparation of B1

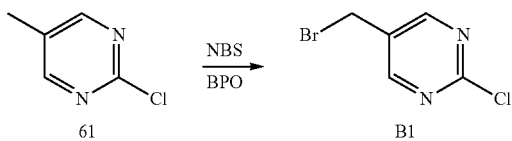

To a solution of 61 (1.5 g, 11.7 mmol) and NBS (2.3 g, 12.8 mmol) in carbon tetrachloride (30 mL) is added BPO (28 mg, 0.12 mmol). After stirring at 80° C. for 6 hours, the mixture is concentrated and purified by silica gel column chromatography (EA:PE=1:10) to give B1 as a colorless oil (850 mg, 35% yield). (MS: [M+H]⁺ 208.9)

Preparation of B2

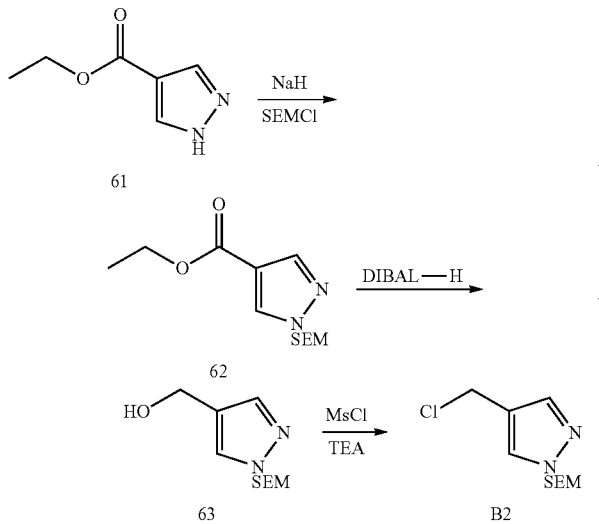

Step 1: Pyrazole 62

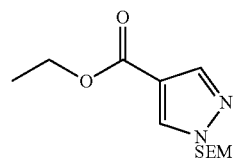 [SMILES: CCOC(=O)c1cnn(COCC[Si](C)(C)C)c1]

To a solution of 61 (1.4 g 10.0 mmol) in THF (30 mL) is added NaH (480 mg 12.0 mmol) followed by 2-(trimethylsilyl)ethoxymethyl chloride (2.5 g 15.0 mmol) at 0° C. After stirring at room temperature overnight, saturated ammonium chloride solution is added and the mixture is extracted with EA (20 mL×3). The combined organic layers are dried over anhydrous sodium sulfate, filtered, concentrated, and purified by silica gel column chromatography (EA:PE=1:20 to 1:5) to give 62 as an oil (2.60 g, 96% yield). (MS: [M+H]⁺ 271.1)

Step 2: Alcohol 63

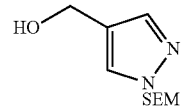 [SMILES: C[Si](C)(C)CCOCn1cc(CO)cn1]

Following Procedure D using 62 (2.00 g, 7.41 mmol), THF (30 mL), and DIBAL-H (1.5 M in toluene, 16.7 mL, 25.0 mmol) and quenching with water (1 mL), 15% NaOH solution (1 mL), water (2.4 mL), and anhydrous sodium sulfate (20 g), then purify with silca gel column chromatography (EA:PE=1:5 to 1:3) to give 63 as an oil (1.3 g, 77% yield). (MS: [M+H]⁺ 229.3)

Step 3: B2

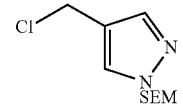

To a solution of 63 (160 mg, 0.70 mmol) in DCM (8 mL) is added TEA (0.2 mL) and MsCl (0.065 mL, 1.05 mmol) at 0° C. After stirring at room temperature for 1 hour, saturated ammonium chloride solution is added and the mixture is extracted with EA (8 mL×3). The combined organic layers are dried over anhydrous sodium sulfate, filtered, concentrated, and purified by silica gel column chromatography (EA:PE=1:20 to 1:5) to give B2 as an oil (130 mg, 76% yield). (MS: [M+H]⁺ 247.2)

Preparation of B3

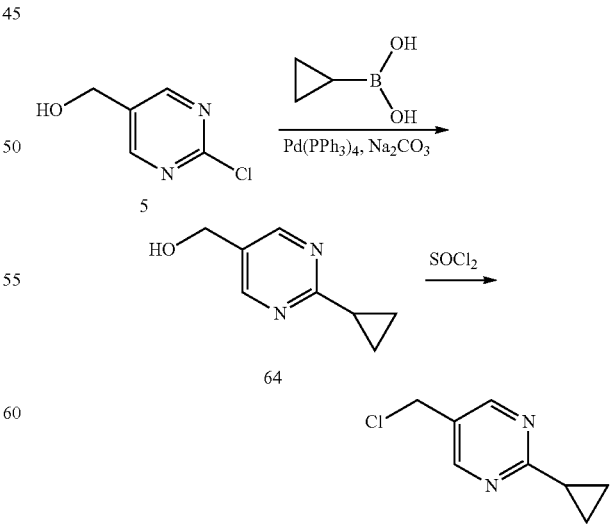

Step 1: Pyrimidine 64

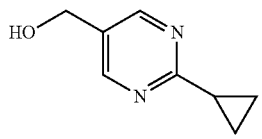 [SMILES: OCc1cnc(C2CC2)nc1]

Following Procedure B using 5 (200 mg, 1.4 mmol), cyclopropylboronic acid (356 mg, 4.15 mmol), sodium carbonate (440 mg, 4.15 mmol), dioxane (10 mL), water (1 mL), and Pd(PPh$_3$)$_4$ (80 mg, 0.07 mmol), react at 100° C. for 3 hours and then purify with silica gel column chromatography (EA:PE=1:10 to 10:1) to give 64 as a white solid (19 mg, 9% yield). (MS: [M+H]$^+$ 151.1)

Step 2: B3

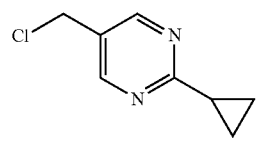 [SMILES: ClCc1cnc(C2CC2)nc1]

Following Procedure F using 64 (19 mg, 0.13 mmol), MeCN (2 mL), and thionyl chloride (0.1 mL) gives crude B3 as a white solid (21.3 mg, 100% yield). (MS: [M+H]$^+$ 169.1)

The following compounds are prepared by essentially the same method as for B3.

| Intermediate | Structure | MS |
|---|---|---|
| B4 | 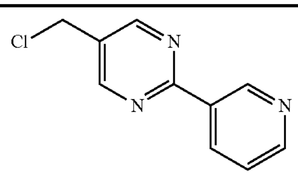 | [M + H]$^+$ 206.0 |
| B5 | 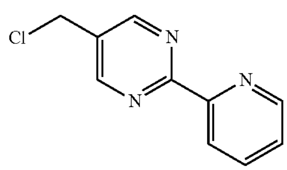 [SMILES: ClCc1cnc(-c2ccccn2)nc1] | [M + H]$^+$ 206.0 |

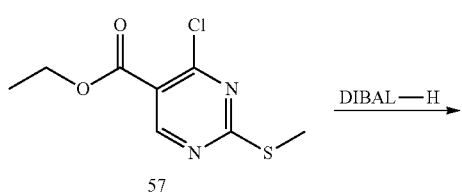

Preparation of B6

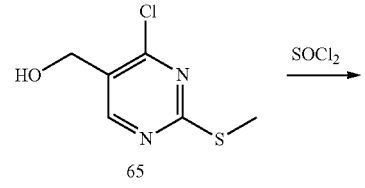

Step 1: Alcohol 65

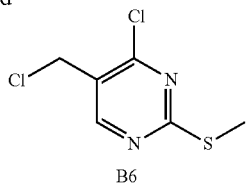

Following Procedure D using 57 (1.20 g, 5.17 mmol), THF (30 mL), and DIBAL-H (1.5 M in toluene, 9.0 mL, 13.1 mmol) and quenching with water (0.6 mL), 15% NaOH solution (0.6 mL), water (1.5 mL), then purify with silica gel column chromatography (EA:PE=1:5 to 1:3) to give 65 as an oil (850 mg, 87% yield). (MS: [M+H]$^+$ 190.1)

Step 2: B6

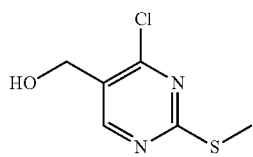

Following Procedure F using 65 (100 mg, 0.53 mmol), MeCN (5 mL), and thionyl chloride (0.20 mL, 2.75 mmol) gives crude B6 as a white solid (108 mg, 100% yield). (MS: [M+H]$^+$ 208.9)

Preparation of B7

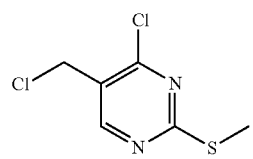

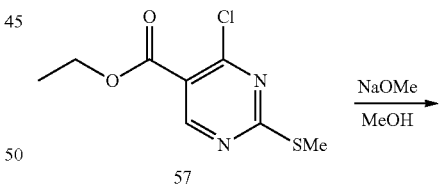

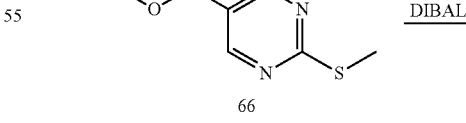

Step 1: Ester 66

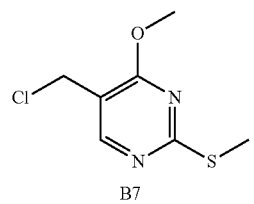
B7

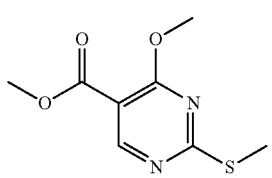

To a solution of 57 (1.20 g 5.1 mmol) in MeOH (40 mL) is added NaOMe (330 mg, 6.08 mmol). After stirring at 50° C. overnight, the mixture is filtered, concentrated, and purified by silica gel column chromatography (EA:PE=1:30 to 1:20) to give 66 as a white solid (1.02 g 93% yield). (MS: [M+H]$^+$ 215.2)

Step 2: Alcohol 67

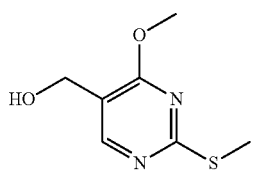

Following Procedure D using 66 (428 mg, 2.0 mmol), THF (30 mL), and DIBAL-H (1.5 M in toluene, 3.3 mL, 5.0 mmol) and quenching water (0.2 mL), 15% NaOH solution (0.2 mL), water (0.5 mL), and anhydrous sodium sulfate (4 g), then purify with silica gel column chromatography (EA:PE=1:5 to 1:3) to give 67 as an oil (260 mg, 70% yield). (MS: [M+H]$^+$ 187.1)

Step 3: B7

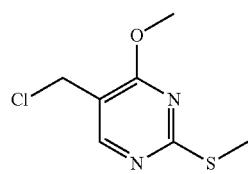

Following Procedure F using 67 (372 mg, 2.0 mmol), MeCN (10 mL), and thionyl chloride (0.36 mL, 5.0 mmol) give crude B7 as a white solid (380 mg, 100% yield). (MS: [M+H]$^+$ 205.1)

Preparation of B8

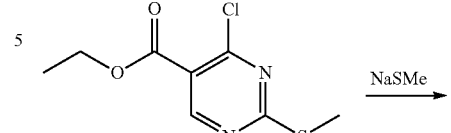

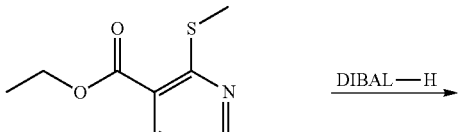

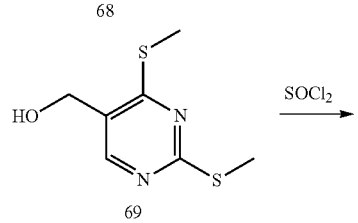

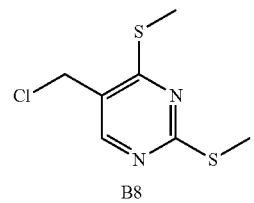
B8

Step 1: Ester 68

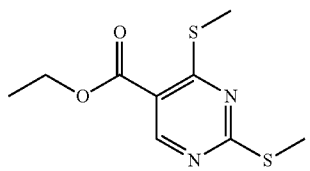

To a solution of 57 (1.16 g, 5.00 mmol) in THF (20 mL) is added sodium methanethiolate (20 wt. % aqueous solution, 5.3 g, 15.0 mmol). After stirring at 50° C. overnight, the mixture is concentrated and purified by silica gel column chromatography (EA:PE=1:30 to 1:20) to give 68 as a white solid (400 mg, 33% yield). (MS: [M+H]$^+$ 245.1)

Step 2: Alcohol 69

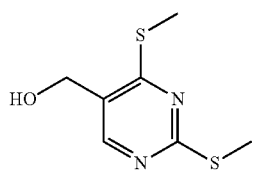

Following Procedure D using 68 (400 mg, 1.64 mmol), THF (15 mL), and DIBAL-H (1.5 M in toluene, 2.7 mL, 4.1 mmol) and quenching with water (0.2 mL), 15% NaOH solution (0.2 mL), water (0.5 mL), and anhydrous sodium sulfate (4 g), then purify with slica gel column chromatography (EA:PE=1:5 to 1:3) to give 69 as an oil (180 mg, 54% yield). (MS: [M+H]$^+$ 203.1)

Step 3: B8

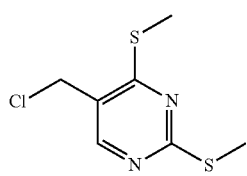

Following Procedure F using 69 (180 mg, 0.89 mmol), MeCN (8 mL), and thionyl chloride (0.20 mL, 2.75 mmol) gives crude B8 as a white solid (186 mg, 100% yield). (MS: [M+H]$^+$ 220.2)

Preparation of B9

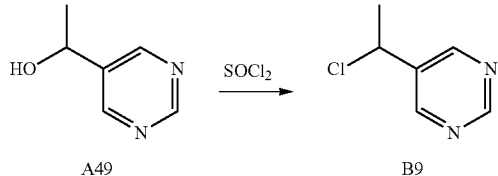

Following Procedure F using A49 (80 mg, 0.65 mmol), MeCN (3 mL), and thionyl chloride (0.5 mL) gives B9 as a white solid (91.2 mg, 100% yield). (MS: [M+H]$^+$ 143.0)

Preparation of B10

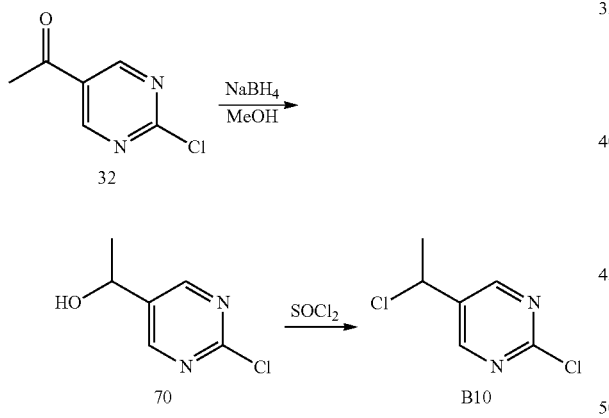

Step 1: Alcohol 70

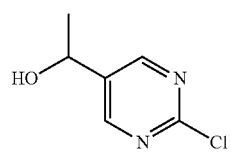

Following Procedure C using 32 (75 mg, 0.48 mmol), MeOH (5 mL), and sodium borohydride (36.2 mg, 0.96 mmol), and purify with silica gel column chromatography (EA) to give 70 as a white solid (37 mg, 49% yield). (MS: [M+H]$^+$ 159.0)

Step 2: B10

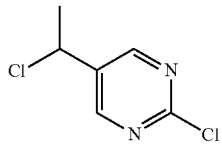

Following Procedure F using 70 (37 mg, 0.23 mmol), DCM (3 mL), and thionyl chloride (55 mg, 0.47 mmol) gives B10 as a white solid (41 mg, 100% yield). (MS: [M+H]$^+$ 177.0)

Preparation of B11

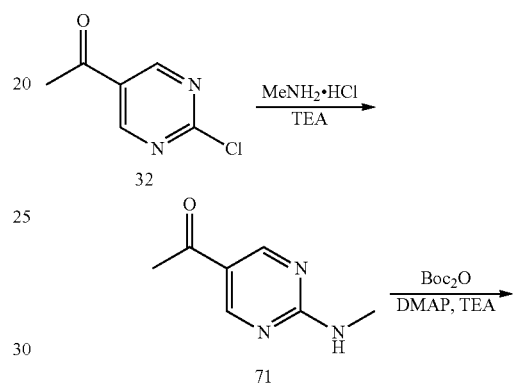

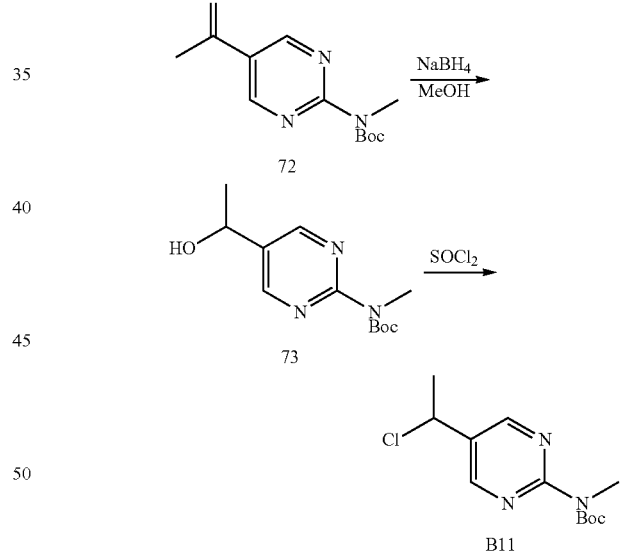

Step 1: Pyrimidine 71

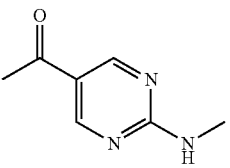

To a solution of 32 (117 mg, 0.76 mmol) in THF (30 mL) is added TEA (383 mg, 3.78 mmol) and methylamine hydrochloride (153 mg, 2.27 mmol). After stirring at room temperature overnight, the mixture is concentrated and purified by silica gel column chromatography (EA:PE=1:4 to 1:1) to give 71 as a pale yellow solid (100 mg, 89% yield). (MS: [M+H]+ 152.1)

Step 2: Pyrimidine 72

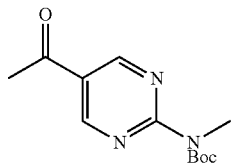 [SMILES: CC(=O)c1cnc(N(C)C(=O)OC(C)(C)C)nc1]

To a solution of 71 (100 mg 0.66 mmol), TEA (201 mg, 1.98 mmol) and DMAP (81 mg, 0.66 mmol) in THF (10 mL) is added di-tert-butyl dicarbonate (360 mg, 1.65 mmol). After stirring at room temperature overnight, the mixture is concentrated and purified by silica gel column chromatography (EA:PE=1:10 to 1:1) to give 72 as a colorless oil (137 mg, 83% yield). (MS: [M+H]+ 252.1)

Step 3: Alcohol 73

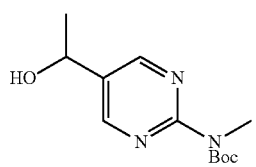 [SMILES: CC(O)c1cnc(N(C)C(=O)OC(C)(C)C)nc1]

Following Procedure C using 72 (200 mg, 0.80 mmol), MeOH (10 mL), sodium borohydride (60 mg, 1.6 mmol), then purify with silica gel column chromatography (EA) to give 73 as a colorless oil (127 mg, 64% yield). (MS: [M+H]+ 254.1)

Step 4: B11

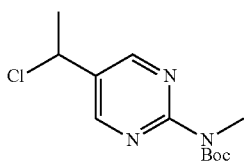 [SMILES: CC(Cl)c1cnc(N(C)C(=O)OC(C)(C)C)nc1]

Following Procedure F using 73 (60 mg, 0.24 mmol), DCM (5 mL), and thionyl chloride (38.82 mg, 0.28 mmol) gives crude B11 as a white solid (64 mg, 100%/yield). (MS: [M+H]+ 272.1)

Preparation of B12

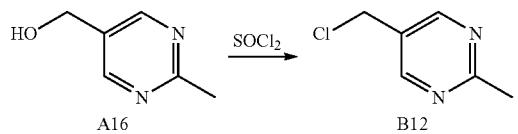

Following Procedure F using A16 (24.8 mg, 0.20 mmol), MeCN (8 mL) and thionyl chloride (0.044 mL, 0.60 mmol) gives crude B12 as a white solid (26 mg, 100% yield). (MS: [M+H]+ 143.1)

The following compounds are prepared by essentially the same method as for B12.

| Intermediate | Structure | MS |
|---|---|---|
| B13 | 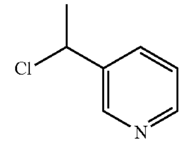 | [M + H]+ 142.0 |
| B14 | 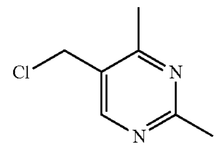 | [M + H]+ 157.0 |

Preparation of B15

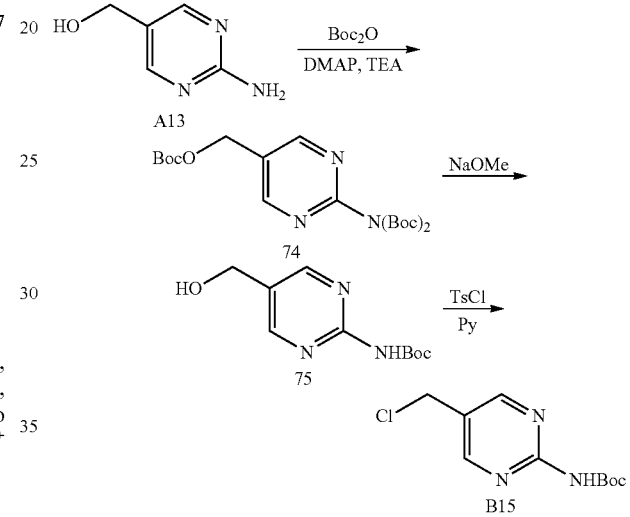

Step 1: Pyrimidine 74

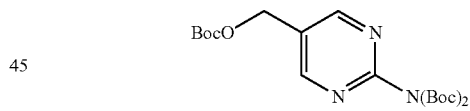

To a solution of A13 (2.0 g 15.9 mmol), TEA (6.47 g, 63.9 mmol), and DMAP (1.95 mmol) in THF (30 mL) is added di-tert-butyl dicarbonate (12.2 g, 55.9 mmol). After stirring at room temperature overnight, the mixture is concentrated and dissolved in EA (100 mL), washed with HCl solution (0.5 M, 30 mL) and brine (30 mL), dried over anhydrous sodium sulfate, filtered, concentrated, and purified by silica gel column chromatography (EA:PE=1:5) to give 74 as a white solid (680 mg, 10% yield). (MS: [M+H]+ 426.2)

Step 2: Alcohol 75

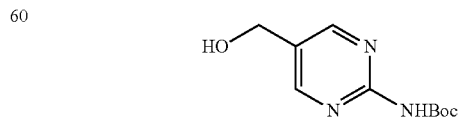

To a solution of 74 (680 mg, 1.6 mmol) in MeOH (30 mL) is added sodium methoxide (518 mg, 9.6 mmol). After stirring at room temperature overnight, the mixture is concentrated and partitioned between EA (50 mL) and water (10 mL). The organic layer is O80 washed with brine (30 mL), dried over anhydrous sodium sulfate, filtered, and concentrated to give crude 75 as a white solid (290 mg, 81% yield). (MS: [M+H]⁺ 226.1)

Step 3: B15

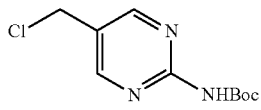 [SMILES: CC(C)(C)OC(=O)Nc1ncc(CCl)cn1]

To a solution of 75 (290 mg, 1.3 mmol) in DCM (50 mL) is added Py (306 mg, 3.9 mmol) and TsCl (368 mg, 1.9 mmol). After stirring at room temperature overnight, the mixture is concentrated and purified by silica gel column chromatography (EA:PE=1:5) to give B15 as a white solid (240 mg, 77% yield). (MS: [M+H]⁺ 244.1)

The following compounds are prepared by essentially the same method as for B15.

| Intermediate | Structure | MS |
|---|---|---|
| B16 | 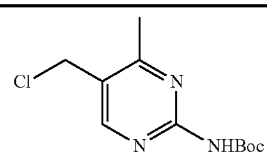 | [M + H]⁺ 258.1 |
| B17 | 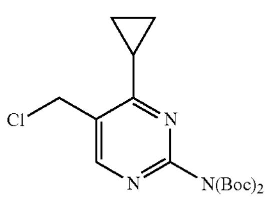 | [M + H]⁺ 384.2 |
| B18 | 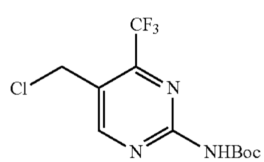 [SMILES: CC(C)(C)OC(=O)Nc1ncc(CCl)c(C(F)(F)F)n1] | [M + H]⁺ 312.1 |

Preparation of B19

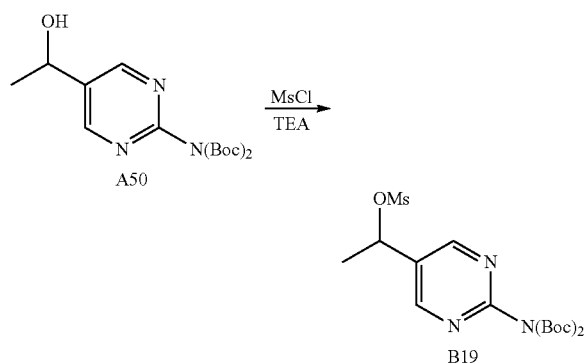

To a solution of A50 (100 mg, 0.29 mmol) in DCM (3 mL) is added TEA (44 mg, 0.44 mmol) and MsCl (40 mg, 0.35 mmol) at 0° C. After stirring at room temperature for 1 hour, the mixture is poured into a saturated ammonium chloride solution (10 mL) and extracted with DCM (20 mL×3). The combined organic layers are dried over anhydrous sodium sulfate, filtered, and concentrated to give crude B19 as an off-white solid (120 mg, 98% yield). (MS: [M+H]⁺ 418.2)

Preparation of B20

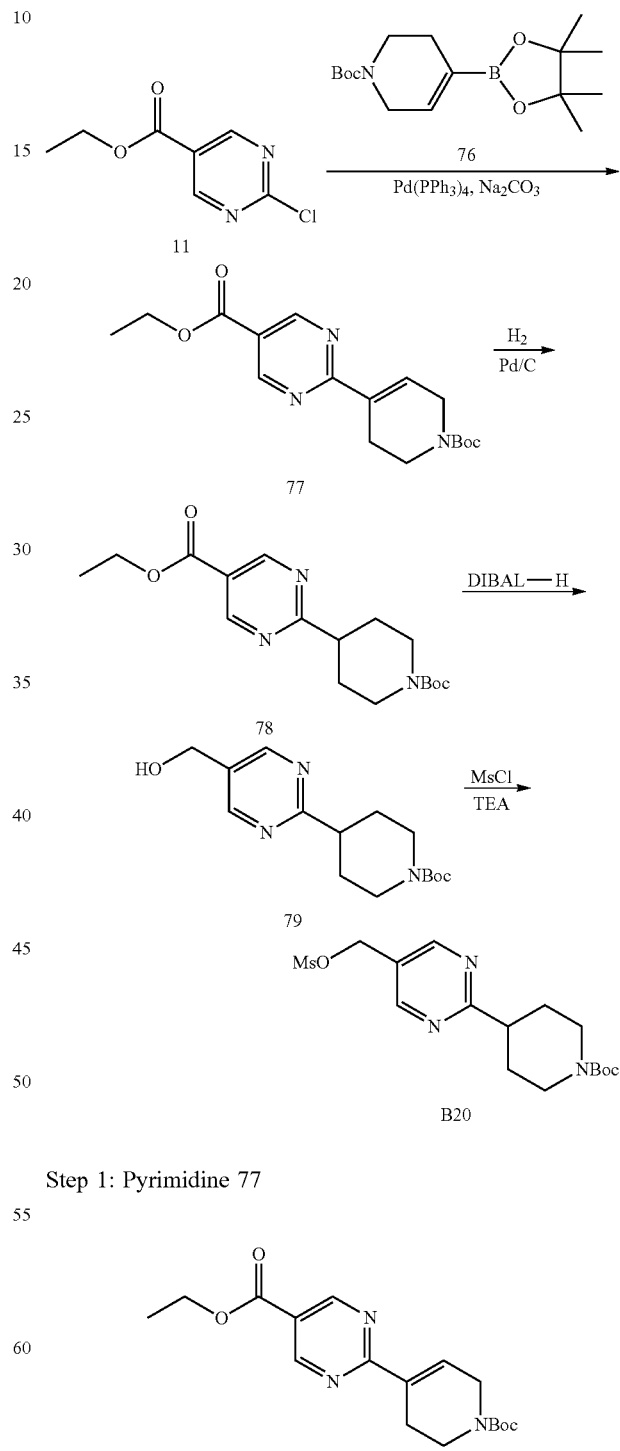

Step 1: Pyrimidine 77

Following Procedure B using 11 (1.0 g, 5.36 mmol), 76 (2.48 g, 8.04 mmol), sodium carbonate (568 mg, 5.36 mmol), dioxane (30 mL), water (3 mL), and Pd(PPh$_3$)$_4$ (100 mg, 0.087 mmol), react at 80° C. for 16 hours and then purify with silica gel column chromatography (EA:PE=1:1) to give 77 as a white solid (890 mg, 50% yield). (MS: [M+H]$^+$ 334.2)

Step 2: Pyrimidine 78

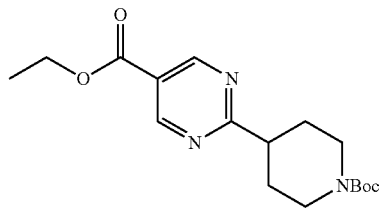 [SMILES: CCOC(=O)c1cnc(C2CCN(C(=O)OC(C)(C)C)CC2)nc1]

To a solution of 77 (890 mg 2.67 mmol) in EA (5 mL) and EtOH (20 mL) is added Pd/C (5 wt. %, 200 mg). After stirring at room temperature for 2 hours, the mixture is filtered through a pad of Celite and concentrated to give crude 78 as a white solid (840 mg, 95% yield). (MS: [M+H]$^+$ 336.2)

Step 3: Alcohol 79

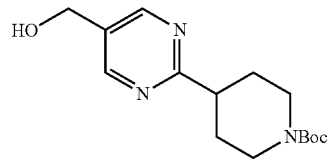 [SMILES: CC(C)(C)OC(=O)N1CCC(c2ncc(CO)cn2)CC1]

Following Procedure D using 78 (110 mg, 0.34 mmol), THF (10 mL), and DIBAL-H (1.5 M in toluene, 0.68 mL, 1.03 mmol) and quenching with aqueous NaOH solution (0.5 mL, 15%) and anhydrous magnesium sulfate (2 g), purify with silica gel column chromatography (EA) to give 79 as a colorless oil (50 mg, 50% yield). (MS: [M+H]$^+$ 294.2)

Step 4: B20

Following the procedure for B19 using 79 (100 mg, 0.34 mmol), TEA (0.2 mL, 1.36 mmol), THF (10 mL), and MsCl (0.1 mL, 1.36 mmol), purify with silica gel column chromatography (DCM:PE=1:2 to 1:1) to give B20 as a colorless oil (80 mg, 59% yield). (MS: [M+H]$^+$ 372.2)

Preparation of B21

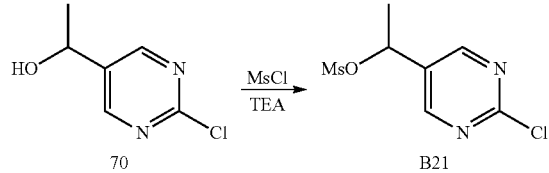

To a solution of 70 (140 mg 0.9 mmol) in THF (10 mL) is added TEA (180 mg 1.8 mmol) followed by MsCl (123 mg 1.1 mmol). After stirring at room temperature for 1 hour, the mixture is concentrated and the residue is partitioned between EA (50 mL) and water (10 mL). The layers are separated and the organic layer is washed with saturated aqueous sodium bicarbonate (15 mL), dried over anhydrous sodium sulfate, filtered, and concentrated to give crude B21 as a white solid (200 mg, 96% yield). (MS: [M+H]$^+$ 237.0)

Preparation of B22

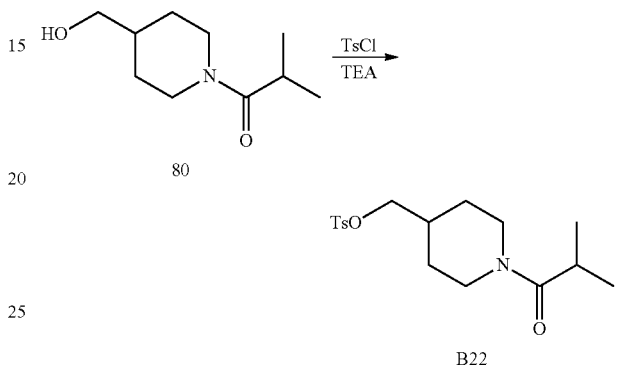

To a solution of 80 (500 mg, 2.70 mmol) and TEA (0.9 mL, 6.75 mmol) in DCM (10 mL) is added p-TsCl (514 mg, 2.70 mmol) at 0° C. After stirring at room temperature overnight, brine (20 mL) is added and the layers are separated. The aqueous layer is extracted with DCM (20 mL×3). The combined organic layers are dried over anhydrous sodium sulfate, filtered, concentrated, and purified by silica gel column chromatography (EA:PE=1:5) to give B22 as a light yellow oil (400 mg, 44% yield). (MS: [M+H]$^+$ 340.5)

Preparation of B23

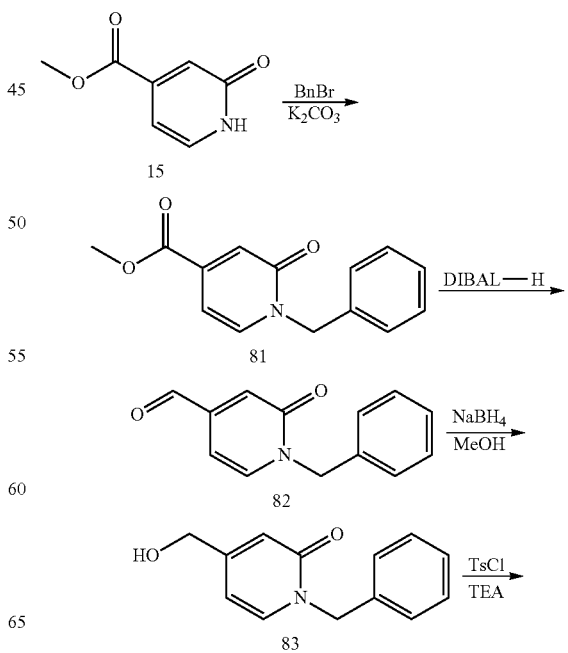

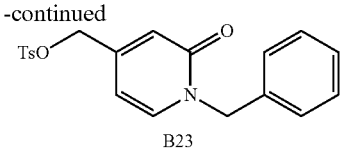

B23

Step 1: Ester 81

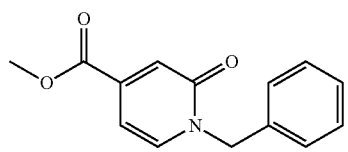 [SMILES: COC(=O)c1ccn(Cc2ccccc2)c(=O)c1]

To a solution of 15 (1.0 g 6.53 mmol) in DMF (20 mL) is added potassium carbonate (1.8 g 13.1 mmol) and benzyl bromide (0.8 mL, 13.1 mmol) at 0° C. After stirring at room temperature overnight, the mixture is diluted with water (20 mL) and extracted with EA (40 mL×3). The combined organic layers are washed with saturated aqueous ammonium chloride solution, dried over anhydrous sodium sulfate, filtered, concentrated, and purified by silica gel column chromatography (EA:PE=1:10) to give 81 as a white solid (1.3 g, 82% yield). (MS: [M+H]$^+$ 244.3)

Step 2: Aldehyde 82

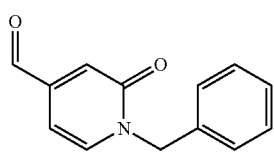 [SMILES: O=Cc1ccn(Cc2ccccc2)c(=O)c1]

To a solution of 81 (600 mg, 2.47 mmol) in DCM (30 mL) is added DIBAL-H (1.5 M toluene solution, 6.5 mL, 9.88 mmol) dropwise at 0° C. After stirring at room temperature for 2 h, saturated ammonium chloride aqueous solution is added at 0° C. and the mixture is stirred at room temperature for 30 minutes, filtered, and concentrated to give crude 82 as a white solid (300 mg, 57.0% yield). (MS: [M+H]$^+$ 214.2)

Step 3: Alcohol 83

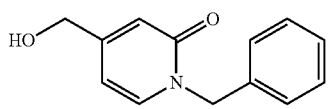 [SMILES: O=c1cc(CO)ccn1Cc1ccccc1]

Following Procedure C using 82 (300 mg, 1.41 mmol), MeOH (10 mL), and sodium borohydride (106 mg, 2.81 mmol) gives 83 as a white solid (200 mg, 66% yield). (MS: [M+H]$^+$ 216.2)

Step 4: B23

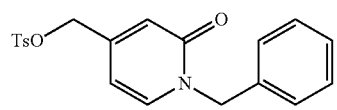

Following the procedure for B22 using 83 (100 mg, 0.46 mmol), DCM (5 mL), TEA (0.2 mL, 1.16 mmol), and TsCl (86 mg, 0.46 mmol) gives B23 as a light yellow oil (100 mg, 58% yield). (MS: [M+H]$^+$ 370.4)

Preparation of B24

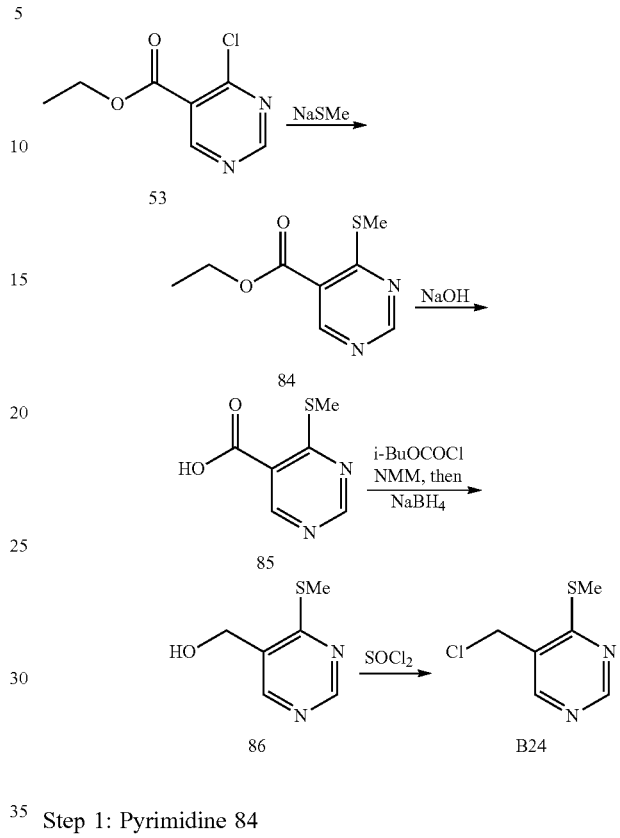

Step 1: Pyrimidine 84

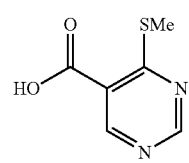 [SMILES: CSc1ncncc1C(=O)O]

Following the procedure for 68 using 53 (500 mg, 2.68 mmol), THF (15 mL), and sodium methanethiolate (20 wt. %, 1.2 mL, 3.22 mmol), then purify with silica gel column chromatography (EA:PE=1:30 to 1:20) to give 84 as a white solid (400 mg, 75% yield). (MS: [M+H]$^+$ 199.1)

Step 2: Acid 85

To a solution of 84 (400 mg, 2.0 mmol) in THF (4 mL) is added a solution of NaOH (400 mg, 10.0 mmol) in water (4 mL) dropwise at 0° C. After stirring at room temperature for 2 hours, concentrated HCl is added to adjust the mixture to pH 5. The solid is then collected by filtration to give crude 85 as a white solid (250 mg, 74% yield). (MS: [M+H]$^+$ 171.1)

Step 3: Alcohol 86

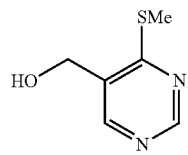

To a solution of crude 85 (237 mg, 1.39 mmol) in THF (20 mL) is added isobutyl chloroformate (0.18 mL, 1.39 mmol) and NMM (154 mg, 1.52 mmol). After stirring at 0° C. for 20 min. The mixture is filtered and concentrated. The residue is dissolved in THF (10 mL) and sodium borohydride (43 mg, 1.11 mmol) in water (3 mL) is added dropwise at −15° C. After stirring for 20 minutes, saturated ammonium chloride solution is added and the mixture is extracted with EA (10 mL×3). The combined organic layers are dried over anhydrous sodium sulfate, filtered, concentrated, and purified by silica gel column chromatography (EA:PE=1:5 to 1:3) to give 86 as an oil (100 mg, 46% yield). (MS: [M+H]+ 156.1)

Step 5: B24

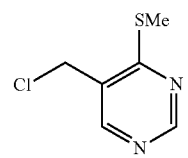

Following Procedure F using 86 (95 mg, 0.60 mmol), MeCN (8 mL), and thionyl chloride (0.10 mL, 1.38 mmol) gives crude B24 as an oil (97 mg, 100% yield). (MS: [M+H]+ 174.1)

Preparation of B25

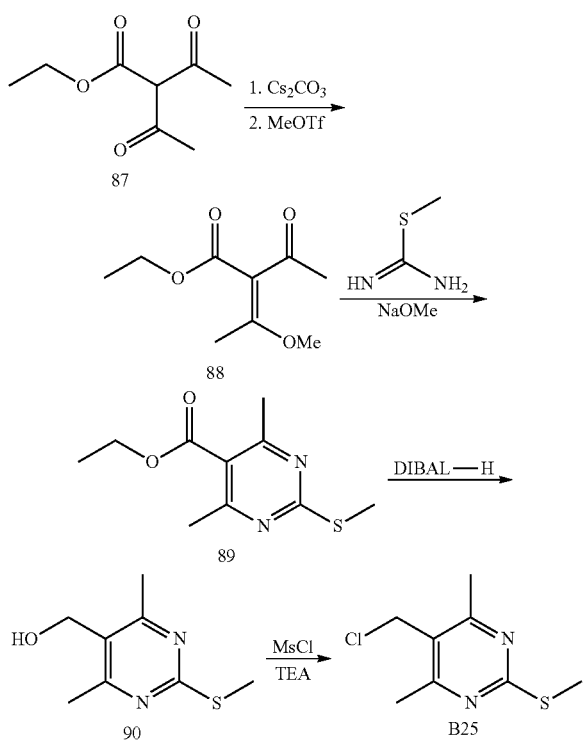

Step 1: Ester 88

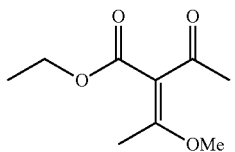

A mixture of 87 (2.0 g, 11.6 mmol), cesium carbonate (6.2 g, 19.0 mmol) in MeCN (20 mL) is stirred at room temperature for 3 hours before methyl trifluoromethanesulfonate (1.4 mL, 12.3 mmol) is added. After stirring at 70° C. overnight, the mixture is diluted with water (20 mL) and extracted with EA (20 mL×3). The combined organic layers are dried over anhydrous sodium sulfate, filtered, and concentrated to give 88 as a yellow oil (2 g, 93% yield).

Step 2: Pyrimidine 89

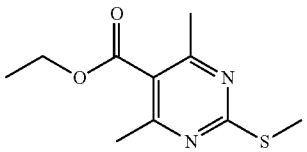

To a solution of crude 88 (2.0 g 10.8 mmol) in EtOH (20 mL) is added S-methylisothiourea hemisulfate salt (5.99 g 21.6 mmol) and MeONa (1.16 g, 21.6 mmol). After stirring at 80° C. overnight, the mixture is concentrated and water (10 mL) is added. The solid is then collected by filtration to give 89 as a white solid (1.0 g 41% yield). (MS: [M+H]+ 227.2)

Step 3: Alcohol 90

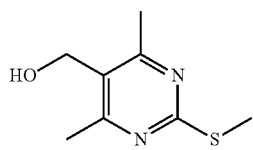

Following Procedure D using 89 (1.0 g, 4.4 mmol), THF (10 mL), and DIBAL-H (1.5 M toluene solution, 88 mL, 13.2 mmol) and quenching with 15% aqueous NaOH solution (1 mL) gives crude 90 as a white solid (0.7 g, 87% yield). (MS: [M+H]+185.1)

Step 4: B25

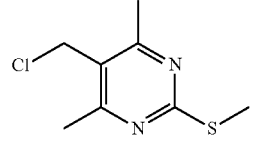

Following the procedure for B2 using 90 (235 mg 1.1 mmol), DCM (5 mL), TEA (0.34 mL, 2.2 mmol) and MsCl (0.18 mL, 2.2 mmol) and quenching with water (3 mL) gives crude B25 as a yellow oil (258 mg 100% yield). (MS: [M+H]+ 203.1)

Preparation of B26

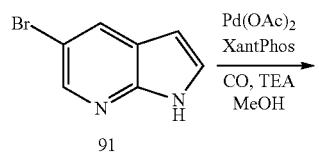
91

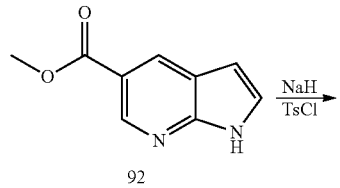
92

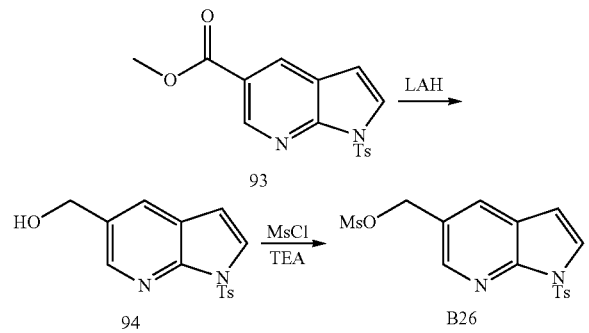
93

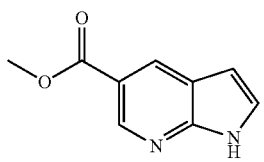
94

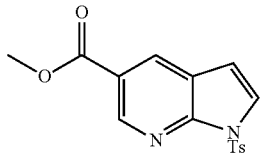 [SMILES: COC(=O)c1cnc2c(ccn2S(=O)(=O)c2ccc(C)cc2)c1]
B26

Step 1: Ester 92

A solution of 91 (3.0 g 15.2 mmol), Pd(OAc)$_2$ (342 mg, 1.52 mmol), Xantphos (881 mg, 1.52 mmol), and TEA (3.08 g, 30.5 mmol, 4.22 mL) in DMF (30 mL), and MeOH (15 mL) is stirred under CO (50 psi) at 80° C. for 10 hours. After filteration and removal of MeOH, the mixture is diluted with EA (200 mL), washed with water (30 mL×3) and brine (30 mL×3), dried over anhydrous sodium sulfate, concentrated, and purified by silica gel column chromatography (EA: PE=1:5 to 1:2) to give 92 as a yellow solid (2.7 g, 71% yield). (MS: [M+H]$^+$ 177.1)

Step 2: Tosylate 93

To a solution of 92 (500 mg, 2.84 mmol) in DMF (10 mL) is added NaH (81.8 mg, 3.41 mmol) in portions at 0° C. After stirring at 15° C. for 10 minutes, TsCl (650 mg, 3.41 mmol) is added and the mixture is stirred at 15° C. for 2 hours before ice is added. The mixture is then extracted with EA (20 mL×2) and the combined organic layers are washed with brine (10 mL), dried over anhydrous sodium sulfate, filtered, and concentrated to give crude 93 as a white solid (0.8 g, 85% yield).

Step 3: Alcohol 94

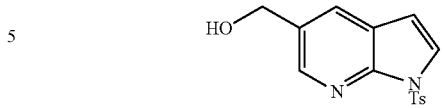

Following Procedure E using 93 (500 mg, 1.51 mmol), THF (20 mL), and LAH (86 mg, 2.27 mmol) and quenching with water (0.2 mL) gives crude 94 as a yellow oil (0.4 g 88% yield). (MS: [M+H]$^+$ 303.1)

Step 4: B26

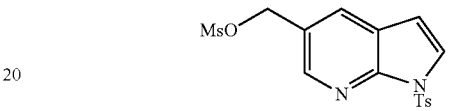

Following the procedure for B19 using 94 (800 mg, 2.65 mmol), TEA (804 mg, 7.95 mmol, 1.10 mL), DCM (20 mL), and MsCl (364 mg, 3.18 mmol, 0.25 mL), then dilute the reaction mixture with DCM (20 mL) and washed with HCl (20 mL) and brine, dry over anhydrous sodium sulfate, and concentrated give crude B26 as a yellow oil (800 mg, 80% yield).

Preparation of B27

91

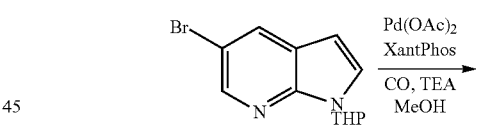
95

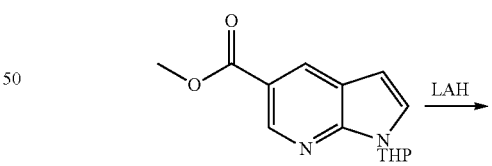
96

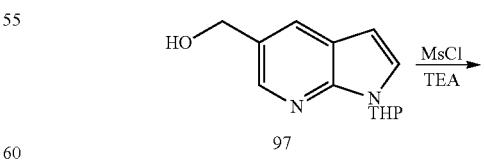
97

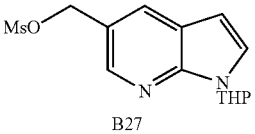
B27

Step 1: Indole 95

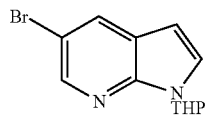

A mixture of 91 (900 mg, 4.54 mmol), DHP (1.91 g, 22.7 mmol, 2.1 mL), and TSA (86 mg, 0.45 mmol) in THF (5.00 mL) is stirred at 70° C. for 3 hours. The mixture is then concentrated and purifed by silica gel column chromatography (EA:PE=1:5 to 1:1) to give 95 as yellow oil (900 mg, 70% yield).

Step 2: Ester 96

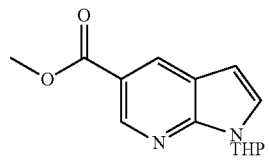

Following the procedure for 92 using 95 (700 mg 2.48 mmol), Pd(OAc)$_2$ (83.5 mg 0.37 mmol), Xantphos (215 mg 0.37 mmol), TEA (753 mg 7.44 mmol, 1.03 mL), DMF (10 mL), and MeOH (10 mL), react 100° C. for 3 hours and purify with silica gel column chromatography to give 96 as a yellow oil (300 mg 46% yield). (MS: [M+H]$^+$ 178.1)

Step 3: Alcohol 97

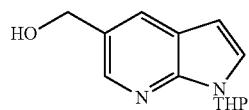

Following Procedure E using 96 (300 mg, 1.15 mmol), THF (10 mL), and LAH (65 mg, 1.72 mmol) and quenching with water (0.2 mL) and solid sodium sulfate gives crude 97 as a yellow oil (100 mg, 37% yield). (MS: [M+H]$^+$ 150.1)

Step 4: B27

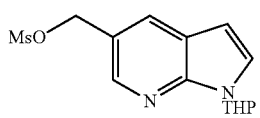

Following the procedure for B19 using 97 (90 mg, 0.386 mmol), TEA (117 mg, 1.16 mmol, 0.16 mL), DCM (10 mL), and MsCl (53 mg, 0.463 mmol, 0.036 mL) gives crude B27 (80 mg, 66.6% yield).

Preparation of B28

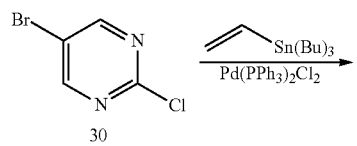

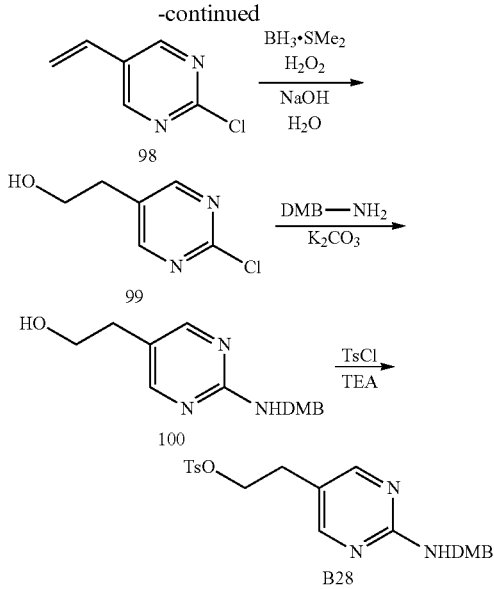

Step 1: Pyrimidine 98

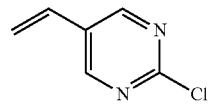

Following the procedure for 31 using 30 (5.0 g, 25.9 mmol), tributyl(vinyl)tin (9.02 g, 28.4 mmol, 8.3 mL), Pd(PPh$_3$)$_2$Cl$_2$ (1.81 g 2.58 mmol), and toluene (5 mL), react at 90° C. for 3 hours, quench with saturated potassium fluoride (200 mL), and purify with silica gel column chromatography (EA:PE=1:100 to 1:20) give 98 as a light yellow solid (2.46 g, 68% yield).

Step 2: Alcohol 99

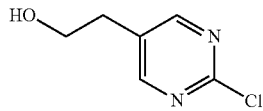

To a solution of 98 (2.5 g 17.8 mmol) in THF (50 mL) is added borane dimethyl sulfide complex (10 M, 1.78 mL) at 0° C. After stirring for 1 hour, NaOH (2.10 g 52.5 mmol) is added and the mixture is stirred at 16° C. for 16 hours. Saturated sodium sulfite (600 mL) is then added and the mixture is extracted with EA (500 mL×3). The combined organic layers are dried over anhydrous sodium sulfate, concentrated, and purified by silica gel column chromatography (EA/PE=1:10 to 1:5 to 1:2) to give 99 as a white solid (1.00 g).

Step 3: Pyrimidine 100

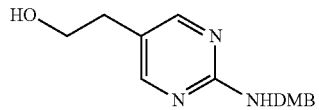

To a solution of 99 (1.0 g 6.31 mmol) in MeCN (10 mL) is added potassium carbonate (1.05 g, 7.57 mmol) and 2,4-dimethoxybenzylamine (1.27 g 7.57 mmol, 1.14 mL). After stirring at 80° C. for 16 hours, the mixture is filtered and concentrated. The residue is then dissolved in EA (20 mL) and washed with 5% aqueous citric acid solution. The aqueous layer is extracted with EA (20 mL) and the combined organic layers are dried over anhydrous sodium sulfate and concentrated to give crude 100 (350 mg). (MS: [M+H]+ 290.1)

Step 4: B28

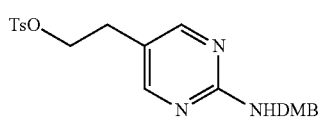

Following the procedure for B15 using 100 (150 mg, 0.52 mmol), DCM (5 mL), TsCl (297 mg, 1.56 mmol), and TEA (157 mg, 1.56 mmol, 0.22 mL), dilute the reaction mixture with DCM (50 mL), washed with water (20 mL) and sodium bicarbonate (20 mL×3), dried over sodium bicarbonate, and concentrated to give crude B28 (300 mg). (MS: [M+H]+ 444.0)

Preparation of B29

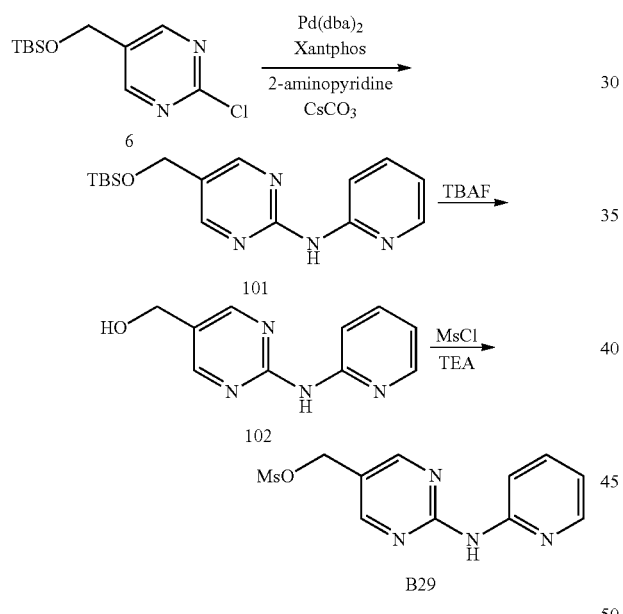

Step 1: Pyrimidine 101

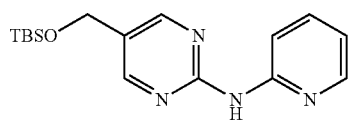 [SMILES: CC(C)(C)[Si](C)(C)OCc1cnc(Nc2ccccn2)nc1]

A mixture of 6 (300 mg, 1.16 mmol), 2-aminopyridine (142 mg, 1.51 mmol), cesium carbonate (755 mg, 2.32 mmol), Xantphos (268 mg, 0.464 mmol), and Pd(dba)₂ (133 mg 0.232 mmol) in dioxane (6 mL) is stirred at 110° C. for 12 hours. The mixture is then filtered, concentrated, and purified by silica gel column chromatography (EA:PE=1:20 to 1:10) to give 101 as a yellow solid (200 mg, 55% yield). (MS: [M+H]+ 316.9)

Step 2: Alcohol 102

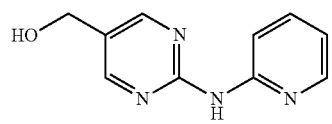 [SMILES: OCc1cnc(Nc2ccccn2)nc1]

To a solution of 101 (200 mg, 0.632 mmol) in THF (10 mL) is added TBAF (1 M, 1.26 mL, 2.0 eq). After stirring at 16° C. for 16 hours, the mixture is concentrated and purified by prep-HPLC to give 102 as a white solid (100 mg, 78% yield). (MS: [M+H]+ 203.0)

Step 3: B29

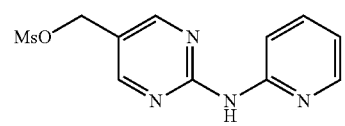 [SMILES: CS(=O)(=O)OCc1cnc(Nc2ccccn2)nc1]

Following the procedure for B19 using 102 (100 mg, 0.495 mmol) in THF (5 mL), TEA (150 mg, 1.48 mmol, 0.21 mL), and MsCl (113 mg, 0.99 mmol, 0.077 mL), then dilute with DCM (100 mL), washed with water (30 mL) and brine (50 mL×2), dried over anhydrous sodium sulfate, and concentrated to give crude B29 (100 mg).

Preparation BA1

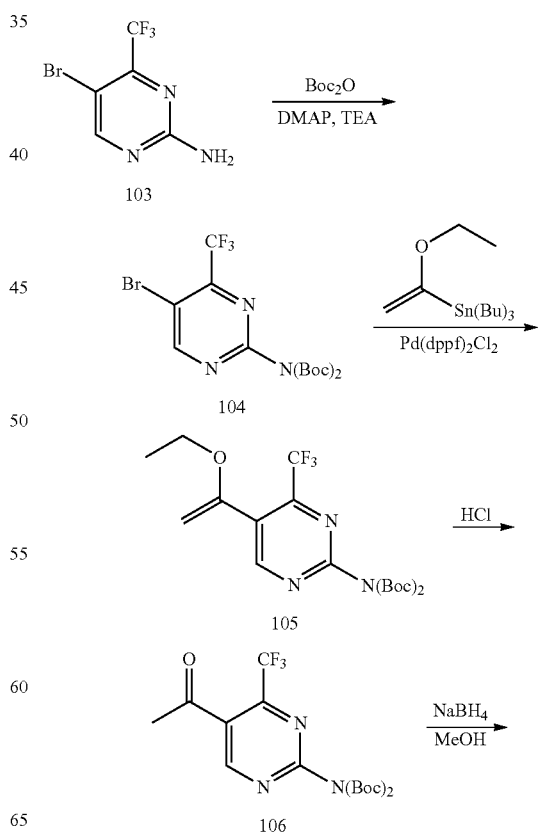

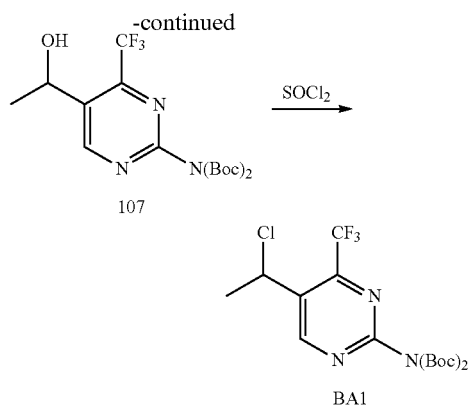

Step 1: Pyrimidine 104

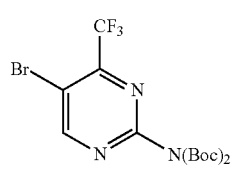

To a solution of 103 (2.42 g, 10.0 mmol) in THF (50 mL) is added DMAP (611 mg, 5.0 mmol), TEA (5.6 mL, 40.0 mmol) and di-tert-butyl dicarbonate (6.9 mL, 30.0 mmol). After stirring at 60° C. overnight, the mixture is cooled, concentrated, and purified by silica gel column chromatography (EA:PE=1:50 to 1:30) to give 104 as a white solid (1.5 g, 34%). (MS: [M+H]$^+$ 442.1)

Step 2: Enol Ether 105

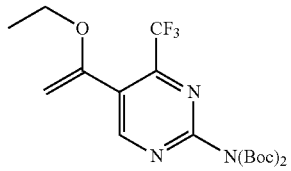

Following the procedure for 31 using 104 (500 mg, 1.13 mmol), DMF (20 mL), Pd(dppf)Cl$_2$ (83 mg, 0.113 mmol), and tributyl(1-ethoxyvinyl)tin (0.49 mL, 1.47 mmol), react at 100° C. overnight and purify with silica gel column chromatography (EA:PE=1:50 to 1:20) to give 105 as an oil (180 mg, 37%). (MS: [M+H]$^+$ 433.2)

Step 3: Ketone 106

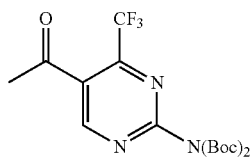

To a solution of 105 (180 mg, 0.42 mmol) in THF (10 mL) is added HCl solution (6 N, 2 mL). After stirring at 60° C. for 2 hours, the mixture is cooled, concentrated, and purified by silica gel column chromatography (EA:PE=1:50 to 1:20) to give 106 as a white solid (120 mg, 70%). (MS: [M+H]$^+$ 406.1)

Step 4: Alcohol 107

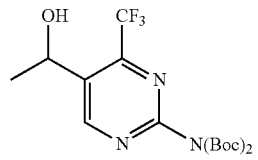

Following Procedure C using 106 (72 mg, 0.18 mmol), MeOH (8 mL), sodium borohydride (4.5 mg, 0.12 mmol), purify with silica gel column chromatography (EA:PE=1:30 to 1:20) to give 107 as a white solid (20 mg, 28%). (MS: [M+H]$^+$ 408.1)

Step 5: BA1

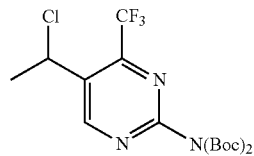

Following Procedure F using 107 (20 mg, 0.049 mmol), MeCN (8 mL), and thionyl chloride (0.20 mL, 2.75 mmol) gives crude BA1 as a white solid (20 mg, 100%). (MS: [M+H]$^+$ 426.1)

Preparation of BA2

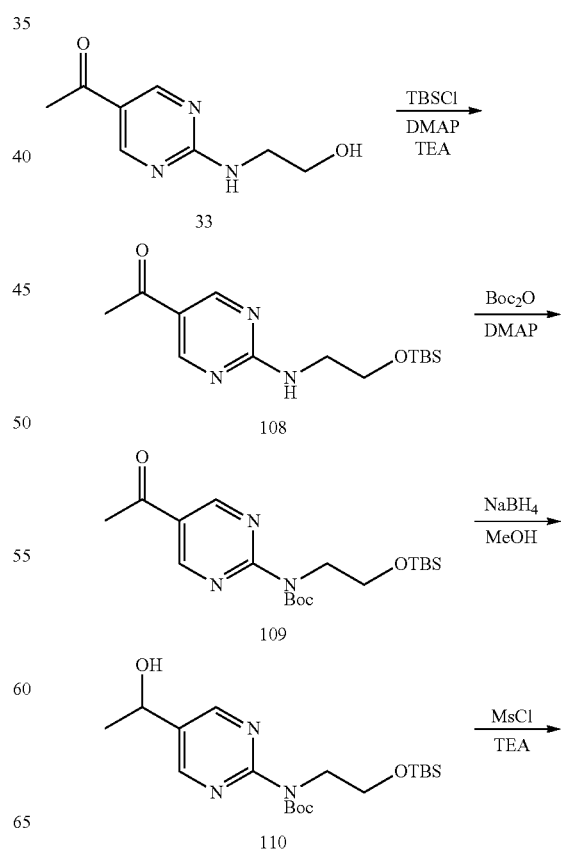

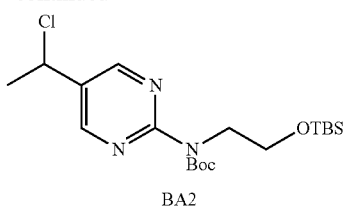

BA2

Step 1: Silyl Ether 108

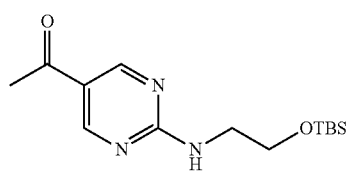 [SMILES: CC(=O)c1cnc(NCCO[Si](C)(C)C(C)(C)C)nc1]

To a solution of 33 (220 mg, 1.21 mmol) in DCM (10 mL) is added TEA (0.4 mL, 2.78 mmol), DMAP (200 mg 1.64 mmol), and TBSCl (252 mg 1.67 mmol). After stirring at room temperature for 16 hours, the mixture is concentrated and is purified by silica gel column chromatography (EA:PE=1:3) to give 108 as a yellow oil (287 mg, 80%). (MS: [M+H]$^+$ 296.2)

Step 2: Carbamate 109

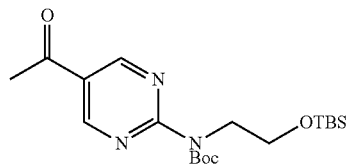 [SMILES: CC(=O)c1cnc(N(CCO[Si](C)(C)C(C)(C)C)C(=O)OC(C)(C)C)nc1]

To a solution of 108 (220 mg, 0.74 mmol) in THF (20 mL) is added DMAP (59 mg, 0.48 mmol) and di-tert-butyl dicarbonate (346 mg, 1.58 mmol). After stirring at room temperature for 16 hours, the mixture is concentrated and purified by silica gel column chromatography (EA:PE=1:5) to give 109 as a yellow oil (290 mg, 99%). (MS: [M+H]$^+$ 396.2)

Step 3: Alcohol 110

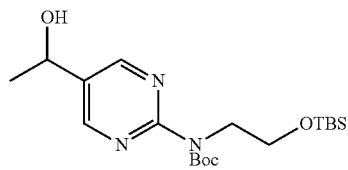 [SMILES: CC(O)c1cnc(N(CCO[Si](C)(C)C(C)(C)C)C(=O)OC(C)(C)C)nc1]

To a solution of 109 (280 mg 0.71 mmol) in THF (20 mL) and MeOH (2 mL) is added sodium borohydride (16 mg, 0.42 mmol). After stirring at room temperature for 3 hours, the mixture is diluted with EA (50 mL), washed with water (20 mL×3), dried over anhydrous sodium sulfate, filtered and concentrated to give crude 110 as a yellow solid (280 mg, 100%). (MS: [M+H]$^+$ 398.2)

Step 4: BA2

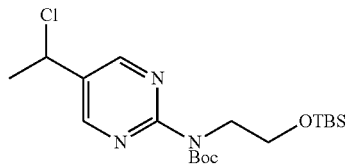 [SMILES: CC(Cl)c1cnc(N(CCO[Si](C)(C)C(C)(C)C)C(=O)OC(C)(C)C)nc1]

Following the procedure for B2 using 110 (280 mg, 0.70 mmol), DCM (10 mL), TEA (0.3 mL, 2.1 mmol), and MsCl (0.08 mL, 1.04 mmol), react at room temperature for 5 hours and purify with silica gel column chromatography (EA:PE=1:5) give BA2 as a yellow solid (200 mg, 68%). (MS: [M+H]$^+$ 416.2)

Preparation of BA3

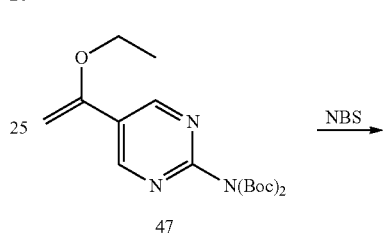

47

To a solution of 47 (2.4 g, 6.5 mmol) in THF (25 mL) and water (9 mL) is added NBS (1.17 g, 6.5 mmol) at 0° C. After stirring for 1 hour, the mixture is diluted with water and extracted with EA (20 mL×2). The combined organic layers are washed with saturated aqueous sodium bicarbonate, brine and concentrated to give BA3 as a yellow solid (2.69 g, 100%). (MS: [M+H]$^+$ 416.1)

Preparation of BA4

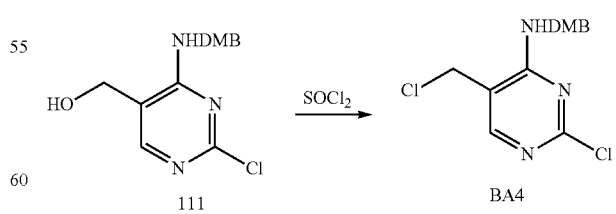

Following Procedure F using 111 (70 mg, 0.18 mmol), DCM (5 mL), and thionyl chloride (43 mg, 0.36 mmol) gives crude BA4 as a white solid (72 mg, 100%). (MS: [M+H]$^+$ 328.1)

Preparation BA5

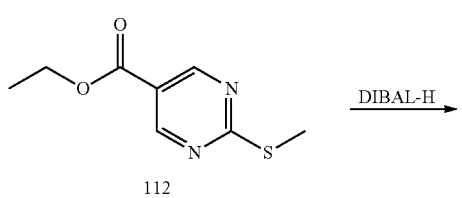

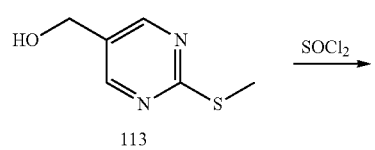

Prepared by essentially the same method as for B6.

Preparation of BB1

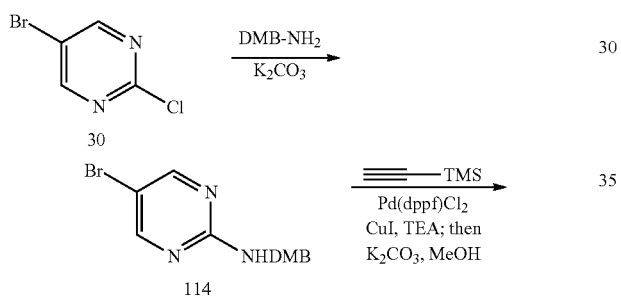

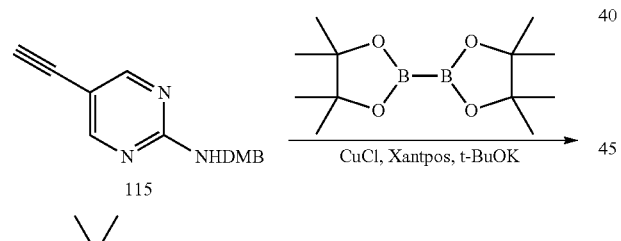

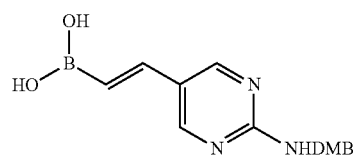

Step 1: Pyrimidine 114

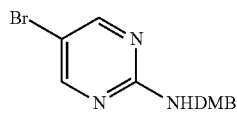

A mixture of 30 (5.5 g, 33 mmol), 2,4-dimethoxybenzylamine (5.5 g, 33 mmol) and potassium carbonate (4.97 g, 36 mmol) in DMF (30 mL) is stirred at 50° C. for 16 hours. The mixture is then cooled to room temperature and diluted with water (100 mL). The solid is collected by filtration and recrystallized from EA/hexanes (1:4) to give 114 as a white solid (9.4 g, 88% yield). (MS: [M+H]$^+$ 324.0).

Step 2: Alkyne 115

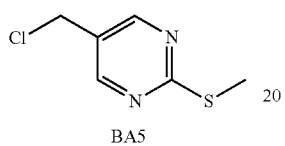

A mixture of 114 (9.4 g, 30 mmol), ethynyltrimethylsilane (3.5 g, 36 mmol), Pd(dppf)Cl$_2$ (1.1 g, 1.5 mmol), CuI (285 mg 1.5 mmol) and TEA (6.0 g, 60 mmol) in THF (30 mL) is stirred at room temperature for 16 hours. The mixture is then filtered, diluted with EA (50 mL), washed with water and brine, dried over anhydrous sodium sulfate, filtered and concentrated. The residue is dissolved in MeOH (50 mL) and K$_2$CO$_3$ (7.8 g, 60 mmol) is added. The mixture is stirred at room temperature for 5 hours and then filtered, concentrated, and purified by silica gel column chromatography (EA:PE=1:5) to give 115 as a solid (4.0 g, 49% yield). (MS: [M+H]$^+$ 270.1).

Step 3: Bronic Ester 116

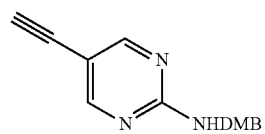

To a solution of 115 in THF (20 mL) is added CuCl (45 mg, 0.45 mmol), bis(pinacolato)diboron (4.5 g, 18 mmol), Xantphos (1.3 g, 2.25 mmol), potassium tert-butoxide (100 mg, 0.9 mmol) and MeOH (960 mg, 30.0 mmol). After stirring at room temperature for 2 hours, the mixture is concentrated and purified by silica gel column chromatography (EA:PE=1:3) to give 116 as a white solid (3.5 g, 29%). (MS: [M+H]$^+$ 398.2).

Step 4: BB1

A mixture of 116 (1.9 g 4.78 mmol) and sodium periodate (2.0 g 9.56 mmol) in acetone (10 mL) and water (10 mL) is stirred at room temperature for 16 hours. The mixture is then diluted with EA (100 mL), washed with water (50 mL×3), dried over anhydrous sodium sulfate, filtered, concentrated, and purified by silica gel column chromatography (EA:PE=1:1) to give BB1 as a white solid (600 mg 40%). (MS: [M+H]+ 316.1)

Preparation of BB2

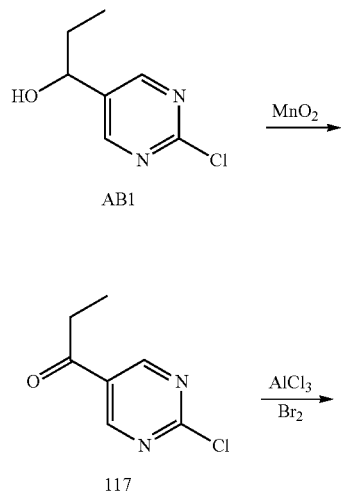

Step 2: Ketone 117

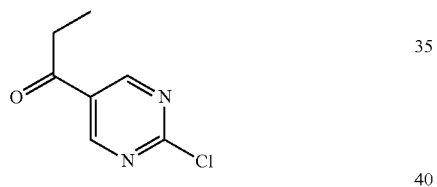

To a solution of AB1 (280 mg, 1.6 mmol) in acetone (5 mL) is added activated manganese(IV) oxide (704 mg, 8.0 mmol). After stirring at room temperature for 3 hours, the mixture is filtered, concentrated, and purified by silica gel column chromatography (EA:PE=1:5) to give 117 as a yellow solid (160 mg, 59%). (MS: [M+H]+ 171.0)

Step 3: BB2

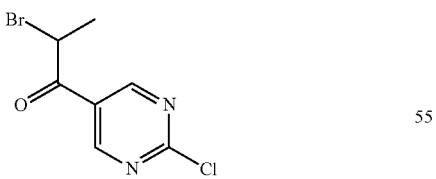

To a solution of 117 (120 mg, 0.7 mmol) in carbon tetrachloride (10 mL) is added bromine (0.07 mL, 1.4 mmol) and aluminum chloride (19 mg, 0.14 mmol). After stirring at room temperature overnight, the mixture is diluted with EA, washed with water and brine, dried over anhydrous sodium sulfate, filtered, concentrated, and purified by silica gel column chromatography (EA:PE=1:3) to give BB2 as a yellow solid (110 mg, 63%). (MS: [M+H]+249.1)

Preparation of BB3

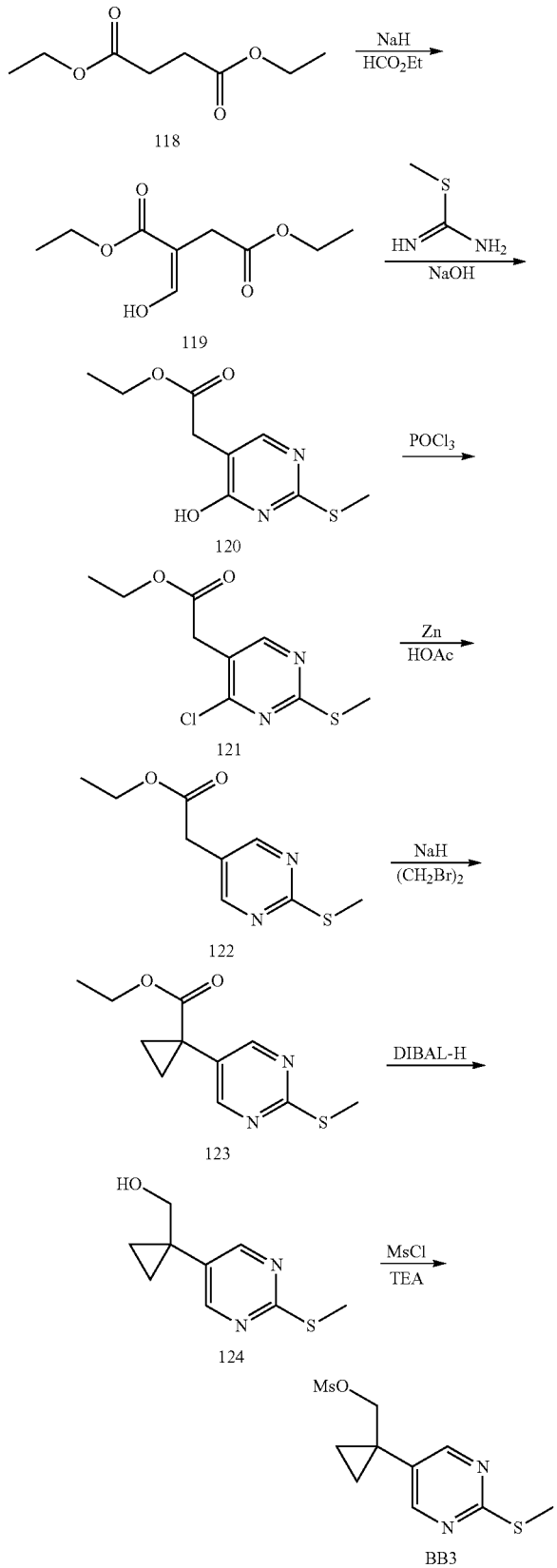

Step 1: Ester 119

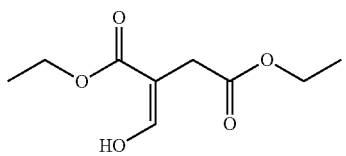

To a mixture of NaH (2.75 g, 114 mmol) in Et$_2$O (75 mL) is added a solution of 118 (20 g, 114 mmol) and ethyl formate (10.2 g, 138 mmol) in EtOH (20 mL). After stirring at room temperature overnight, water (50 mL) is added and the layers are separated. The aqueous layer is neutralized with 2 M HCl and extracted with ether (50 mL×3). The combined organic layers are washed with brine, dried over anhydrous sodium sulfate, filtered, and concentrated to give crude 119 (12 g, 52%). (MS: [M+H]$^+$ 203.1)

Step 2: Pyrimidine 120

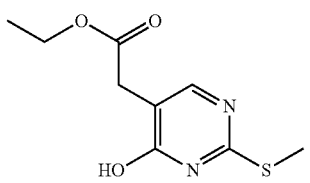

To a solution of crude 119 (53.4 g, 0.26 mol) and S-methylisothiourea hemisulfate salt (36.8 g, 0.264 mol) in water (240 mL) is added NaOH (15.8 g, 0.40 mol) in water (60 mL). After stirring at 100° C. for 1 hour, the mixture is neutralized with acetic acid. The solid is collected by filtration, washed with water, and dried to give 120 (32.6 g, 55% yield). (MS: [M+H]$^+$ 229.1)

Step 3: Pyrimidine 121

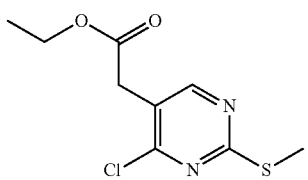

A mixture of 120 (28.8 g, 0.128 mol) in phosphoryl chloride (240 mL) is stirred under reflux for 4 hours. After cooling to room temperature, the mixture is concentrated, co-evaporated with benzene twice, and purified by silica gel column chromatography (EA:hexanes=1:3) to give 121 as a yellow oil (29.7 g 94% yield). (MS: [M+H]$^+$ 247.1)

Step 4: Pyrimidine 122

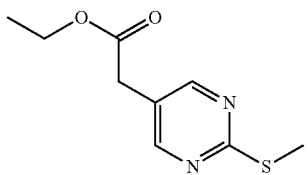

To a solution of 121 (2.6 g, 10 mmol) in EtOH (20 mL) is added zinc powder (2.6 g, 40 mmol) and HOAc (2 mL). After stirring at room temperature overnight, the mixture is filtered and concentrated. The residue is dissolved in EA (30 mL), washed with brine, dried over anhydrous sodium sulfate, filtered, and concentrated to give 122 as a yellow oil (1.2 g, 56% yield). (MS: [M+H]$^+$ 213.1)

Step 5: Pyrimidine 123

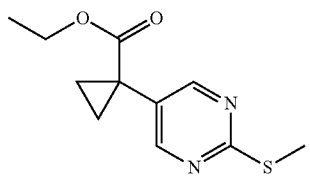 [SMILES: CCOC(=O)C1(c2cnc(SC)nc2)CC1]

To a mixture of 122 (500 mg 2.44 mmol) and NaH (142 mg 3.6 mmol) in DMF (5 mL) is added 1,2-dibromoethane (900 mg 4.8 mmol). After stirring at room temperature overnight, the mixture is diluted with EA (10 mL), washed with brine, dried over anhydrous sodium sulfate, filtered, concentrated, and purified by silica gel column chromatography (EA:PE=1:5) to give 123 as a yellow oil (240 mg, 41%). (MS: [M+H]$^+$ 239.1)

Step 7: alcohol 124

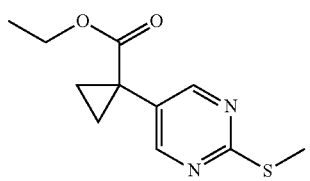 [SMILES: CCOC(=O)C1(c2cnc(SC)nc2)CC1]

Prepared by using Procedure D.

Step 7: BB3

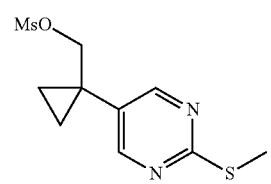 [SMILES: CSc1ncc(C2(COS(C)(=O)=O)CC2)cn1]

Prepared by essentially the same method as for B20. (MS: [M+H]$^+$ 275.1)

Preparation of BB4

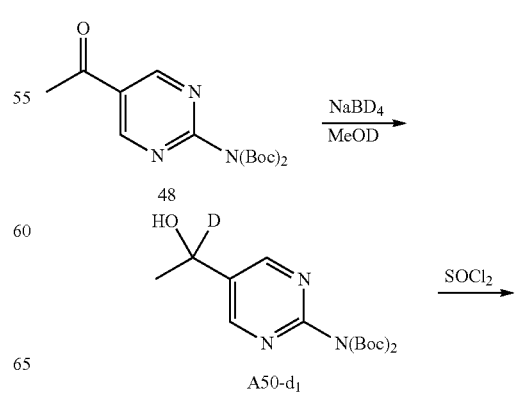

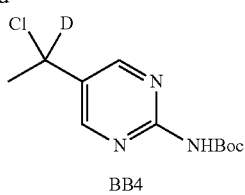

BB4

Step 1: Alcohol A50-d₁

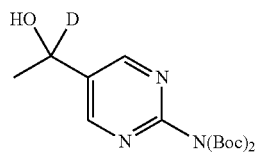

Prepared by essentially the same method as for A50 using 48, sodium borodeuteride, THF, and MeOD. (MS: [M+H]⁺ 341.2)

Step 3: BB4

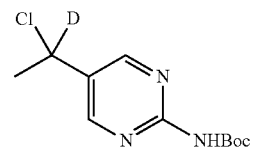 [SMILES: [2H]C(C)(Cl)c1cnc(NC(=O)OC(C)(C)C)nc1]

Following Procedure G using A50-di (80 mg, 0.23 mmol), DCM (5 mL) and thionyl chloride (55 mg, 0.47 mmol) gives crude BB4 (60 mg, 100%). (MS: [M+H]⁺ 259.1)

Preparation of BB5

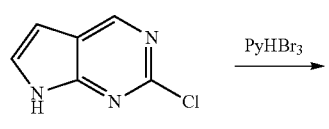

125

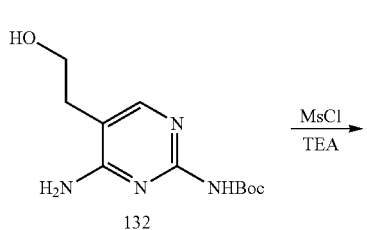

129

130

131

132

BB5

Step 1: Dibromide 126

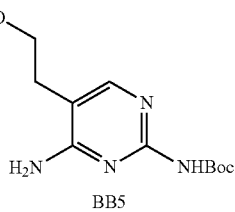

To a mixture of 125 (2.0 g, 13.02 mmol) in t-butanol (100 mL) is added pyridinium tribromide (25.0 g 78.1 mmol). After stirring at room temperature for 16 hours, the mixture is concentrated and the residue is dissolved in EA (100 mL), washed with brine (50 mL×3), dried over anhydrous sodium sulfate, filtered, concentrated, and purified by silica gel column chromatography (EA:PE=2:1) to give 126 as a solid (3.5 g 82%). (MS: [M+H]⁺ 327.8)

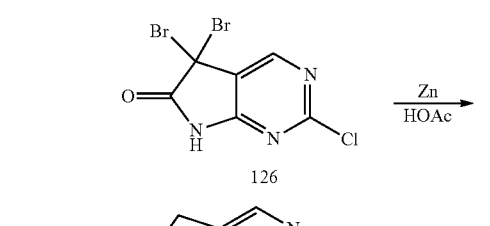

126

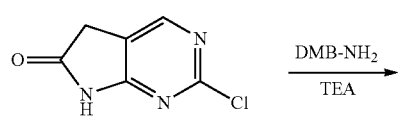

127

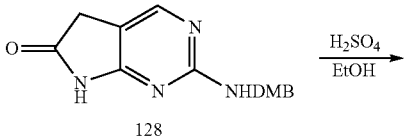

128

Step 2: Chloride 127

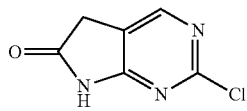 [SMILES: O=C1Cc2cnc(Cl)nc2N1]

To a mixture of 126 (3.5 g, 10.7 mmol) in HOAc (50 mL) is added Zn dust (7.0 g, 107 mmol). After stirring at room temperature for 2 hours, the mixture is concentrated and the residue is dissolved in EA (100 mL), washed with saturated sodium bicarbonate aqueous solution (50 mL×3), brine (50 mL×3), dried over anhydrous sodium sulfate, filtered, concentrated, and purified by silica gel column chromatography (EA:PE=1:2) to give 127 as a solid (1.3 g, 72%). (MS: [M+H]$^+$ 170.0)

Step 3: Amine 128

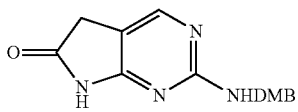

To a mixture of 127 (600 mg, 3.54 mmol) and 2,4-dimethoxybenzylamine (887 mg, 5.31 mmol) in n-butanol (10 mL) is added TEA (716 mg, 7.08 mmol). After stirring at 130° C. for 30 minutes under microwave irradiation, the mixture is concentrated and purified by silica gel column chromatography (EA:PE=1:1) to give 128 as a white solid (700 mg, 66%). (MS: [M+H]$^+$ 301.1)

Step 4: Ester 129

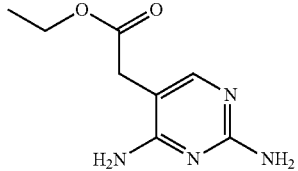

To a solution of 128 (700 mg, 2.33 mmol) in EtOH (10 mL) is added concentrated H$_2$SO$_4$ (0.5 mL). After stirring at 80° C. for 30 minutes, the mixture is diluted with EA (100 mL), neutralized with saturated sodium bicarbonate aqueous solution, washed with brine (30 mL×3), dried over sodium sulfate, filtered, and concentrated to give crude 129 (280 mg, 61% yield). (MS: [M+H]$^+$ 301.1)

Step 5: Alcohol 130

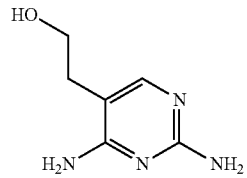 [SMILES: Nc1ncc(CCO)c(N)n1]

Prepared by using Procedure E.

Step 6: Carbamate 131

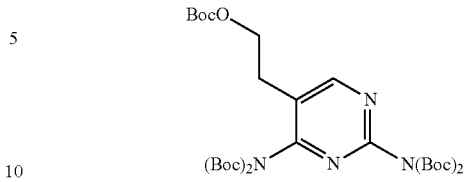

Prepared by essentially the same method as for 74.

Step 7: Alcohol 132


Prepared by essentially the same method as for 75.

Step 8: BB5

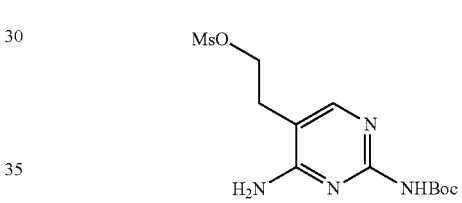

Prepared by using the method essentially the same as for B20. (MS: [M+H]$^+$333.1)

Preparation of BA5-d$_2$

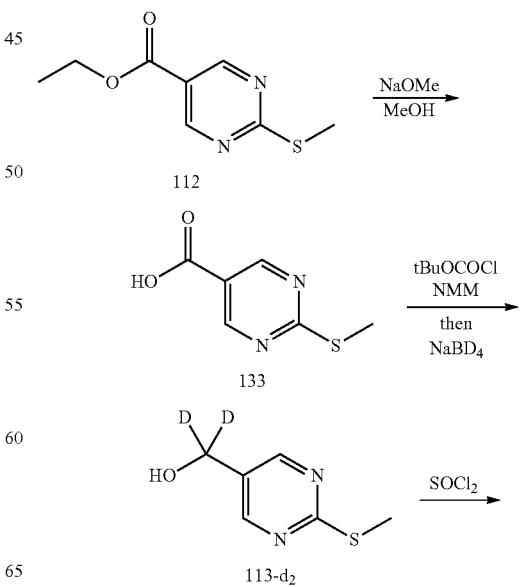

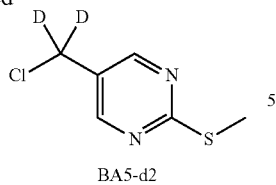

Step 1: Acid 133

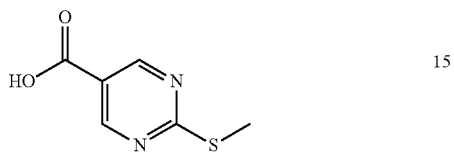

To a solution of 112 (1.0 g, 5 mmol) in MeOH (15 mL) is added 1N NaOH solution (6 mL). After stirring at room temperature for 1 hour, the mixture is concentrated and concentrated HCl (0.5 mL) is added. The solid is collected by filtration, washed with water, and dry to give 133 as a yellow solid (811 mg, 95%). (MS: [M+H]$^+$ 171.1)

Step 2: Alcohol 113-d$_2$

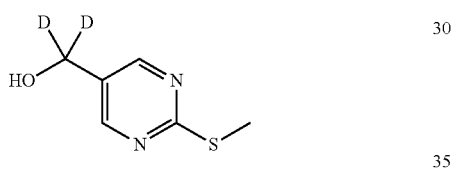

Following the procedure for A38 using 133 (1.18 g 6.9 mmol), NMM (695 mg, 6.9 mmol), THF (20 mL), isobutyl chloroformate (1.13 g, 8.25 mmol), sodium borodeuteride (289 mg, 6.9 mmol), and deueterate water (0.5 mL), then purify with silica gel column chromatography (EA:PE=1:5) to give 113-d$_2$ as a light yellow solid (290 mg, 25%). (MS: [M+H]$^+$ 159.1)

Step 3: BA5-d$_2$

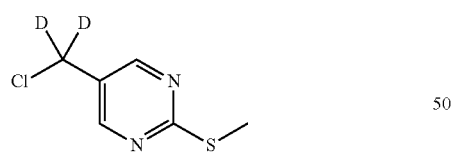

Prepared by essentially the same method as for A50. (MS: [M+H]$^+$ 177.1)

Preparation of BB6

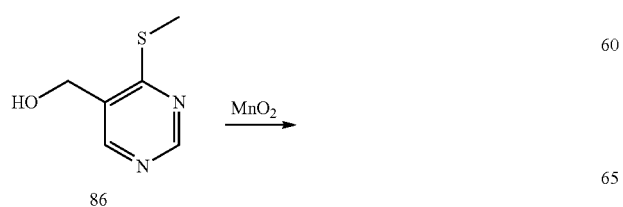

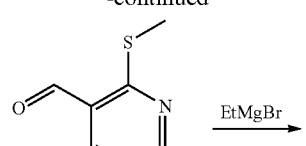

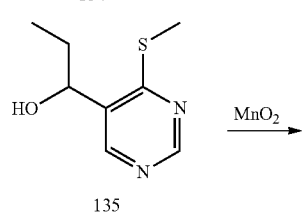

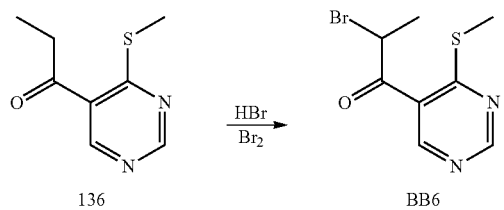

Step 1: Aldehyde 134

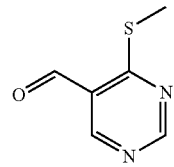

Prepared by essentially the same method as for 8. (MS: [M+H]$^+$ 155.0).

Step 1: Alcohol 135

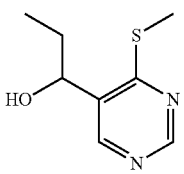

Prepared by essentially the same method as for AA2.

Step 1: Ketone 136

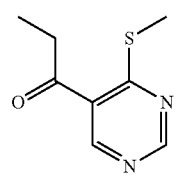

Prepared by essentially the same method as for 8.

Step 1: BB6

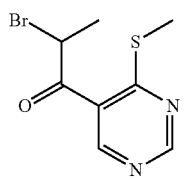

Prepared by essentially the same method as for BB2. (MS: [M+H]⁺ 261.0)

Preparation of BB7

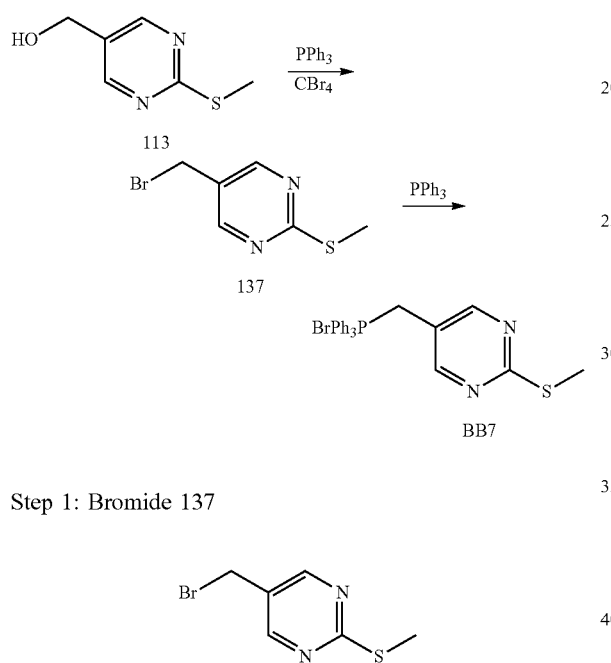

Step 1: Bromide 137

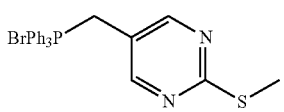

To a mixture of 113 (1.02 g, 6.53 mmol) and PPh₃ (3.4 g, 13.1 mmol) in DCM (50 mL) is added carbon tetrabromide (4.3 g, 13.1 mmol). After stirring at room temperature for 16 hours, the mixture is diluted with DCM, washed with brine, dried over anhydrous sodium sulfate, filtered, concentrated, and purified by silica gel column chromatography (EA: PE=1:20) to give 137 as a pale yellow oil (900 mg, 63%). (MS: [M+H]⁺ 219.0)

Step 2: BB7

A mixture of 137 (255 mg, 1.16 mmol) and PPh₃ (457 mg, 1.75 mmol) in toluene (15 mL) is stirred at 110° C. for 16 hours. The mixture is then cooled and filtered to give BB7 as a white solid (476 mg, 44%). (MS: [M-Br]⁺ 401.1)

The following compounds are prepared by essentially the same method as for BB7.

| Intermediate | Structure | MS |
|---|---|---|
| BB8 | BrPh₃P-CH₂-(pyrimidine)-N(2,5-dimethylpyrrole) | [M + H]⁺ 528.1 |

Preparation of C

Preparation of C1

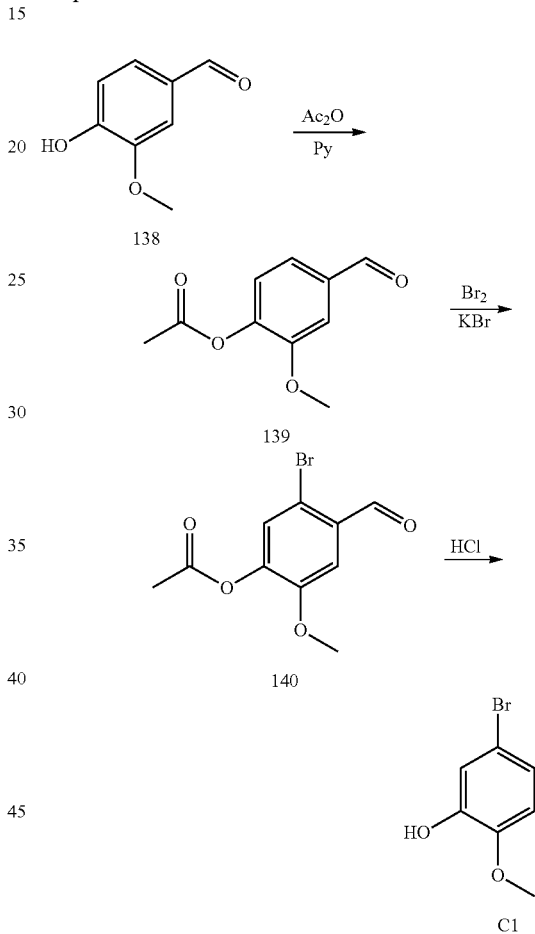

Step 1: Acetate 139

To a solution of 138 (50.0 g, 329 mmol) in DCM (250 mL) is added acetic anhydride (37.5 mL, 399 mmol) and Py (32 mL, 79 mmol). After stirring at room temperature for 18 hours, water (100 mL) is added and the mixture is extracted with EA (100 mL×3). The combined organic layers are washed with 1 N HCl solution (100 mL) and saturated aqueous sodium bicarbonate solution (100 mL), dried over anhydrous sodium sulfate, filtered, and concentrated to give crude 139 (60.0 g, 94% yield). (MS: [M+H]$^+$ 195.2)

Step 2: Bromide 140

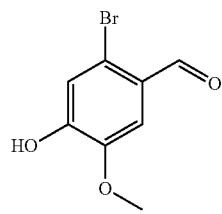

To a suspension of 139 (5.0 g, 25.5 mmol) and potassium bromide (10.0 g, 85 mmol) in water (50 mL) is added bromine (1.5 mL, 28.5 mmol) dropwise at 0° C. After stirring at room temperature for 15 hours, the solid is collected by filtration, washed with water, and dried to give crude 140 as a white solid (6.0 g, 87% yield). (MS: [M+H]$^+$ 274.1)

Step 3: C1

A mixture of 140 (66 g, 243 mmol) in 6 N HCl aqueous solution (1.0 L) is stirred at 90° C. for 10 hours and then cooled to room temperature. The solid is collected by filtration, washed with water, and dried to give $C_1$ as a white solid (50 g, 90% yield). (MS: [M+H]$^+$ 232.2)

The following compound is prepared by essentially the same method as for C1.

| Intermediate | Structure | MS |
|---|---|---|
| C2 | 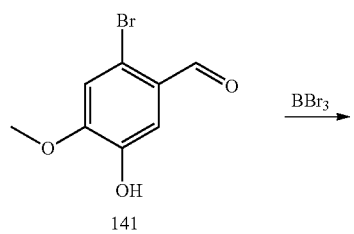 | [M + H]$^+$ 248.9 |

Preparation of C3

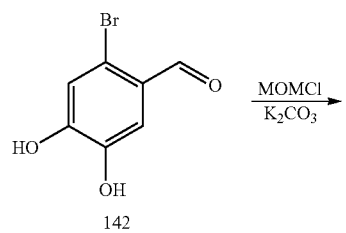

Step 1: Catechol 142

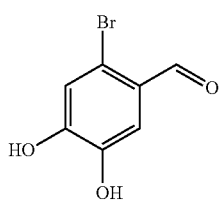

To a solution of 141 (30 g, 130 mmol) in DCM (500 mL) is added boron tribromide (65.3 g, 261 mmol) dropwise at 0° C. After stirring at room temperature for 16 hours, MeOH (100 mL) is added and the mixture is concentrated and purified by silica gel column chromatography (MeOH:DCM=1:15) to give 142 as a solid (12 g 42% yield). (MS: [M+H]$^+$ 218.2)

Step 2 C3

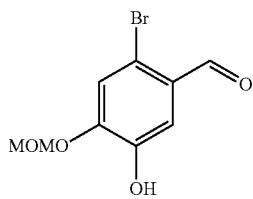

To a suspension of 142 (4.32 g, 20 mmol) and potassium carbonate (4.14 g, 30 mmol) in acetone (20 mL) is added MOMCl (1.7 g, 22 mmol) dropwise at room temperature. After stirring at room temperature for 12 hours, saturated aqueous ammonium chloride solution (20 mL) is added and the mixture is extracted with EA (50 mL×3). The combined organic layers are dried over anhydrous sodium sulfate, filtered, concentrated, and purified by silica gel column chromatography (EA:PE=1:4) to give C3 as an oil (2.2 g, 42% yield). (MS: [M+H]$^+$ 262.2)

Preparation of C4

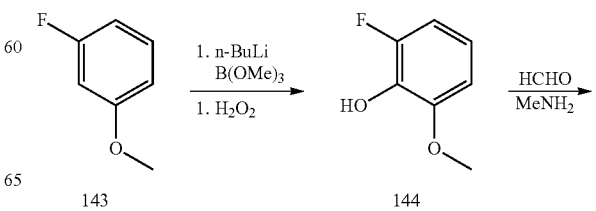

115

-continued

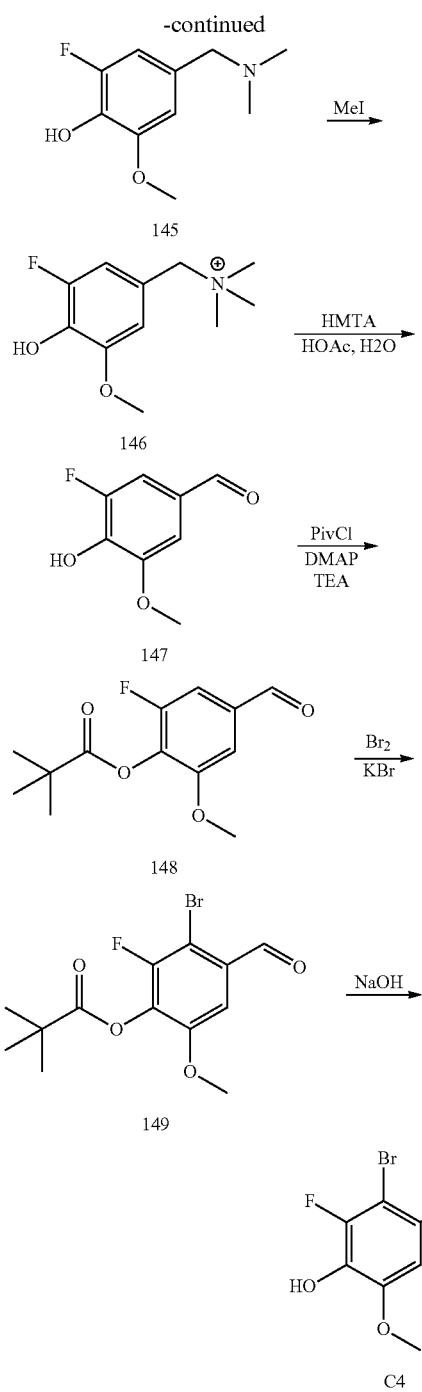

145

146

147

148

149

C4

Step 1: Phenol 144

To a solution of 143 (100 g, 794 mmol) in THF (800 mL) is added n-BuLi (2.5 M in THF, 300 mL, 7.5 mol) at −78°

116

C. dropwise over 1 hour. After stirring for 2 hours, trimethyl borate (90 mL, 807 mmol) in THF (200 mL) is added dropwise over 1 hour and the mixture is stirred at −78° C. for 30 minutes before HCl solution (2 N, 1.0 L) and 30% hydrogen peroxide (100 mL, 880 mmol) is added at 0° C. After stirring at room temperature overnight, saturated sodium thiosulfate solution (200 mL) is added and the mixture is extracted with MTBE (800 mL×2). The combined organic layers are washed with water (300 mL×2), dried over anhydrous magnesium sulfate, filtered, and concentrated to give 144 (54.9 g 49% yield). (MS: [M+H]$^+$ 143.1)

Step 2: Amine 145

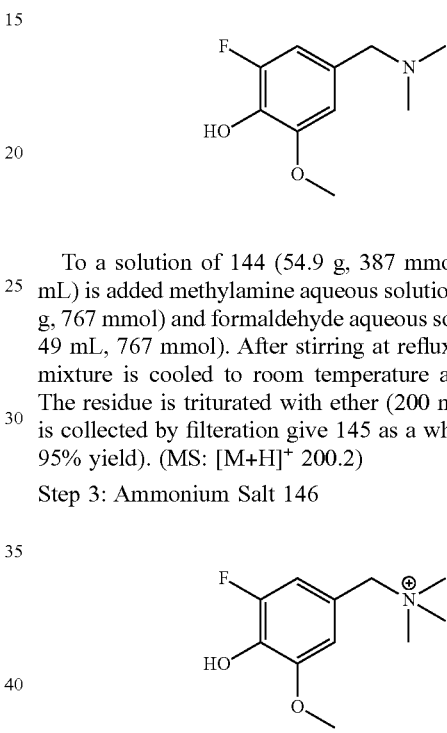

To a solution of 144 (54.9 g, 387 mmol) in EtOH (400 mL) is added methylamine aqueous solution (40 wt. %, 82.4 g, 767 mmol) and formaldehyde aqueous solution (37 wt. %, 49 mL, 767 mmol). After stirring at reflux for 2 hours, the mixture is cooled to room temperature and concentrated. The residue is triturated with ether (200 mL) and the solid is collected by filteration give 145 as a white solid (73.0 g, 95% yield). (MS: [M+H]$^+$ 200.2)

Step 3: Ammonium Salt 146

To a solution of 145 (73.0 g, 380 mmol) in chloroform (900 mL) is added MeI (380 mL). After stirring at room temperature overnight, the solid is collected by filtration to give crude 146 as an off-white solid (124 g, 95% yield).

Step 4: Aldehyde 147

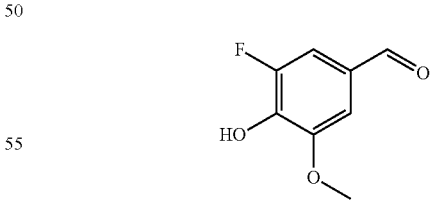

To a solution of 146 (124 g, 362 mmol) in HOAc (300 mL) and water (300 mL) is added HMTA (196 g, 1.4 mol) under reflux. After stirring for 2 hour, concentrated HCl solution (80 mL) is added and the mixture is stirred for 5 minutes, cooled, and extracted with MTBE (800 mL×3). The combined organic layers are washed with water (800 mL×2), dried over anhydrous magnesium sulfate, and concentrated to give 147 as a white solid (46 g, 75% yield).

Step 5: Pivalate 148

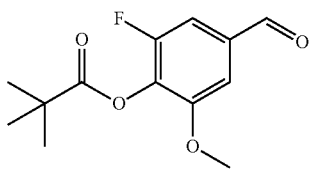 [SMILES: COc1cc(C=O)cc(F)c1OC(=O)C(C)(C)C]

To a solution of 147 (46 g, 271 mmol), TEA (90 mL, 649 mmol), and DMAP (1.65 g, 13.5 mmol) in DCM (500 mL) is added pivaloyl chloride (39 mL, 325 mmol) at 0° C. After stirring at room temperature for 2 hours, the mixture is diluted with DCM (200 mL), washed with water (100 mL×3), dried over anhydrous magnesium sulfate, filtered, concentrated, and purified by silica gel column chromatography (EA:PE=1:20) to give 148 as a yellow solid (62 g 91% yield). (MS: [M+H]⁺ 254.1)

Step 6: Bromide 149

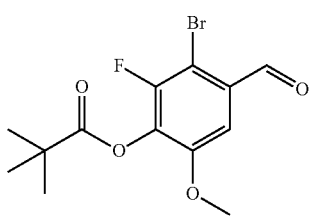 [SMILES: COc1cc(C=O)c(Br)c(F)c1OC(=O)C(C)(C)C]

Following the procedure for 140 using 148 (10.0 g, 39.4 mmol), potassium bromide (32.7 g, 275 mmol), water (100 mL), and bromine (12 mL, 236 mmol) gives crude 149 as a yellow solid (26.3 g, 99% yield). (MS: [M+H]⁺ 334.1)

Step 7: C4

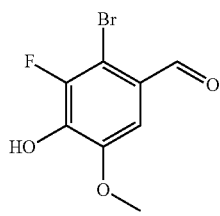

To a solution of 149 (333 mg, 1 mmol) in EtOH (5 mL) is added NaOH aqueous solution (4 N, 1 mL, 4 mmol). After stirring at reflux overnight, the mixture is cooled to room temperature, acidified with 6 N HCl aqueous solution to pH 5, and extracted with DCM (20 mL×3). The combined organic layers are dried over anhydrous sodium sulfate, filtered, and concentrated to give crude C4 as a yellow solid (195 mg, 78% yield). (MS: [M+H]⁺ 249.0)

Preparation of C5

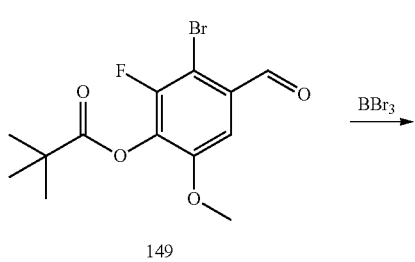

149

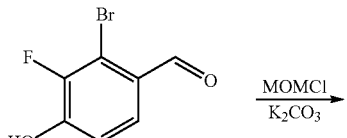

150

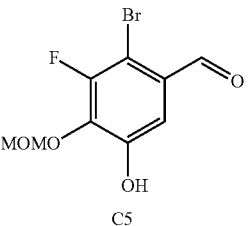

C5

Prepared by essentially the same method as for C3 to give C5 (MS: [M+H]⁺280.2)

Preparation of C6

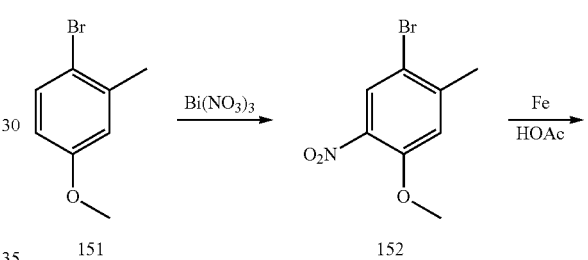

151      152

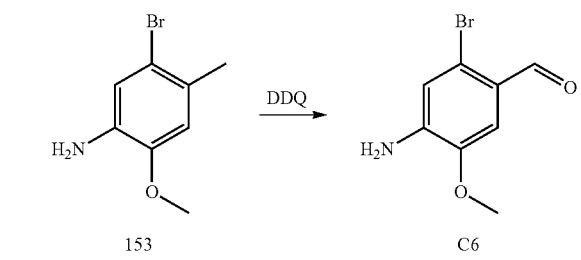

153      C6

Step 1: Nitroarene 152

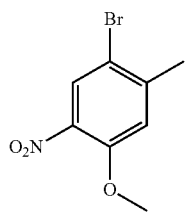

To a suspension 151 (2.5 g, 12.5 mmol) in DCE (20 mL) is added bismuth nitrate pentahydrate (7.28 g, 15 mmol) at room temperature. After stirring at 80° C. overnight, the mixture is cooled to room temperature, filtered, concentrated, and purified by silica gel column chromatography (EA:PE=1:10) to give 152 as a light yellow solid (1.19 g, 39% yield). (MS: [M+H]⁺ 246.0)

Step 2: Aniline 153

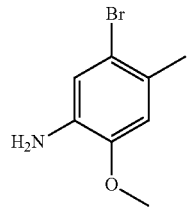

To a suspension of 152 (1.19 g, 4.86 mmol) and iron powder (0.82 g 14.6 mmol) in water (1.2 mL) is added HOAc (2.8 mL) at room temperature. After stirring at 100° C. for 4 hours, the mixture is cooled to room temperature and concentrated. Aqueous potassium hydroxide solution (10%, 20 mL) is then added and the mixture is filtered, extracted with EA (10 mL×3). The combined organic layers are washed with water and brine, dried over anhydrous sodium sulfate, filtered, concentrated, and purified by silica gel column chromatography (EA:PE=1:10) to give 153 as a white solid (0.63 g, 60% yield). (MS: [M+H]+ 216.0)

Step 3: C6

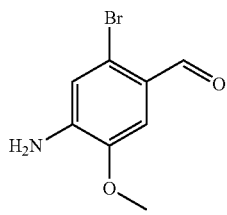

To a solution of 153 (0.63 g, 2.92 mmol) in MeOH (24 mL), THF (1.5 mL), and water (6.0 mL) is added DDQ (1.99 g, 8.77 mmol) at 0° C. After stirring at room temperature for 15 minutes, the mixture is extracted with EA (20 mL×3). The combined organic layers are washed with saturated aqueous sodium bicarbonate solution and brine, dried over anhydrous sodium sulfate, filtered, concentrated, and purified by silica gel column chromatography (EA:PE=1:5) to give C6 as a brown solid (390 mg, 58% yield). (MS: [M+H]+ 230.0)

Preparation of C7

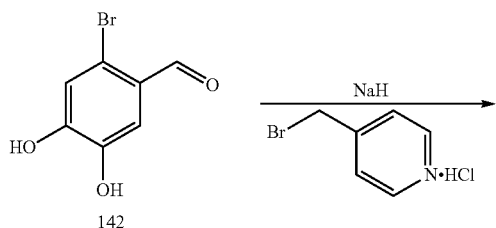

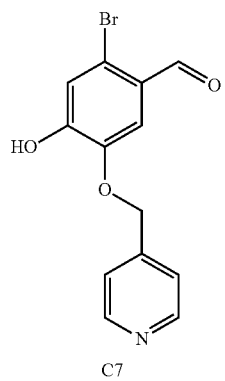

To a solution of 142 (217 mg, 1 mmol) in DMF (8 mL) is added NaH (120 mg, 3 mmol) at 0° C. and stirred at 25° C. for 30 minutes before 4-(bromomethyl)pyridine hydrochloride (252 mg, 1 mmol) is added at 0° C. After stirring at 25° C. overnight MeOH (1 mL) is added at 0° C. and the mixture is concentrated and purified by silica gel column chromatography (MeOH:DCM=1:50) to give C7 as a yellow solid (100 mg, 35% yield). (MS: [M+H]+ 308.1)

Preparation of C8

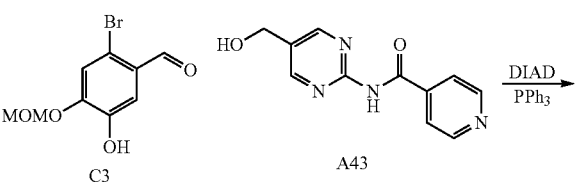

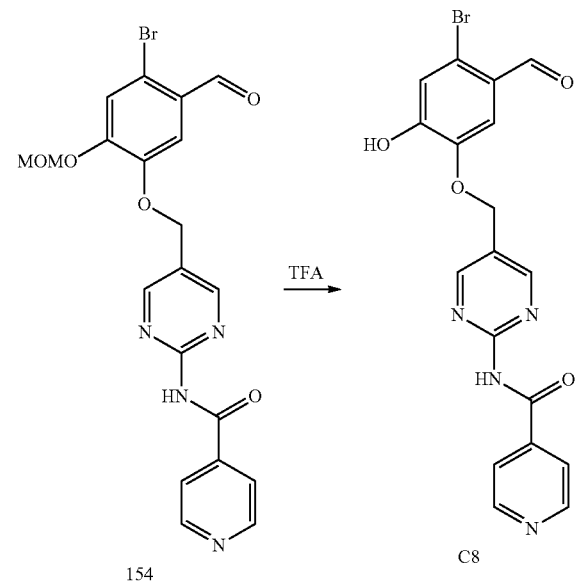

Step 1: Aldehyde 154

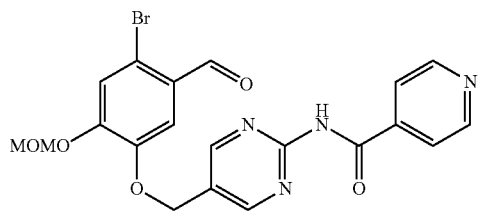

To a solution of A43 (200 mg, 0.87 mmol) in THF (3 mL) is added C3 (190 mg 0.73 mmol), PPh$_3$ (455 mg 1.74 mmol), and DIAD (351 mg 1.74 mmol) at room temperature. After stirring at 30° C. overnight, the mixture is concentrated and purified by silica gel column chromatography (MeOH: DCM=1:50) to give 154 as a yellow solid (100 mg, 29% yield). (MS: [M+H]$^+$ 473.1)

Step 2: C8

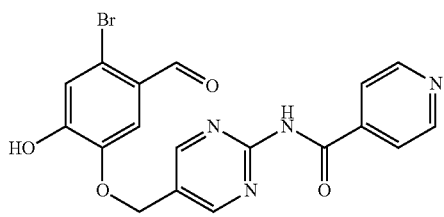 [SMILES: O=Cc1cc(OCc2cnc(NC(=O)c3ccncc3)nc2)c(O)cc1Br]

To a solution of 154 (50 mg 0.11 mmol) in DCM (4 mL) is added TFA (0.4 mL) dropwise at 0° C. After stirring at room temperature for 20 minutes, the mixture is basified with a saturated aqueous sodium bicarbonate solution. The solid is collected by filtration, washed with water (3 mL), and dried to crude C8 as a yellow solid (23 mg, 50% yield). (MS: [M+H]$^+$ 429.0)

The following compounds are prepared by essentially the same method as for C8.

Preparation of C11

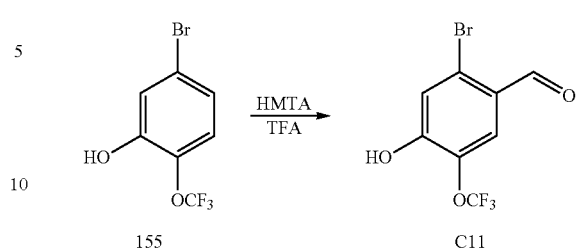

A solution of 155 (52 mg, 0.2 mmol), HMTA (56 mg, 0.4 mmol) and TFA (1 ml) is stirred at 70° C. for 3 hours. The mixture is then concentrated and the residue is dissolved in EA (10 mL), washed with saturated aqueous sodium carbonate solution (10 mL), dried over anhydrous sodium sulfate, filtered, concentrated, and purified by silica gel column chromatography (DCM) to give C11 as a yellow solid (10 mg, 17% yield). (MS: [M+H]$^+$286.3)

Preparation of C12

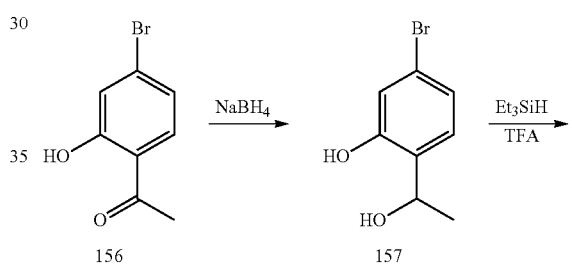

| Intermediate | Structure | MS |
|---|---|---|
| C9 | (structure shown) | [M + H]$^+$ 428.0 |
| C10 | (structure shown) | [M + H]$^+$ 428.0 |

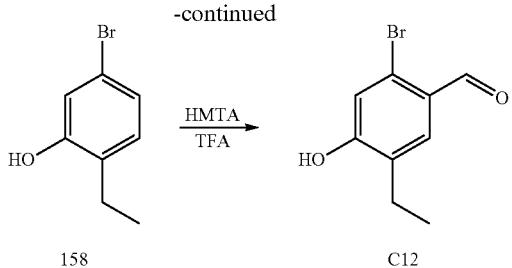

A solution of 158 (0.1 g 0.5 mmol), TFA (3 mL), and HMTA (0.14 g, 1.0 mmol) is stirred at 105° C. for 30 minutes and then diluted with EA (100 mL), washed with saturated sodium bicarbonate (20 mL×2), dried over anhydrous sodium sulfate, filtered, concentrated, and purified by silica gel column chromatography (EA:PE=1:10) to give C12 as a yellow oil (30 mg, 30% yield). (MS: [M+H]+ 229.2)

Preparation of C13

Step 1: Alcohol 157

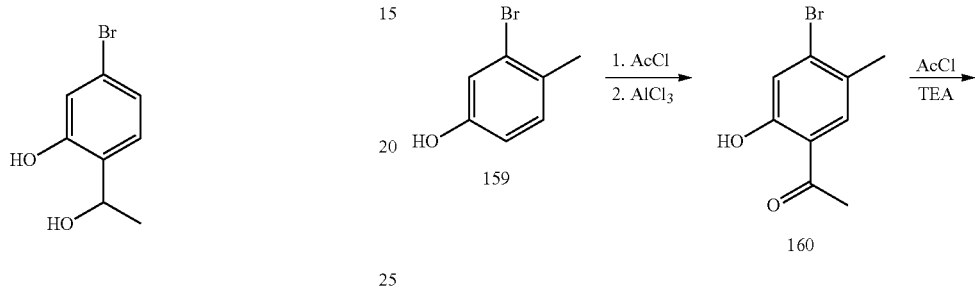

Following Procedure C using 156 (2.0 g, 9.3 mmol), MeOH (10 mL) and sodium borohydride (0.2 g, 5.3 mmol), dilute the reaction mixture with EA (50 mL), wash with water (50 mL) and brine (20 mL), dry over anhydrous sodium sulfate, filter, and concentrate to give 157 as a yellow solid (2 g, 100% yield). (MS: [M+H]+ 215.1)

Step 2: Phenol 158

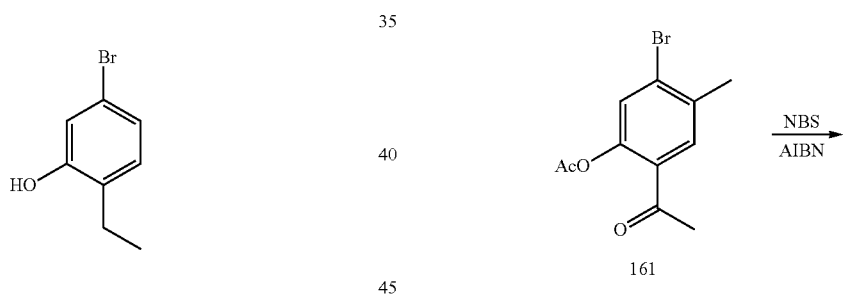

A solution of 157 (0.5 g, 2.3 mmol), DCM (5 mL), triethylsilane (0.7 mL, 4.6 mmol), and TFA (1 mL) is stirred at room temperature overnight and then concentrated and purified by silica gel column chromatography (EA:PE=1:10) to give 158 as a yellow oil (0.3 g, 60% yield). (MS: [M+H]+ 201.2)

Step 3: C12

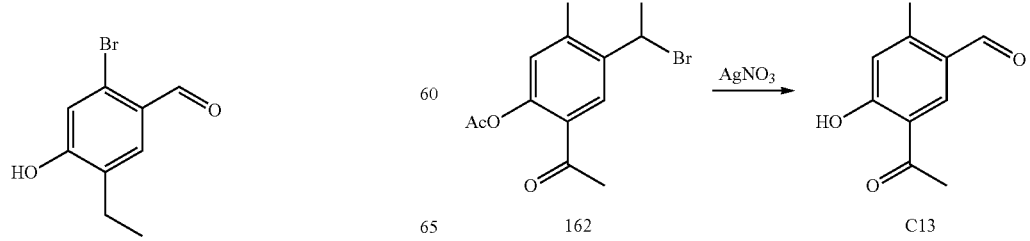

Step 1: Ketone 160

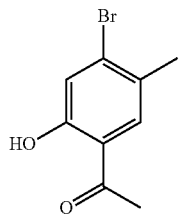

A mixture of 159 (5.0 g, 26.7 mmol) and acetyl chloride (10.5 g, 134 mmol) is stirred at 60° C. for 1 hour before aluminum chloride (5.4 g, 40.1 mmol) is added at room temperature. After stirring at 160° C. for 2 hours, the mixture is cooled to room temperature, poured into saturated ammonium chloride solution (50 mL), and extracted with EA (50 mL×5). The combined organic layers are dried over anhydrous sodium sulfate, filtered, and concentrated to crude 160 as an off-white solid (5.5 g, 90% yield). (MS: [M+H]$^+$ 229.0)

Step 2: Acetate 161

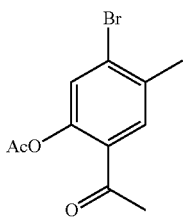

To a solution of 160 (3.0 g, 13.1 mmol) and TEA (2.6 g, 26.2 mmol) in DCM (30 mL) is added acetyl chloride (1.54 g 19.6 mmol) dropwise at room temperature. After stirring for 1 hour, the mixture is poured into a saturated ammonium chloride solution (20 mL) and extracted with EA (50 mL×5). The combined organic layers are dried over anhydrous sodium sulfate, filtered, and concentrated, and purified by silica gel column chromatography (EA:PE=1:10) to give 161 as an off-white solid (3.3 g, 93% yield).

Step 3: Bromide 162

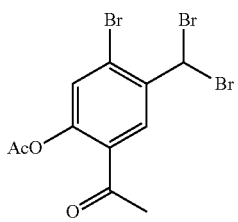 [SMILES: CC(=O)Oc1cc(Br)c(C(Br)Br)cc1C(C)=O]

To a solution of 161 (2.0 g, 7.4 mmol) in carbon tetrachloride (15 mL) is added NBS (2.6 g, 14.7 mmol) and AIBN (200 mg, 1.2 mmol). After stirring at 90° C. for 16 hours, the mixture is cooled, concentrated, and purified by silica gel column chromatography (EA:PE=1:10) to give 162 as an off-white solid (3.0 g, 94% yield).

Step 4: C13

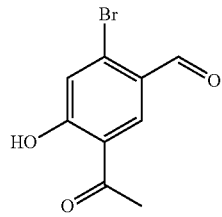

To a solution of 162 (3.0 g, 6.9 mmol) in EtOH (30 mL) is added a solution of silver nitrate (5.9 g, 34.9 mmol) in water (20 mL) dropwise. After stirring at 75° C. for 16 hours, the mixture is extracted with EA (20 mL×3). The combined organic layers are dried over anhydrous sodium sulfate, filtered, concentrated, and purified by silica gel column chromatography (EA:PE=1:8) to give C13 as an off-white solid (1.6 g 94% yield). (MS: [M+H]$^+$ 243.0)

Preparation of C14

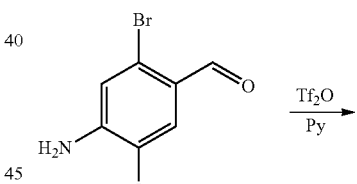

163

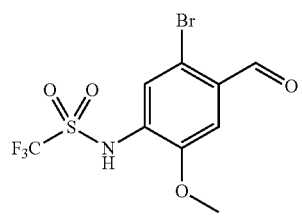

C14

To a solution of 163 (230 mg, 1.0 mmol) and Py (0.25 ml, 3.1 mmol) in DCM (5 mL) is added trifluoromethanesulfonic anhydride (338 mg, 1.2 mmol) dropwise at 0° C. After stirring at room temperature overnight, the mixture is concentrated and purified by prep-TLC (MeOH:DCM=1:20) to give C14 as a yellow solid (303 mg, 84% yield). (MS: [M+H]$^+$ 362.0)

Preparation of C15

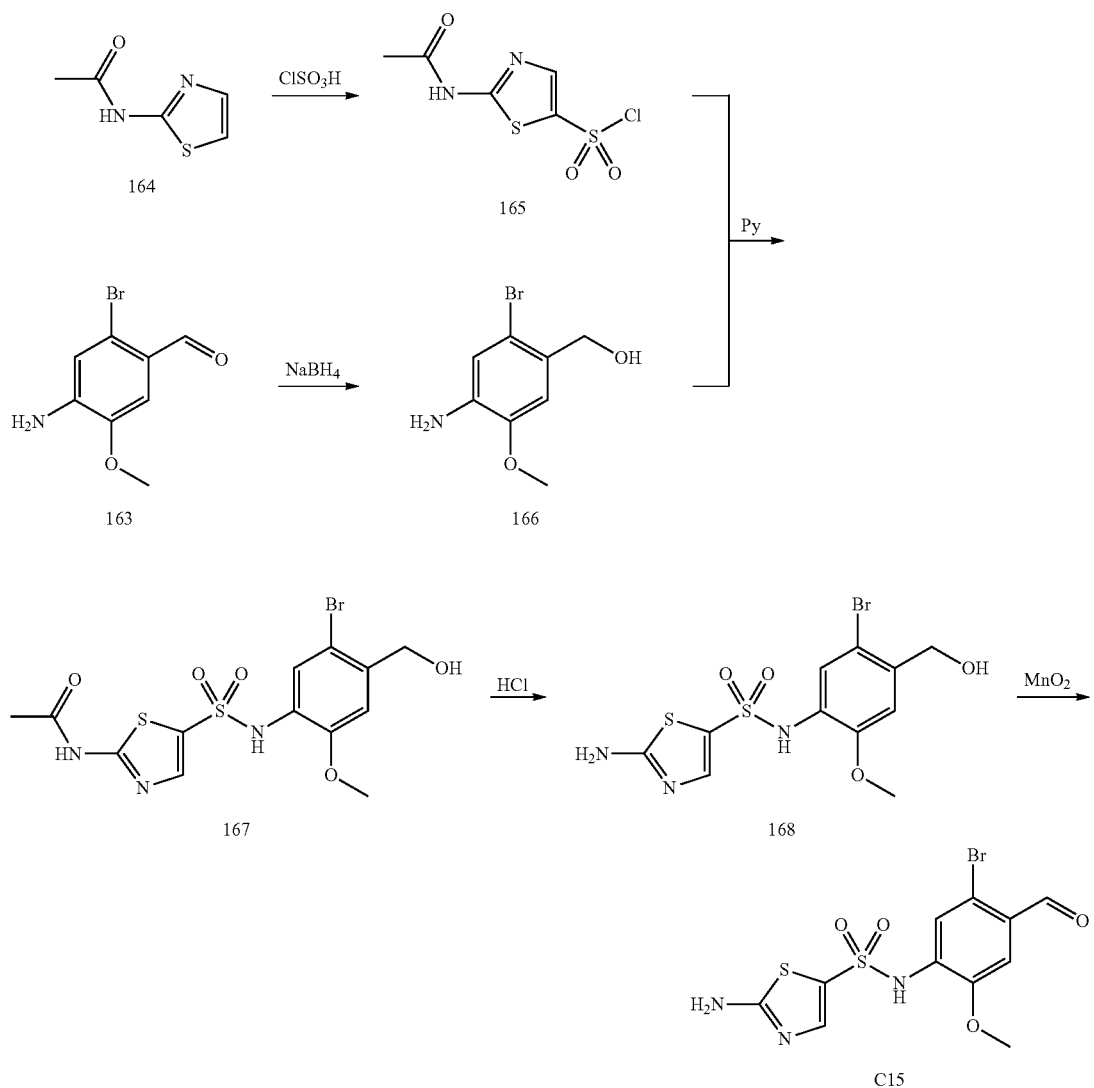

Step 1: Sulfonyl Chloride 165

To chlorosulfonic acid (4.1 g, 35.2 mmol) is added 164 (1.0 g 7.04 mmol) in portions. After stirring at 100° C. for 16 hours, the mixture is cooled to room temperature, poured into ice water (100 mL), and extracted with EA (50 mL×2). The combined organic layers are washed with brine (100 mL), dried over anhydrous sodium sulfate, filtered, concentrated, and purified by silica gel column chromatography (EA:PE=1:5) to give 165 as a yellow solid (100 mg, 6% yield). (MS: $[M+H]^+$ 241.0)

Step 2: Alcohol 166

Following Procedure C using 163 (671 mg, 2.92 mmol), MeOH (3 mL), and sodium borohydride (220 mg, 5.84 mmol), workup with saturated aqueous sodium bicarbonate solution (3 mL) and water (5 mL), extract with EA (30 mL×3), wash the combined organic layers with brine (100 mL), dry over anhydrous sodium sulfate, filter, concentrate, and purify with silica gel column chromatography (EA: PE=1:3 to 1:2) give 166 as a pale yellow solid (550 mg, 81% yield). (MS: $[M+H]^+$ 232.0)

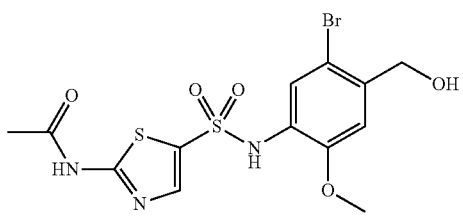 [SMILES: COc1cc(CO)c(Br)cc1NS(=O)(=O)c1cnc(NC(C)=O)s1]

Step 3: Sulfonamide 167

To a solution of 165 (100 mg 0.41 mmol) in Py (2 mL) is added 166 (230 mg, 1.0 mmol). After stirring at room temperature for 16 hours, the mixture is acidified with 1 N HCl solution to pH 7 and extracted with EA (30 mL×3). The combined organic layers are washed with brine (100 mL), dried over anhydrous sodium sulfate, filtered, and concentrated to give 167 as a yellow solid (130 mg, 72% yield). (MS: [M+H]$^+$ 436.0)

Step 4: Alcohol 168

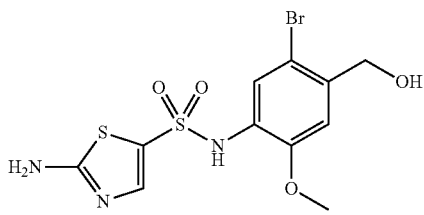 [SMILES: COc1cc(CO)c(Br)cc1NS(=O)(=O)c1cnc(N)s1]

To a solution of 167 (130 mg, 0.30 mmol) in EtOH (2 mL) is added HCl (4 M in 1,4-dioxane, 2 mL, 8.0 mmol) at room temperature. After stirring at 80° C. for 2 hours, the mixture is cooled to room temperature, basified with 1 N aqueous NaOH solution to pH 9, and extracted with EA (50 mL×3). The combined organic layers are washed with brine (100 mL), dried over anhydrous sodium sulfate, filtered, concentrated, and purified by silica gel column chromatography (MeOH:DCM=1:50) to give 168 as a pale yellow solid (100 mg, 85% yield). (MS: [M+H]$^+$ 394.0)

Step 5: C15

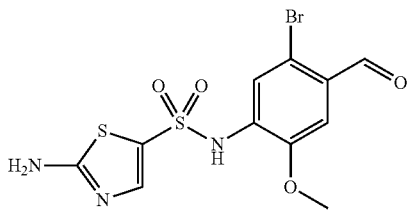 [SMILES: COc1cc(C=O)c(Br)cc1NS(=O)(=O)c1cnc(N)s1]

To a solution of 168 (100 mg, 0.25 mmol) in DMF (2 mL) and DCM (5 mL) is added activated manganese(IV) oxide (376 mg, 4.33 mmol). After stirring at room temperature for 2 hours, the mixture is filtered through a pad of Celite and concentrated to give C15 as a yellow solid (80 mg, 81% yield). (MS: [M+H]$^+$ 392.0)

Preparation of C16

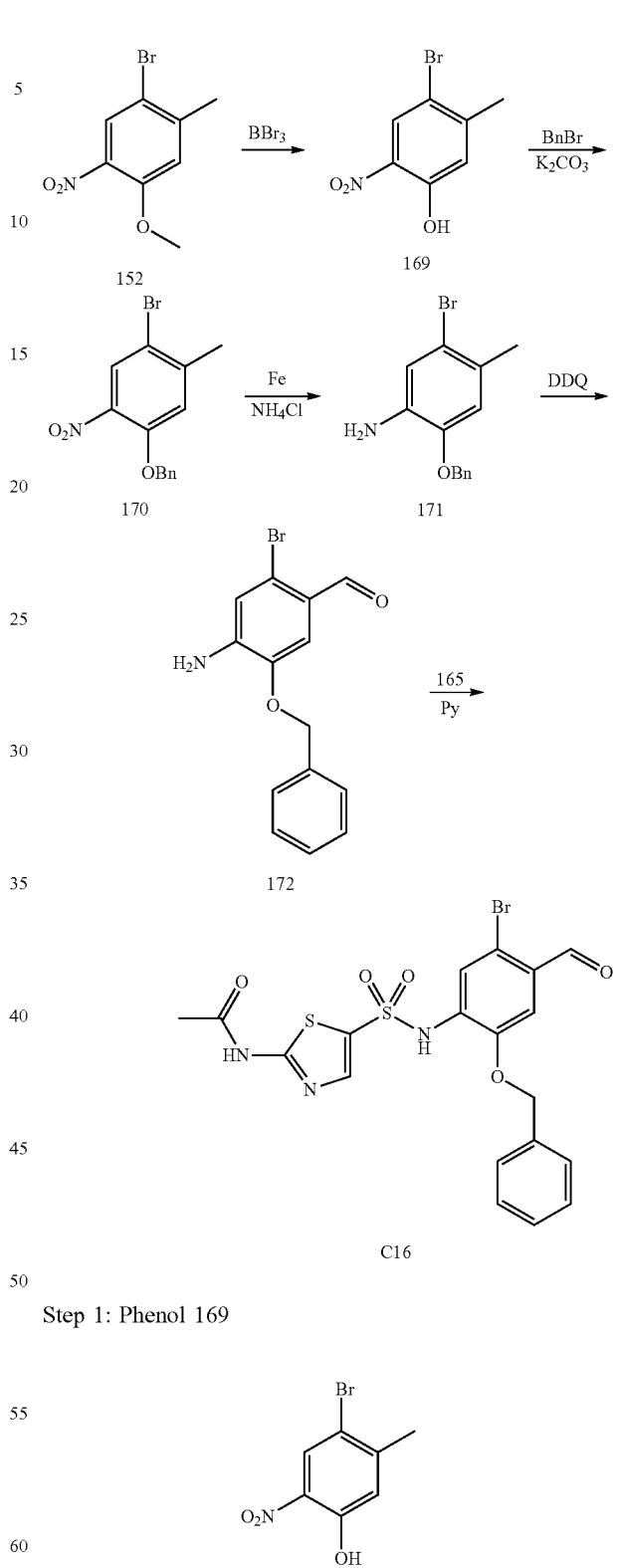

Step 1: Phenol 169

To a solution of 152 (2.5 g, 10.2 mmol) in DCM (30 mL) is added boron tribromide (3.0 mL, 30.5 mmol) dropwise at −78° C. After stirring at room temperature overnight, MeOH (2 mL) is added at 0° C. and the mixture is extracted with DCM (20 mL×3). The combined organic layers are dried over anhydrous sodium sulfate, filtered, concentrated, and purified by silica gel column chromatography (MeOH:DCM=1:100) to give 169 as a yellow solid (2.3 g, 98% yield). (MS: [M+H]$^+$ 233.0)

Step 2: Benzyl Ether 170

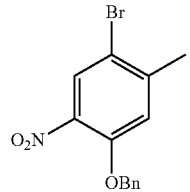 [SMILES: Cc1cc(OCc2ccccc2)c([N+](=O)[O-])cc1Br]

To a solution of 169 (2.3 g, 9.91 mmol) in DMF (20 mL) is added potassium carbonate (4.11 g, 29.7 mmol) and benzyl bromide (1.4 mL, 11.9 mmol). After stirring at 80° C. overnight, the mixture is cooled to room temperature followed by addition of EA (40 mL) and water (20 mL). The layers are separated and the aqueous layer is extracted with EA (40 mL×3). The combined organic layers are washed with saturated ammonium chloride aqueous solution, dried over anhydrous sodium sulfate, filtered, concentrated, and purified by silica gel column chromatography (MeOH:DCM=1:100) to give 170 as a yellow solid (2.7 g, 85% yield). (MS: [M+H]$^+$ 323.2)

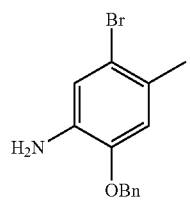

Step 3: Aniline 171

To a mixture of 170 (1.7 g, 5.28 mmol) in saturated ammonium chloride aqueous solution (4 mL) and EtOH (20 mL) is added iron powder (1.8 g, 31.66 mmol). After stirring at 90° C. overnight, the mixture is filtered, and extracted with EA (40 mL×3). The combined organic layers are dried over anhydrous sodium sulfate, filtered, concentrated, and purified by silica gel column chromatography (MeOH:DCM=1:100) to give 171 as a white solid (1.1 g, 71% yield). (MS: [M+H]$^+$ 293.2)

Step 4: Aldehyde 172

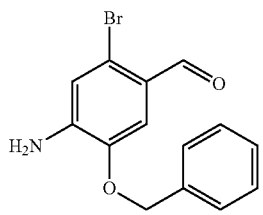 [SMILES: Nc1cc(Br)c(C=O)cc1OCc1ccccc1]

To a solution of 171 (1.1 g, 3.76 mmol) in THF (25 mL), MeOH (5 mL), and water (1 mL) is added DDQ (2.6 g 11.3 mmol) at 0° C. After stirring at room temperature for 30 minutes, the mixture is extracted with EA (30 mL×3). The combined organic layers are washed with brine, dried over anhydrous sodium sulfate, filtered, concentrated, and puri-fied by silica gel column chromatography (EA:PE=1:10) to give 172 as a brown solid (1.1 g, 95% yield). (MS: [M+H]$^+$ 307.2)

Step 5: C16

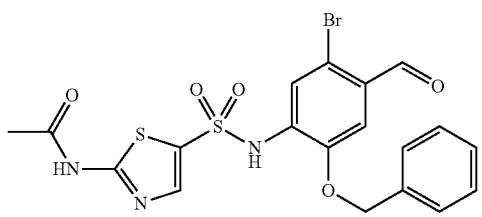 [SMILES: CC(=O)Nc1ncc(S(=O)(=O)Nc2cc(Br)c(C=O)cc2OCc2ccccc2)s1]

To a solution of 172 (700 mg 2.29 mmol) and Py (0.7 mL, 9.15 mmol) in DCM (10 mL) is added 165 (660 mg 2.74 mmol) at 0° C. After stirring at room temperature overnight, the mixture is concentrated and purified by silica gel column chromatography (MeOH:DCM=1:100) to give C16 as a grey solid (430 mg 37% yield). (MS: [M+H]$^+$ 511.4)

Preparation of C17

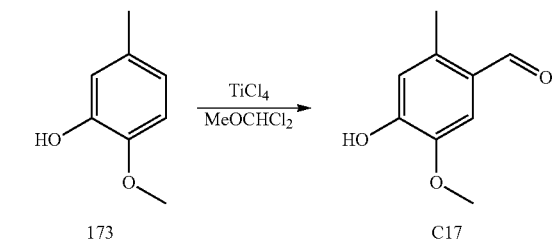

To a solution of 173 (1.0 g, 7.2 mmol) in DCM (20 mL) is added TiCl$_4$ solution (1M, 15 mL, 15.0 mmol) at −78° C. After stirring for 10 minutes, dichloromethyl methyl ether (1.1 mL, 12.2 mmol) is added and the mixture is stirred at room temperature for 4 hours. The mixture is then poured onto ice and the solid is collected by filtration, washed with EA and ether, and dried to give crude C17 as a brown powder (131 mg, 11% yield).

Preparation of C18

Step 4: indoline 178

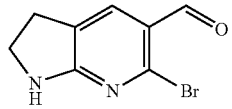

To a solution of 177 (1.0 g, 2.9 mmol) in DCM (5 mL) is added TFA (10 mL). After stirring at room temperature for 16 hours, the mixture is concentrated and purified by silica gel column chromatography (EA:PE=1:10) to give 178 as an off-white solid (600 mg, 92% yield). (MS: [M+H]$^+$ 226.0)

Step 5: C18

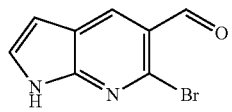

To a solution of 178 (800 mg, 3.5 mmol) in DCM (8 mL) is added activated manganese(IV) oxide (1.2 g, 14.1 mmol). After stirring at room temperature for 16 hours, the mixture is filtered and concentrated to give crude C18 as a white solid (700 mg, 87% yield). (MS: [M+H]$^+$ 224.0)

Preparation of C19

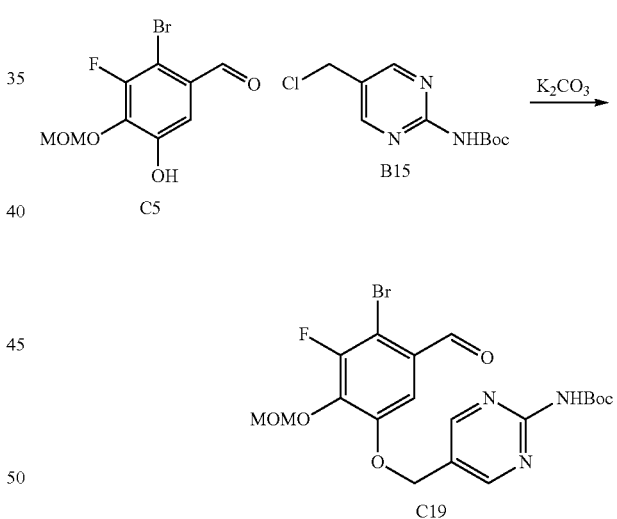

To a solution of C5 (100 mg, 0.36 mmol) in DMF (5 mL) is added B15 (100 mg, 0.43 mmol) and potassium carbonate (99.4 mg, 0.72 mmol). After stirring at 50° C. for 2 hours, the mixture is diluted with EA (10 mL), washed with aqueous lithium chloride solution (10 mL×3), dried over anhydrous sodium sulfate, fitered, concentrated, and purified by silica gel column chromatography (MeOH:DCM=1:50) to give C19 as a white solid (120 mg, 86% yield). (MS: [M+H]$^+$ 487.3)

The following compounds are prepared by essentially the same method as for C19 from B26, B27, B28, and B29, respectively, with an option of removing MOMO group using essentially the same method as for C8.

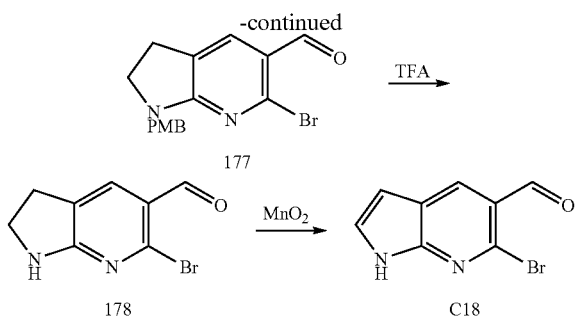

Step 1: Indoline 175

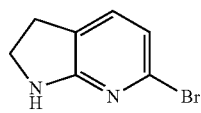

To a mixture of 174 (5.0 g, 25.5 mmol) in HOAc (10 mx) is added sodium cyanoborohydride (4.8 g, 76.5 mmol) at 0° C. After stirring at room temperature for 2 hours, the mixture is poured into saturated sodium bicarbonate solution (100 mL) slowly and extracted with EA (50 mL×6). The combined organic layers are dried over anhydrous sodium sulfate, filtered, concentrated, and purified by silica gel column chromatography (EA:PE=1:10) to give 175 as a white solid (3.5 g 69% yield). (MS: [M+H]$^+$ 198.0)

Step 2: Indoline 176

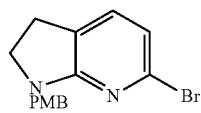

To a mixture of 175 (8801.2 g, 4.4 mmol) in DMF (10 methoxybenzyl chloride (835 m 5.3 mmol) in DMF (8 mL) is added potassium carbonate (920 mg, 6.6 mmol) and sodium iodide (88 mg, 0.6 mmol). After stirring at 50° C. for 16 hours, the mixture is poured into saturated ammonium chloride solution (20 mL), and extracted with EA (50 mL×3). The combined organic layers are dried over anhydrous sodium sulfate, filtered, concentrated, and purified by silica gel column chromatography (EA:PE=1:30) to give 176 as a colorless oil (1.2 g 85% yield). (MS: [M+H]$^+$ 318.0)

Step 3: Aldehyde 177

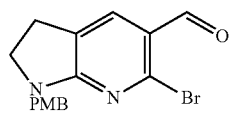

To a mixture of 176 (1.2 g 3.8 mmol) in DMF (10 mL) is added phosphoryl chloride (867 mg, 5.7 mmol) dropwise at 0° C. After stirring at room temperature for 1 hour and at 50° C. for 1 hour, the mixture is poured into saturated ammonium chloride solution (30 mL) and extracted with EA (50 mL×3). The combined organic layers are dried over anhydrous sodium sulfate, filtered, concentrated, and purified by silica gel column chromatography (EA:PE=1:10) to give 177 as a light yellow oil (1.2 g, 91% yield). (MS: [M+H]$^+$ 346.0)

| Intermediate | Structure | MS |
|---|---|---|
| C20 | 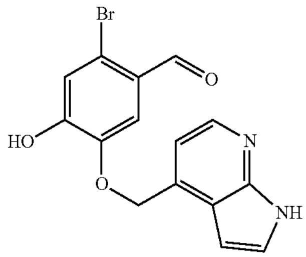 [SMILES: O=Cc1cc(OCc2ccnc3[nH]ccc23)c(O)cc1Br] | [M + H]+ 349.0 |
| C21 | 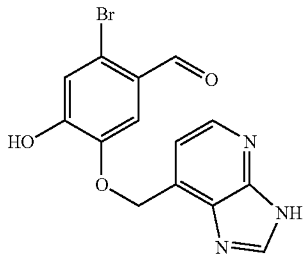 [SMILES: O=Cc1cc(OCc2ccnc3[nH]cnc23)c(O)cc1Br] | [M + H]+ 349.9 |
| C22 | 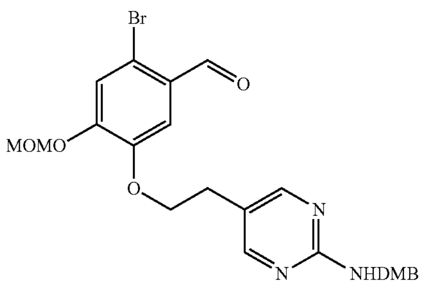 | [M + H]+ 533.9 |
| C23 | 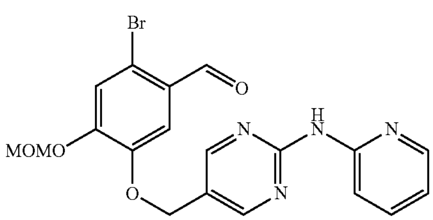 | [M + H]+ 446.8 |

Preparation of C24

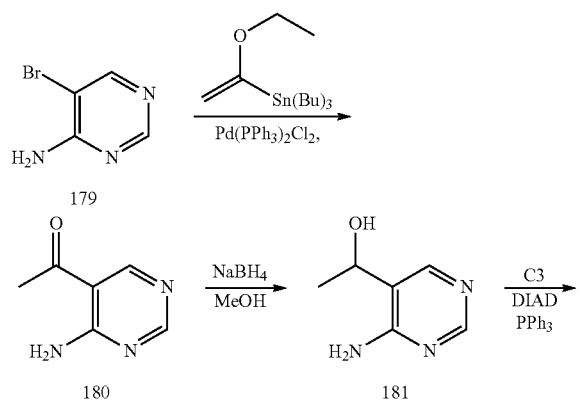

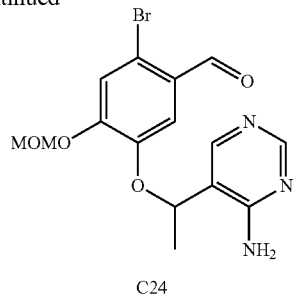

Step 1: Ketone 180

To a solution of 179 (260 mg, 1.5 mmol) in DMF (4 mL) is added tributyl(1-ethoxyvinyl)tin (543 mg, 1.5 mmol) and Pd(dppf)Cl$_2$ (110 mg, 0.15 mmol). After stirring at 100° C. for 16 hours, the mixture is cooled to room temperature, filtered, concentrated, and purified by silica gel column chromatography (MeOH:DCM=1:50) to give 180 as a brown solid (30 mg, 15% yield). (MS: [M+H]+ 138.1)

Step 2: Alcohol 181

Following Procedure C using 180 (137 mg, 1.0 mmol), MeOH, and sodium borohydride (19 mg 0.5 mmol), purify with silica gel column chromatography (MeOH:DCM=1:30) to give 181 as a white solid (100 mg, 73% yield). (MS: [M+H]+ 140.2)

Step 3: C24

To a mixture of C3 (130 mg, 0.5 mmol), 181 (70 mg, 0.5 mmol), and PPh$_3$ (262 mg, 1.0 mmol) in THF is added DIAD (200 mg, 1.0 mmol) at room temperature. After stirring at room temperature for 30 minutes, the mixture is concentrated and purified by silica gel column chromatography (MeOH:DCM=1:30) to give C24 as a white solid (60 mg, 32% yield). (MS: [M+H]+ 383.3)

Preparation of C25

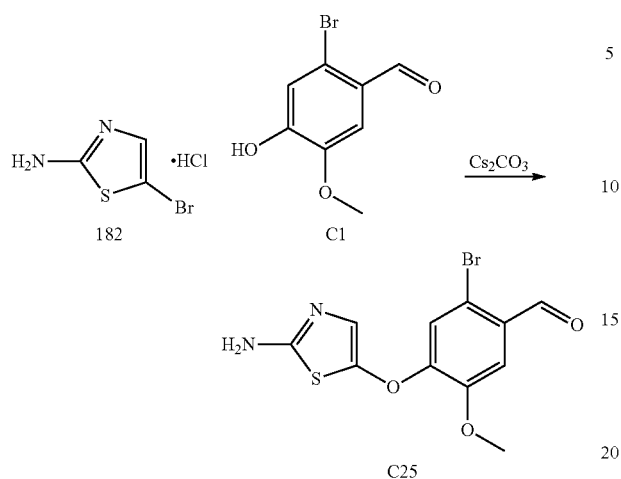

A mixture of 182 (113 mg, 0.44 mmol), C1 (50 mg, 0.22 mmol) and cesium carbonate (143 mg, 0.44 mmol) in MeCN (2 mL) is stirred at 70° C. for 1.5 hours. The mixture is then cooled to room temperature, diluted with DCM (10 mL), washed with water (10 mL×3), dried over anhydrous sodium sulfate, and concentrated to give crude C25 as a brown solid (80 mg, 56% yield). (MS: [M+H]$^+$ 330.1)

Preparation of C26

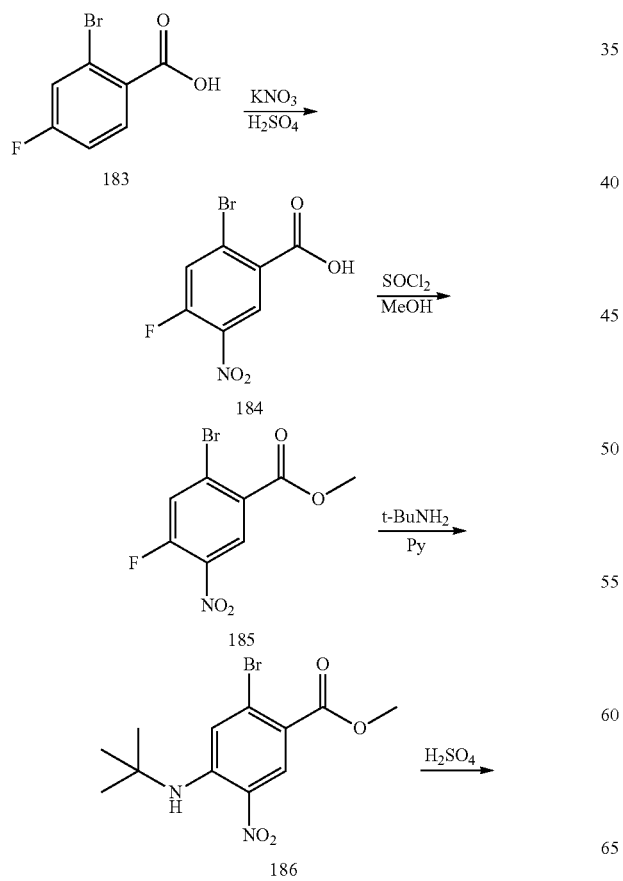

Step 1: Acid 184

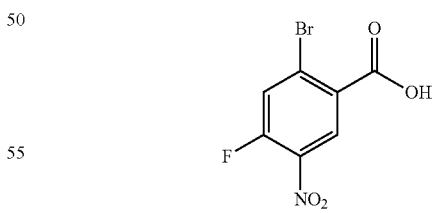

To a solution of 183 (25 g, 114 mmol) in sulfuric acid (228 mL) is added potassium nitrate (11.5 g 114 mmol) at 0° C. over 10 minutes. After stirring at room temperature for 3 hours, the mixture is poured onto ice and the solid is collected by filtration, washed with water, dried, and purified by prep-HPLC (water/MeOH with 0.1% TFA, 35% to 60%) to give 184 as a white solid (5.6 g, 52% yield). (MS: [M+H]$^+$ 265.2)

Step 2: Ester 185

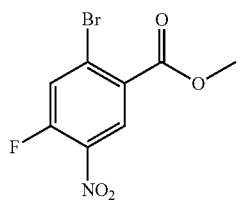

To a solution of 184 (5.5 g, 20.9 mmol) in MeOH (50 mL) is added thionyl chloride (5 g, 42 mmol) dropwise at 0° C. After stirring at 120° C. for 4 hours, the mixture is concentrated and purified by silica gel column chromatography (EA:PE=1:4) to give 185 as a white solid (4.0 g, 70% yield). (MS: [M+H]$^+$ 279.1)

Step 3: Aniline 186

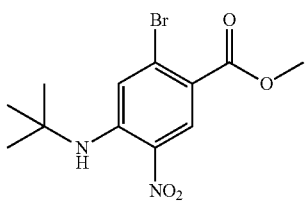 [SMILES: COC(=O)c1cc([N+](=O)[O-])c(NC(C)(C)C)cc1Br]

A mixture of 185 (55 mg, 0.2 mmol), tert-butylamine (29.2 mg, 0.4 mmol), and Py (1 mL) is stirred at room temperature for 18 hours. The mixture is then diluted with EA (20 mL), washed with 1N HCl solution (5 mL), dried over anhydrous sodium sulfate, and concentrated to give crude 186 as a yellow solid (30 mg, 45% yield). (MS: [M+H]$^+$ 332.1)

Step 4: Aniline 187

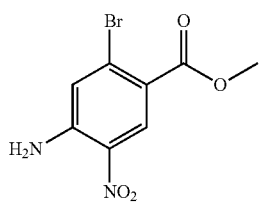

To a solution of crude 186 (4.0 g 12.1 mmol) in MeOH (20 mL) is added concentrated sulfuric acid (1 mL) at 0° C. After stirring at 100° C. for 16 hours, the mixture is diluted with saturated aqueous sodium bicarbonate solution (20 mL) and extracted with EA (50 mL×3). The combined organic layers are dried over anhydrous sodium sulfate, filtered, and concentrated to give crude 187 as a brown solid (3.0 g, 91% yield). (MS: [M+H]$^+$ 276.2)

Step 5: Ester 188

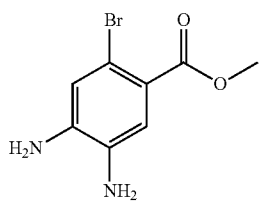

A mixture of 187 (3.0 g, 11 mmol), iron powder (3.0 g, 55 mmol), saturated aqueous ammonium chloride solution (10 mL), and EtOH (10 mL) is stirred at 80° C. for 1.5 hours. The mixture is then filtered, diluted with water and extracted with EA (50 mL×3). The combined organic layers are dried over anhydrous sodium sulfate, filtered, and concentrated to give crude 188 as a brown solid (2.4 g 92% yield). (MS: [M+H]$^+$ 246.1)

Step 6: Benzotriazole 189

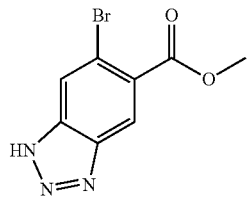

To a solution of crude 188 (2.0 g 8.20 mmol) in MeOH is added 1 N HCl (120 mL) and sodium nitrite (622 mg, 9.0 mmol) at 0° C. After stirring at room temperature for 1 hour, saturated aqueous sodium bicarbonate solution (50 mL) is added and the mixture is extracted with EA (100 mL×3). The combined organic layers are dried over anhydrous sodium sulfate, filtered, and concentrated to give crude 189 as a brown solid (1.5 g, 83% yield). (MS: [M+H]$^+$ 256.2)

Step 7: alcohol 190

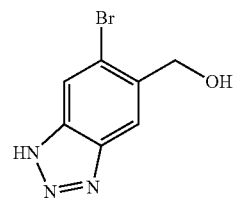 [SMILES: OCc1cc2nn[nH]c2cc1Br]

Following Procedure E using 189 (1.0 g, 3.92 mmol), THF (10 mL), and LAH (300 mg, 8.0 mmol), quench the reaction with water (10 mL), acidify the mixture with 6 N HCl solution to pH 3, extract with THF (30 mL×3), dry the combined organic layers over anhydrous sodium sulfate, filter, and concentrate to give crude 190 as a brown solid (700 mg, 79% yield). (MS: [M+H]$^+$ 229.1)

Step 8: C26

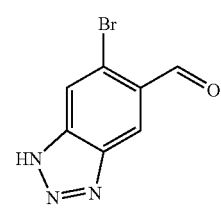

A mixture of 190 (700 mg, 3.08 mmol), PDC (1.27 g, 3.39 mmol) in acetone (20 mL) is stirred at room temperature for 4 hours. The mixture is then concentrated and purified by silica gel column chromatography (EA:PE=1:2) to give C26 as a gray solid (200 mg, 29% yield). (MS: [M+H]$^+$ 227.2)

Preparation of C27

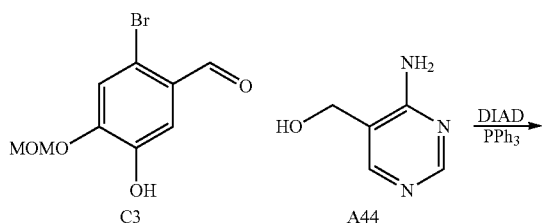

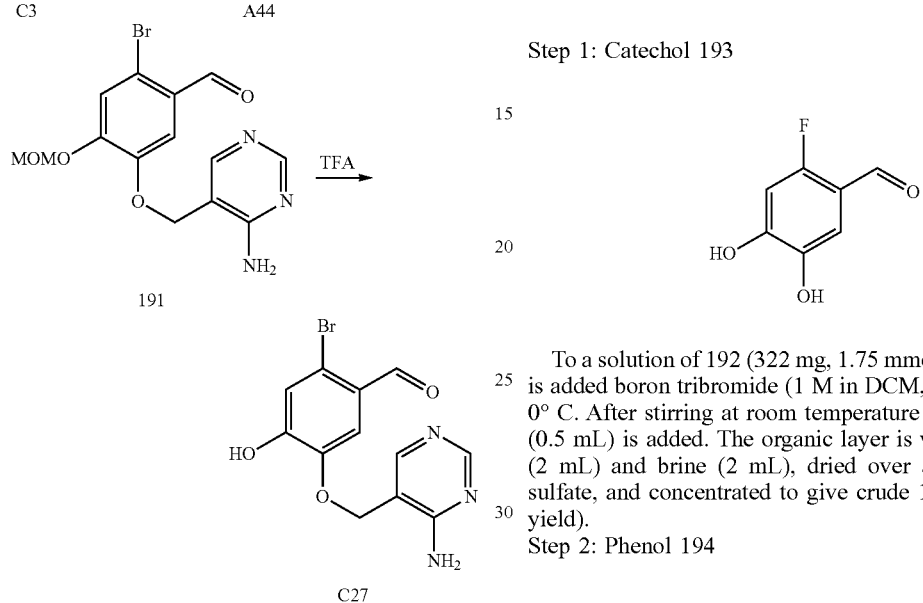

Prepared by essentially the same methods as for C8 to give C27 as an off-white solid. (MS: [M+H]⁺ 323.9)

Preparation of C28

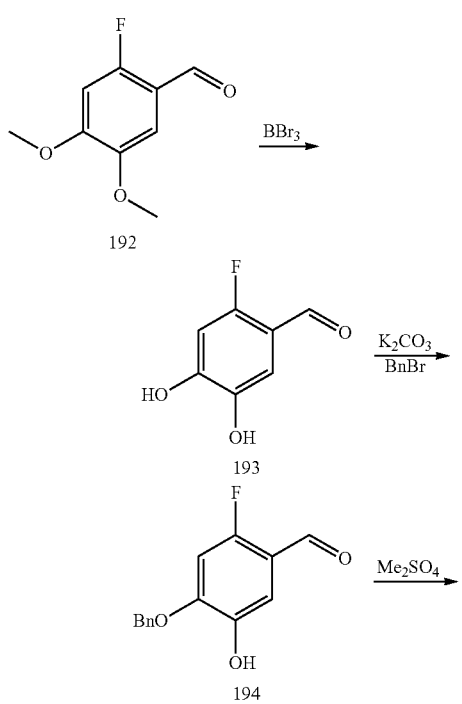

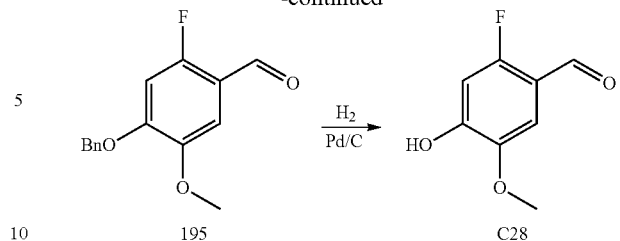

Step 1: Catechol 193

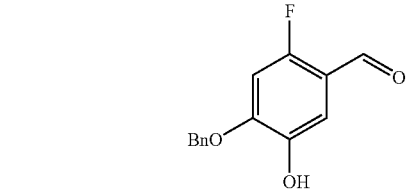 [SMILES: O=Cc1cc(O)c(OCc2ccccc2)cc1F]

To a solution of 192 (322 mg, 1.75 mmol) in DCM (2 mL) is added boron tribromide (1 M in DCM, 4 mL, 4 mmol) at 0° C. After stirring at room temperature for 2 hours, water (0.5 mL) is added. The organic layer is washed with water (2 mL) and brine (2 mL), dried over anhydrous sodium sulfate, and concentrated to give crude 193 (280 mg, 99% yield).

Step 2: Phenol 194

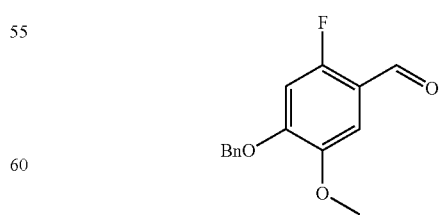

To a mixture of crude 193 (34 mg) and potassium carbonate (45 mg, 0.33 mmol) in acetone (2 mL) is added benzyl bromide (0.03 mL, 0.24 mmol). After stirring overnight, water (1 mL) and EA (10 mL) are added. The layers are separated and the organic layer is washed with water (2 mL) and brine (2 mL), dried over anhydrous sodium sulfate, concentrated, and purified by silica gel column chromatography (EA:hexanes=1:3) to give 194 as white solid (30 mg, 55% yield).

Step 3: Methyl Ether 195

To a mixture of 194 (13 mg, 0.05 mmol) and potassium carbonate (11 mg, 0.08 mmol) in acetone (1.5 mL) is added dimethyl sulfate (0.015 mL, 0.16 mmol). After stirring at reflux for 2 hours and cooled back to room temperature, the mixture is concentrated and then EA (10 mL) is added. The organic layer is washed with 5% ammonium chloride aqueous solution (2 mL), water (5 mL), and brine (5 mL), dried over anhydrous sodium sulfate, and concentrated to give crude 195 (15 mg, 99% yield).

Step 4: C28

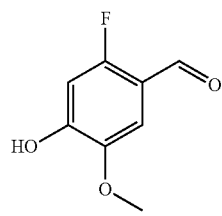

To a solution of 195 (15 mg, 0.058 mmol) in MeOH (1.0 mL) is added Pd/C (20 wt. %, 3 mg). After stirring overnight, the mixture is purified by silica gel column chromatography (EA/hexanes=1:3) to give C28 as a white solid (8 mg, 81% yield). (MS: [M+H]+ 171.2).

Preparation of C29

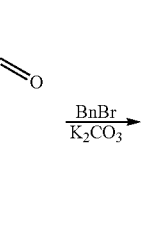

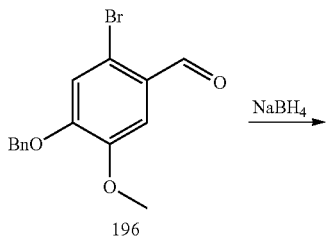

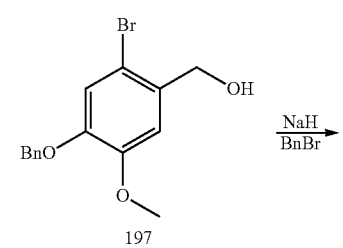

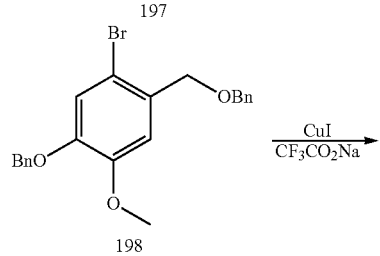

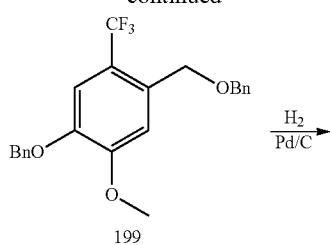

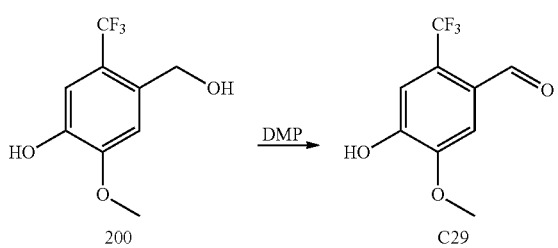

Step 1: Benzyl Ether 196

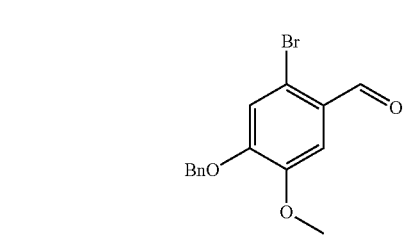

To a mixture of C1 (230 mg, 1.0 mmol) and potassium carbonate (180 mg, 1.3 mmol) in DMF (1.0 mL) is added benzyl bromide (0.125 mL, 1.15 mmol). After stirring at 60° C. for 1.5 hours, the mixture is cooled to room temperature and water (2 mL) and EA (10 mL) are added. The layers are separated and the organic layer is washed by brine (5 mL), dried over anhydrous sodium sulfate, and concentrated to give crude 196 (300 mg, 94% yield).

Step 2: Alcohol 197

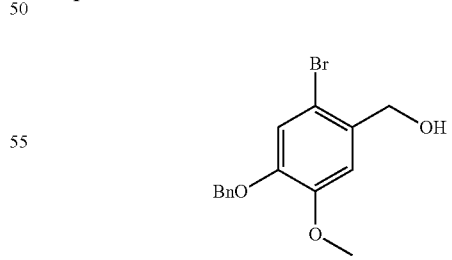

Following Procedure C using crude 196 (300 mg, 0.94 mmol), THF (1.5 mL), water (0.3 mL), and sodium borohydride (20 mg, 0.54 mmol), dilute the reaction mixture with EA (15 mL), washed with brine (5 mL), dried over anhydrous sodium sulfate, and concentrate to give crude 197 (286 mg, 95% yield).

Step 3: Benzyl Ether 198

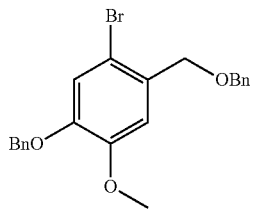 [SMILES: COc1cc(COCc2ccccc2)c(Br)cc1OCc1ccccc1]

To a mixture of NaH (53 mg 1.33 mmol) in THF (1 mL) is added a solution of 197 (286 mg, 0.89 mmol) at 0° C. After stirring for 30 min, benzyl bromide (0.14 mL, 1.15 mmol) is added and the mixture is stirred at room temperature overnight. The mixture is then cooled to 0° C. and saturated ammonium chloride solution (1 mL) is added. The mixture is then extracted with EA (10 mL) and the organic layer is washed with brine (5 mL), dried over anhydrous sodium sulfate, concentrated and purified by silica gel flash chromatography (EA:hexanes=1:10) to give 198 as a white solid (330 mg, 91% yield).

Step 4: Trifluoride 199

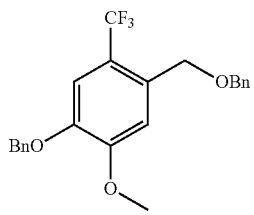 [SMILES: COc1cc(COCc2ccccc2)c(C(F)(F)F)cc1OCc1ccccc1]

A mixture of 198 (52 mg, 0.125 mmol), sodium trifluoroacetate (51 mg, 0.38 mmol), and CuI (48 mg, 0.25 mmol) in DMF (1 mL) and dimethyl acetamide (0.5 mL) is stirred at 152° C. After cooling to room temperature, water (2 mL) and EA (15 mL) are added. The organic layer is washed with brine (5 mL), dried over anhydrous sodium sulfate, and concentrated to give crude 199 (50 mg).

Step 5: Alcohol 200

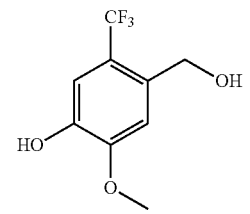

A solution of crude 199 (10 mg) and Pd/C (30 wt. %, 1.5 mg) in MeOH (1.0 mL) and THF (0.2 mL) is stirred at 50° C. under hydrogen for 2 hours. The mixture is then purified by prep-TLC (EA:hexanes=1:2) to give 200 as a white solid (5 mg, 89% yield for two steps). (MS: [M+H]$^+$ 223.0)

Step 6: C29

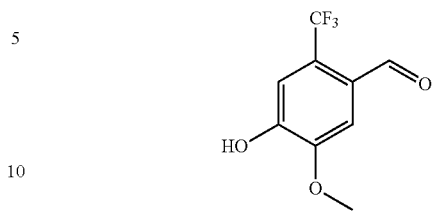

Following Procedure G using 200 (5 mg, 0.022 mmol), DCM (1.0 mL), DMP (15 mg, 0.045 mmol), and water (0.6 µL, 0.045 mmol), react for 30 minutes and then add EA (5 mL), wash with brine (5 mL), dried over anhydrous sodium sulfate, and concentrated to give crude C29 (1.2 mg, 24% yield). (MS: [M+H]$^+$ 221.1)

Preparation C30

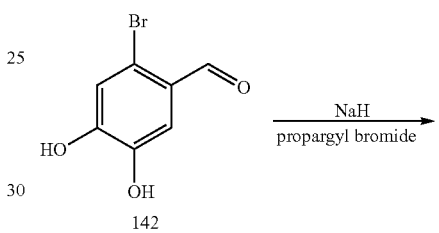

A mixture of NaH (95 mg, 2.4 mmol) in DMSO (1 mL) is stirred for 10 minutes before a solution of 142 (235 mg, 1.1 mmol) in DMSO (1 mL) is added. After stirring for 30 minutes, propargyl bromide (0.13 mL, 1.2 mmol) is added dropwise and the mixture is stirred overnight before ice water (0.5 mL) is added at 0° C. The mixture is then extracted with EA (5 mL), and the organic layer is washed with water (1 mL) and brine (1 mL), dried over anhydrous sodium sulfate, concentrated, and purified by silica gel column chromatography (EA:hexanes=1:3) to give C30 as a white solid (180 mg, 65% yield). (MS: [M-1]$^-$ 253.2)

Preparation of C31

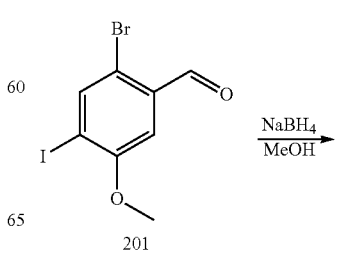

Step 2: Cyanide 203

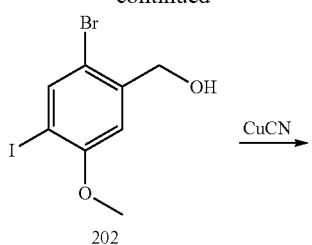

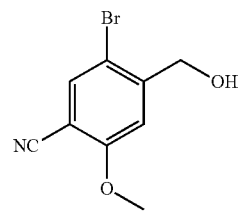

A mixture of 202 (1.37 g, 4.0 mmol) and CuCN (0.39 g 4.4 mmol) in DMF (10 mL) is stirred at 85° C. overnight. After cooling to room temperature, the mixture is diluted with EA (50 mL), filtered, washed with saturated sodium bicarbonate (50 mL) and brine (50 mL), dried over anhydrous sodium sulfate, concentrated, and purified by silica gel flash chromatography (EA:hexanes=1:3) to give 203 as a white solid (0.57 g, 59% yield). (MS: [M+H]$^+$ 242.2)

Step 3: Tetrazole 204

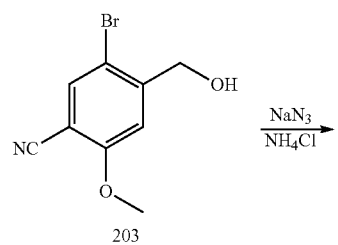

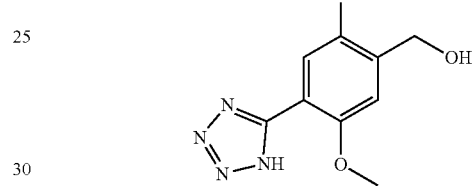

A mixture of 203 (0.12 g 0.5 mmol), ammonium chloride (0.11 g 4 mmol) and sodium azide in DMF (2 mL) is stirred at 100° C. overnight. After cooling to room temperature, the mixture is diluted with EA (10 mL) and 1 N HCl (4 mL). The layers are separated and the organic layer is washed with water (5 mL) and brine (5 mL), dried over anhydrous sodium sulfate, and concentrated to give crude 204 (96 mg, 67% yield). (MS: [M+H]$^+$ 285.2)

Step 4: C31

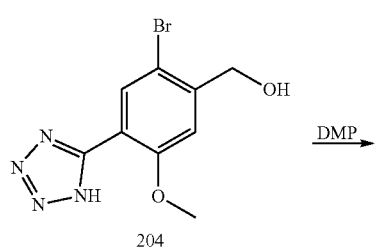

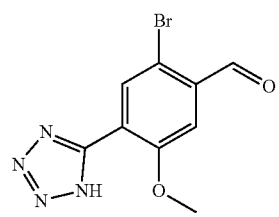 [SMILES: COc1cc(C=O)c(Br)cc1-c1nnn[nH]1]

Following Procedure G using 204 (29 mg, 0.1 mmol), DCM (1.0 mL), and DMP (64 mg, 0.15 mmol) to give C31 (30 mg, 99% yield). (MS: [M+H]$^+$ 283.2)

Preparation of C32

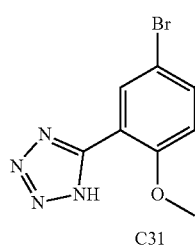

Step 1: Alcohol 202

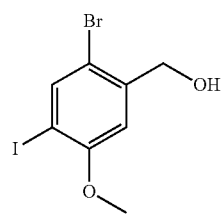

Follow Procedure C using 201 (3.0 g, 8.8 mmol), MeOH (30 mL), and sodium borohydride (0.57 g, 15 mmol), quench with saturated ammonium chloride (50 mL) and dilute with EA (200 mL), wash with water (100 mL) and brine (50 mL), dried over anhydrous sodium sulfate, and concentrate to give 202 (2.9 g, 99% yield). (MS: [M+H]$^+$ 343.0)

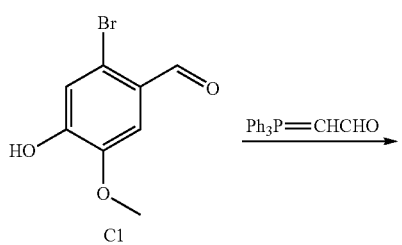

149

-continued

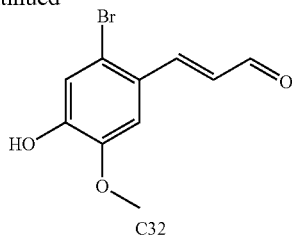

C32

A solution of C1 (200 mg, 0.87 mmol) and (triphenylphosphoranyliden)acetaldehyde (264 mg, 0.87 mmol) in toluene (5 mL) is stirred at 80° C. overnight. The mixture is then concentrated and purified by prep-TLC (EA: hexanes=7:10) to give C32 as a yellow solid (5 mg, 2% yield).

Preparation of C33

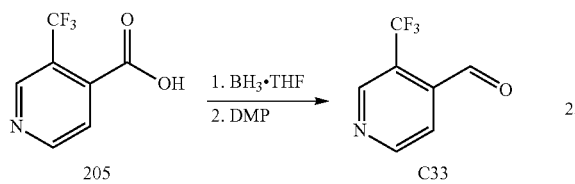

205 → C33

To a solution of 205 (100 mg, 0.52 mmol) in THF (2 mL) is added borane tetrahydrofuran complex (1.0 M, 1.57 mL, 1.57 mmol) at 0° C. After stirring at room temperature overnight, water (1 mL) is added the mixture is diluted with EA (10 mL). The organic layer is washed with 1 N HCl (5 mL) and brine (5 mL×3), dried over anhydrous sodium sulfate, and concentrated. Next follow Procedure G using half of the residue obtained above, DCM (2.0 mL), and DMP (250 mg, 0.6 mmol) to give C32 as a white solid (36 mg, 79% yield for two steps). (MS: [M+H]⁺ 176.2).

Preparation of C34

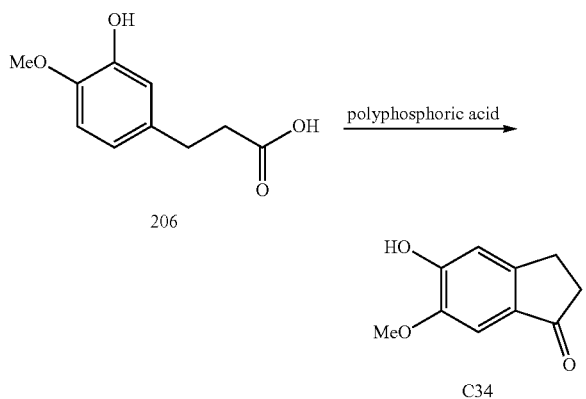

206

C34

A mixture of 206 (147 mg, 1 mmol) and polyphosphoric acid (2.11 g) in chloroform (0.1 mL) is stirred at 80° C. for 2 hours. After cooling to room temperature, saturated sodium bicarbonate (200 mL) is added slowly and the mixture is extracted with EA (300 mL×4). The combined organic layers are washed with brine (150 mL×3), dried over anhydrous sodium sulfate, concentrated to give C34 as a yellow solid (75 mg, 42% yield). (MS: [M+H]⁺ 179.2)

150

Preparation of C35

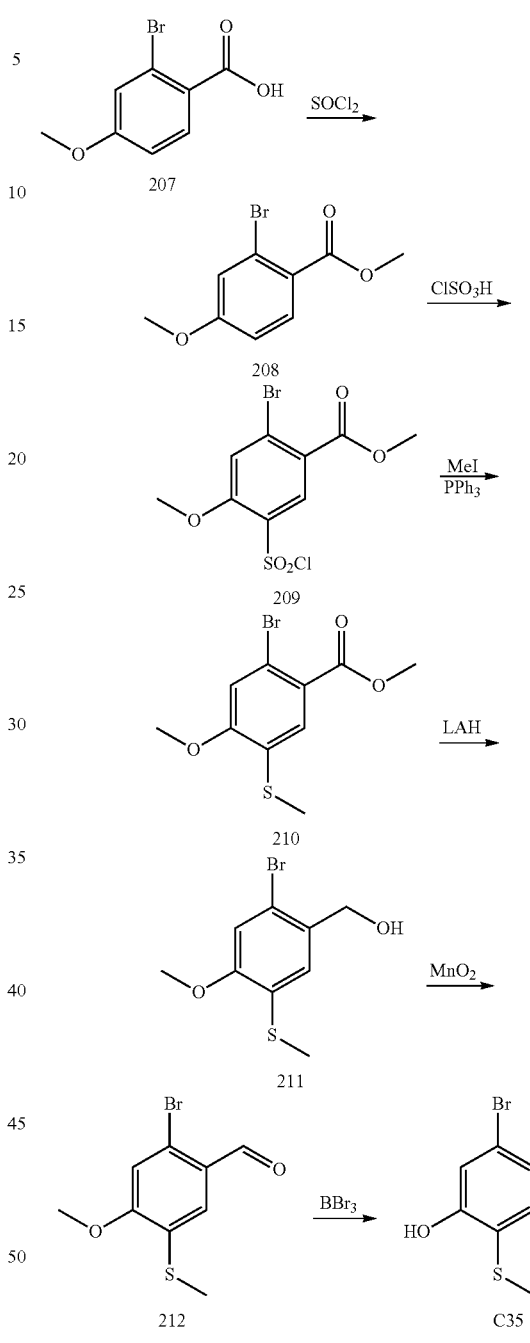

Step 1: Ester 208

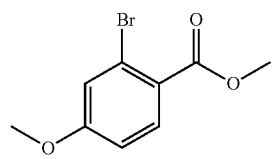

To a solution of 207 (5.0 g 21.6 mmol) in MeOH (50 mL) is added thionyl chloride (7.7 g 64.9 mmol, 4.7 mL) at 0° C. After stirring at 80° C. for 2 hours, the mixture is concentrated and the residue is dissolved in DCM (200 mL), washed with saturated sodium bicarbonate solution (50 mL×3), dried over anhydrous sodium sulfate, and concentrated to give crude 208 as a yellow oil (4.80 g 91% yield).
Step 2: Sulfonyl Chloride 209

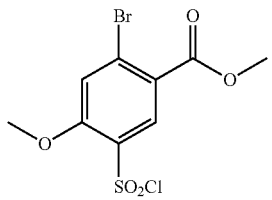

To A mixture of 208 (500 mg, 2.04 mmol) and chlorosulfonic acid (1.19 g 10.2 mmol, 0.68 mm) is stirred at 60° C. for 12 hours, the mixture is diluted with DCM (10 mL), washed with water (3 mL×3) and brine (3 mL×3), dried over anhydrous sodium sulfate, concentrated, and purified by prep-TLC (EA:PE=1:3) to provide 209 as a white solid (500 mg, 71% yield).
Step 3: Methyl Sulfide 210

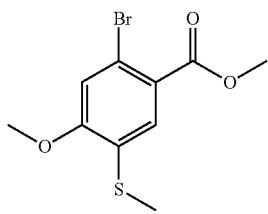

To a solution of 209 (2.0 g, 5.82 mmol) in toluene (20 mo) is added PPh$_3$ (4.58 g 17.5 mmol) in toluene (20 ms) at 0° C. After stirring at 15° C. for 2 hours, TEA (1.77 g, 17.5 mmol, 2.4 mL) and methyl iodide (2.48 g 17.5 dried mmol, 1.1 m) are added and the mixture is stirred at 15° C. for another 30 minutes before it is concentrated and purified by silica gel column chromatography (EA:PE=1:10 to 1:5) to give 210 as a white solid (1.69 g, 30% yield).
Step 4: Alcohol 211

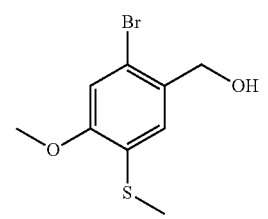

Following Procedure E using 210 (500 mg, 1.72 mmol), THF (10 mL), and LAH (98 mg, 2.58 mmol), react at −20° C. to give 211 as a white solid (400 mg, 88% yield).
Step 5: Aldehyde 212

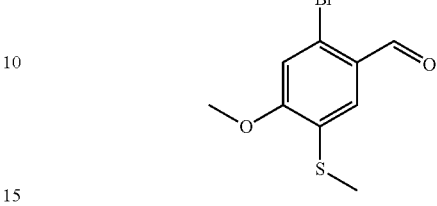

Following the procedure for 8 using 211 (350 mg, 1.33 mmol), DCM (5 mL), activated manganese(IV) oxide (1.16 g, 13.3 mmol), react at 15° C. for 12 hours to give crude 212 as a yellow solid (320 mg, 92% yield).
Step 6: C35

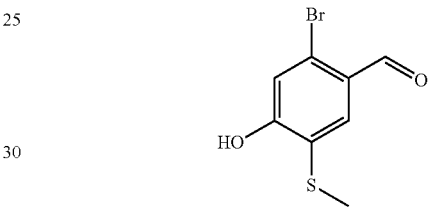

To a solution of 212 (320 mg, 1.23 mmol) in DCM (5 mL) is added with boron tribromide (308 mg, 1.23 mmol, 0.12 mL) at −40° C. After stirring at 15° C. for 12 hours, MeOH is added and the mixture is washed with saturated sodium carbonate (20 mL×3). The aqueous solution is adjusted with 1 N HCl to pH 4-5 and then extracted with DCM (30 mL×3). The combined organic layers are dried over anhydrous sodium sulfate and concentrated to give C35 as a white solid (130 mg, 43% yield).

The following compound is prepared by essentially the same method as for C19.

| Intermediate | Building blocks | Structure | MS |
|---|---|---|---|
| CA1 | C5, B19 | (Br, F, MOMO, pyrimidine-N(Boc)₂ structure) | [M + H]⁺ 600.1 |

Preparation of CB1

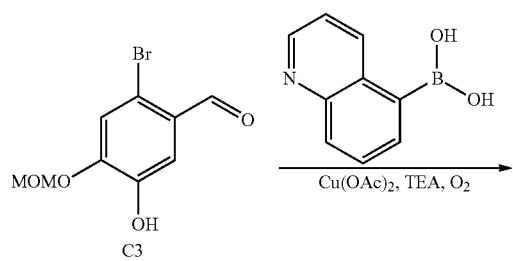

To a solution of C3 (200 mg 1.2 mmol) and 5-quinolinylboronic acid (200 mg 1.5 mmol) in DCM (30 mL) is added Cu(OAc)₂ (130 mg 1.03 mmol) and TEA (300 mg 3.11 mmol). After stirring at room temperature under an oxygen atmosphere for 2 hours, the mixture is concentrated and purified by silica gel column chromatography (EA:PE=1:10 to 1:3) to give CB1 (85 mg, 29%) as a colorless oil. (MS: [M+H]⁺ 388.0)

The following compounds are prepared by essentially the same method as for C36.

| Intermediate | Structure | MS |
|---|---|---|
| CB2 | (structure) | [M + H]⁺ 388.0 |
| CB3 | (structure) | [M + H]⁺ 414.0 |
| CB4 | (structure) | [M + H]⁺ 393.0 |
| CB5 | (structure) | [M + H]⁺ 414.0 |

Preparation of CB6

(reaction scheme: 213 → 214 → CB6; reagents: acetohydroxamic acid, K₂CO₃; then HMTA, TFA)

Step 1: Phenol 214

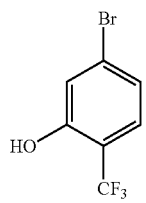

To a mixture of 213 (2.0 g, 8.23 mmol) and acetohydroxamic acid (2.47 g, 32.9 mmol) in DMSO (10 mL) is added potassium carbonate (5.69 g, 41.2 mmol). After stirring at 80° C. for 16 hours, the mixture is diluted EA (150 mL), washed with brine (50 mL×3), dried over anhydrous sodium sulfate, filtered, concentrated, and purified by silica gel column chromatography (EA:PE=1:5) to give 214 as a white solid (1.3 g, 66%). (MS: [M+H]$^+$ 240.9)

Step 2: CB6

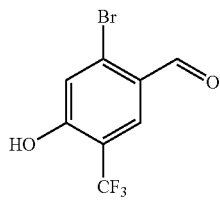

A mixture of 214 (1.3 g, 5.39 mmol), TFA (20 mL) and HMTA (1.51 g, 10.8 mmol) is stirred at 70° C. for 30 minutes. The mixture is then concentrated and purified by silica gel column chromatography (EA:PE=1:3) to give CB6 as a white solid (1.1 g, 76% yield). (MS: [M+H]$^+$ 268.9)

Preparation of CB7

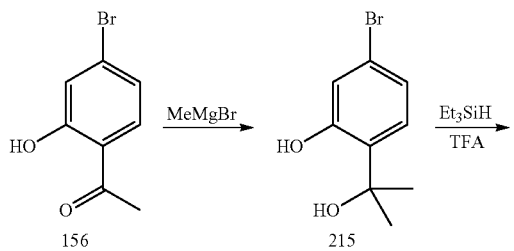

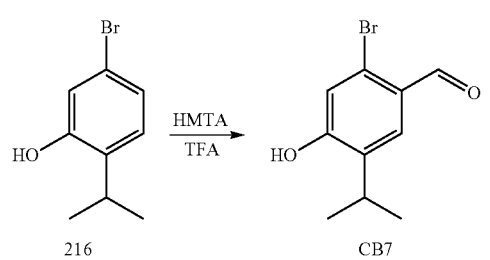

Step 1: Alcohol 215

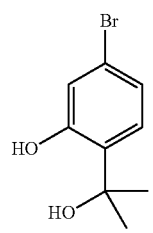

To a solution of 156 (1.0 g, 4.65 mmol) in THF (20 mL) is added MeMgBr (1M in THF, 14 mL, 14.0 mmol) at 0° C. After stirring at room temperature for 12 hours, water (20 mL) is added and the mixture is extracted with EA (20 mL×3). The combined organic layers are dried over anhydrous sodium sulfate, concentrated and purified by silica gel column chromatography (EA:PE=1:15) to give 215 as a yellow solid. (1.0 g, 93%). (MS: [M+H]$^+$232.8)

Step 2: Phenol 216

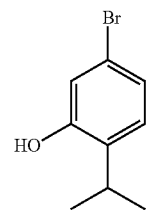

To a solution of 215 (1.0 g, 4.32 mmol) in DCM (10 mL) is added triethylsilane (1.5 mL, 9.5 mmol) and TFA (2 mL). After stirring at room temperature for 12 hours, the mixture is concentrated and purified by silica gel column chromatography (EA:PE=1:10) to give 216 as an oil (0.9 g, 97%). (MS: [M+H]$^+$ 216.7)

Step 3: CB7

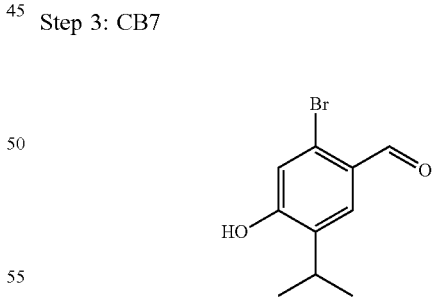

To a solution of 216 (900 mg, 4.19 mmol) in TFA (30 mL) is added HMTA (1.4 g, 10.3 mmol). After stirring at 70° C. for 2 hours, saturated sodium bicarbonate aqueous solution (50 mL) is added and the mixture is extracted with EtOAc (100 mL×3). The combined organic layers are dried, concentrated and purified by silica gel column chromatography (EA:PE=1:5) to give CB7 as an oil. (150 mg, 15%). (MS: [M+H]$^+$ 243.2)

Preparation of CB8

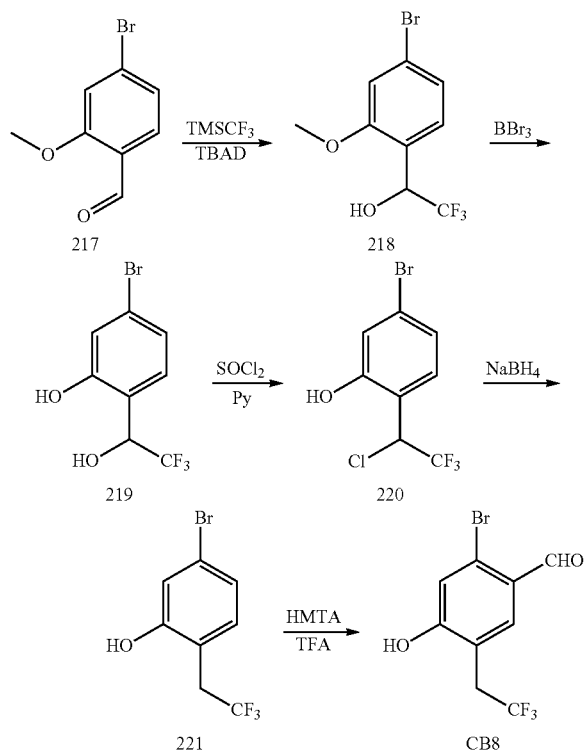

Step 1: Alcohol 218

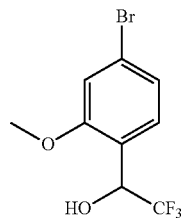

To a solution of 217 (214 mg, 1.0 mmol) in THF is added trimethyl(trifluoromethyl)silane (170 mg, 1.2 mmol) at 0° C. followed by TBAF (107 mg, 0.41 mmol). After stirring at room temperature for 1 hour, water is added and the mixture is extracted with EA (20 mL×3). The combined organic layers are dried over anhydrous sodium sulfate, concentrated and purified by silica gel column chromatography (PE 100%) to give 218 as an oil (170 mg, 62%). (MS: $[M+H]^+$ 285.0)

Step 2: Phenol 219

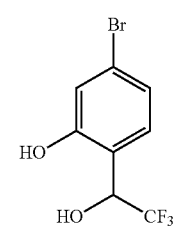

To a solution of 218 (660 mg, 2.32 mmol) in DCM (20 mL) is added boron tribromide (580 mg, 2.32 mmol) at 0° C. slowly. After stirring at room temperature for 3 hours, IN HCl is added and the mixture is extracted with DCM (10 mL×3). The combined organic layers are dried, concentrated, and purified by silica gel column chromatography (EA:PE=1:20) to give 219 as an oil. (480 mg, 77%). (MS: $[M+H]^+$ 269.0)

Step 3: Chloride 220

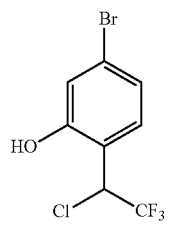

To a solution of 219 (480 mg, 1.77 mmol), Py (0.15 mL, 1.77 mmol) in toluene is added thionyl chloride (0.25 mL, 3.54 mmol). After stirring at room temperature for 1 hour, the mixture is concentrated and partitioned between DCM and IN HCl aqueous solution. The organic layer is washed with water, dried, filtered, and concentrated to give 220 as an oil (500 mg, 98%). (MS: $[M+H]^+$ 287.0)

Step 4: Phenol 221

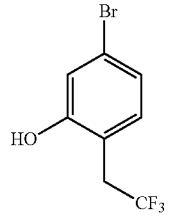

To a solution of 220 (500 mg, 1.736 mmol) in THF (20 mL) is added sodium borohydride (131 mg, 3.47 mmol). After stirring at room temperature for 3 hours, IN HCl is added and the mixture is extracted with EA, dried, and concentrated to give 221 as an oil (360 mg, 82%). (MS: $[M+H]^+$ 255.1)

Step 5: CB8

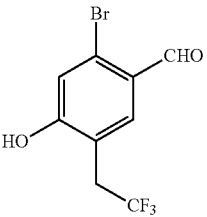

Prepared by essentially the same method as for C11. (MS: $[M+H]^+$ 283.0)

Preparation of CB9

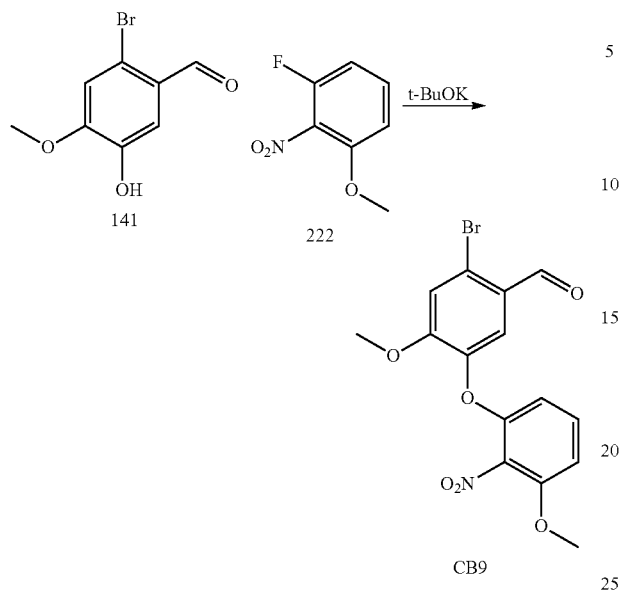

To a solution of 141 (231 mg, 1.0 mmol) and 222 (200 mg, 1.2 mmol) in DMF (15 mL) is added potassium tert-butoxide (135 mg, 1.2 mmol). After stirring at 100° C. for 8 hours, the mixture is concentrated and purified by silica gel column chromatography (EA:PE=1:3) to give CB9 as a yellow solid (175 mg, 54%). (MS: [M+H]$^+$ 383.2)

Preparation of CB10

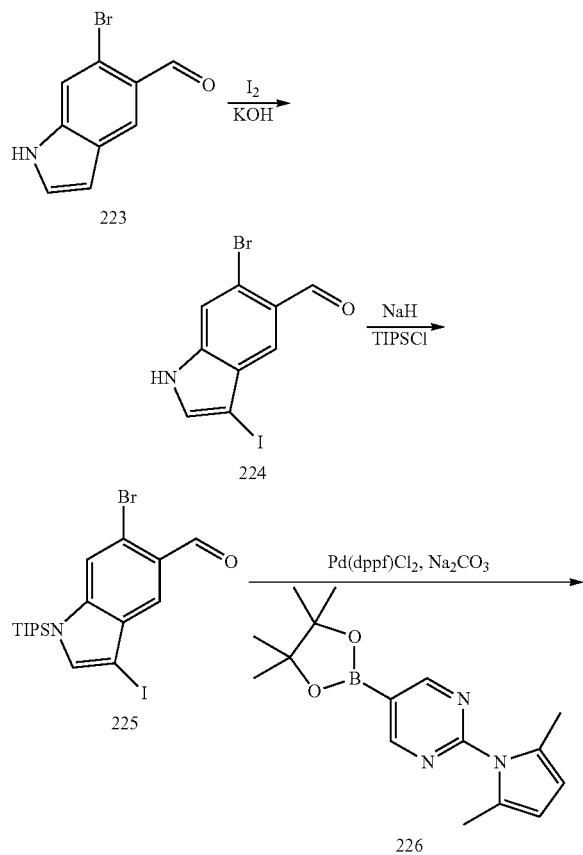

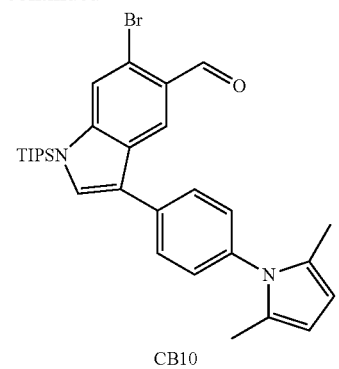

Step 1: Iodide 224

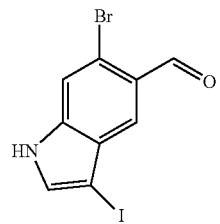

To a solution of 223 (300 mg, 1.34 mmol) in DMF (5 mL) is added potassium hydroxide (98 mg 1.74 mmol) followed by iodine (408 mg 1.61 mmol). After stirring at room temperature for 2 hours, the mixture is diluted with EA (100 mL), washed with brine (30 mL×3), dried over anhydrous sodium sulfate, filtered, concentrated and purified by silica gel column chromatography (EA:PE=1:3) to give 224 as a white solid (310 mg, 66%). (MS: [M+H]$^+$349.9)

Step 2: Iodide 225

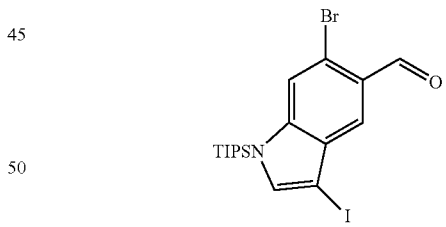

To a solution of 224 (300 mg, 0.85 mmol) in THF (10 mL) is added NaH (51 mg, 1.29 mmol) and stirred for 10 minutes before triisopropylsilyl chloride (198 mg, 1.03 mmol) is added at 0° C. After stirring at room temperature for 2 hours, saturated ammonium chloride aqueous solution and EA (100 mL) are added. The organic layer is washed with brine (30 mL×3), dried over anhydrous sodium sulfate, filtered, concentrated, and purified by silica gel column chromatography (EA:PE=1:5) to give 225 as a white solid (400 mg, 92%). (MS: [M+H]$^+$ 506.0)

Step 3: CB10

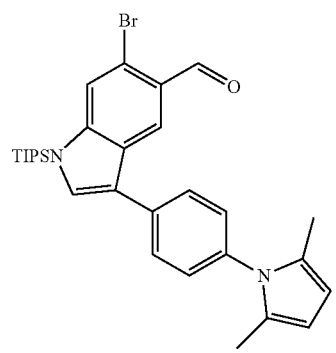

To a mixture of 225 (200 mg, 0.39 mmol), 226 (118 mg, 0.39 mmol), and sodium carbonate (83.7 mg, 0.79 mmol) in dioxane (5 mL) and water (0.5 mL) is added Pd(dppf)Cl$_2$ (50 mg, 0.07 mmol). After stirring at 90° C. for 2 hours, the mixture is diluted with EA (50 mL), filtered, concentrated, and purified by silica gel column chromatography (EA:PE=1:3) to give CB10 as a white solid (87 mg, 40%). (MS: [M+H]$^+$ 553.2)

Preparation of CB11

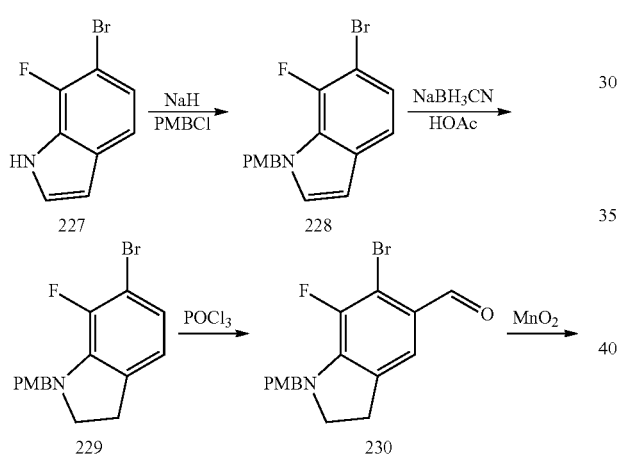

Prepared by essentially the same method as for C18. (MS: [M+H]$^+$ 362.0)

Preparation of CB12

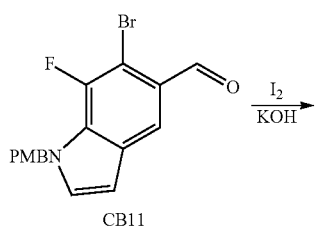

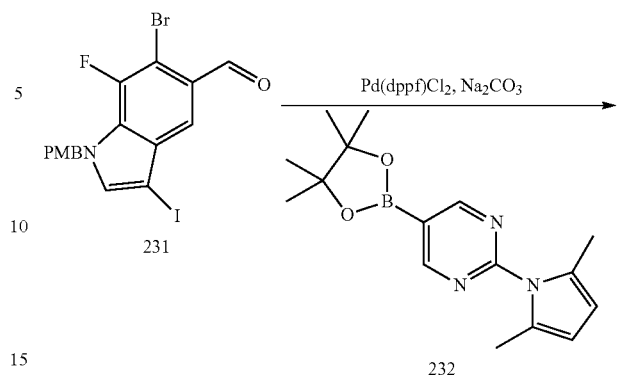

Prepared by essentially the same method as for CB10. (MS: [M+H]$^+$ 533.1)

Preparation of D

Preparation of D1

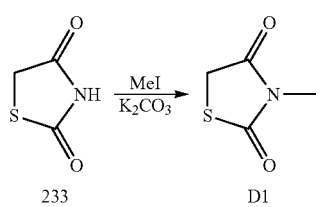

To a mixture of 233 (20 g, 171 mmol) and potassium carbonate (47.3 g, 342 mmol) in DMF (100 mL) is added MeI (32 mL, 513 mmol) dropwise at 0° C. After stirring at room temperature for 12 hours, the mixture is concentrated and the residue is partitioned between water (100 mL) and DCM (100 mL). The aqueous layer is extracted with DCM (60 mL×4). The combined organic layers are dried over anhydrous sodium sulfate, filtered, concentrated, and purified by silica gel column chromatography (DCM) to give D1 as an off-white solid (10 g, 50% yield). (MS: [M+H]$^+$ 132.2)

The following compound is prepared by essentially the same method as for D1.

| Intermediate | Structure | MS |
|---|---|---|
| D2 | 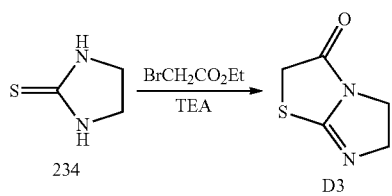 | [M + H]⁺ 146.0 |

Preparation D3

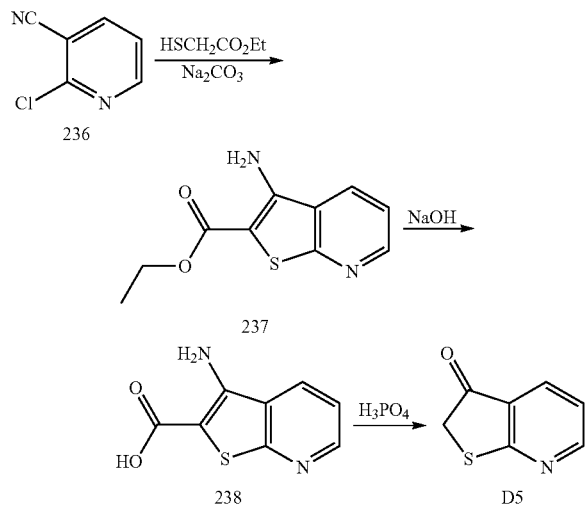

To a solution of 234 (500 mg, 4.9 mmol) and TEA (1.1 mL, 7.4 mmol) in EtOH (10 mL) is added ethyl 2-bromoacetate (814 mg, 4.9 mmol). After stirring at 60° C. for 2 hours, the mixture is cooled to room temperature, diluted with water (5 mL) and EA (100 mL). The layers are separated and the organic layer is washed with water (10 mL×3), dried over anhydrous sodium sulfate, and concentrated to give D3 as a white solid (77 mg, 7% yield)

The following compound is prepared by essentially the same method as for D3.

| Intermediate | Structure | MS |
|---|---|---|
| D4 | 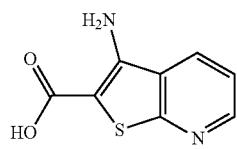 | — |

Preparation of D5

Step 1: Ester 237

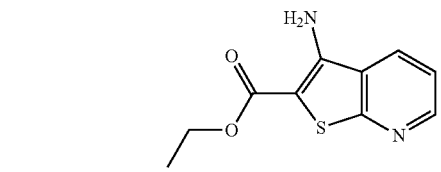

To a solution of 236 (30 g, 218 mmol) in EtOH (300 mL) is added sodium carbonate (25 g, 237 mmol) and ethyl 2-mercaptoacetate (31 mL, 283 mmol). After stirring at 90° C. for 2.5 hours, the mixture is cooled to room temperature and water (500 mL) is added. The solid is collected by filtration, washed with water, and dried to give 237 as a yellow solid (45 g, 94% yield). (MS: [M+H]⁺ 223.3)

Step 2: Acid 238

To a solution of 237 (20.0 g, 90.1 mmol) in EtOH (500 mL) and water (500 mL) is added NaOH (7.2 g, 180 mmol) in portions. After stirring at 70° C. for 45 minutes, the mixture is cooled to 0° C. and is acidified with concentrated HCl to pH 5. The yellow solid is then collected by filtration and dried to give 238 (17 g, 98% yield). (MS: [M+H]⁺ 195.2)

Step 3: D5

A solution of 238 (17 g, 87 mmol) in phosphoric acid (150 mL, 85% aqueous solution) is stirred at 100° C. for 45 minutes. Saturated aqueous sodium bicarbonate solution is then added at room temperature to adjust to pH 8. The solid is collected by filtration and washed with EtOH (100 mL×2) to give D5 as an orange solid (9.0 g, 54% yield). (MS: [M+H]⁺ 152.1)

The following compounds are prepared by essentially the same method as for D5 except DMF was used as the solvent for the first step.

| Intermediate | Structure | MS |
|---|---|---|
| D6 | 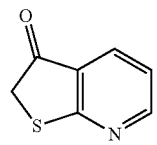 | [M + H]⁺ 169.9 |

| Intermediate | Structure | MS |
|---|---|---|
| D7 | ![D7 structure] | [M + H]+ 152.1 |
| D8 | ![D8 structure] | [M + H]+ 153.0 |
| D9 | ![D9 structure] | — |

Preparation D10

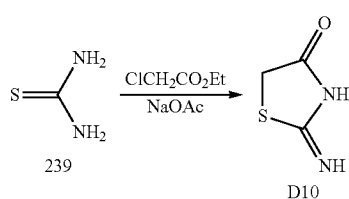

A solution of 239 (0.76 g 10 mmol), ethyl 2-chloroacetate (2.1 mL, 20 mmol), and sodium acetate in EtOH (100 mL) is stirred at 60° C. overnight. After cooling to room temperature, the solid is collected to give D10 as a white solid (0.65 g, 55% yield). (MS: [M+H]+ 117.2)

Preparation of DA1

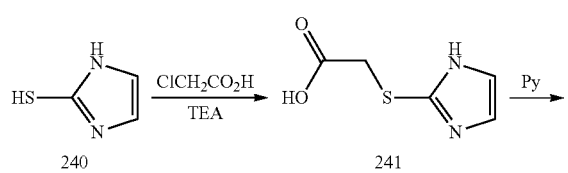

Step 1: Acid 241

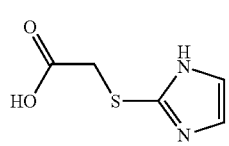

A mixture of 240 (1.0 g, 10 mmol) and NaOH (0.8 g, 2.0 mmol) in EtOH (20 mL) is stirred at 80° C. for 1 hour before chloroacetic acid (1.03 g, 1.1 mmol) is added. After stirring at 80° C. for 2 hours, the mixture is concentrated and concentrated HCl (4 mL) is added. The mixture is then stirred at room temperature for 10 minutes before concentrated to give 241 as a yellow solid (2.5 g, 100%). (MS: [M+H]+ 159.1)

Step 2: DA1

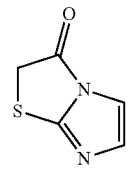

To a solution of 241 (1.0 g 6.3 mmol) in Py (10 mL) is added acetic anhydride (3 mL). After stirring at 55° C. for 40 minutes, the mixture is diluted with EA (100 mL), washed with water (40 mL×3), dried over anhydrous sodium sulfate, filtered, concentrated, and purified by silica gel column chromatography (EA:PE=1:2) to give DA1 as a yellow solid (150 mg, 17%). (MS: [M+H]+ 141.1)

Preparation of DB1

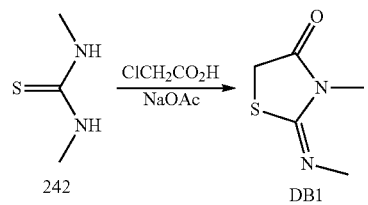

To a mixture of 242 (500 mg, 4.81 mmol) and sodium acetate (1.97 g, 24.1 mmol) in EtOH (20 mL) is added ethyl 2-chloroacetate (1.17 g, 9.62 mmol). After stirring at 60° C. overnight, the mixture is concentrated and purified by silica gel column chromatography (EA:PE=1:10) to give DB1 as a white solid (619 mg, 90%). (MS: [M+H]+145.0)

Preparation of DB2

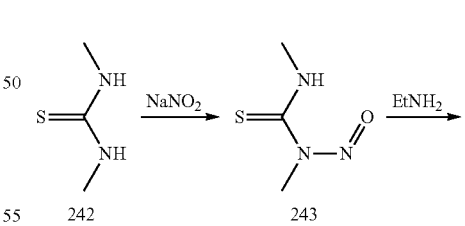

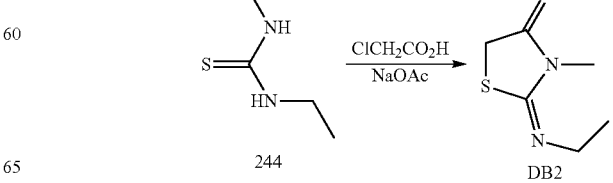

Step 1: Nitrosothiourea 242

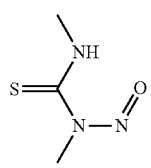

To a mixture of 242 (1.04 g, 10 mmol) and sodium nitrite (696 mg, 10.1 mmol) in DCM (10 mL) is added 0.1 N HCl (20 mL, 200 mmol). After stirring at −10° C. to 5° C. for 4 hours, the mixture is extracted with DCM (100 mL×3). The combined organic layers are dried over anhydrous sodium sulfate, filtered, and purified by silica gel column chromatography (EA:PE=1:30) to give 243 as a yellow oil (224 mg, 17%). (MS: [M+H]$^+$134.0)

Step 2: Thiourea 244

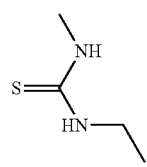

To a mixture of 243 (224 mg, 1.66 mmol) in MeCN (3 mL) is added ethylamine (225 mg, 5 mmol). After stirring at room temperature overnight, the mixture is concentrated and purified by silica gel column chromatography (EA:PE=1:10) to give 244 as a solid (90 mg, 46%). (MS: [M+H]$^+$ 119.0)

Step 3: DB2

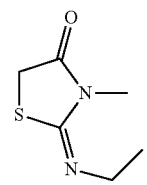

Prepared by essentially the same method as for DB1. (MS: [M+H]$^+$ 159.2)

Preparation of DB3

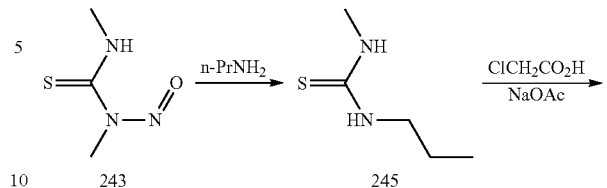

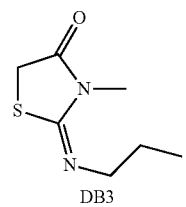

Prepared by essentially the same method as for DB2. (MS: [M+H]$^+$ 173.2)

Preparation of E

Preparation of E1

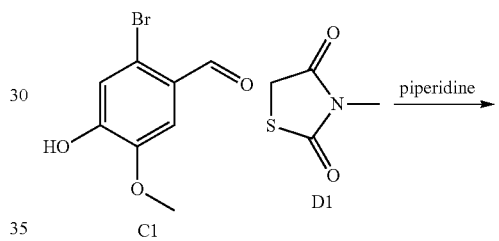

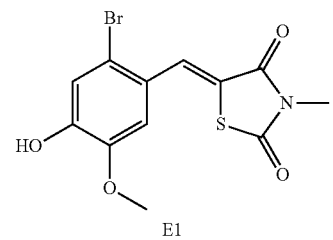

To a solution of C1 (100 mg, 0.43 mmol) in EtOH (5 mL) is D1 (57 mg, 0.43 mmol) and piperidine (37 mg, 0.43 mmol). After stirring at 80° C. for 4 hours, the solid is collected by filtration and washed with EtOH. Recrystallization from EtOH gives E1 (32 mg, 21% yield) as a yellow solid. (MS: [M+H]$^+$ 344.2)

The following compounds are prepared by essentially the same method as for E1.

| Intermediate | Building blocks | | Structure | MS |
|---|---|---|---|---|
| E2 | 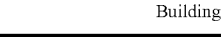 C3 | 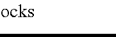 D1 | 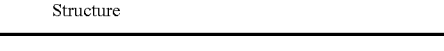 | [M + H]$^+$ 374.0 |

| Intermediate | Building blocks | Structure | MS |
|---|---|---|---|
| E3 | C5, D1 | 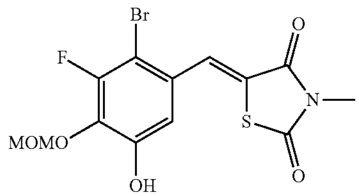 | [M + H]+ 392.0 |
| E4 | C6, D1 | 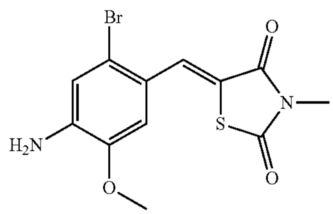 [SMILES: COc1cc(/C=C2\SC(=O)N(C)C2=O)c(Br)cc1N] | [M + H]+ 343.0 |
| E5 | C3, D5 | 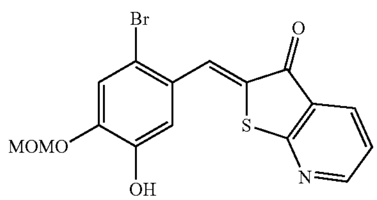 | [M + H]+ 394.0 |
| E6 | C5, D5 | 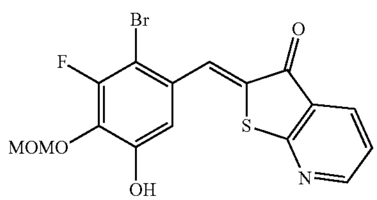 | [M + H]+ 412.0 |
| E7 | C4, D1 | 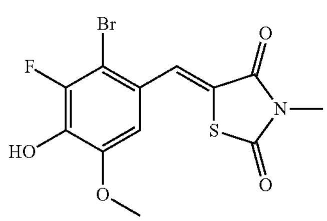 [SMILES: COc1cc(/C=C2\SC(=O)N(C)C2=O)c(Br)c(F)c1O] | [M + H]+ 361.9 |
| E8 | C1, D5 | 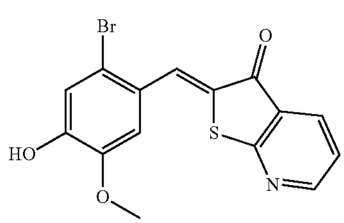 [SMILES: COc1cc(/C=C2\Sc3ncccc3C2=O)c(Br)cc1O] | [M + H]+ 364.0 |

| Intermediate | Building blocks | Structure | MS |
|---|---|---|---|
| E9 | C13, D1 | 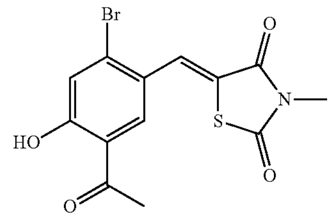 [SMILES: CC(=O)c1cc(/C=C2\SC(=O)N(C)C2=O)c(Br)cc1O] | [M + H]⁺ 354 |
| E10 | C18, D1 | 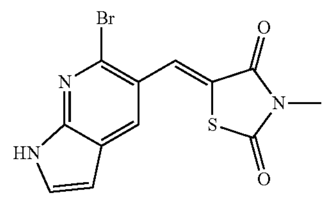 [SMILES: CN1C(=O)S/C(=C\c2cc3cc[nH]c3nc2Br)C1=O] | [M + H]⁺ 338 |
| E11 | D1 | 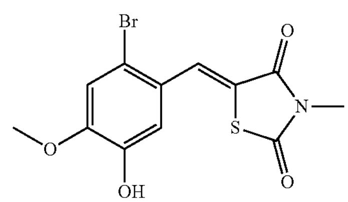 | [M + H]⁺ 343.9 |

Preparation of E12

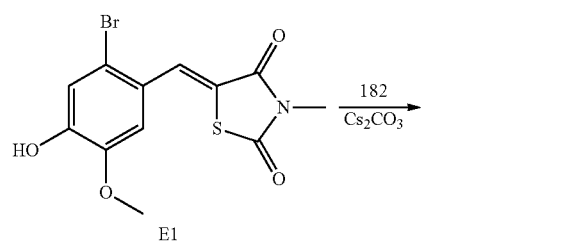

E1

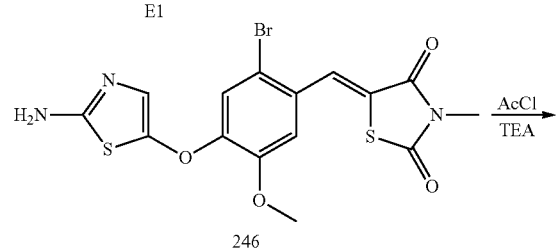

246

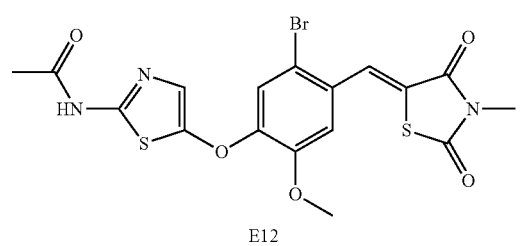

E12

Step 1: Ether 246

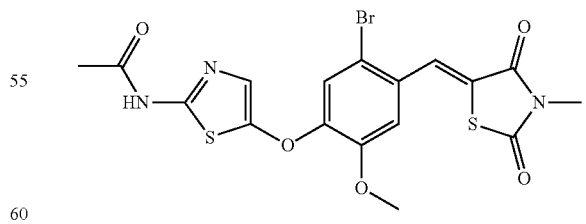

To a solution of E1 (200 mg, 0.58 mmol) in MeCN (5 mL) is added 182 (104 mg, 0.58 mmol) and cesium carbonate (474 mg, 1.46 mmol). After stirring at 70° C. for 3 hours, the mixture is concentrated and purified by silica gel column chromatography (MeOH:DCM=0:100 to 1:200) to give 246 as a yellow solid (100 mg, 39% yield). (MS: [M+H]⁺ 442.1)

Step 2: E12

To a solution of 246 (200 mg, 0.45 mmol) and TEA (0.3 mL, 2.26 mmol) in DCM (10 mL) is added acetyl chloride (0.06 mL, 0.9 mmol) dropwise at room temperature. After stirring for 3 hours, water is added and the solid is collected by filtration, washed with water, and dried to give crude E12 as a yellow solid (170 mg, 78% yield). (MS: [M+H]⁺484.2)

Preparation of E13

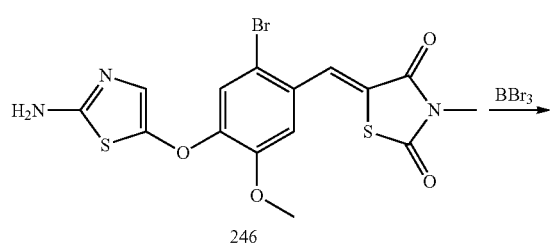

To a solution of 246 (100 mg, 0.23 mmol) in DCM (10 mL) is added boron tribromide (180 mg, 0.7 mmol) dropwise at 0° C. After stirring at room temperature for 3 hours, water (2 mL) is added at 0° C. The organic layer is dried over anhydrous sodium sulfate, filtered, and concentrated to crude E13 as a yellow solid (80 mg, 52% yield). (MS: [M+H]$^+$ 428.1)

Preparation of E14

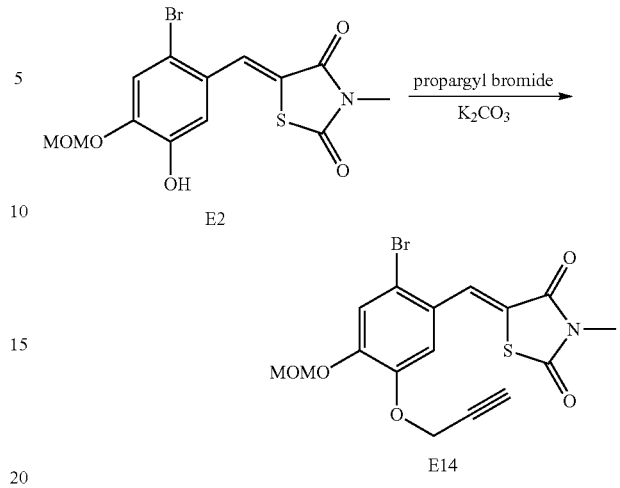

A mixture of E2 (200 mg, 0.53 mmol), DMF (3 mL), potassium carbonate (148 mg, 1.07 mmol), and propargyl bromide (0.1 mL, 1.04 mmol) is stirred at room temperature for 3 hours. The mixture is then diluted with water (10 mL) and extracted with EA (10 mL×3). The combined organic layers are dried over anhydrous sodium sulfate, filtered, and concentrated to crude E14 as a yellow solid (228 mg, 100% yield). (MS: [M+H]$^+$412.1)

The following compounds are prepared by essentially the same method as for E14.

| Intermediate | Building blocks | | Structure | MS |
|---|---|---|---|---|
| E15 | ![E2] | ![B6] | ![E15 structure] | [M + H]$^+$ 545.9 |
| E16 | ![E2] | ![B7] | ![E16 structure] | [M − MOM + 2H]$^+$ 498 |

-continued
| Intermediate | Building blocks | Structure | MS |
|---|---|---|---|
| E17 | 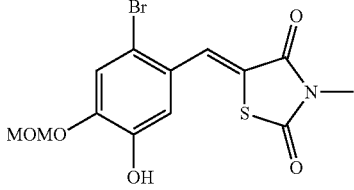 E2 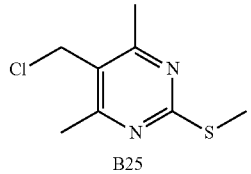 B25 | 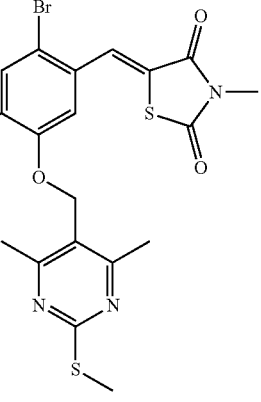 | [M − MOM + 2H]⁺ 496 |
| E18 | 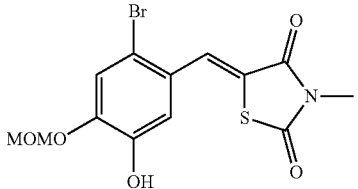 E2 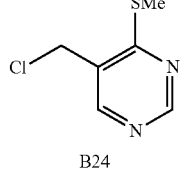 B24 | 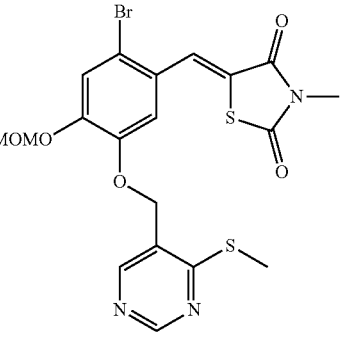 | [M − MOM + 2H]⁺ 470 |
| E19 | 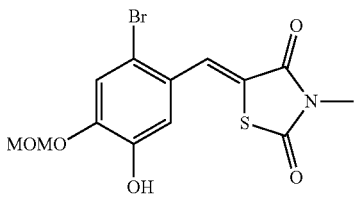 E2 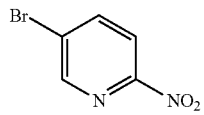 | 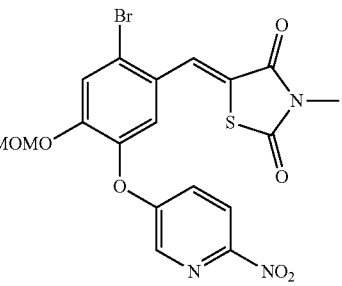 | [M − MOM + 2H]⁺ 454 |

Preparation of E20

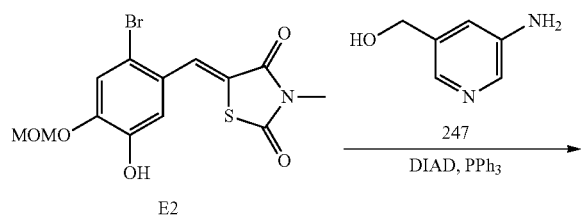

A E2 (55 mg 0.1 mmol), 247 (22 mg 0.1 mmol), and triphenylphosphine (58 mg 0.2 mmol) in THF (3 mL) is stirred at room temperature for 10 minutes. DIAD (44 mg 0.2 mmol) is then added at −5° C. After stirring at room temperature for 16 hours, the mixture is concentrated and purified by silica gel column chromatography (MeOH: DCM=1:100) to give E20 as a yellow solid (35 mg, 45% yield). (MS: [M+H]⁺ 480.0)

The following compounds are prepared by essentially the same method as for E20.

| Intermediate | Building blocks | | Structure | MS |
|---|---|---|---|---|
| E21 | E2 | A24 | 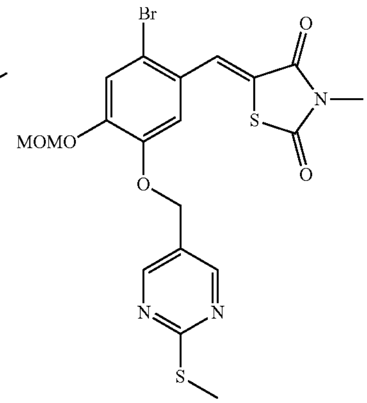 | [M + H]⁺ 512.0 |
| E22 | E5 | A24 | 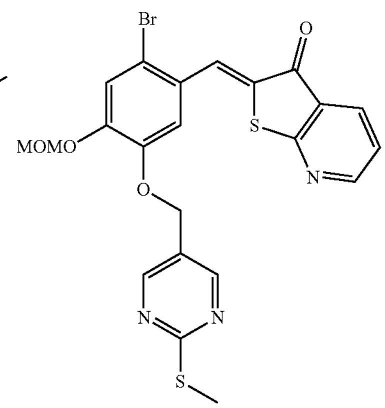 | [M + H]⁺ 532.0 |

-continued

Preparation of E23

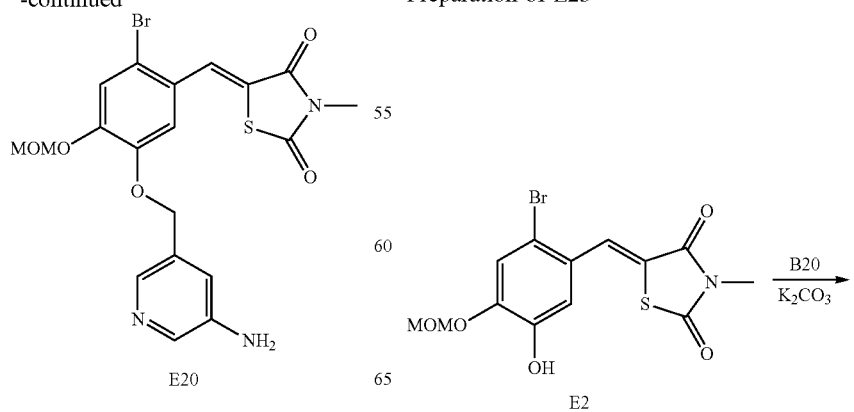

-continued

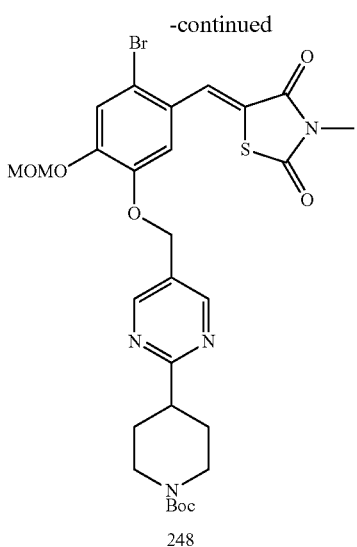
248

TFA →

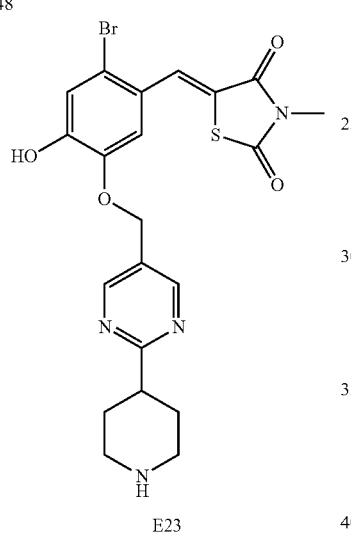
E23

Step 1: Ether 248

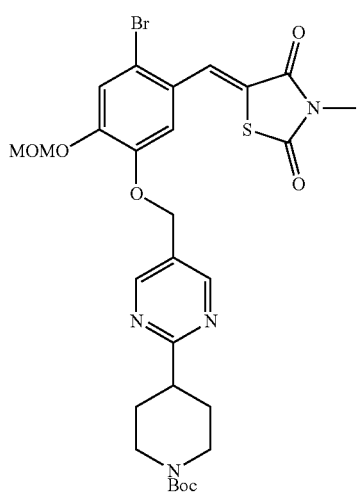

To a solution of B20 (100 mg, 0.27 mmol) and E2 (100 mg, 0.27 mmol) in DMF (5 mL) is added potassium carbonate (74.4 mg, 0.54 mmol) at room temperature. After stirring at room temperature for 1 hour, the mixture is filtered, concentrated, and purified by silica gel column chromatography (EA:PE=1:1) to give 248 as a yellow solid (150 mg, 86% yield). (MS: [M+H]$^+$ 651.1)

Step 2: E23

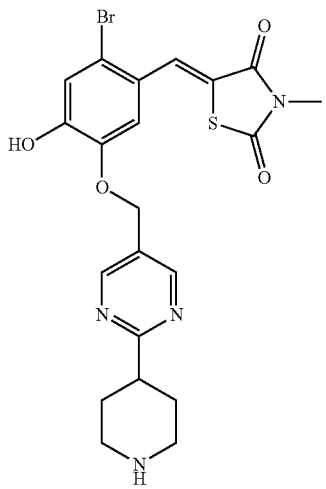 [SMILES: CN1C(=O)S/C(=C\c2cc(OCc3cnc(C4CCNCC4)nc3)c(O)cc2Br)C1=O]

To a solution of 248 (150 mg 0.23 mmol) in DCM (4 mL) is added TFA (2 mL) dropwise at 0° C. After stirring at room temperature for 2 hours, the mixture is concentrated and triturated with MeOH (5 mL). The solid is collected by filtration and dried to give E23 as a light yellow solid (78 mg 67% yield). (MS: [M+H]$^+$ 507.0)

Preparation of E24

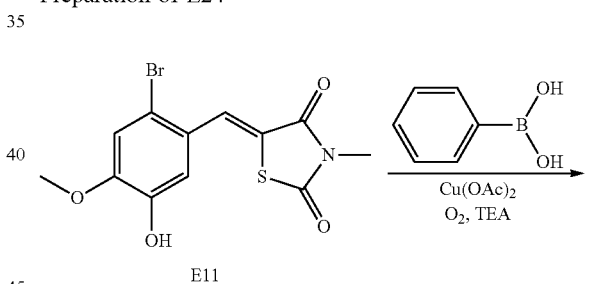

E11

E24

To a mixture of E11 (400 mg, 1.16 mmol) and phenylboronic acid (425 mg, 3.49 mmol) in DCM (10 mL) is added Cu(OAc)$_2$ (253 mg, 1.39 mmol) and TEA (588 mg, 5.81 mmol). After stirring at room temperature overnight, the mixture is filtered, concentrated, and triturated with EtOH (5 mL). The solid is collected by filtration to give E24 as a yellow solid (208 mg, 43% yield). (MS: [M+H]$^+$ 420.1)

The following compounds are prepared by essentially the same method as described above.

| Intermediate | Building blocks | | Structure | MS | Reference of preparation |
|---|---|---|---|---|---|
| EA1 | C3 | DA1 | EA1 | [M − H]⁻ 398.0 | E1 |
| EA2 | E3 | AA3 | EA2 | [M + H]⁺ 695.1 | E20 |
| EA3 | E6 | BA5 | EA3 | [M + H]⁺ 550.0 | E14 |
| EA4 | E6 | B8 | EA4 | [M + H]⁺ 596.0 | E14 |

| Intermediate | Building blocks | Structure | MS | Reference of preparation |
|---|---|---|---|---|
| EA5 | 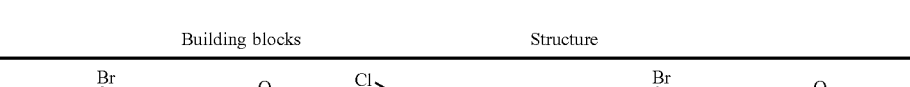 E3, B24 | 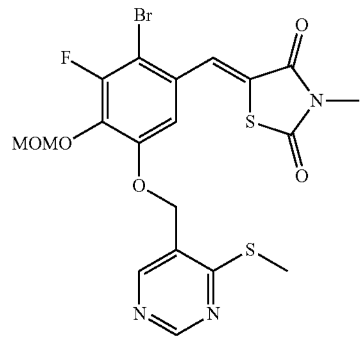 | — | E14 |

EXAMPLES

The following examples of compounds of the invention were made and tested according to the procedures and methods described herein.

Chemistry

Example 1

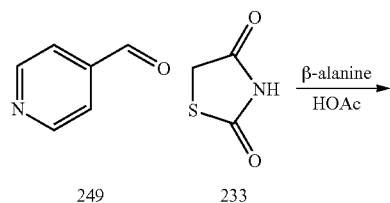
249   233

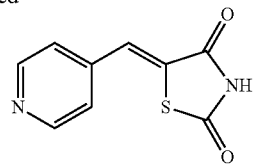
Ex1

A solution of 249 (11 mg, 0.1 mmol), 233 (12 mg, 0.1 mmol), and β-alanine (11 mg, 0.12 mmol) in acetic acid (0.5 mL) is stirred under refluxed for 3 hours. The solid is collected and washed with acetic acid (0.5 mL) to give Ex1 as a white solid (20 mg, 97% yield). (MS: $[M+H]^+$ 207.2)

The following compounds are prepared by essentially the same method as for Ex1.

| Example | Building blocks | Structure | MS |
|---|---|---|---|
| Ex2 | 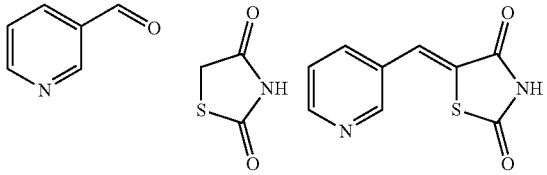 233 | 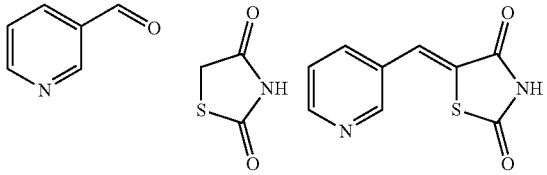 | $[M + H]^+$ 207.2 |
| Ex3 | 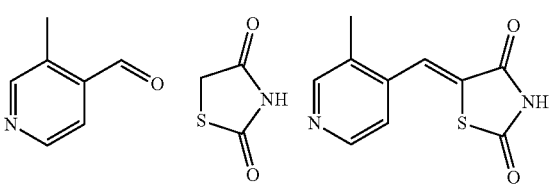 233 | 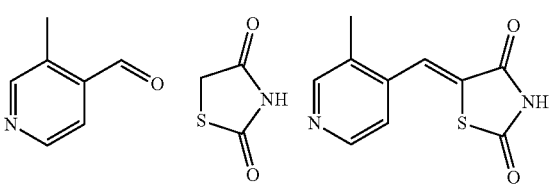 | $[M + H]^+$ 221.2 |

| Example | Building blocks | Structure | MS |
|---|---|---|---|
| Ex4 | C33 / 233 | 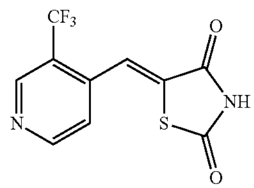 [SMILES: O=C1NC(=O)/C(=C/c2ccncc2C(F)(F)F)S1] | [M + H]⁺ 275.2 |
| Ex5 | / 233 | 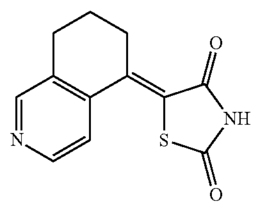 [SMILES: O=C1NC(=O)/C(=C2\CCCc3cnccc32)S1] | [M + H]⁺ 247.2 |
| Ex6 | 25 / 233 | 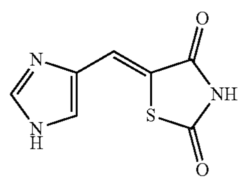 [SMILES: O=C1NC(=O)/C(=C/c2c[nH]cn2)S1] | [M + Na]⁺ 218.0 |
| Ex7 | / 233 | 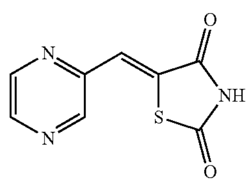 [SMILES: O=C1NC(=O)/C(=C/c2cnccn2)S1] | [M + H]⁺ 208.2 |
| Ex8 | 47 / 233 | 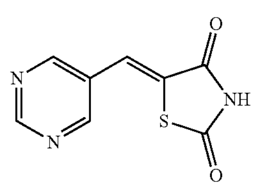 [SMILES: O=C1NC(=O)/C(=C/c2cncnc2)S1] | [M − H]⁻ 206.2 |
| Ex9 | 213 / D10 | 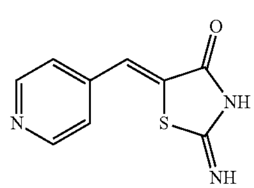 | [M + H]⁺ 206.2 |

Example 10

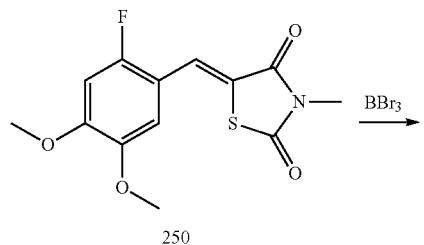

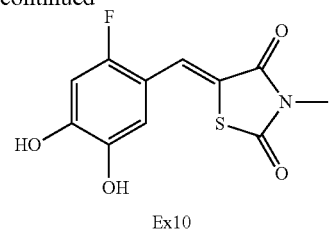

To a solution of 250 (79 mg, 0.27 mmol) in DCM (0.6 mL) is added boron tribromide (1 M in DCM, 0.4 mL, 0.4 mmol) at 0° C. After stirring at room temperature for 3 hours, the mixture is concentrated and purified by silica gel flash chromatography (EA:hexanes=1:1) to give Ex10 as a brown solid (40 mg, 56% yield). (MS: [M−H]⁻ 268.2)

The following compound is prepared by essentially the same method as for Ex10.

| Example | Building blocks | Structure | MS |
|---|---|---|---|
| Ex11 | C1, D1 | (Br, HO, OH substituted thiazolidinedione benzylidene) | [M + H]⁺ 330.2 |

The following compound is prepared by essentially the same method as for Ex1.

| Example | Building blocks | Structure | MS |
|---|---|---|---|
| Ex12 | 233 | (pyridin-4-yl ethylidene thiazolidinedione) | [M + H]⁺ 221.0 |
| Ex13 | D1 | (indanone-derived thiazolidinedione) | [M + H]⁺ 292.2 |

Example 14

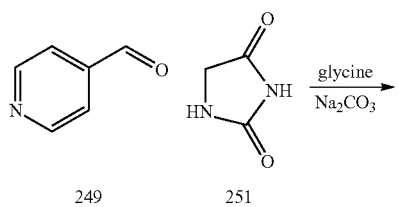

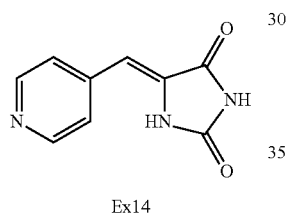

Ex14

A mixture of 249 (200 mg, 1.87 mmol), 251 (187 mg, 1.87 mmol), glycine (140 mg, 1.87 mmol), and sodium carbonate (98 mg, 0.94 mmol) in water (2 mL) is stirred at reflux for 3 hours. After cooling to room temperature, the solid is collected and washed with water (0.5 mL) to give Ex14 as a pink solid (28 mg, 8% yield). (MS: [M+H]$^+$ 190.2)

The following compound is prepared by essentially the same method as for Ex14.

Example 16

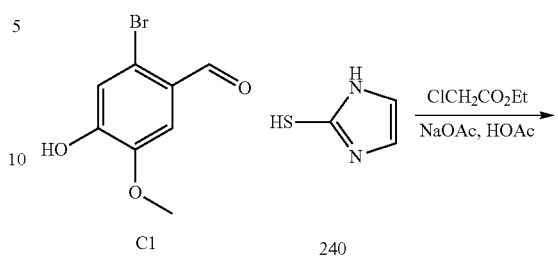

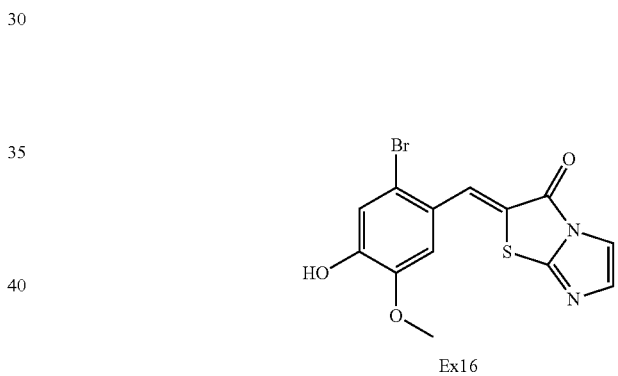

Ex16

A mixture of C1 (200 mg, 0.87 mmol), 240 (87 mg, 0.87 mmol), ethyl 2-chloroacetate (0.082 mL, 0.87 mmol), and sodium acetate in HOAc (5 mL) is stirred at reflux overnight. After cooling to room temperature, the solid is collected, washed with water (0.5 mL), and purified by prep-TLC (EA:hexanes=1:1) to give Ex16 as a yellow solid (0.8 mg, 0.3% yield). (MS: [M+H]$^+$ 354.9)

The following compound is prepared by essentially the same method as for Ex16.

| Example | Building blocks | Structure | MS |
|---|---|---|---|
| Ex15 | ![pyridazine-4-carbaldehyde and hydantoin 251] | ![Ex15 structure] | [M + H]$^+$ 191.2 |

| Example | Building blocks | Structure | MS |
|---|---|---|---|
| Ex17 | 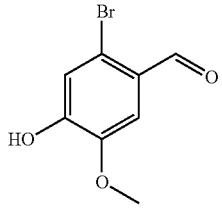 C1 | 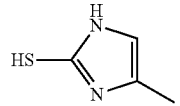 | [M + H]⁺ 367.0 |
The structure column shows: 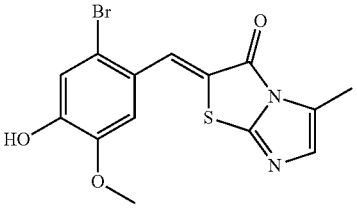 [SMILES: COc1cc(/C=c2\sc3ncc(C)n3c2=O)c(Br)cc1O]
Example 18
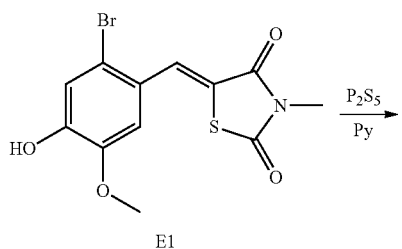
E1
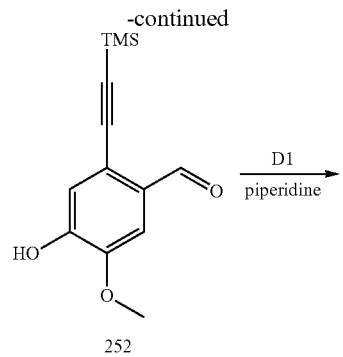
252
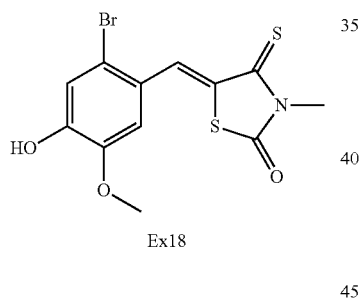
Ex18
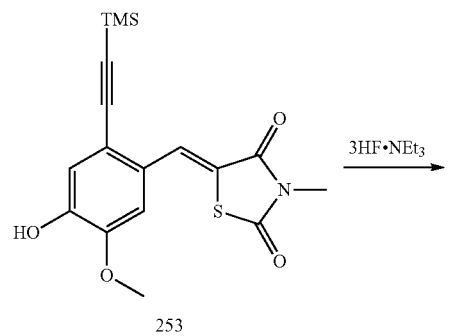
253
A solution of E1 (17 mg, 0.05 mmol) and phosphorus pentasulfide (33 mg, 0.075 mmol) in Py (1.0 mL) is stirred at 120° C. for 3 hours. After cooling to room temperature, one-fifth of the mixture is purified by HPLC (MeCN:water with 0.1% TFA=1:1 to 1:0) to give Ex18 as a yellow solid (1.5 mg, 42% yield). (MS: [M+H]⁺ 360.2)
Example 19
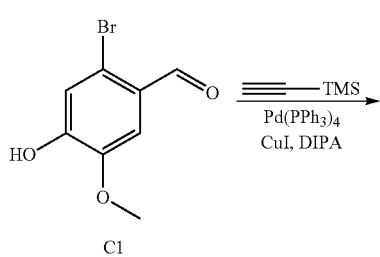
C1
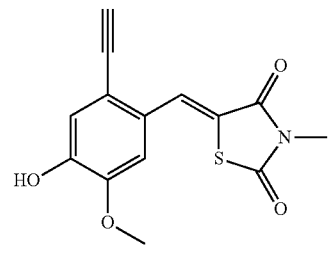
Ex19

193

Step 1: Alkyne 252

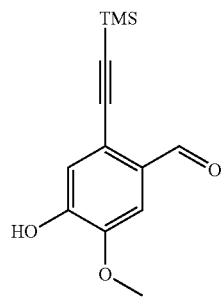

To a solution of C1 (115 mg, 0.5 mmol), CuI (10 mg, 0.05 mmol), trimethylsilylacetylene (0.083 mL, 0.55 mmol), and DIPA (0.5 mL) in DMF (1.0 mL) and THF (5.0 mL) is added Pd(PPh$_3$)$_4$ (30 mg, 0.026 mmol) at room temperature. After stirring at 88° C. for 1 hour, the mixture is cooled to room temperature, filtered, diluted with EA (10 mL), washed with water (5 mL) and brine (5 mL), dried over anhydrous sodium sulfate, and purified by prep-TLC (EA:hexanes=1:2) to give 252 as a white solid (50 mg, 40% yield). (MS: [M+H]$^+$ 249.0)

Step 2: Thiazolidinedione 253

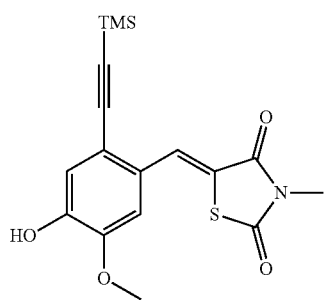 [SMILES: COc1cc(/C=C2\SC(=O)N(C)C2=O)c(C#C[Si](C)(C)C)cc1O]

A solution of 252 (10 mg, 0.04 mmol), D1 (7 mg, 0.05 mmol), and piperidine (0.002 mL, 0.02 mmol) in EtOH (0.4 mL) is stirred under reflux for 2 hours and then cooled to room temperature. The mixture is purified on prep-TLC (EA:hexanes=1:1) to give 253 as a white solid (10 mg, 69% yield). (MS: [M+H]$^+$ 362.2)

Step 3: Ex19

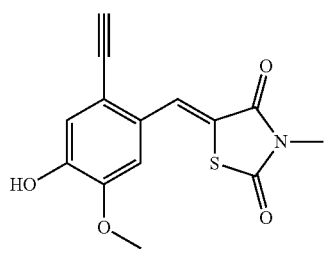 [SMILES: C#Cc1cc(O)c(OC)cc1/C=C1\SC(=O)N(C)C1=O]

To a solution of 253 (3.5 mg, 0.01 mmol) in THF (0.5 mL) is added triethylamine trihydrofluoride (0.005 mL, 0.03 mmol). After stirring for 2 hours, the mixture is purified by HPLC (MeCN:water with 0.1% TFA=2:3 to 1:0) to give Ex19 as a white solid (2.0 mg, 71% yield). (MS: [M+H]$^+$ 290.2)

194

Example 20

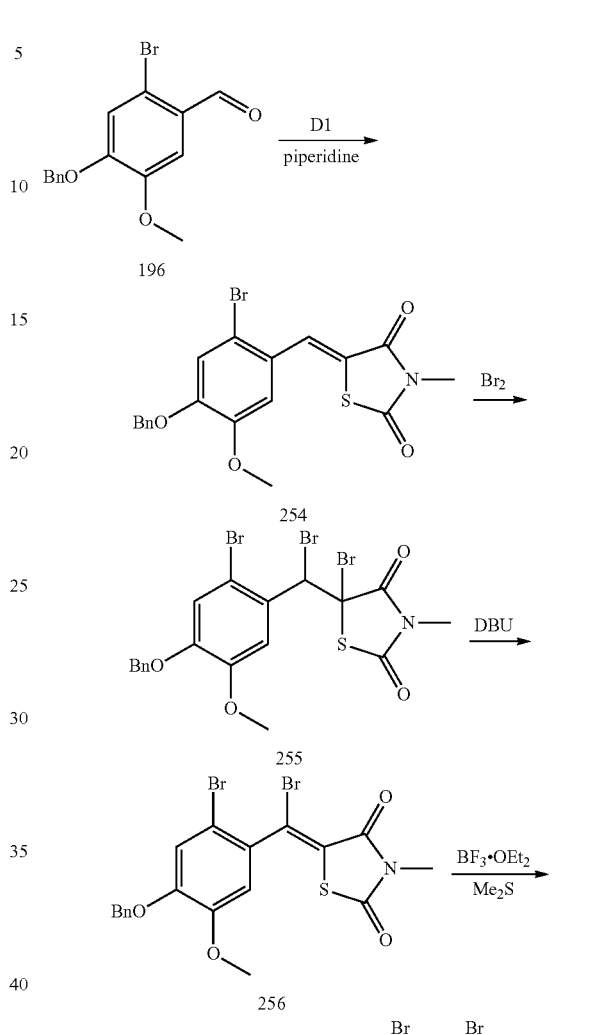

Step 1: Thiazolidinedione 254

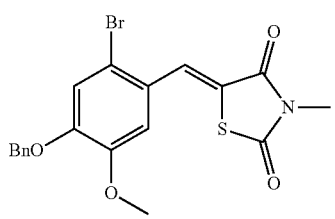 [SMILES: COc1cc(/C=C2\SC(=O)N(C)C2=O)c(Br)cc1OCc1ccccc1]

A solution of crude 196 (394 mg), D1 (161 mg, 1.23 mmol), and piperidine (0.03 mL, 0.25 mmol) in EtOH (2 mL) is stirred at reflux for 2 hours and then cooled to room temperature. The solid is collected to give 254 as a white solid (256 mg, 68% yield for two steps). (MS: [M+H]+ 434.2)

Step 2: Bromide 255

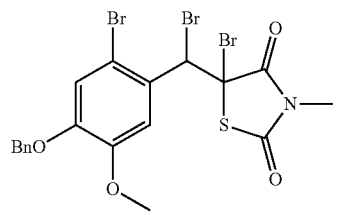 [SMILES: COc1cc(C(Br)C2(Br)SC(=O)N(C)C2=O)c(Br)cc1OCc1ccccc1]

To a solution of 254 (256 mg, 0.46 mmol) in DCM (4 mL) is added bromine (0.03 mL, 0.58 mmol) at 0° C. After stirring at room temperature for 1.5 hours, saturated sodium thiosulfate (0.5 mL) is added and the mixture is extracted with EA (10 mL×3). The combined organic layers are washed with water (5 mL) and brine (5 mL), dried over anhydrous sodium sulfate, concentrated and purified by silica gel column chromatography (EA:hexanes=1:1) to give 255 as a white solid (37 mg, 14% yield).

Step 3: Bromide 256

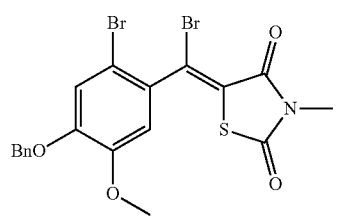 [SMILES: COc1cc(/C(Br)=C2\SC(=O)N(C)C2=O)c(Br)cc1OCc1ccccc1]

To a solution of 255 (37 mg, 0.062 mmol) in DCM (2 mL) is added DBU (0.02 mL, 0.124 mmol) at 0° C. After stirring at room temperature for 4 hours, 1 N HCl (0.5 mL) is added and the mixture is extracted with EA (5 mL×3). The combined organic layers are washed with water (3 mL) and brine (3 mL), dried over anhydrous sodium sulfate, concentrated, and purified by prep-TLC (EA:hexanes=1:1) to give 256 as a colorless oil (5 mg, 16% yield). (MS: [M+H]+ 512.0)

Step 4: Ex20

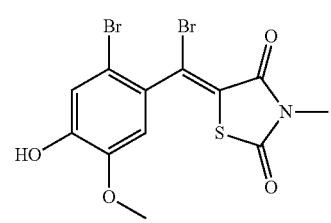 [SMILES: COc1cc(/C(Br)=C2\SC(=O)N(C)C2=O)c(Br)cc1O]

To a solution of 256 (77 mg, 0.15 mmol) and dimethylsulfide (0.03 mL, 0.45 mmol) in DCM (3 mL) is added boron trifluoride diethyl etherate (0.06 mL, 0.45 mmol) at 0° C. After stirring at room temperature for 5 hours, saturated sodium bicarbonate (1 mL) is added and the mixture is extracted with EA (10 mL×3). The combined organic layers are washed with water (10 mL) and brine (10 mL), dried over anhydrous sodium sulfate, concentrated, and purified by prep-TLC (EA:hexanes=1:2) to give Ex20 as a yellow oil (24 mg, 38% yield). (MS: [M+H]+ 422.0)

Example 21

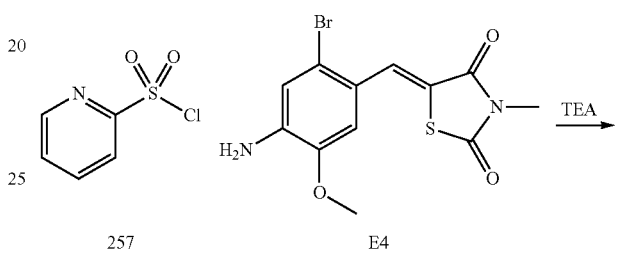

To a solution of E4 (100 mg 0.29 mmol) and TEA (88 mg 0.87 mmol) in DCM (2.5 mL) and DCE (2.5 mL) is added 257 (100 mg 0.58 mmol) at 0° C. After stirring at 60° C. overnight, the mixture is filtered, concentrated, and purified by silica gel column chromatography (MeOH:DCM=1:30) to give Ex21 as a yellow solid (7 mg, 5% yield). (MS: [M+H]+ 486)

The following compounds are prepared by essentially the same method as for Ex21.

| Example | Building blocks | Structure | MS |
|---|---|---|---|
| Ex22 |  E4 | 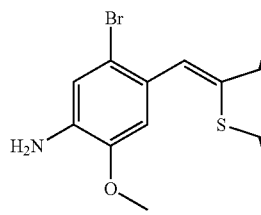 | [M + Na]+ 443.0 |
| Ex23 | 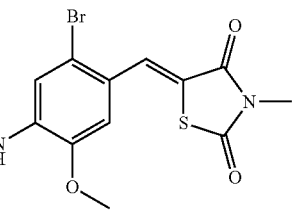 E4 | 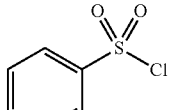 | [M + Na]+ 504.8 |
| Ex24 | 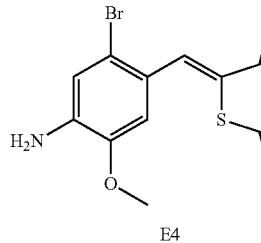 E4 | 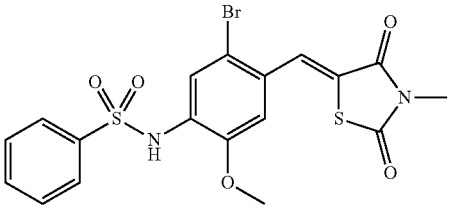 | [M + H]+ 497.2 |
Example 25
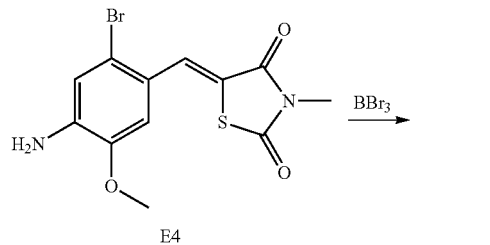
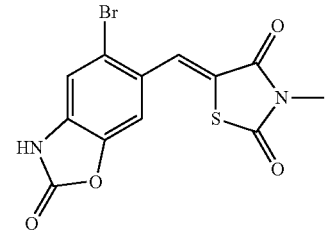
Ex25
Step: Phenol 258N
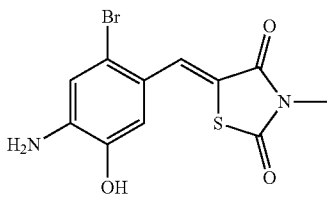 [SMILES: CN1C(=O)S/C(=C\c2cc(O)c(N)cc2Br)C1=O]
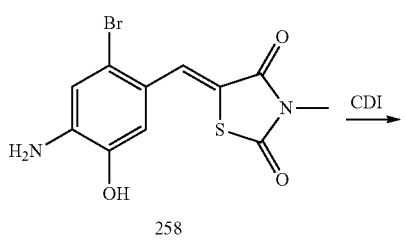
258
To a solution of E4 (250 mg, 0.73 mmol) in DCM (10 mL) is added boron tribromide (547 mg, 2.19 mmol) at −78° C. slowly. After stirring at −78° C. for 1 hour and then at room temperature for 1.5 hours, water (2 mL) is added at −30° C. The solid is collected by filtration and dried to provide 258 as a yellow solid (230 mg, 96% yield). (MS: [M+H]+ 329.1)

Step 2: Ex25

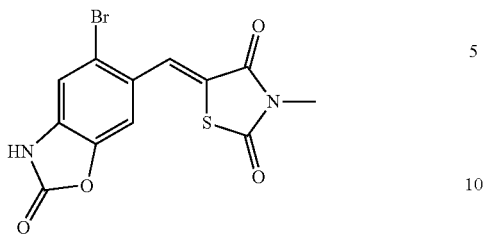

A mixture of 258 (50 mg, 0.15 mmol) and CDI (49 mg, 0.30 mmol) in THF (2 mL) is stirred at room temperature overnight. The mixture is then filtered and triturated with MeOH (5 mL) to give Ex25 as a yellow solid (20 mg, 37% yield). (MS: [M+H]$^+$ 355.1)

The following compound is prepared by essentially the same method as for Ex25.

| Example | Building blocks | Structure | MS |
|---|---|---|---|
| Ex26 | C6, D5 | 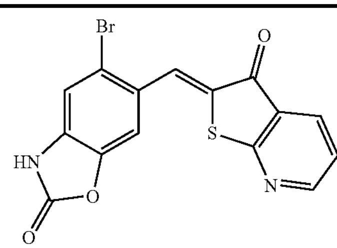 | [M + H]$^+$ 374.9 |

Example 27

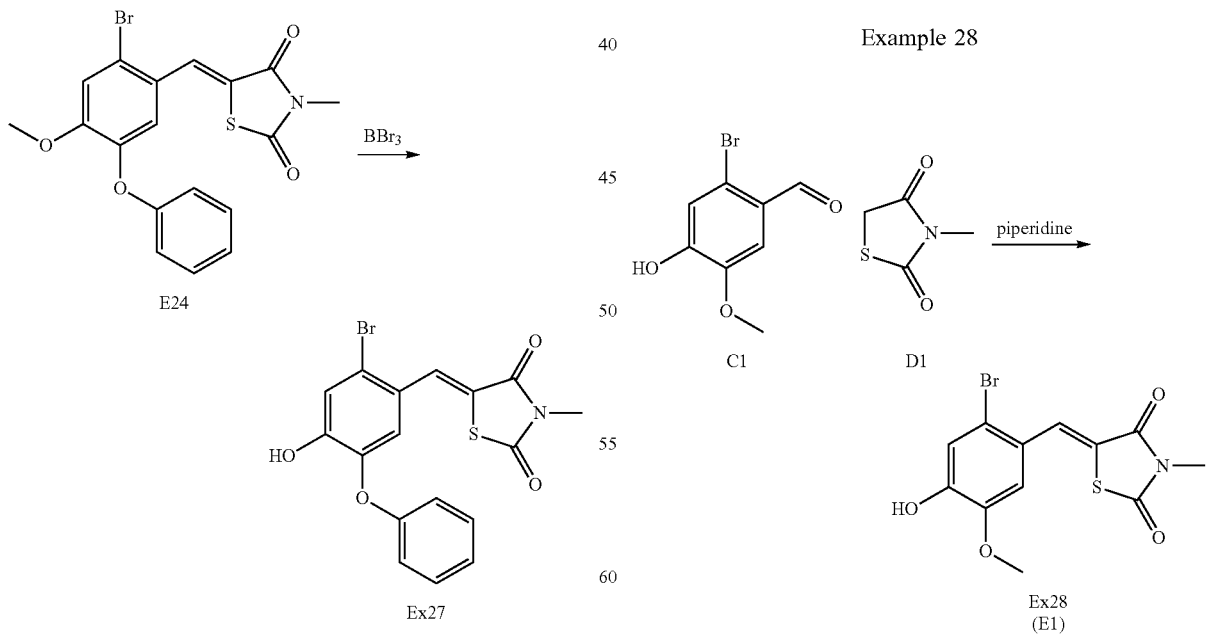

the mixture is concentrated and purified by prep-HPLC to give Ex27 as a white solid (15 mg, 31% yield). (MS: [M+H]$^+$ 406.1)

Example 28

To a solution of E24 (50 mg, 0.12 mmol) in DCM (5 mL) is added boron tribromide (89.4 mg, 0.36 mmol) at −78° C. slowy. After stirring at −78° C. for 1 hour and then at room temperature overnight, water (2 mL) is added at −30° C. and Prepared as described above for E1.

The following compounds are prepared by essentially the same method as for Ex28.

| Example | Building blocks | Structure | MS |
|---|---|---|---|
| Ex29 | C28 (2-fluoro-4-hydroxy-5-methoxybenzaldehyde); D1 | 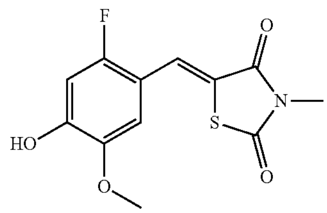 | [M + H]+ 284.0 |
| Ex30 | (2-chloro-4-hydroxy-5-methoxybenzaldehyde); D1 | 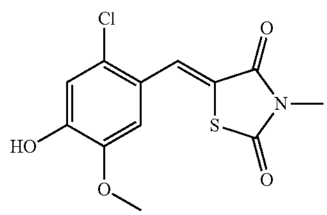 | [M + H]+ 300.2 |
| Ex31 | C29 (4-hydroxy-5-methoxy-2-(trifluoromethyl)benzaldehyde); D1 | 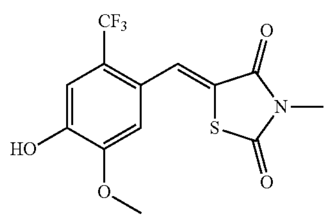 | [M + H]+ 334.1 |
| Ex32 | (2-bromo-5-ethoxy-4-hydroxybenzaldehyde); D1 | 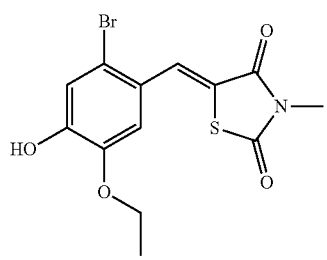 [SMILES: CCOc1cc(/C=C2\SC(=O)N(C)C2=O)c(Br)cc1O] | [M + Na]+ 380.0 |
| Ex33 | C30 (2-bromo-4-hydroxy-5-(prop-2-yn-1-yloxy)benzaldehyde); D1 | 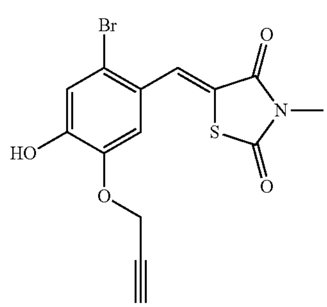 [SMILES: C#CCOc1cc(/C=C2\SC(=O)N(C)C2=O)c(Br)cc1O] | [M + Na]+ 390.0 |
| Ex34 | (2-bromo-3-chloro-4-hydroxy-5-methoxybenzaldehyde); D1 | 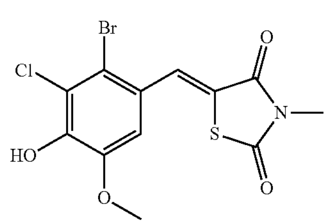 | [M + Na]+ 399.8 |

-continued

| Example | Building blocks | Structure | MS |
|---|---|---|---|
| Ex35 | C31 / D1 | 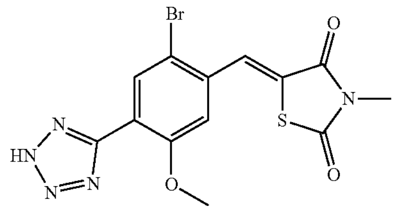 [SMILES: COc1cc(/C=C2\SC(=O)N(C)C2=O)c(Br)cc1-c1nn[nH]n1] | [M + H]+ 396.2 |
| Ex36 | C26 / D1 | 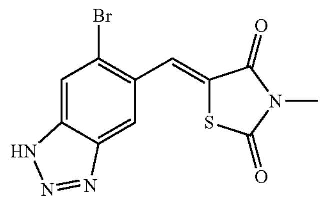 [SMILES: CN1C(=O)S/C(=C\c2cc3nn[nH]c3cc2Br)C1=O] | [M + H]+ 339.2 |
| Ex37 | C32 / D1 | 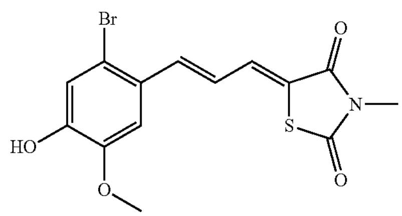 [SMILES: COc1cc(/C=C/C=C2\SC(=O)N(C)C2=O)c(Br)cc1O] | [M + Na]+ 392.0 |
| Ex38 | C1 | 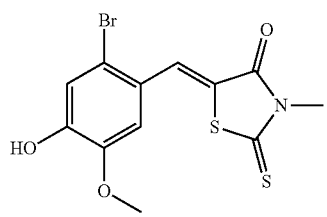 | [M + Na]+ 381.8 |
| Ex39 | C1 / D2 | 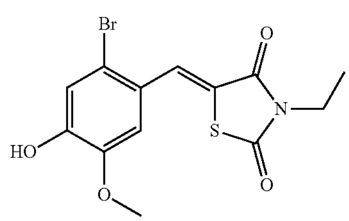 [SMILES: CCN1C(=O)S/C(=C\c2cc(OC)c(O)cc2Br)C1=O] | [M + H]+ 358.1 |
| Ex40 | C1 / D3 | 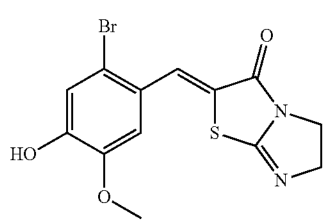 | [M + H]+ 355.0 |

-continued
| Example | Building blocks | Structure | MS |
|---|---|---|---|
| Ex41 | 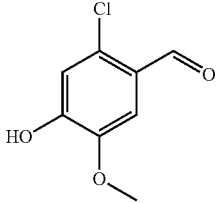 C1, D3 | 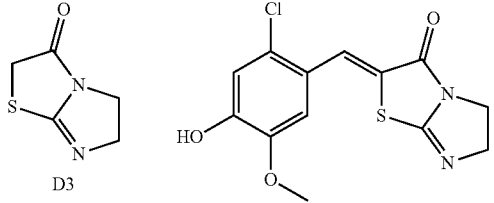 | [M + H]+ 311.0 |
| Ex42 | 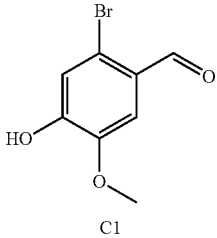 C1, D4 | 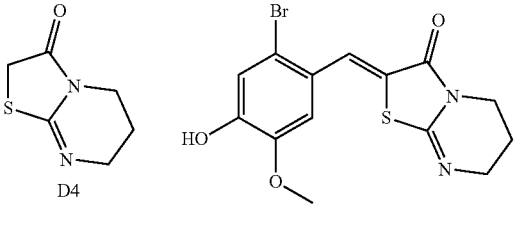 | [M + H]+ 369.0 |
| Ex43 | 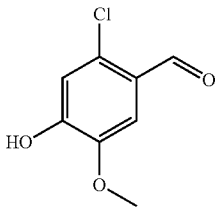 D4 | 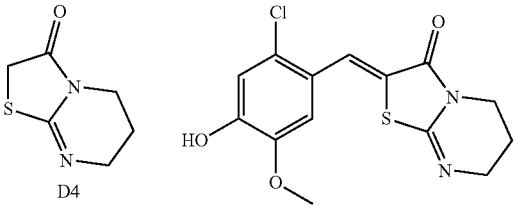 | [M + H]+ 325.0 |
| Ex44 | 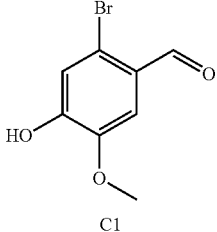 C1 | 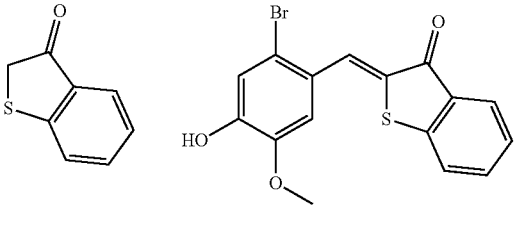 | [M + H]+ 362.9 |
| Ex45 | 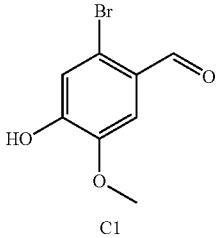 C1, D5 | 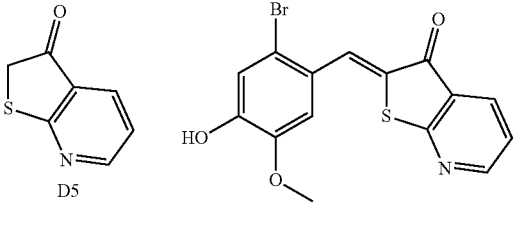 | [M + H]+ 364.0 |
| Ex46 | 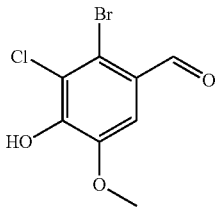 D5 | 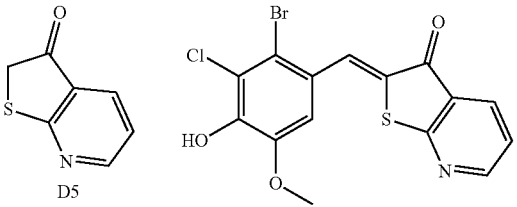 | [M + H]+ 398.2 |

| Example | Building blocks | | Structure | MS |
|---|---|---|---|---|
| Ex47 | 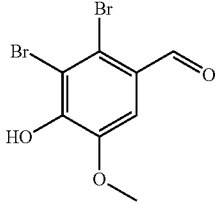 | 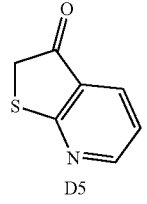   D5 | 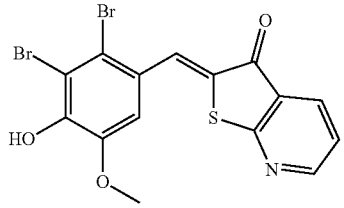 [SMILES: COc1cc(/C=C2\Sc3ncccc3C2=O)c(Br)c(Br)c1O] | [M + H]+ 441.8 |
| Ex48 | 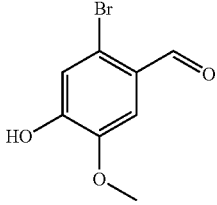   C1 | 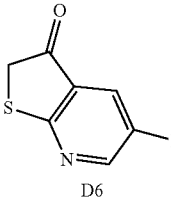   D6 | 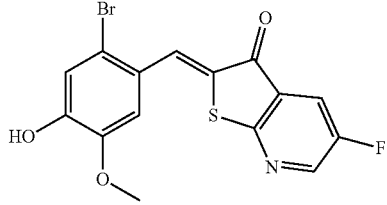 [SMILES: COc1cc(/C=C2\Sc3ncc(F)cc3C2=O)c(Br)cc1O] | [M + H]+ 382.0 |
| Ex49 | 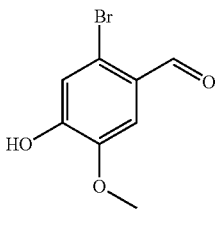   C1 | 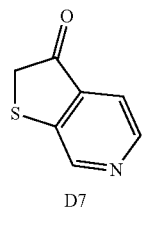   D7 | 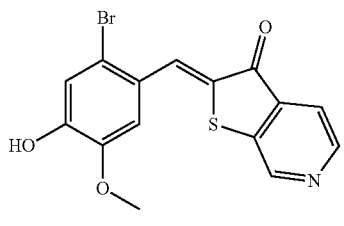 [SMILES: COc1cc(/C=C2\Sc3cnccc3C2=O)c(Br)cc1O] | [M + H]+ 364.0 |
| Ex50 | 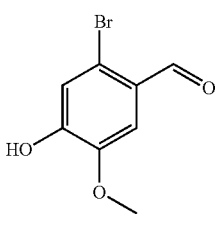   C1 |    D8 | 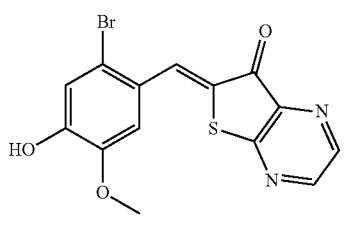 [SMILES: COc1cc(/C=C2\Sc3nccnc3C2=O)c(Br)cc1O] | [M + H]+ 365.0 |
| Ex51 | 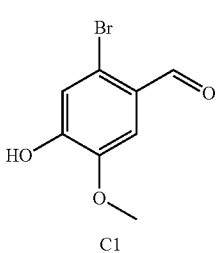   C1 | 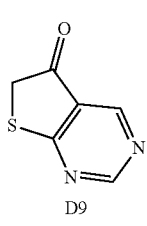   D9 | 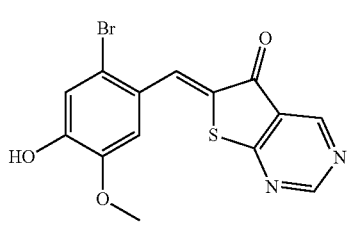 [SMILES: COc1cc(/C=C2\Sc3ncncc3C2=O)c(Br)cc1O] | [M + H]+ 365.2 |
| Ex52 | 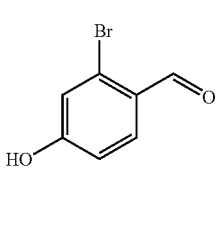 | 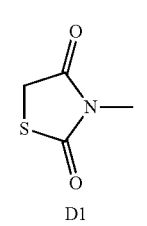   D1 | 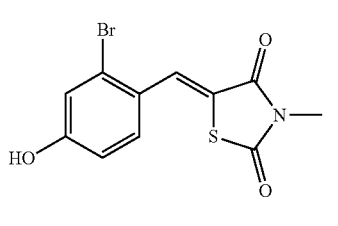 [SMILES: CN1C(=O)S/C(=C\c2ccc(O)cc2Br)C1=O] | [M + H]+ 313.9 |

-continued
| Example | Building blocks | Structure | MS |
|---|---|---|---|
| Ex53 | 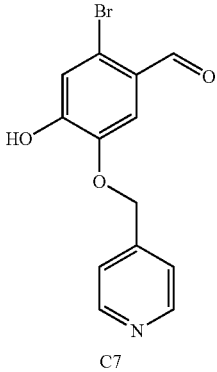 C7, D1 | 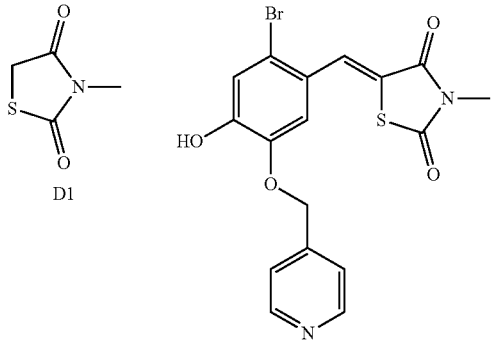 | [M + H]+ 420.9 |
| Ex54 | 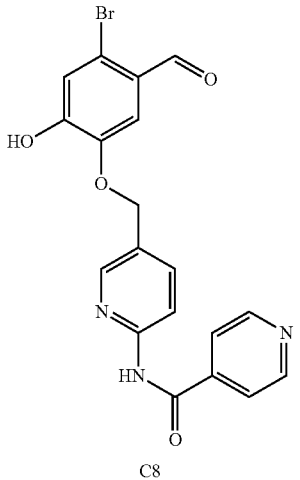 C8, D1 | 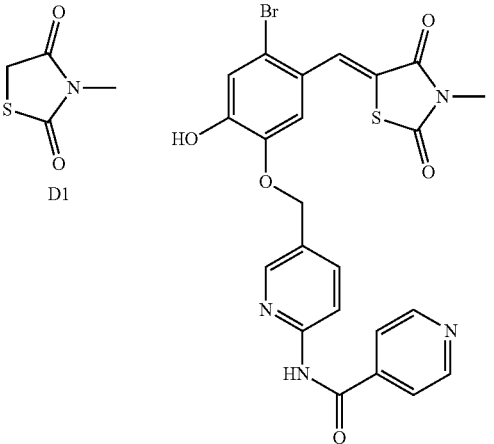 | [M + H]+ 541.0 |
| Ex55 | 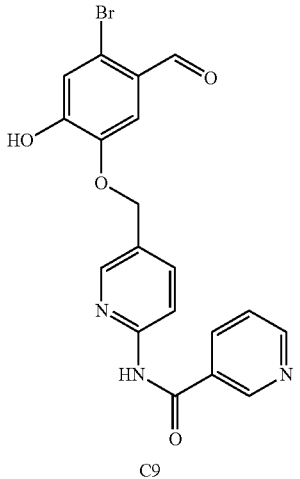 C9, D1 | 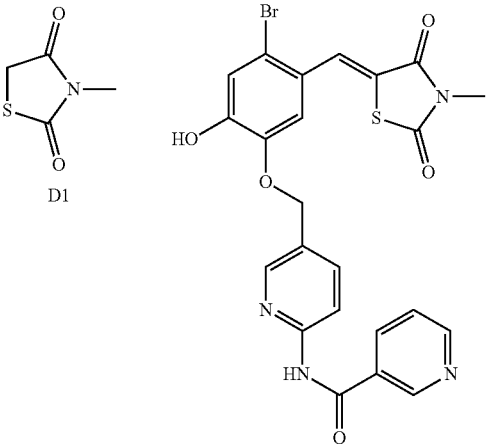 | [M + H]+ 541.0 |

-continued
| Example | Building blocks | Structure | MS |
|---|---|---|---|
| Ex56 | 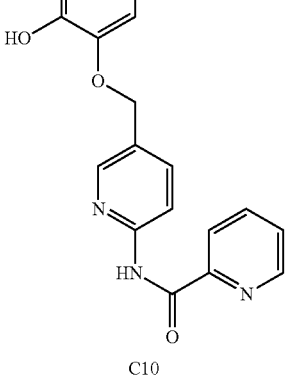 C10 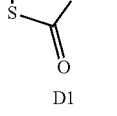 D1 | 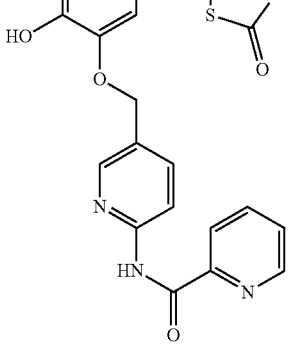 | [M + H]+ 541.0 |
| Ex57 | 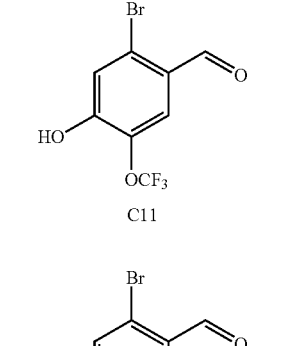 C11 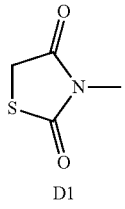 D1 | 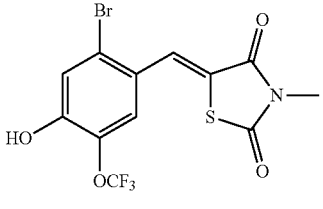 [SMILES: CN1C(=O)S/C(=C\c2cc(OC(F)(F)F)c(O)cc2Br)C1=O] | [M + H]+ 397.9 |
| Ex58 | 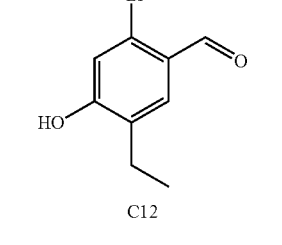 C12 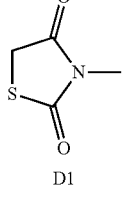 D1 | 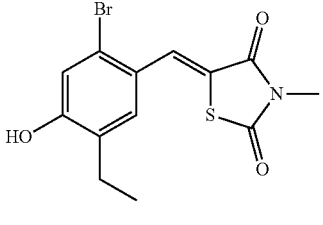 [SMILES: CCc1cc(/C=C2\SC(=O)N(C)C2=O)c(Br)cc1O] | [M + H]+ 342.1 |
| Ex59 | 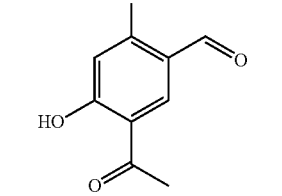 C13 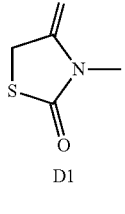 D1 | 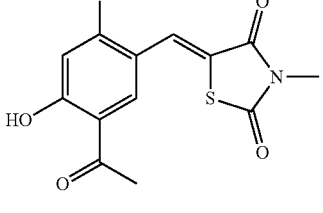 | [M − H]− 354 |
| Ex60 | 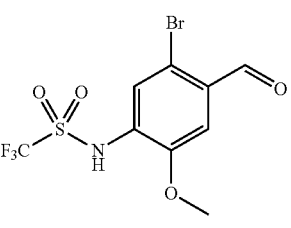 C14 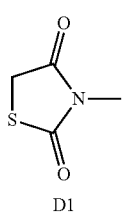 D1 | 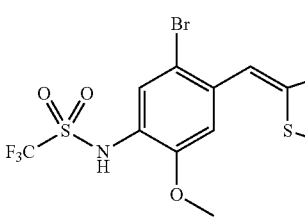 | [M + H]+ 474.9 |

-continued

| Example | Building blocks | Structure | MS |
|---|---|---|---|
| Ex61 | C15 | 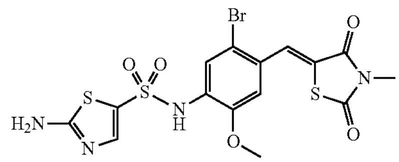 [SMILES: COc1cc(/C=C2\SC(=O)N(C)C2=O)c(Br)cc1NS(=O)(=O)c1cnc(N)s1] | [M + H]+ 504.9 |
| Ex62 | C16 | 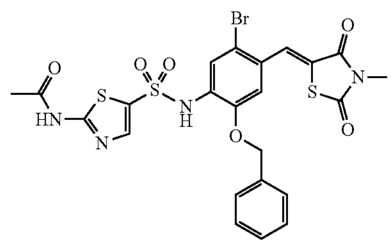 [SMILES: CC(=O)Nc1ncc(S(=O)(=O)Nc2cc(Br)c(/C=C3\SC(=O)N(C)C3=O)cc2OCc2ccccc2)s1] | [M + H]+ 623.1 |
| Ex63 | C4 | 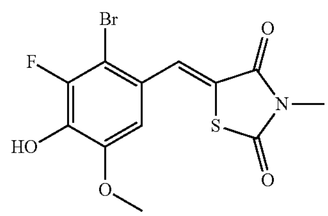 [SMILES: COc1cc(/C=C2\SC(=O)N(C)C2=O)c(Br)c(F)c1O] | [M + H]+ 361.9 |
| Ex64 | C17 | 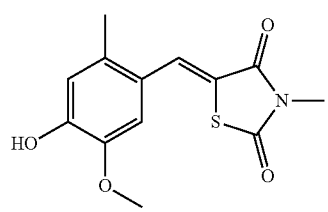 [SMILES: COc1cc(/C=C2\SC(=O)N(C)C2=O)c(C)cc1O] | [M + H]+ 280.1 |
| Ex65 | C2 | 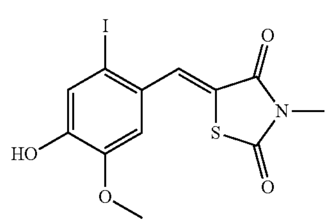 [SMILES: COc1cc(/C=C2\SC(=O)N(C)C2=O)c(I)cc1O] | [M + H]+ 391.9 |
| Ex66 | C18 | 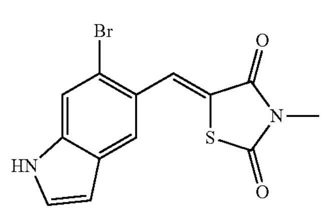 [SMILES: CN1C(=O)S/C(=C\c2cc3cc[nH]c3cc2Br)C1=O] | [M + H]+ 337.1 |

-continued
| Example | Building blocks | Structure | MS |
|---|---|---|---|
| Ex67 | 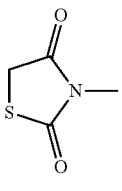 C20, D1 | 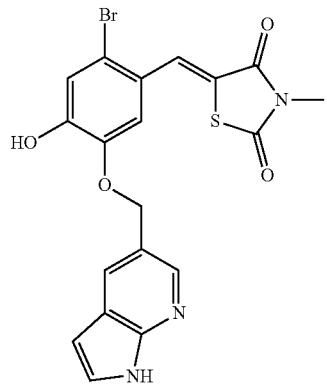 [SMILES: CN1C(=O)S/C(=C\c2cc(OCc3cnc4[nH]ccc4c3)c(O)cc2Br)C1=O] | — |
| Ex68 | 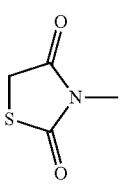 C21, D1 | 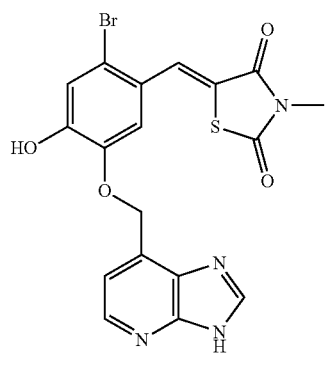 | [M + H]+ 463.0 |
| Ex69 | 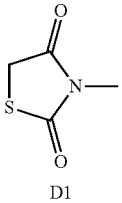 C35, D1 | 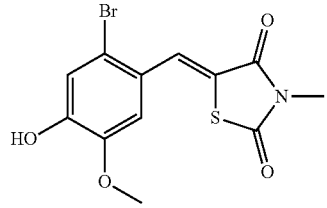 | — |
| Ex70 | 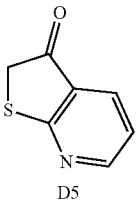 C11, D5 | 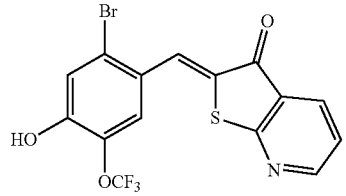 [SMILES: O=C1/C(=C/c2cc(OC(F)(F)F)c(O)cc2Br)Sc2ncccc21] | [M + H]+ 417.9 |
| Ex71 | 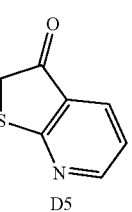 D5 | 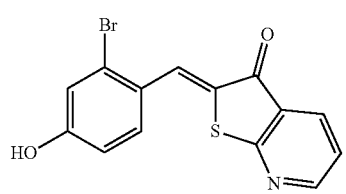 [SMILES: O=C1/C(=C/c2ccc(O)cc2Br)Sc2ncccc21] | [M + Na]+ 358.1 |

-continued

| Example | Building blocks | Structure | MS |
|---|---|---|---|
| Ex72 | C7 | 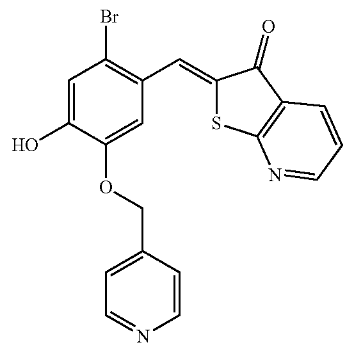 [SMILES: O=C1/C(=C/c2cc(OCc3ccncc3)c(O)cc2Br)Sc2ncccc21] | [M + H]+ 441.0 |
| Ex73 | C24 | 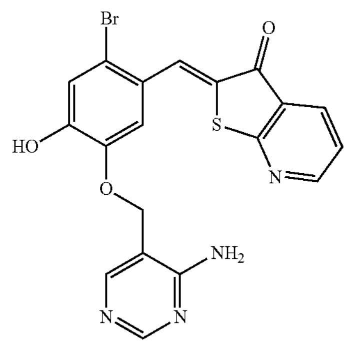 | [M + H]+ 457.0 |
| Ex74 | C25 | 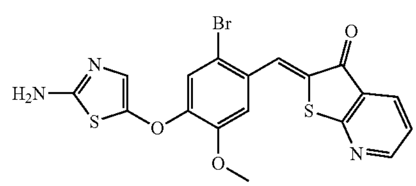 [SMILES: COc1cc(/C=C2\Sc3ncccc3C2=O)c(Br)cc1Oc1cnc(N)s1] | [M + H]+ 462.0 |
| Ex75 | C4 | 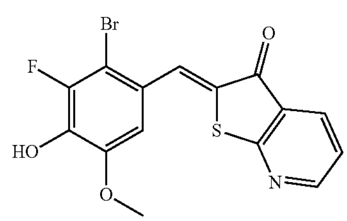 [SMILES: COc1cc(/C=C2\Sc3ncccc3C2=O)c(Br)c(F)c1O] | [M + H]+ 381.9 |
| Ex76 | C17 | 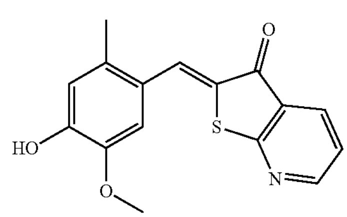 [SMILES: COc1cc(/C=C2\Sc3ncccc3C2=O)c(C)cc1O] | [M + H]+ 300.1 |

-continued
| Example | Building blocks | Structure | MS |
|---|---|---|---|
| Ex77 | 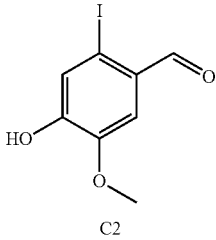 C2    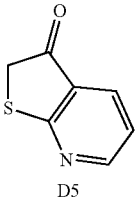 D5 | 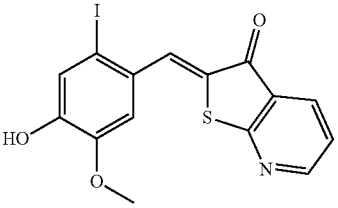 [SMILES: COc1cc(/C=C2\Sc3ncccc3C2=O)c(I)cc1O] | [M + H]⁺ 411.9 |
| Ex78 | 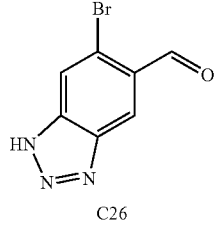 C26    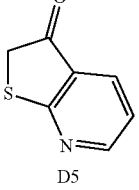 D5 | 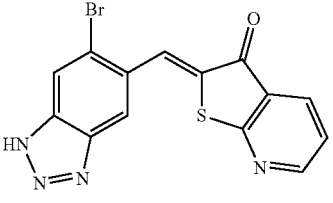 [SMILES: O=C1/C(=C/c2cc3nn[nH]c3cc2Br)Sc2ncccc21] | [M + H]⁺ 359.1 |
| Ex79 | 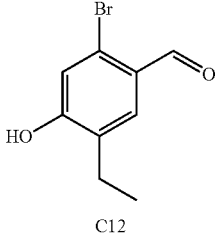 C12    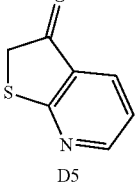 D5 | 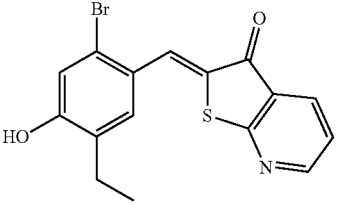 [SMILES: CCc1cc(/C=C2\Sc3ncccc3C2=O)c(Br)cc1O] | [M + H]⁺ 362.0 |
Example 80
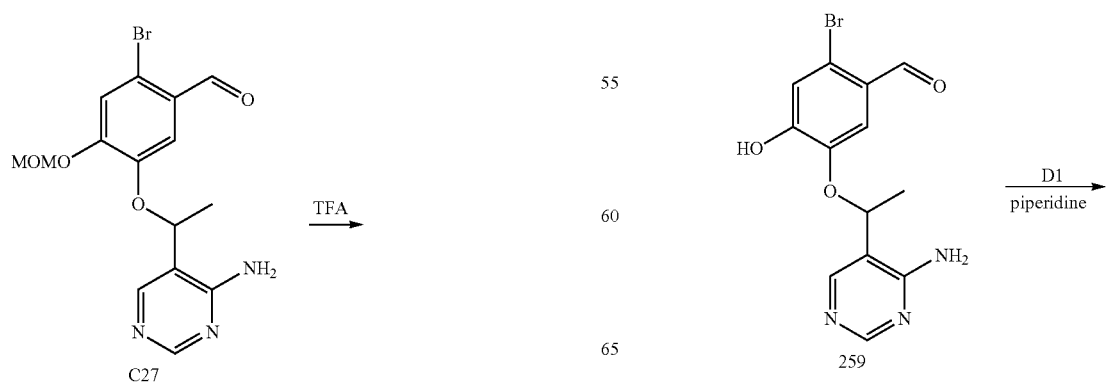

-continued

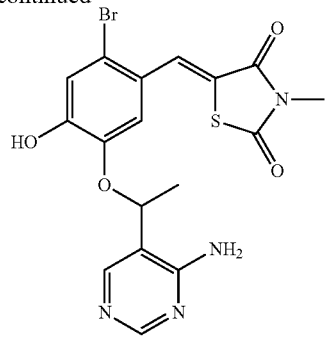

Ex80

Step 1: Phenol 222

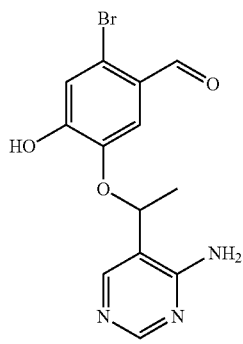 [SMILES: CC(Oc1cc(C=O)c(Br)cc1O)c1cncnc1N]

To a solution of C27 (60 mg, 0.16 mmol) in DCM is added TFA (1 mL) dropwise at 0° C. After stirring at room temperature for 2 hours, the mixture is concentrated to give crude 259 as a yellow oil (40 mg, 75% yield). (MS: [M+H]$^+$ 339.3)

Step 2: Ex80

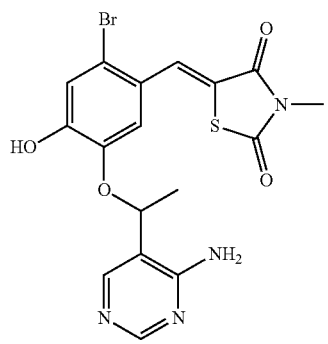 [SMILES: CC(Oc1cc(/C=C2\SC(=O)N(C)C2=O)c(Br)cc1O)c1cncnc1N]

To a solution of 259 (40 mg, 0.12 mmol) in EtOH (1 mL) is added piperidine (10 mg, 0.12 mmol) and D1 (16 mg, 0.12 mmol). After stirring at 60° C. for 12 hours, the mixture is concentrated and purified by prep-HPLC to give Ex80 as a yellow solid (3.6 mg, 7% yield). (MS: [M+H]$^+$ 453)

The following compounds are prepared by essentially the same method as for Ex80.

| Example | Building blocks | | Structure | MS |
|---|---|---|---|---|
| Ex81 | C19 | D1 | 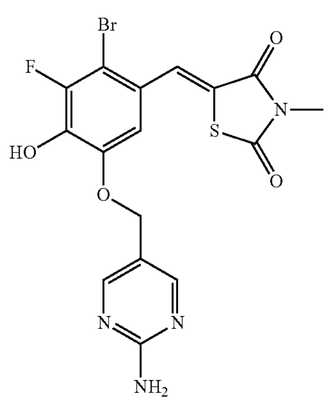 [SMILES: CN1C(=O)S/C(=C\c2cc(OCc3cnc(N)nc3)c(O)c(F)c2Br)C1=O] | [M + H]$^+$ 455.1 |

-continued

| Example | Building blocks | Structure | MS |
|---|---|---|---|
| Ex82 | C22 / D1 | 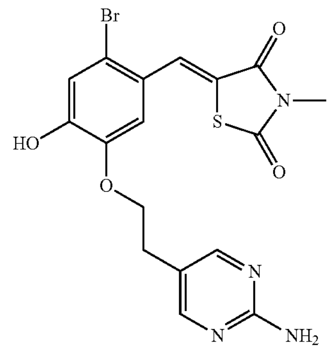 [SMILES: CN1C(=O)S/C(=C\c2cc(OCCc3cnc(N)nc3)c(O)cc2Br)C1=O] | [M + H]+ 452.8 |
| Ex83 | C23 / D1 | 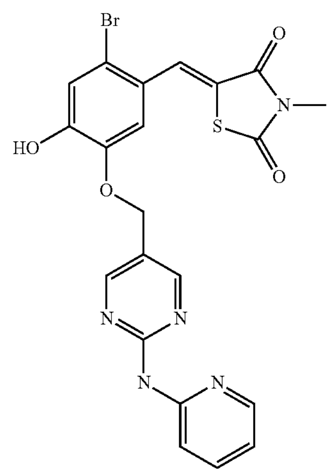 [SMILES: CN1C(=O)S/C(=C\c2cc(OCc3cnc(Nc4ccccn4)nc3)c(O)cc2Br)C1=O] | [M + H]+ 514 |

The following compounds are prepared by essentially the same method as for E23.

| Example | Building blocks | Structure | MS |
|---|---|---|---|
| Ex84 | E2 / B19 | 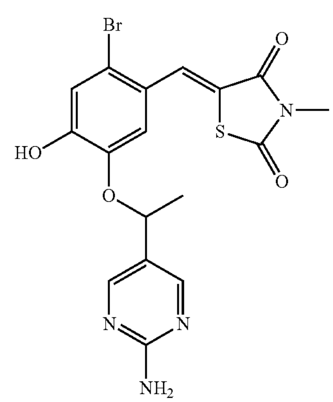 | [M + H]+ 451.0 |

-continued
| Example | Building blocks | | Structure | MS |
|---|---|---|---|---|
| Ex85 | 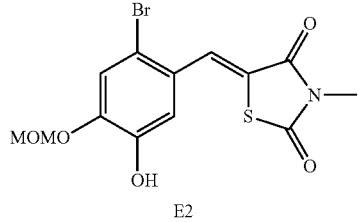 E2 | 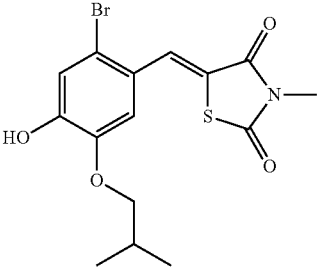 [SMILES: CC(C)COc1cc(/C=C2\SC(=O)N(C)C2=O)c(Br)cc1O] | 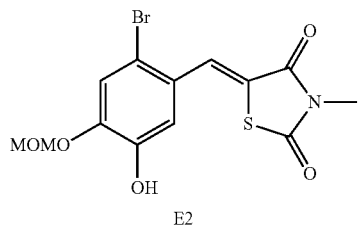 | [M + H]⁺ 386.0 |
| Ex86 | 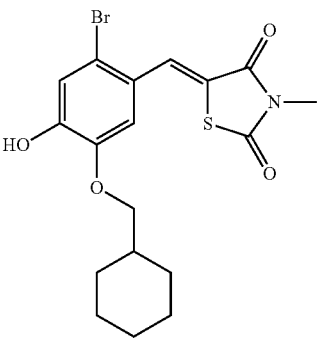 E2 | 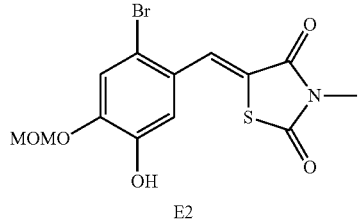 | 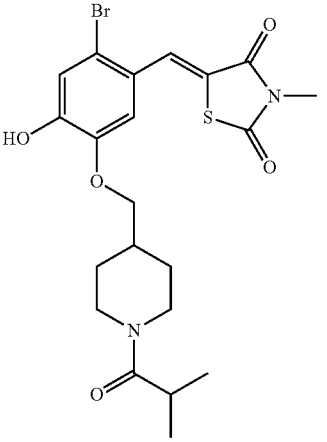 | [M + H]⁺ 426.0 |
| Ex87 | 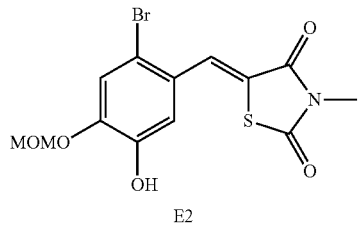 E2 | B22 | (see structure) | [M + H]⁺ 497.0 |
| Ex88 | 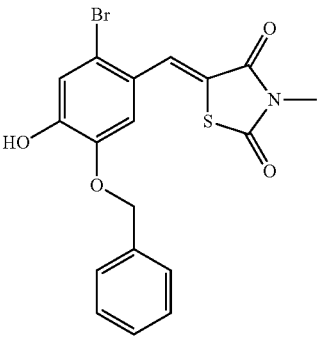 E2 | | 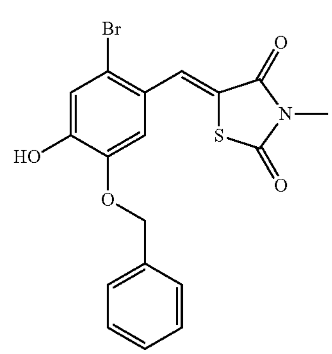 [SMILES: CN1C(=O)S/C(=C\c2cc(OCc3ccccc3)c(O)cc2Br)C1=O] | [M + H]⁺ 420.0 |

-continued
| Example | Building blocks | | Structure | MS |
|---|---|---|---|---|
| Ex89 | 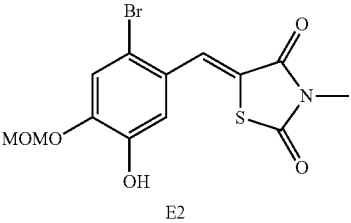 E2 | 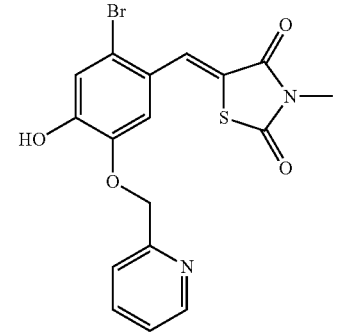 [SMILES: CN1C(=O)S/C(=C\c2cc(OCc3ccccn3)c(O)cc2Br)C1=O] | 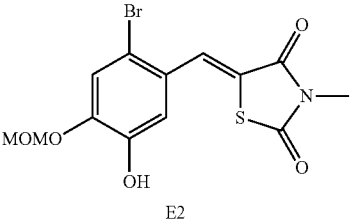 | [M + H]+ 421.0 |
| Ex90 | 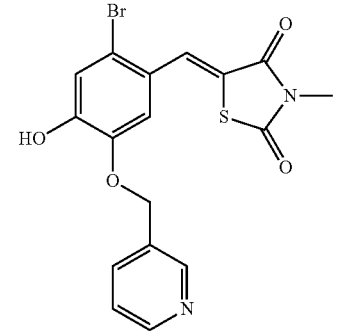 E2 | 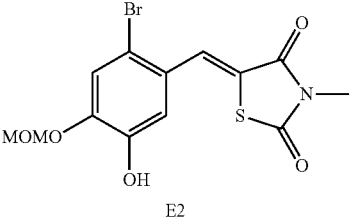 | 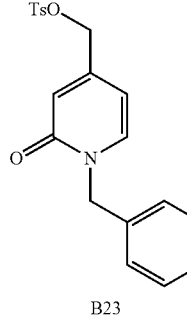 | [M + H]+ 421.0 |
| Ex91 | 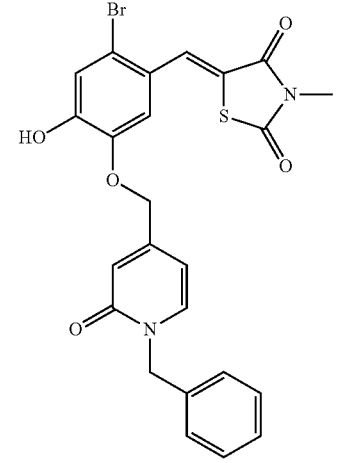 E2 | 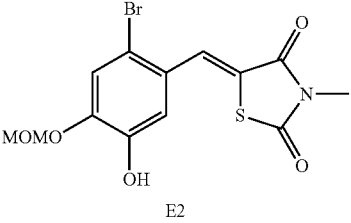 B23 | 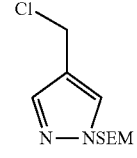 | [M + H]+ 527.0 |
| Ex92 | 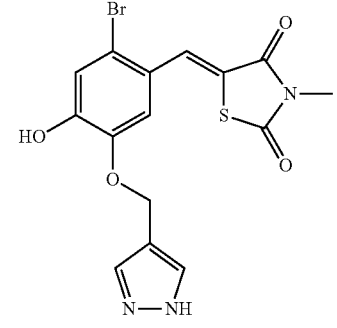 E2 | | 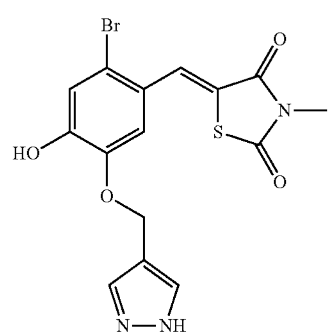 [SMILES: CN1C(=O)S/C(=C\c2cc(OCc3cn[nH]c3)c(O)cc2Br)C1=O] | [M + H]+ 410.0 |

-continued
| Example | Building blocks | | Structure | MS |
|---|---|---|---|---|
| Ex93 | 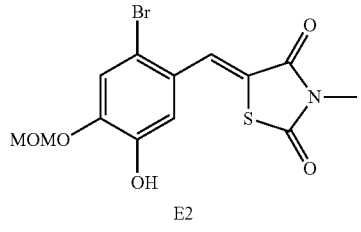 E2 | 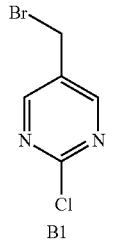 B1 | 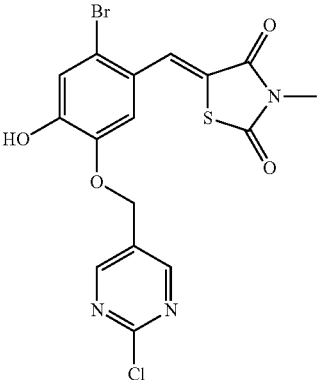 [SMILES: CN1C(=O)S/C(=C\c2cc(OCc3cnc(Cl)nc3)c(O)cc2Br)C1=O] | [M + H]+ 455.9 |
| Ex94 | 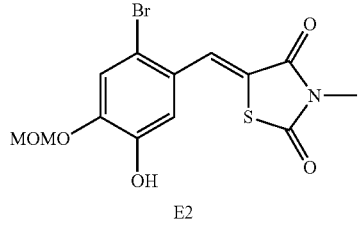 E2 | 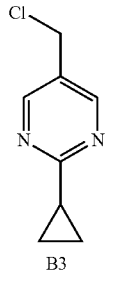 B3 | 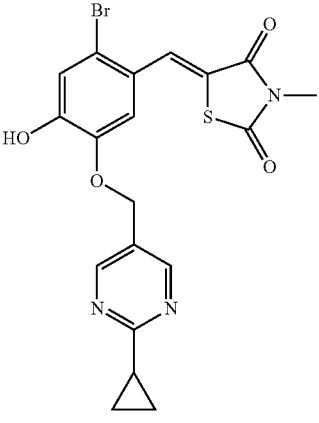 [SMILES: CN1C(=O)S/C(=C\c2cc(OCc3cnc(C4CC4)nc3)c(O)cc2Br)C1=O] | [M + H]+ 462.1 |
| Ex95 | 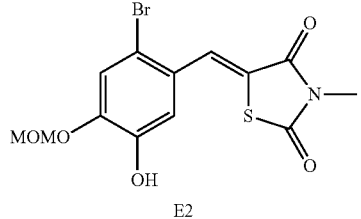 E2 | 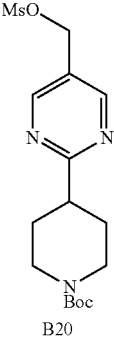 B20 | 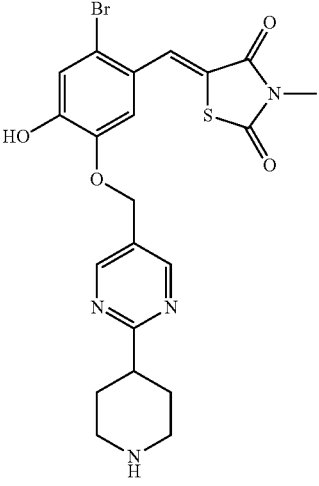 [SMILES: CN1C(=O)S/C(=C\c2cc(OCc3cnc(C4CCNCC4)nc3)c(O)cc2Br)C1=O] | [M + H]+ 507.0 |

-continued
| Example | Building blocks | | Structure | MS |
|---|---|---|---|---|
| Ex96 | 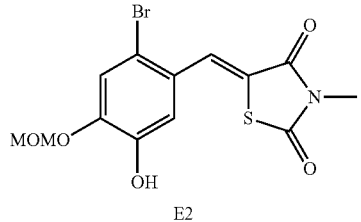<br>E2 | 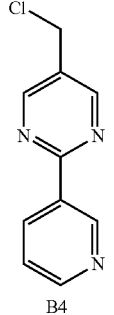<br>B4 | 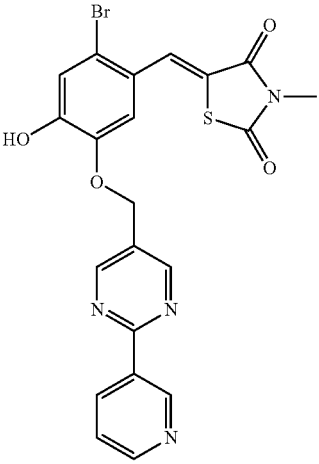 [SMILES: CN1C(=O)S/C(=C\c2cc(OCc3cnc(-c4cccnc4)nc3)c(O)cc2Br)C1=O] | [M + H]+ 499.0 |
| Ex97 | 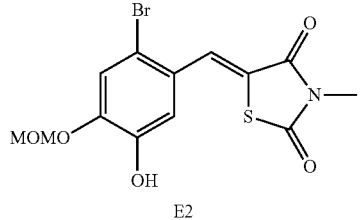<br>E2 | 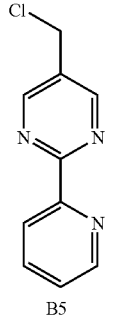<br>B5 | 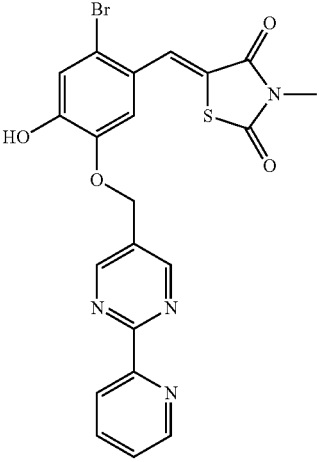 [SMILES: CN1C(=O)S/C(=C\c2cc(OCc3cnc(-c4ccccn4)nc3)c(O)cc2Br)C1=O] | [M + H]+ 499.0 |
| Ex98 | 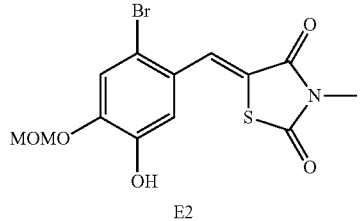<br>E2 | 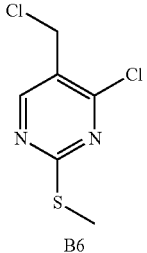<br>B6 | 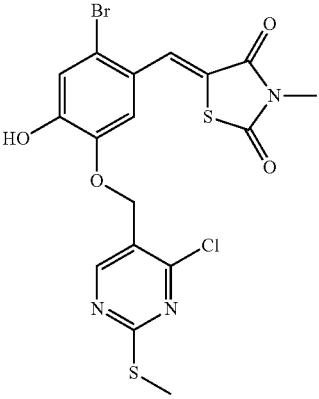 [SMILES: CSc1ncc(COc2cc(/C=C3\SC(=O)N(C)C3=O)c(Br)cc2O)c(Cl)n1] | [M + H]+ 501.9 |

-continued
| Example | Building blocks | | Structure | MS |
|---|---|---|---|---|
| Ex99 | 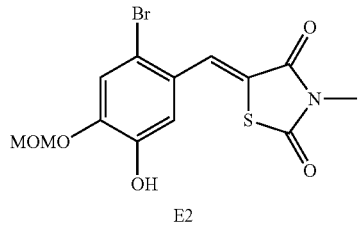 E2 | 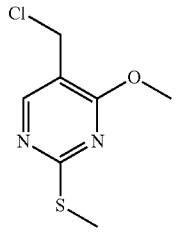 B7 | 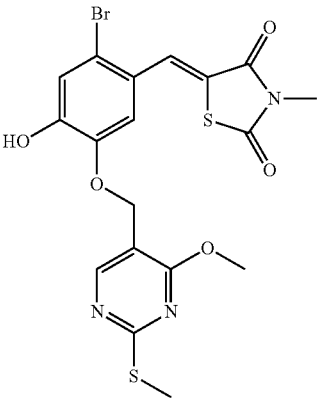 [SMILES: COc1nc(SC)ncc1COc1cc(/C=C2\SC(=O)N(C)C2=O)c(Br)cc1O] | [M + H]+ 498.0 |
| Ex100 | 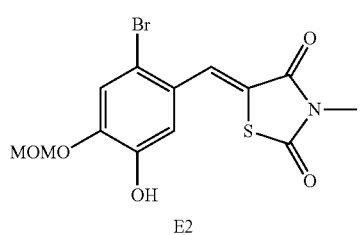 E2 | 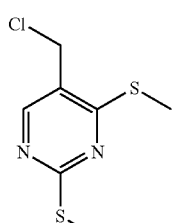 B7 | 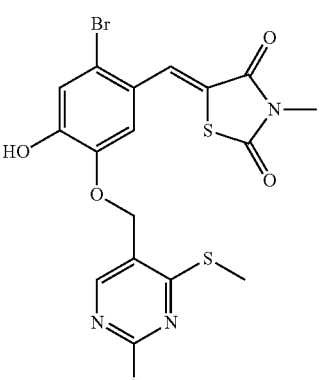 | [M + H]+ 513.9 |
| Ex101 | 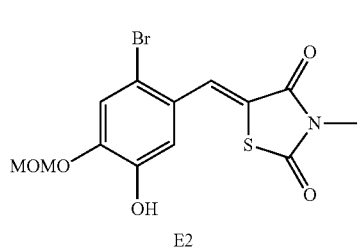 E2 | 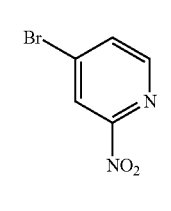 | 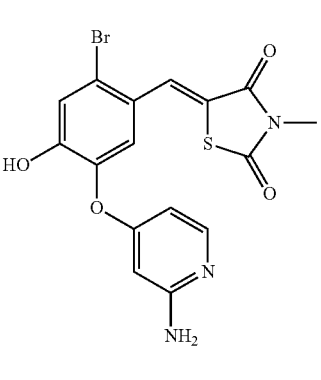 | [M + H]+ 422.0 |
| Ex102 | 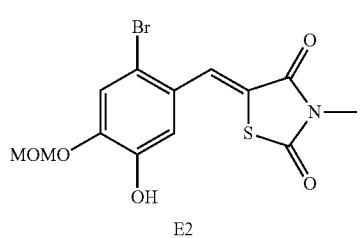 E2 | 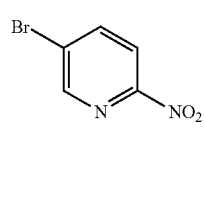 | 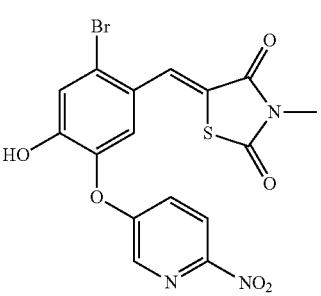 [SMILES: CN1C(=O)S/C(=C\c2cc(Oc3ccc([N+](=O)[O-])nc3)c(O)cc2Br)C1=O] | [M + H]+ 451.9 |

-continued
| Example | Building blocks | | Structure | MS |
|---|---|---|---|---|
| Ex103 | 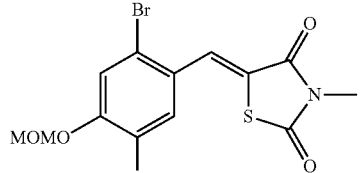 E2 | 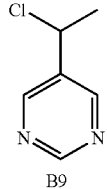 B9 | 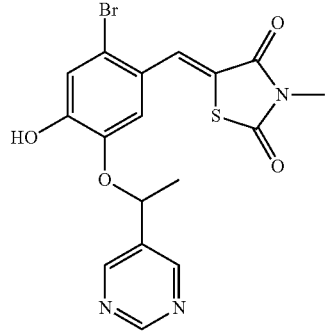 [SMILES: CC(Oc1cc(/C=C2\SC(=O)N(C)C2=O)c(Br)cc1O)c1cncnc1] | [M + H]+ 436.0 |
| Ex104 | 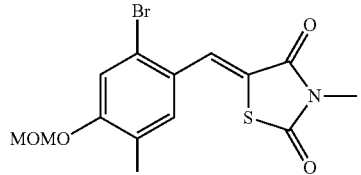 E2 | 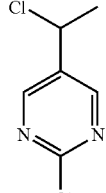 B10 | 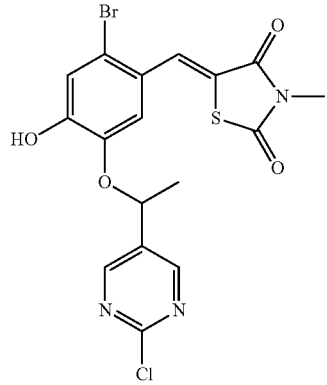 [SMILES: CC(Oc1cc(/C=C2\SC(=O)N(C)C2=O)c(Br)cc1O)c1cnc(Cl)nc1] | [M + H]+ 469.9 |
| Ex105 | 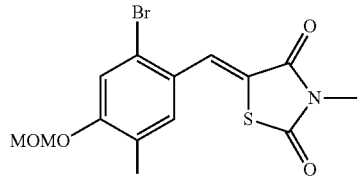 E2 | 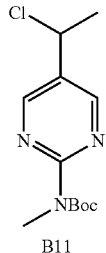 B11 | 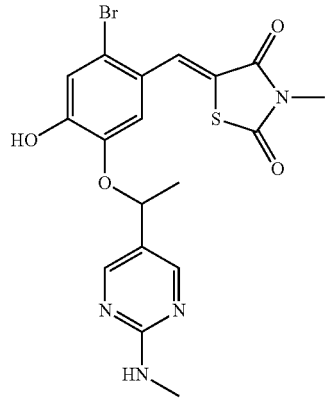 [SMILES: CNc1ncc(C(C)Oc2cc(/C=C3\SC(=O)N(C)C3=O)c(Br)cc2O)cn1] | [M + H]+ 465.0 |
| Ex106 | 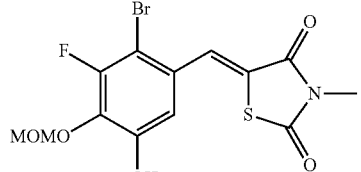 E3 | 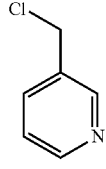 | 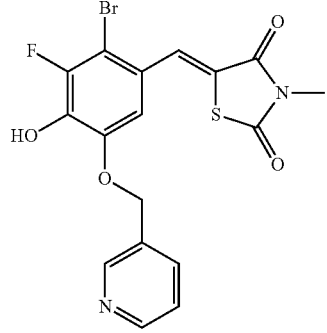 [SMILES: CN1C(=O)S/C(=C\c2cc(OCc3cccnc3)c(O)c(F)c2Br)C1=O] | [M + H]+ 439.0 |

| Example | Building blocks | | Structure | MS |
|---|---|---|---|---|
| Ex107 | E3 | B1 | 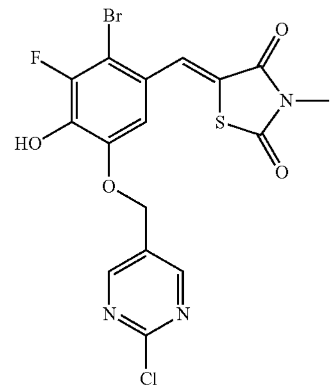 [SMILES: CN1C(=O)S/C(=C\c2cc(OCc3cnc(Cl)nc3)c(O)c(F)c2Br)C1=O] | [M + H]+ 473.9 |
| Ex108 | E3 | B16 | 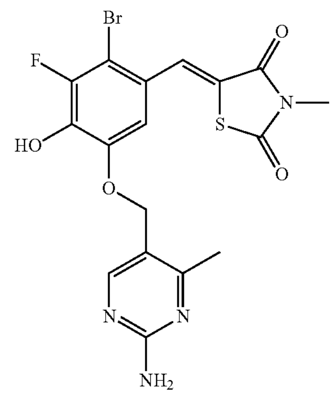 [SMILES: Cc1nc(N)ncc1COc1cc(/C=C2\SC(=O)N(C)C2=O)c(Br)c(F)c1O] | [M + H]+ 469.0 |
| Ex109 | E3 | | 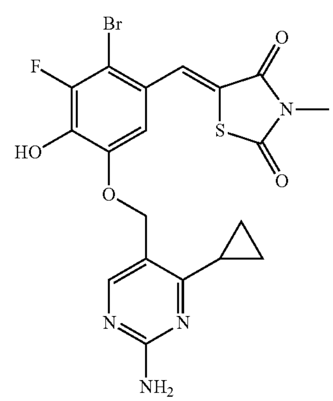 [SMILES: CN1C(=O)S/C(=C\c2cc(OCc3cnc(N)nc3C3CC3)c(O)c(F)c2Br)C1=O] | [M + H]+ 495.0 |
| Ex110 | E3 | B19 | 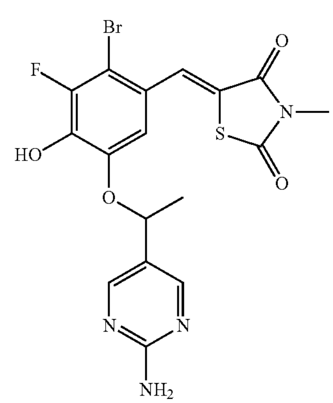 [SMILES: CC(Oc1cc(/C=C2\SC(=O)N(C)C2=O)c(Br)c(F)c1O)c1cnc(N)nc1] | [M + H]+ 469.0 |

-continued
| Example | Building blocks | | Structure | MS |
| --- | --- | --- | --- | --- |
| Ex111 | 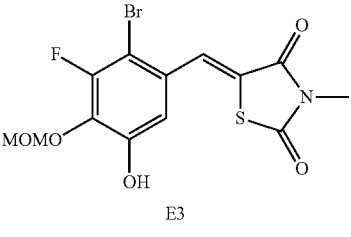 E3 | 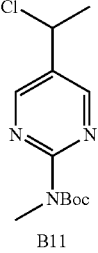 B11 | 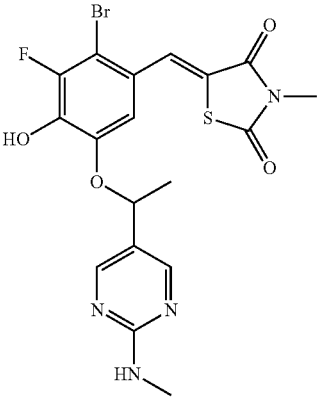 [SMILES: CNc1ncc(C(C)Oc2cc(/C=C3\SC(=O)N(C)C3=O)c(Br)c(F)c2O)cn1] | [M + H]+ 483.0 |
| Ex112 | 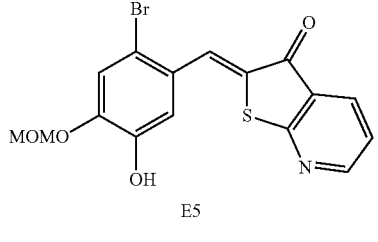 E5 |  | 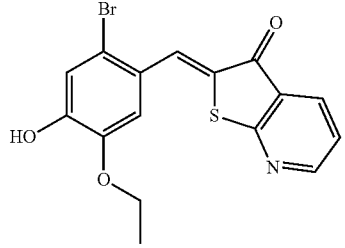 | [M + H]+ 387.0 |
| Ex113 | 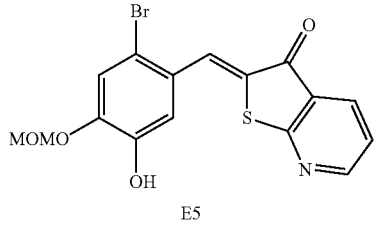 E5 | 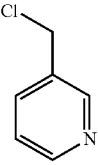 | 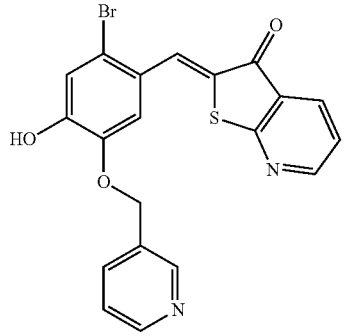 [SMILES: O=C1/C(=C/c2cc(OCc3cccnc3)c(O)cc2Br)Sc2ncccc21] | [M + H]+ 441.0 |
| Ex114 | 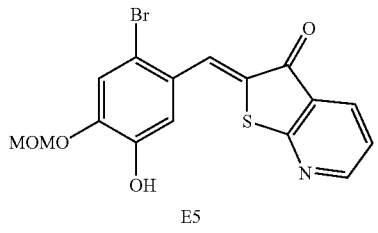 E5 | 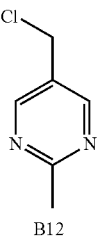 B12 | 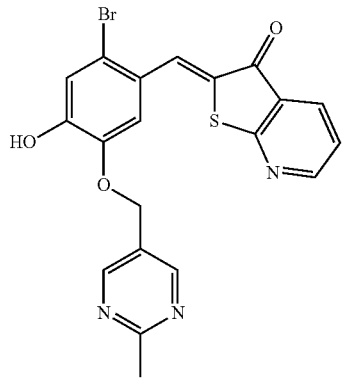 [SMILES: Cc1ncc(COc2cc(/C=C3\Sc4ncccc4C3=O)c(Br)cc2O)cn1] | [M + H]+ 456.0 |

-continued

| Example | Building blocks | Structure | MS |
|---|---|---|---|
| Ex115 | E5, B1 | 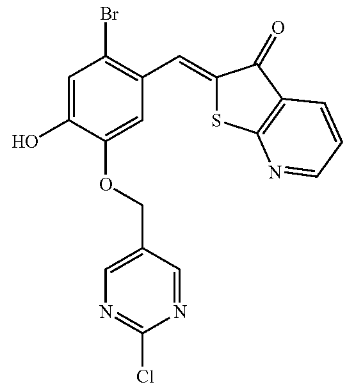 [SMILES: O=C1/C(=C/c2cc(OCc3cnc(Cl)nc3)c(O)cc2Br)Sc2ncccc21] | [M + H]+ 475.9 |
| Ex116 | E5, B16 | 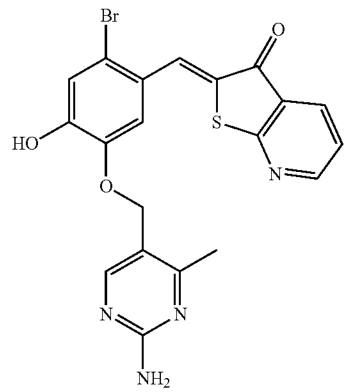 [SMILES: Cc1nc(N)ncc1COc1cc(/C=C2\Sc3ncccc3C2=O)c(Br)cc1O] | [M + H]+ 471.0 |
| Ex117 | E5, B17 | 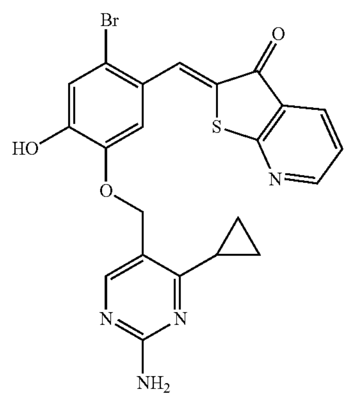 [SMILES: Nc1ncc(COc2cc(/C=C3\Sc4ncccc4C3=O)c(Br)cc2O)c(C2CC2)n1] | [M + H]+ 497.0 |
| Ex118 | E5, B18 | 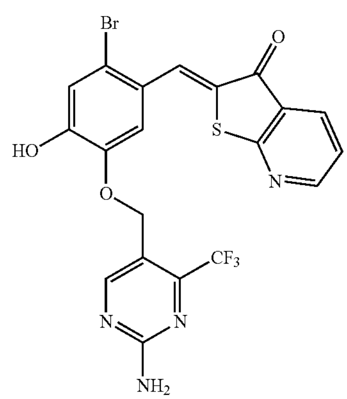 [SMILES: Nc1ncc(COc2cc(/C=C3\Sc4ncccc4C3=O)c(Br)cc2O)c(C(F)(F)F)n1] | [M + H]+ 525.0 |

-continued
| Example | Building blocks | | Structure | MS |
|---|---|---|---|---|
| Ex119 | 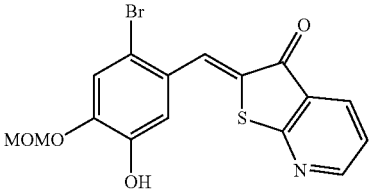 E5 | 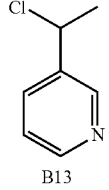 B13 | 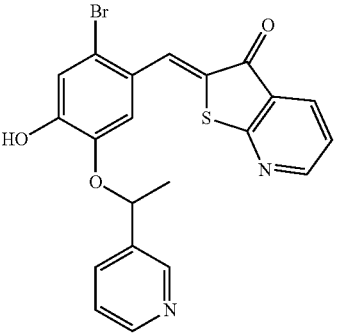 [SMILES: CC(Oc1cc(/C=C2\Sc3ncccc3C2=O)c(Br)cc1O)c1cccnc1] | [M + H]+ 455.0 |
| Ex120 | 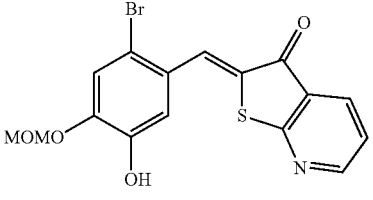 E5 | 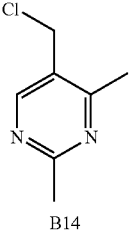 B14 | 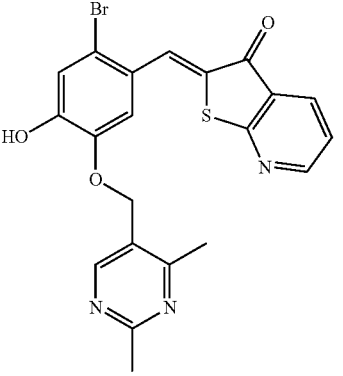 [SMILES: Cc1ncc(COc2cc(/C=C3\Sc4ncccc4C3=O)c(Br)cc2O)c(C)n1] | [M + H]+ 470.0 |
| Ex121 | 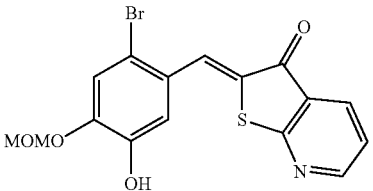 E5 | 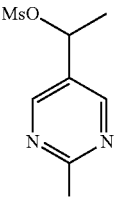 B21 | 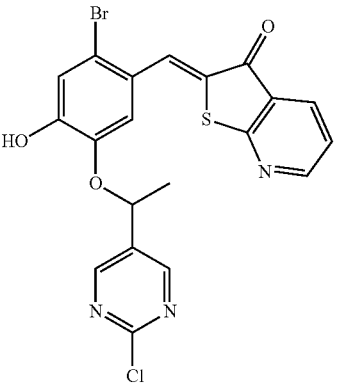 [SMILES: CC(Oc1cc(/C=C2\Sc3ncccc3C2=O)c(Br)cc1O)c1cnc(Cl)nc1] | [M + H]+ 490.0 |
| Ex122 | 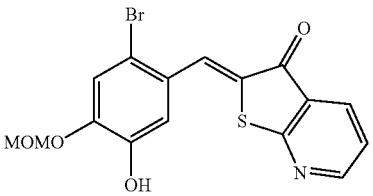 E5 | 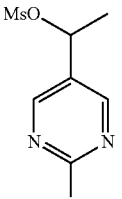 B19 | 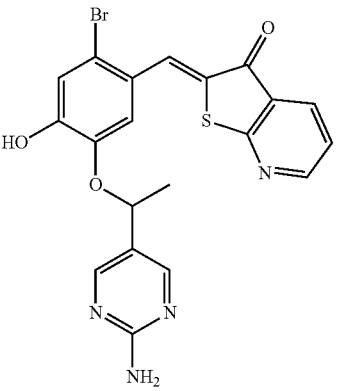 [SMILES: CC(Oc1cc(/C=C2\Sc3ncccc3C2=O)c(Br)cc1O)c1cnc(N)nc1] | [M + H]+ 471.0 |

-continued
| Example | Building blocks | Structure | MS |
|---|---|---|---|
| Ex123 | 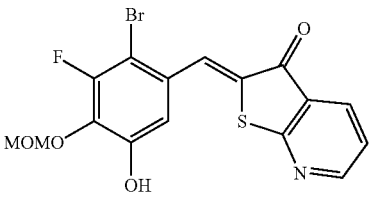 | 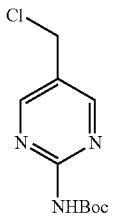 | [M + H]⁺ 475.0 |
| Ex124 | 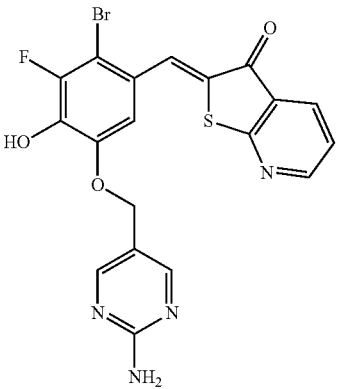 | 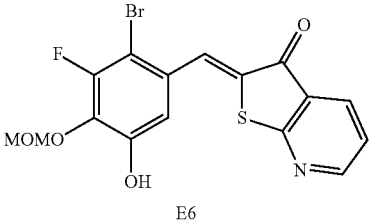 | [M + H]⁺ 489.0 |
Example 125
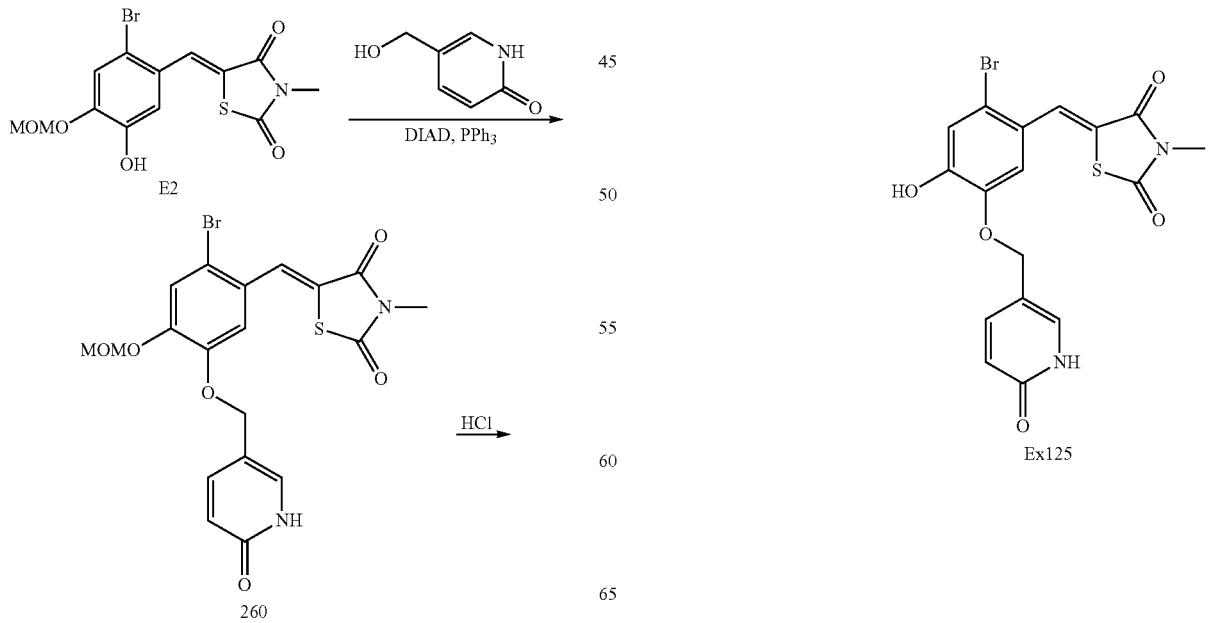

Step 1: pyridinone 260

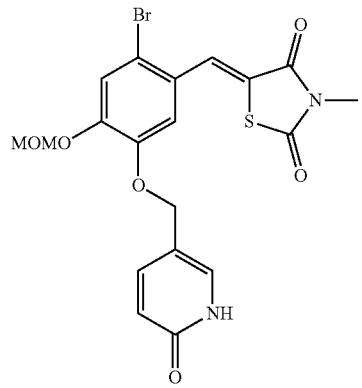

Step 2: Ex125

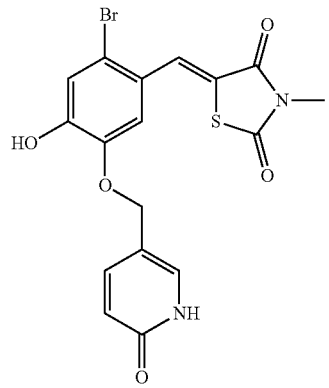 [SMILES: CN1C(=O)S/C(=C\c2cc(OCc3ccc(=O)[nH]c3)c(O)cc2Br)C1=O]

To a solution of E2 (50 mg 0.14 mmol), 5-(hydroxymethyl)pyridin-2(1H)-one (20 mg, 0.16 mmol), and PPh₃ (42 mg, 0.16 mmol) in THF (2 mL) is added DIAD (54 mg 0.27 mmol) at room temperature. After stirring at 30° C. overnight, the mixture is concentrated, triturated with EtOH (3 mL), and collected by filtration to give 260 as a white solid (23 mg 36% yield). (MS: [M+H]⁺ 481.1)

A mixture of 260 (20 mg, 0.05 mmol) and 2M HCl in MeOH (5 mL) is stirred at room temperature for 3 hours. The mixture is then concentrated and purified by prep-TLC (MeOH:DCM=1:20) to give Ex125 as a yellow solid (4 mg, 22% yield). (MS: [M+H]⁺437.2)

The following compounds are prepared by essentially the same method as for Ex125.

| Example | Building blocks | | Structure | MS |
|---|---|---|---|---|
| Ex126 | (E2) | (piperidine building block) | 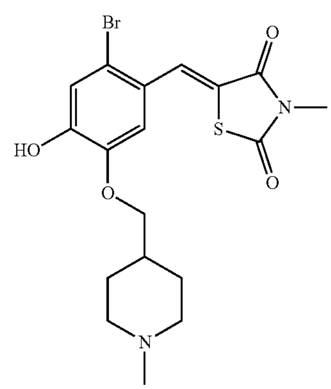 [SMILES: CN1CCC(COc2cc(/C=C3\SC(=O)N(C)C3=O)c(Br)cc2O)CC1] | [M + H]⁺ 441.0 |
| Ex127 | (E2) | (A1) | 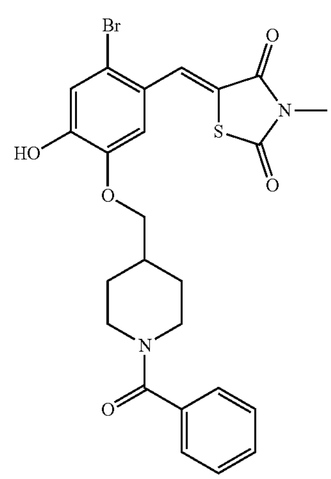 [SMILES: CN1C(=O)S/C(=C\c2cc(OCC3CCN(C(=O)c4ccccc4)CC3)c(O)cc2Br)C1=O] | [M + H]⁺ 531.1 |

-continued
| Example | Building blocks | Structure | MS |
|---|---|---|---|
| Ex128 | 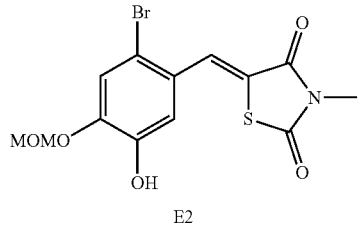 E2  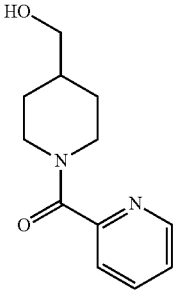 A2 | 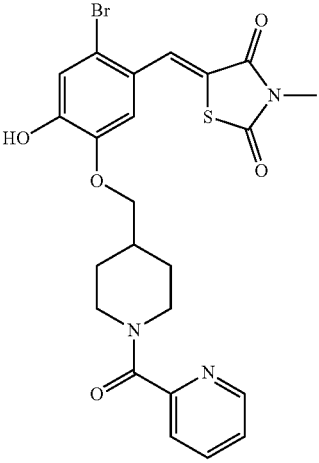 [SMILES: CN1C(=O)S/C(=C\c2cc(OCC3CCN(C(=O)c4ccccn4)CC3)c(O)cc2Br)C1=O] | [M + H]⁺ 532.0 |
| Ex129 | 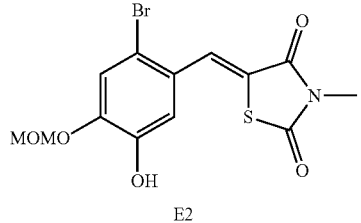 E2  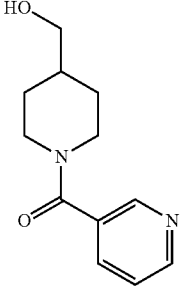 A3 | 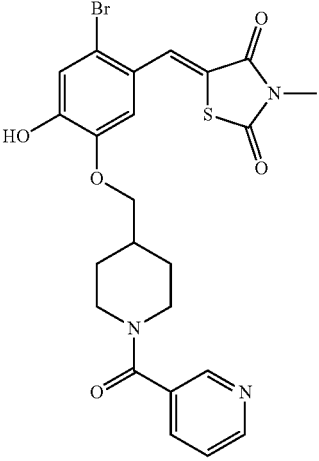 [SMILES: CN1C(=O)S/C(=C\c2cc(OCC3CCN(C(=O)c4cccnc4)CC3)c(O)cc2Br)C1=O] | [M + H]⁺ 532.0 |
| Ex130 | 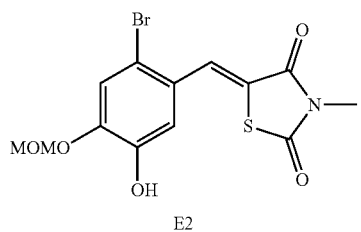 E2  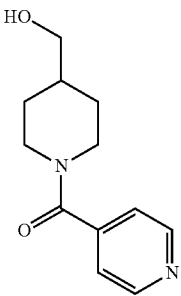 A4 | 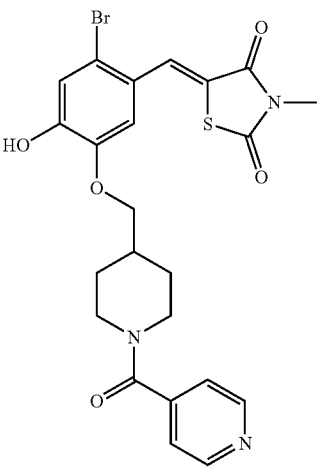 [SMILES: CN1C(=O)S/C(=C\c2cc(OCC3CCN(C(=O)c4ccncc4)CC3)c(O)cc2Br)C1=O] | [M + H]⁺ 532.0 |

-continued
| Example | Building blocks | | Structure | MS |
|---|---|---|---|---|
| Ex131 | 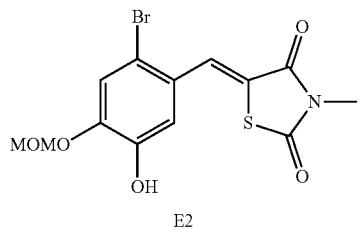 E2 | 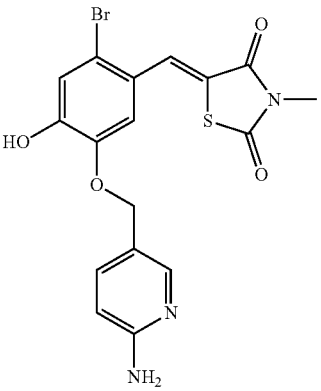 [SMILES: CN1C(=O)S/C(=C\c2cc(OCc3ccc(N)nc3)c(O)cc2Br)C1=O] | 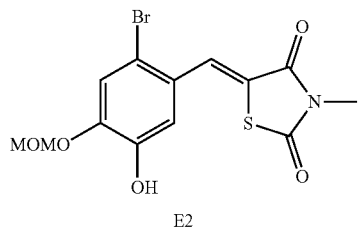 | [M + H]+ 436.0 |
| Ex132 | 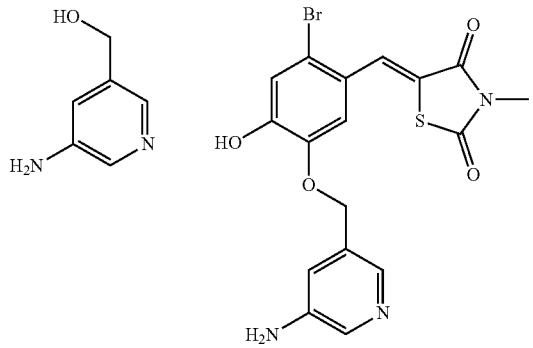 E2 | 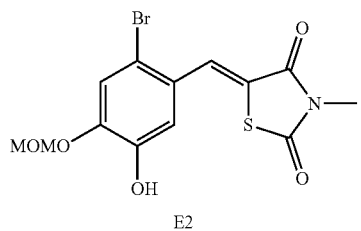 | 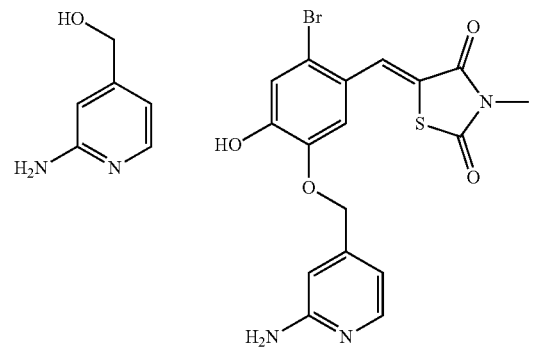 | [M + H]+ 436.0 |
| Ex133 | 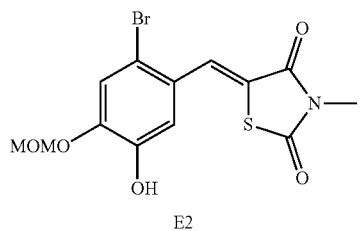 E2 | (structure) | (structure) | [M + H]+ 436.0 |
| Ex134 | 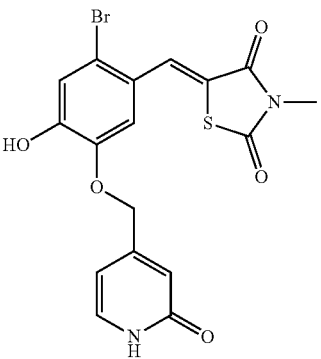 E2 | (structure) | (structure) | [M + H]+ 437.0 |

-continued
| Example | Building blocks | | Structure | MS |
|---|---|---|---|---|
| Ex135 | 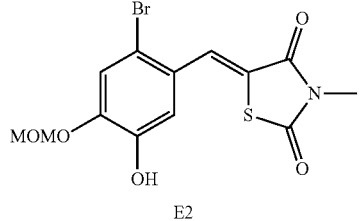 E2 | 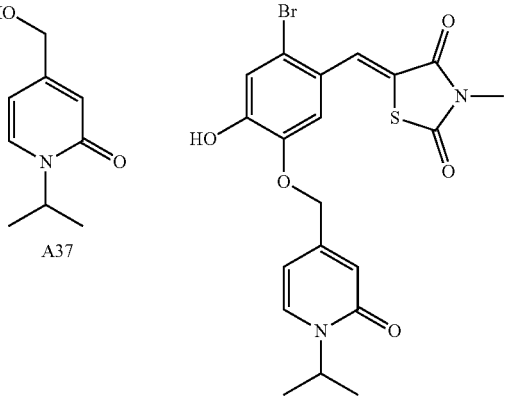 A37 | 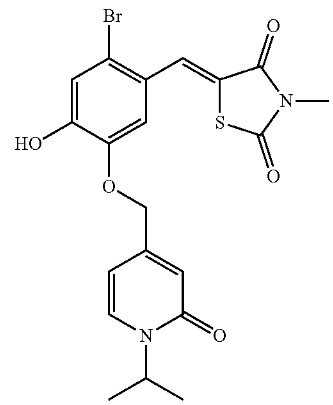 [SMILES: CC(C)n1ccc(COc2cc(/C=C3\SC(=O)N(C)C3=O)c(Br)cc2O)cc1=O] | [M + H]+ 479.0 |
| Ex136 | 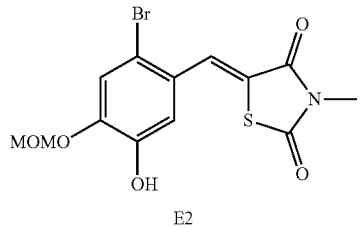 E2 | 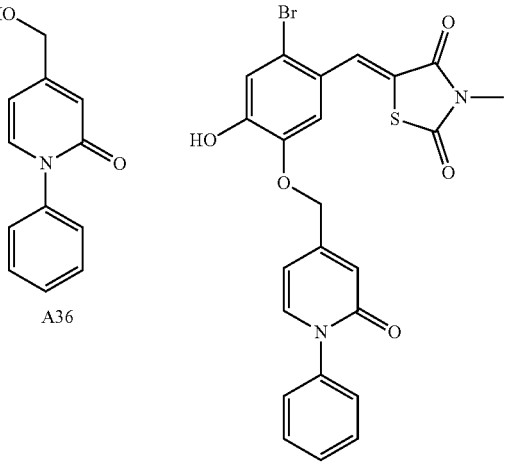 A36 | 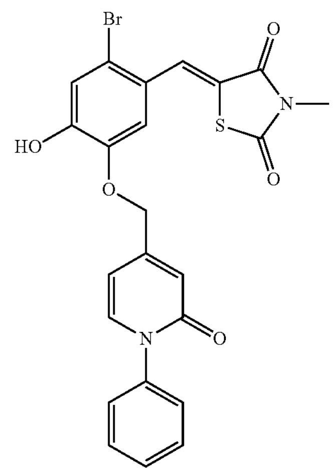 [SMILES: CN1C(=O)S/C(=C\c2cc(OCc3ccn(-c4ccccc4)c(=O)c3)c(O)cc2Br)C1=O] | [M + H]+ 513.0 |
| Ex137 | 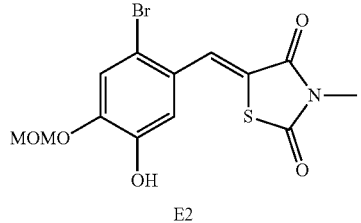 E2 | 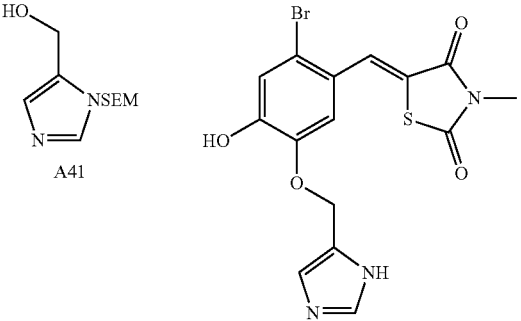 A41 | 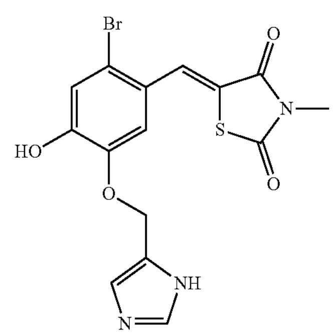 [SMILES: CN1C(=O)S/C(=C\c2cc(OCc3cnc[nH]3)c(O)cc2Br)C1=O] | [M + H]+ 410.0 |
| Ex138 | 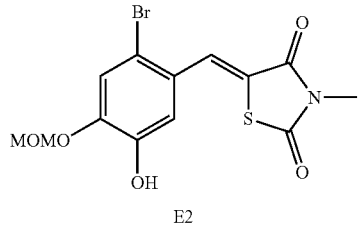 E2 | 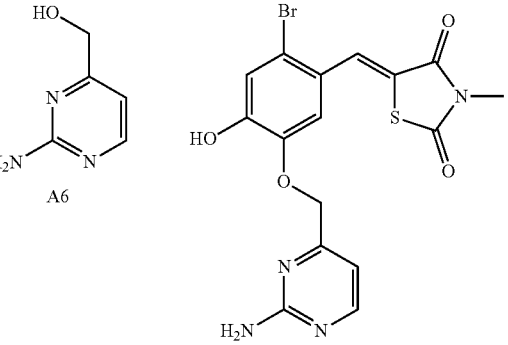 A6 | 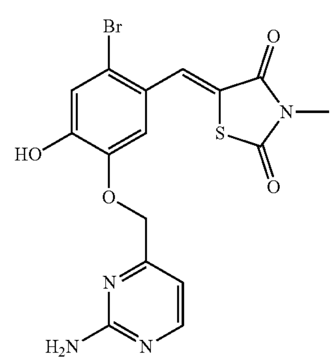 [SMILES: CN1C(=O)S/C(=C\c2cc(OCc3ccnc(N)n3)c(O)cc2Br)C1=O] | [M + H]+ 437.0 |

-continued
| Example | Building blocks | | Structure | MS |
|---|---|---|---|---|
| Ex139 | 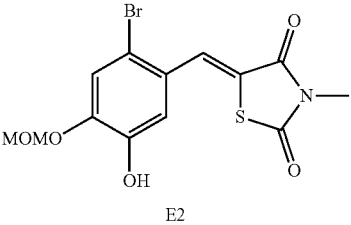 E2 | 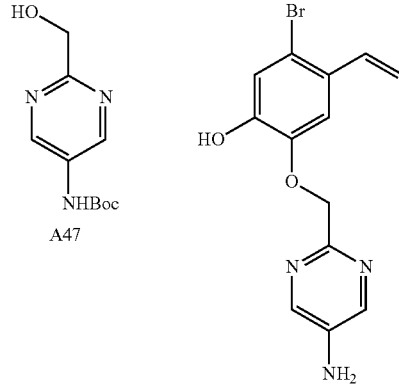 A47 | 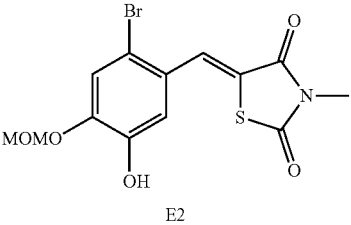 | [M + H]⁺ 437.0 |
| Ex140 | 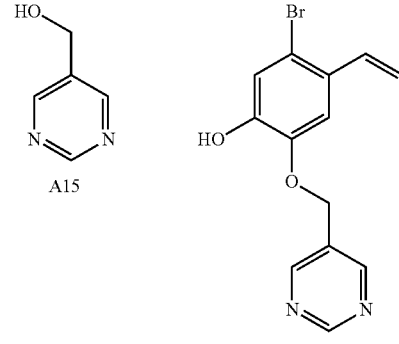 E2 | 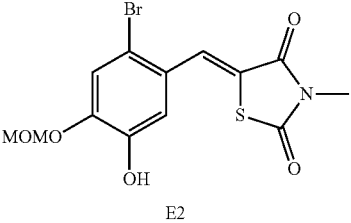 A15 | 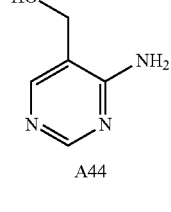 | [M + H]⁺ 422.0 |
| Ex141 | 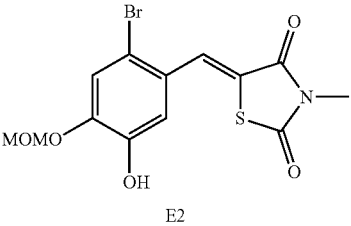 E2 | A44 | 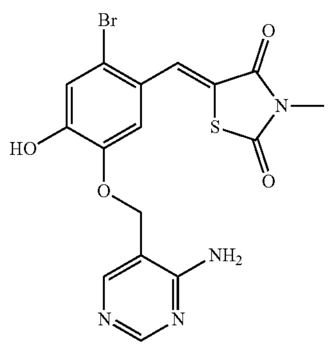 [SMILES: CN1C(=O)S/C(=C\c2cc(OCc3cncnc3N)c(O)cc2Br)C1=O] | [M + H]⁺ 437.0 |
| Ex142 | 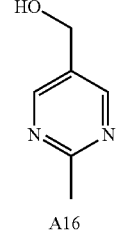 E2 | A16 | 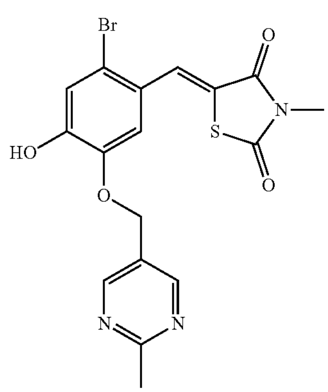 [SMILES: Cc1ncc(COc2cc(/C=C3\SC(=O)N(C)C3=O)c(Br)cc2O)cn1] | [M + H]⁺ 436.0 |

-continued
| Example | Building blocks | | Structure | MS |
|---|---|---|---|---|
| Ex143 | 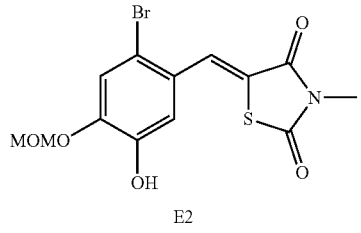 E2 | 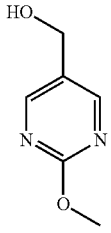 A24 | 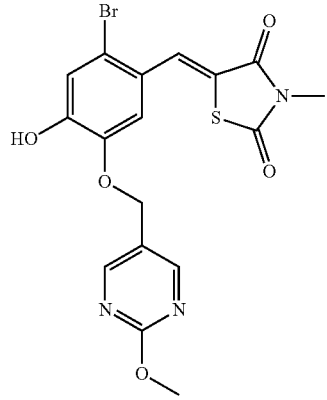 [SMILES: COc1ncc(COc2cc(/C=C3\SC(=O)N(C)C3=O)c(Br)cc2O)cn1] | [M + H]+ 452.0 |
| Ex144 | 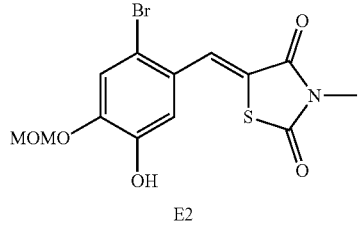 E2 | 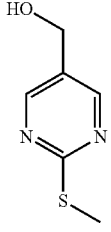 A25 | 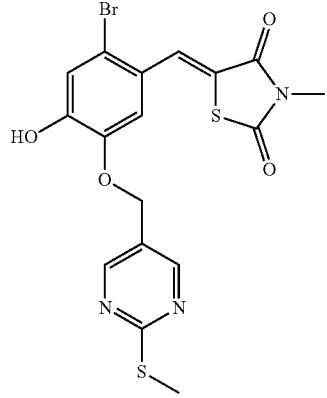 [SMILES: CSc1ncc(COc2cc(/C=C3\SC(=O)N(C)C3=O)c(Br)cc2O)cn1] | [M + H]+ 468.0 |
| Ex145 | 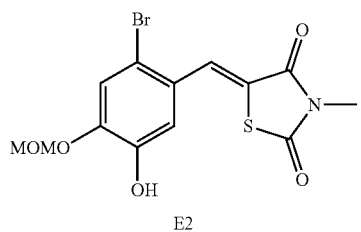 E2 | 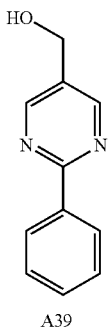 A39 | 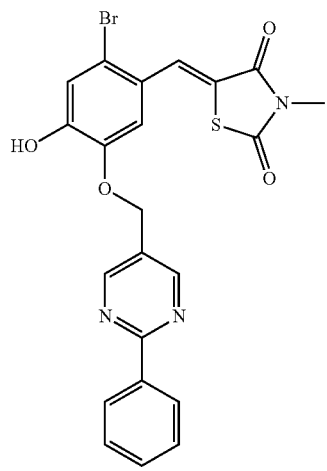 [SMILES: CN1C(=O)S/C(=C\c2cc(OCc3cnc(-c4ccccc4)nc3)c(O)cc2Br)C1=O] | [M + H]+ 498.0 |

-continued
| Example | Building blocks | Structure | MS |
|---|---|---|---|
| Ex146 | 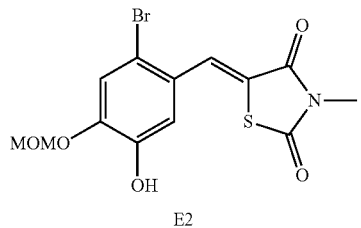 E2    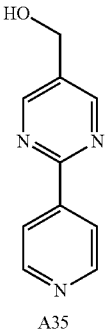 A35 | 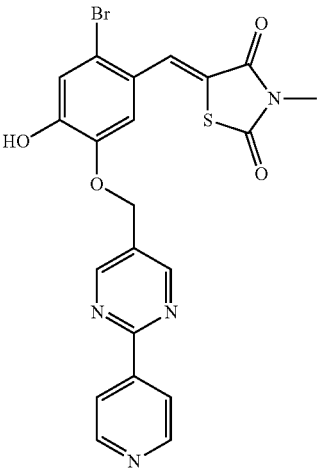 [SMILES: CN1C(=O)S/C(=C\c2cc(OCc3cnc(-c4ccncc4)nc3)c(O)cc2Br)C1=O] | [M + H]+ 499.0 |
| Ex147 | 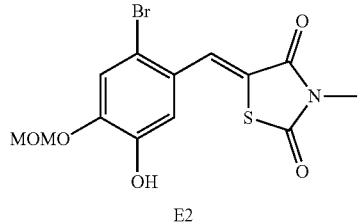 E2    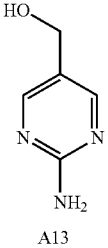 A13 | 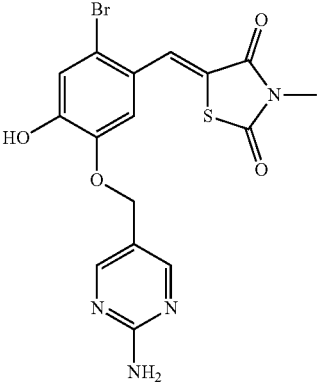 [SMILES: CN1C(=O)S/C(=C\c2cc(OCc3cnc(N)nc3)c(O)cc2Br)C1=O] | [M + H]+ 437.0 |
| Ex148 | 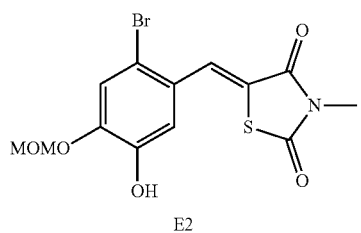 E2    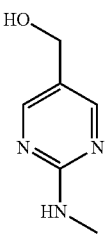 A18 | 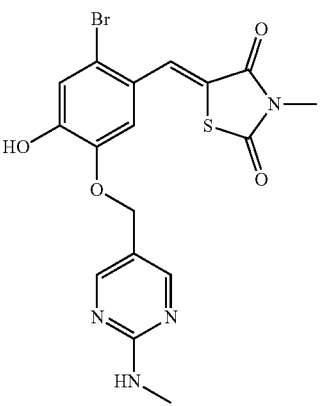 [SMILES: CNc1ncc(COc2cc(/C=C3\SC(=O)N(C)C3=O)c(Br)cc2O)cn1] | [M + H]+ 451.0 |

-continued
| Example | Building blocks | | Structure | MS |
|---|---|---|---|---|
| Ex149 | 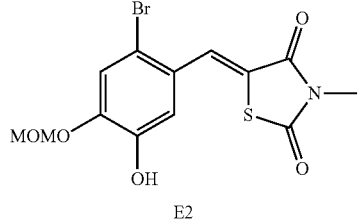<br>E2 | 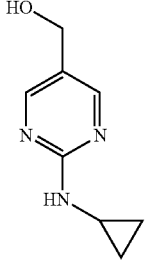<br>A19 | 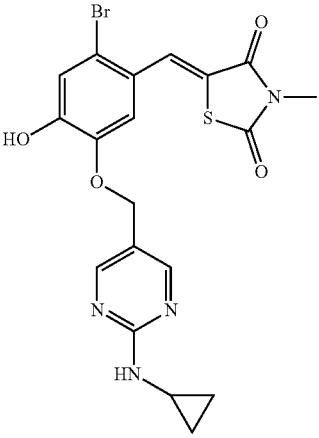 [SMILES: CN1C(=O)S/C(=C\c2cc(OCc3cnc(NC4CC4)nc3)c(O)cc2Br)C1=O] | [M + H]⁺ 477.0 |
| Ex150 | 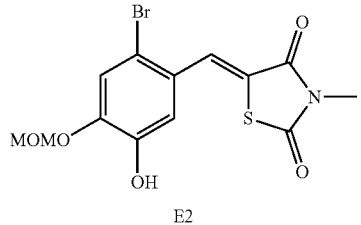<br>E2 | 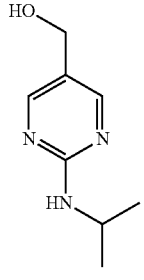<br>A20 | 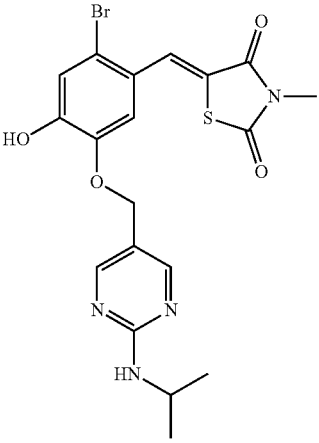 [SMILES: CC(C)Nc1ncc(COc2cc(/C=C3\SC(=O)N(C)C3=O)c(Br)cc2O)cn1] | [M + H]⁺ 479.0 |
| Ex151 | 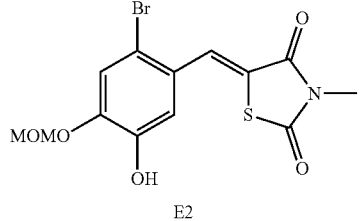<br>E2 | 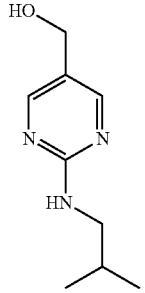<br>A21 | 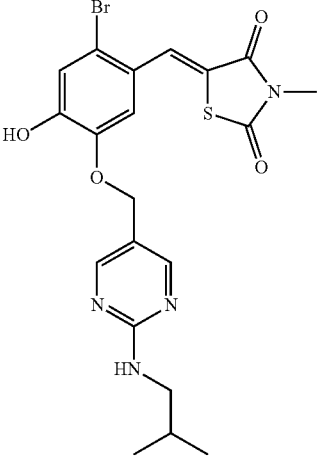 [SMILES: CC(C)CNc1ncc(COc2cc(/C=C3\SC(=O)N(C)C3=O)c(Br)cc2O)cn1] | [M + H]⁺ 493.0 |

-continued
| Example | Building blocks | | Structure | MS |
|---|---|---|---|---|
| Ex152 | 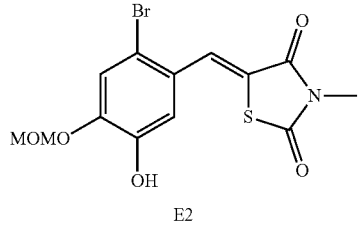 E2 | 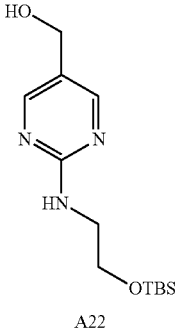 A22 | 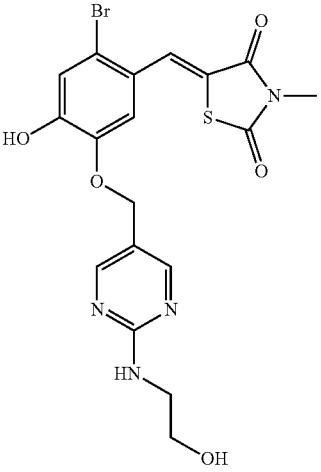 | [M + H]⁺ 499.0 |
| Ex153 | 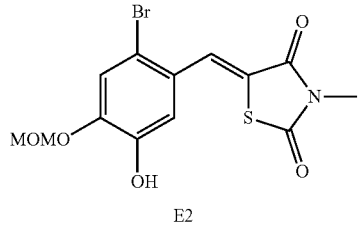 E2 | 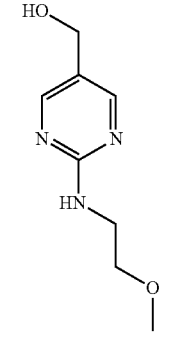 A23 | 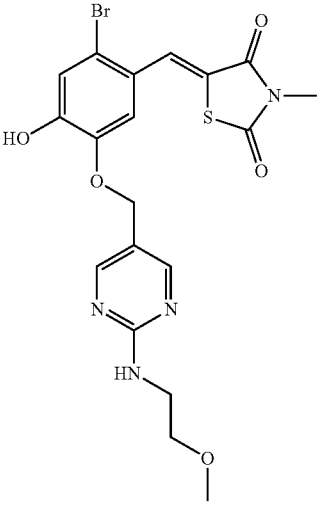 | [M + H]⁺ 515 |
| Ex154 | 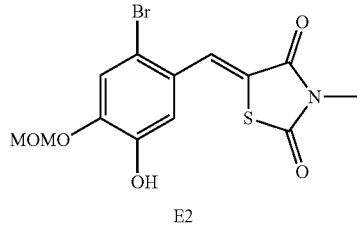 E2 | 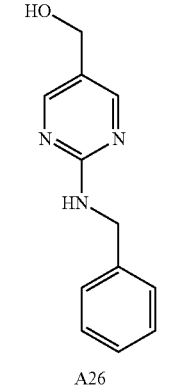 A26 | 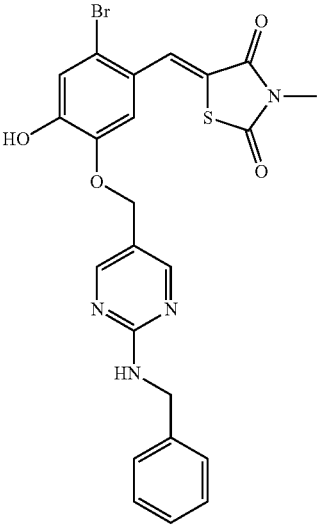 [SMILES: CN1C(=O)S/C(=C\c2cc(OCc3cnc(NCc4ccccc4)nc3)c(O)cc2Br)C1=O] | [M + H]⁺ 527.0 |

-continued
| Example | Building blocks | | Structure | MS |
|---|---|---|---|---|
| Ex155 | 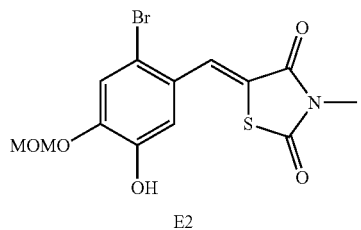 E2 | 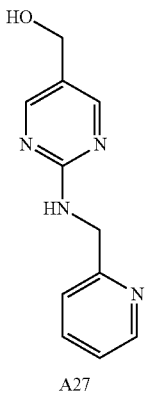 A27 | 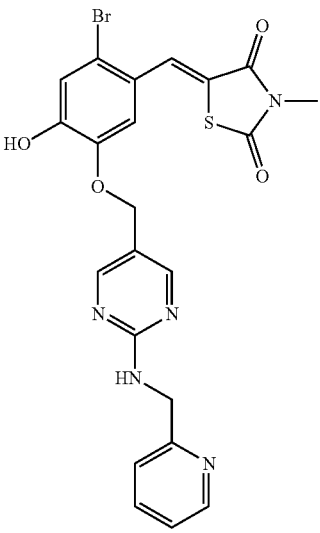 [SMILES: CN1C(=O)S/C(=C\c2cc(OCc3cnc(NCc4ccccn4)nc3)c(O)cc2Br)C1=O] | [M + H]+ 528.0 |
| Ex156 | 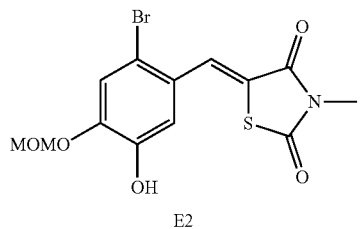 E2 | 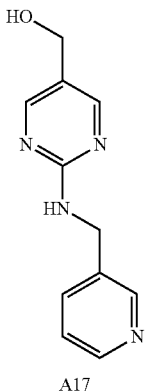 A17 | 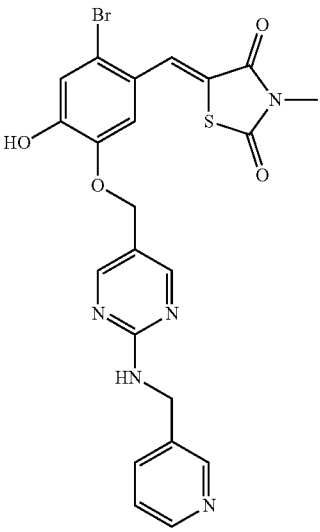 [SMILES: CN1C(=O)S/C(=C\c2cc(OCc3cnc(NCc4cccnc4)nc3)c(O)cc2Br)C1=O] | [M + H]+ 528.0 |
| Ex157 | 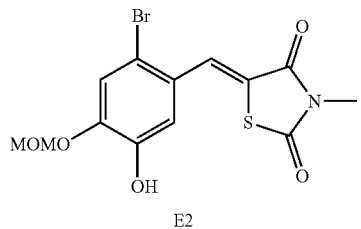 E2 | 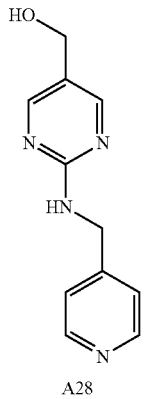 A28 | 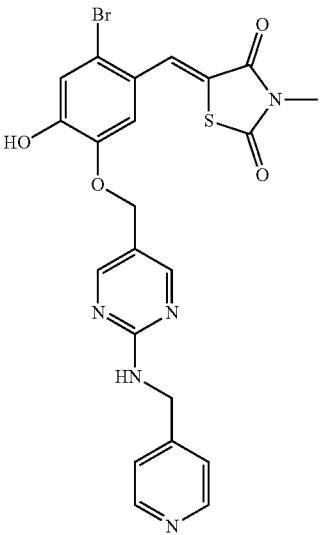 [SMILES: CN1C(=O)S/C(=C\c2cc(OCc3cnc(NCc4ccncc4)nc3)c(O)cc2Br)C1=O] | [M + H]+ 528.0 |

-continued
| Example | Building blocks | | Structure | MS |
|---|---|---|---|---|
| Ex158 | 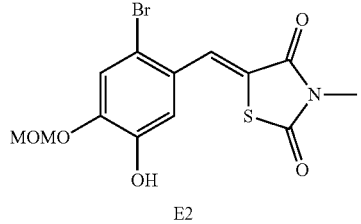 E2 | 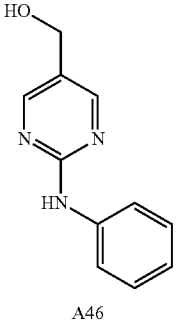 A46 | 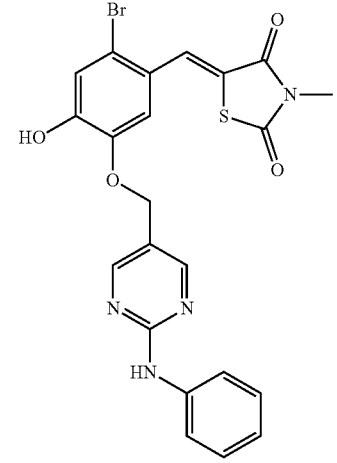 [SMILES: CN1C(=O)S/C(=C\c2cc(OCc3cnc(Nc4ccccc4)nc3)c(O)cc2Br)C1=O] | [M + H]+ 513.0 |
| Ex159 | 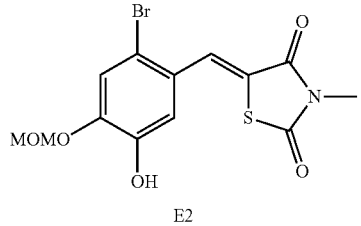 E2 | 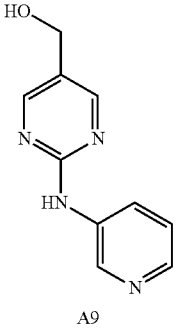 A9 | 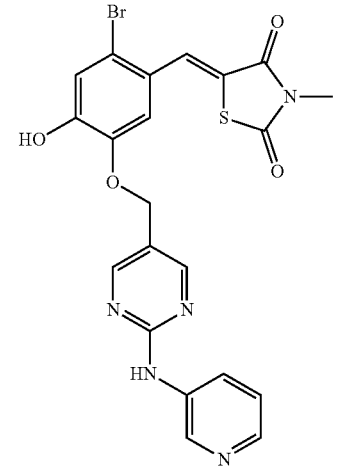 [SMILES: CN1C(=O)S/C(=C\c2cc(OCc3cnc(Nc4cccnc4)nc3)c(O)cc2Br)C1=O] | [M + H]+ 514.0 |
| Ex160 | 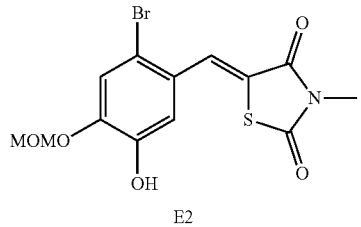 E2 | 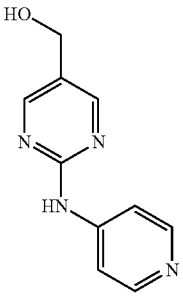 A7 | 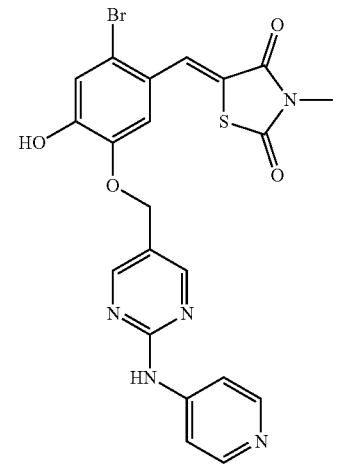 [SMILES: CN1C(=O)S/C(=C\c2cc(OCc3cnc(Nc4ccncc4)nc3)c(O)cc2Br)C1=O] | [M + H]+ 514.0 |

-continued
| Example | Building blocks | | Structure | MS |
|---|---|---|---|---|
| Ex161 | 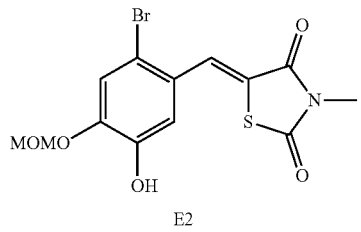 E2 | 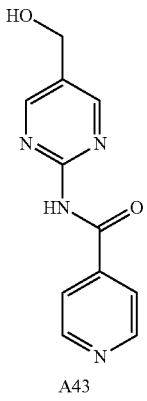 A43 | 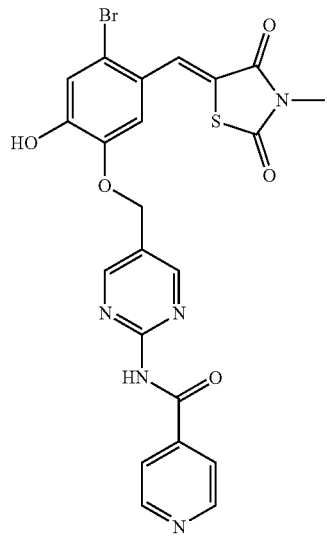 [SMILES: CN1C(=O)S/C(=C\c2cc(OCc3cnc(NC(=O)c4ccncc4)nc3)c(O)cc2Br)C1=O] | [M + H]+ 542.0 |
| Ex162 | 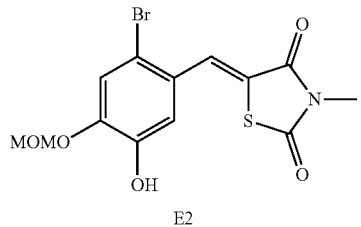 E2 | 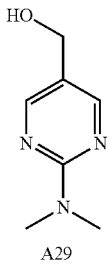 A29 | 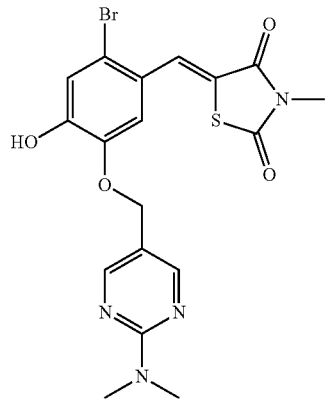 [SMILES: CN1C(=O)S/C(=C\c2cc(OCc3cnc(N(C)C)nc3)c(O)cc2Br)C1=O] | [M + H]+ 465.0 |
| Ex163 | 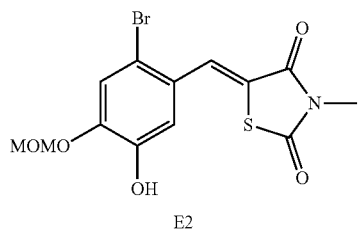 E2 | 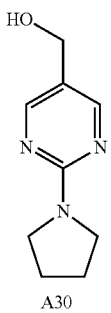 A30 | 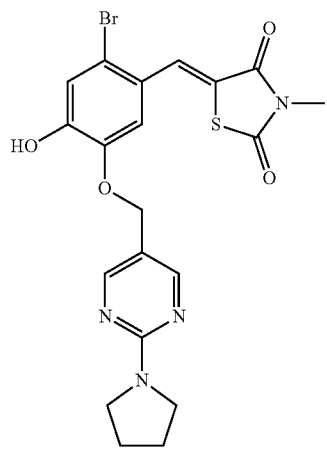 [SMILES: CN1C(=O)S/C(=C\c2cc(OCc3cnc(N4CCCC4)nc3)c(O)cc2Br)C1=O] | [M + H]+ 490.0 |

-continued
| Example | Building blocks | | Structure | MS |
|---|---|---|---|---|
| Ex164 | 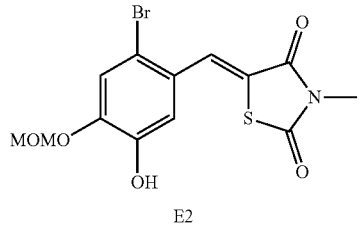 E2 | 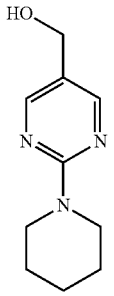 A31 | 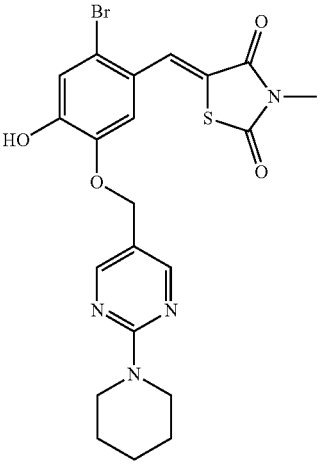 [SMILES: CN1C(=O)S/C(=C\c2cc(OCc3cnc(N4CCCCC4)nc3)c(O)cc2Br)C1=O] | [M + H]+ 505.0 |
| Ex165 | 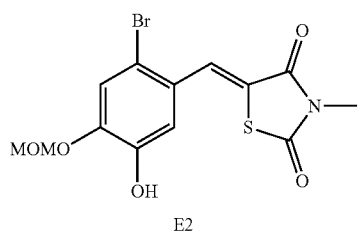 E2 | 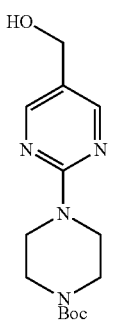 A32 | 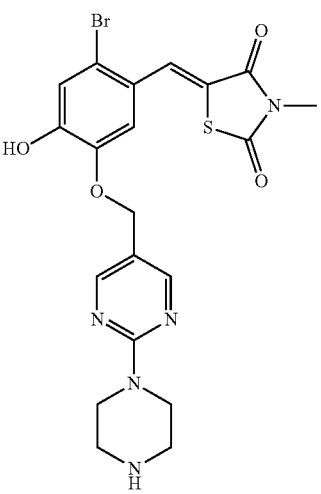 [SMILES: CN1C(=O)S/C(=C\c2cc(OCc3cnc(N4CCNCC4)nc3)c(O)cc2Br)C1=O] | [M + H]+ 506.0 |
| Ex166 | 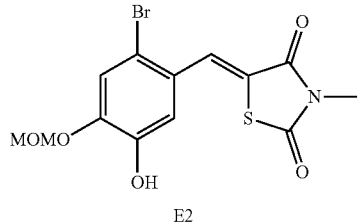 E2 | 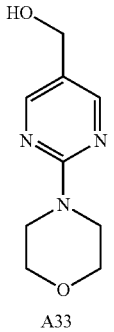 A33 | 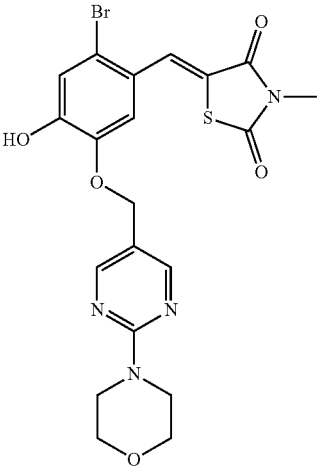 [SMILES: CN1C(=O)S/C(=C\c2cc(OCc3cnc(N4CCOCC4)nc3)c(O)cc2Br)C1=O] | [M + H]+ 507.0 |

-continued
| Example | Building blocks | | Structure | MS |
|---|---|---|---|---|
| Ex167 | 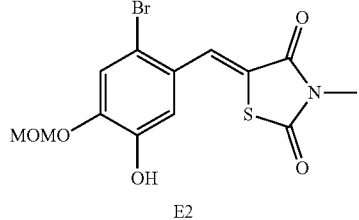 E2 | 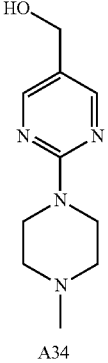 A34 | 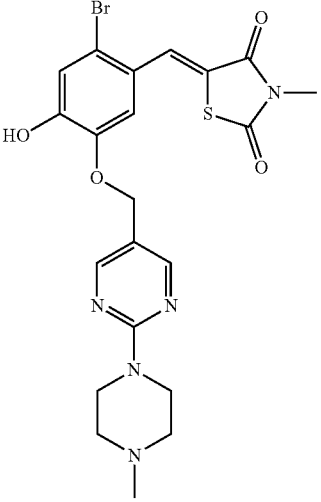 [SMILES: CN1CCN(c2ncc(COc3cc(/C=C4\SC(=O)N(C)C4=O)c(Br)cc3O)cn2)CC1] | [M + H]+ 520.3 |
| Ex168 | 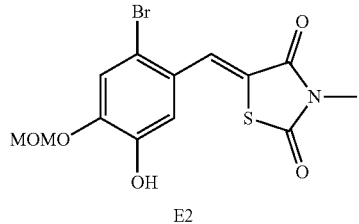 E2 | 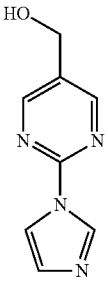 A11 | 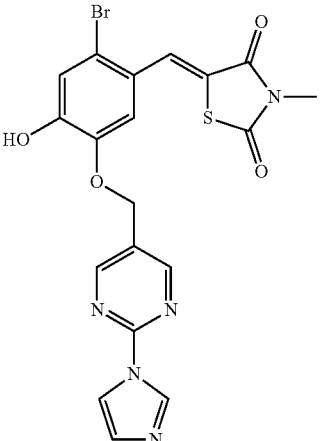 | [M + H]+ 488.0 |
| Ex169 | 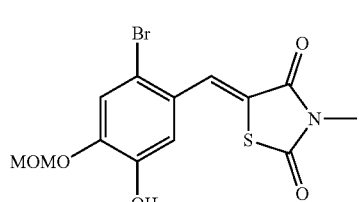 E2 | 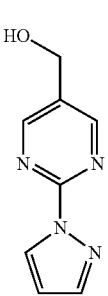 A8 | 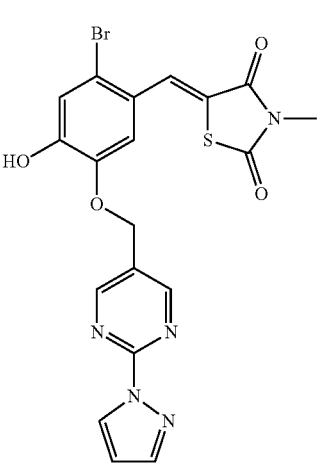 [SMILES: CN1C(=O)S/C(=C\c2cc(OCc3cnc(-n4cccn4)nc3)c(O)cc2Br)C1=O] | [M + H]+ 488.0 |

-continued
| Example | Building blocks | | Structure | MS |
|---|---|---|---|---|
| Ex170 | 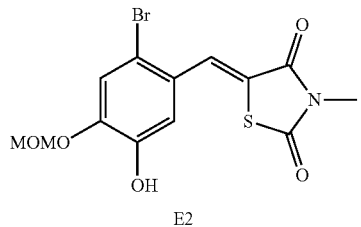 E2 | 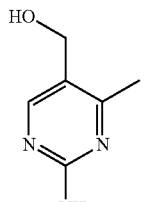 A48 | 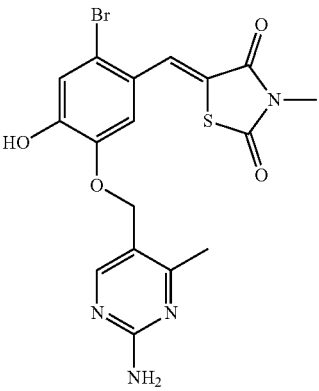 [SMILES: Cc1nc(N)ncc1COc1cc(/C=C2\SC(=O)N(C)C2=O)c(Br)cc1O] | [M + H]⁺ 451.0 |
| Ex171 | 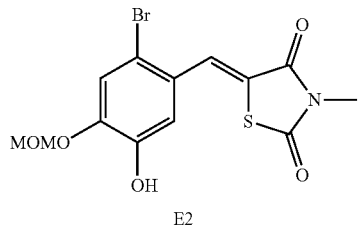 E2 | 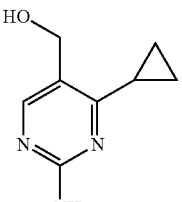 A40 | 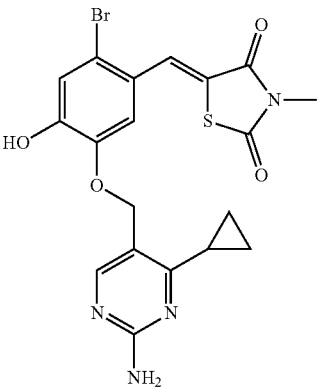 [SMILES: CN1C(=O)S/C(=C\c2cc(OCc3cnc(N)nc3C3CC3)c(O)cc2Br)C1=O] | [M + H]⁺ 477.0 |
| Ex172 | 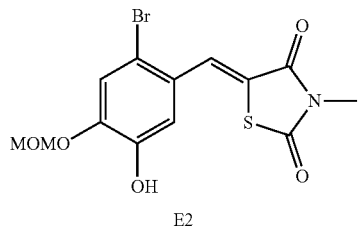 E2 | 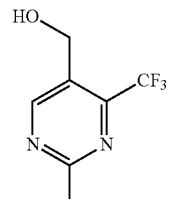 A38 | 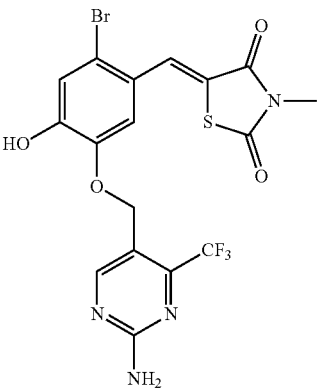 [SMILES: CN1C(=O)S/C(=C\c2cc(OCc3cnc(N)nc3C(F)(F)F)c(O)cc2Br)C1=O] | [M + H]⁺ 505.0 |
| Ex173 | 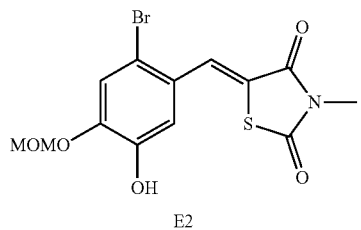 E2 | 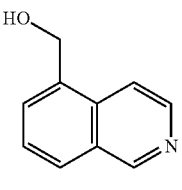 | 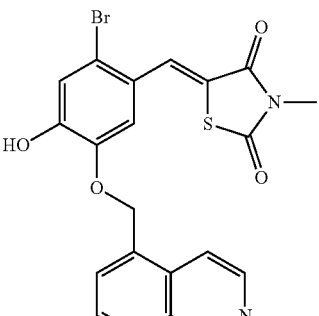 | [M + H]⁺ 471.0 |

-continued
| Example | Building blocks | | Structure | MS |
|---|---|---|---|---|
| Ex174 | 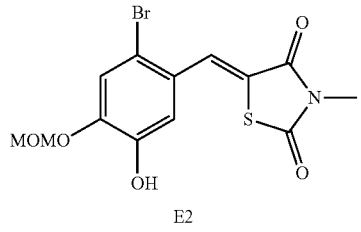 E2 | 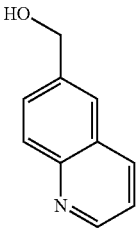 [SMILES: OCc1ccc2ncccc2c1] | 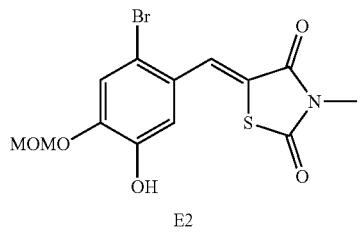 | [M + H]+ 471.0 |
| Ex175 | 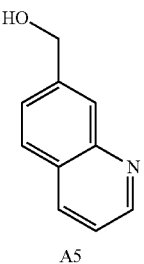 E2 | 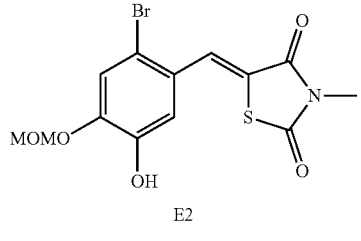 A5 | 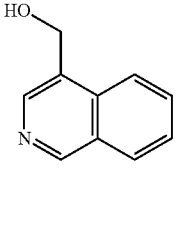 | [M + H]+ 471.0 |
| Ex176 | 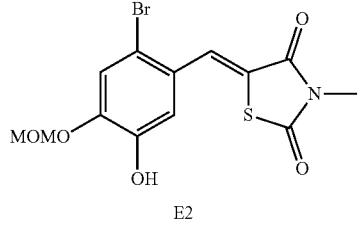 E2 | 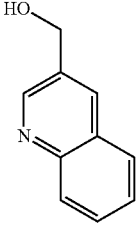 | 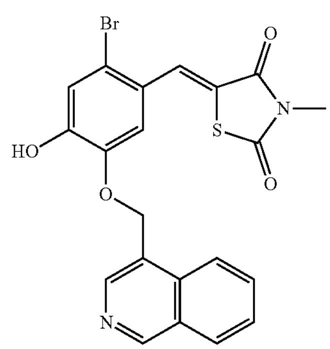 [SMILES: CN1C(=O)S/C(=C\c2cc(OCc3cncc4ccccc34)c(O)cc2Br)C1=O] | [M + H]+ 471.0 |
| Ex177 |  E2 |  | 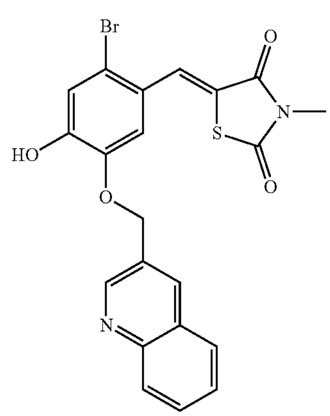 [SMILES: CN1C(=O)S/C(=C\c2cc(OCc3cnc4ccccc4c3)c(O)cc2Br)C1=O] | [M + H]+ 471.0 |

| Example | Building blocks | | Structure | MS |
|---|---|---|---|---|
| Ex178 | (E2) | (quinolin-4-yl)methanol | 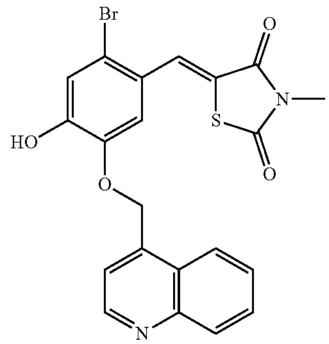 [SMILES: CN1C(=O)S/C(=C\c2cc(OCc3ccnc4ccccc34)c(O)cc2Br)C1=O] | [M + H]+ 471.0 |
| Ex179 | (E2) | 2-(pyridin-4-yl)ethanol | 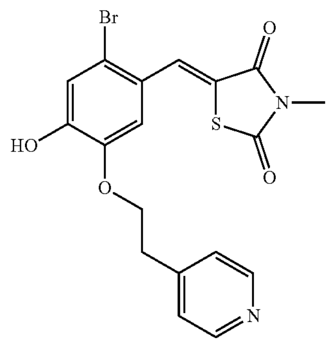 [SMILES: CN1C(=O)S/C(=C\c2cc(OCCc3ccncc3)c(O)cc2Br)C1=O] | [M + H]+ 435.0 |
| Ex180 | (E2) | 1-(2-methylpyrimidin-5-yl)ethanol (A42) | 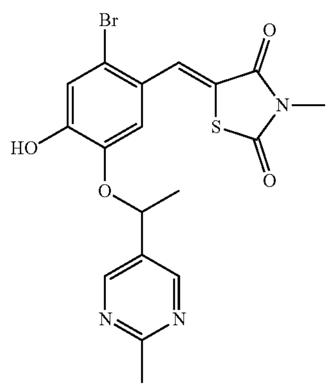 [SMILES: Cc1ncc(C(C)Oc2cc(/C=C3\SC(=O)N(C)C3=O)c(Br)cc2O)cn1] | [M + H]+ 450.0 |
| Ex181 | (E2) | 2-((2-hydroxyethyl)amino)pyrimidin-5-yl ethanol (A45) | 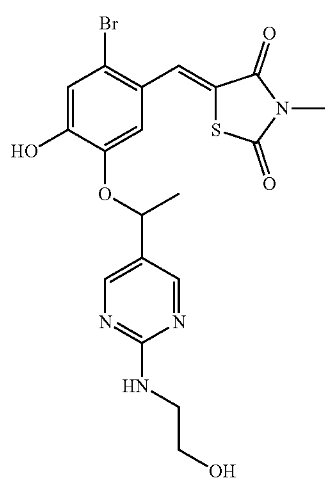 [SMILES: CC(Oc1cc(/C=C2\SC(=O)N(C)C2=O)c(Br)cc1O)c1cnc(NCCO)nc1] | [M + H]+ 495.0 |

-continued
| Example | Building blocks | | Structure | MS |
|---|---|---|---|---|
| Ex182 | 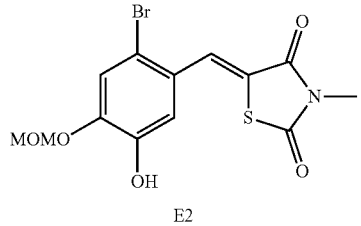 E2 | 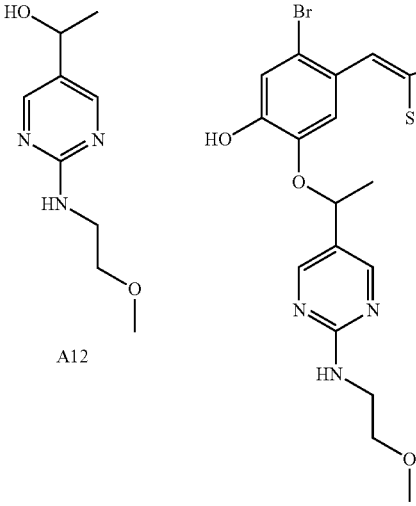 A12 | 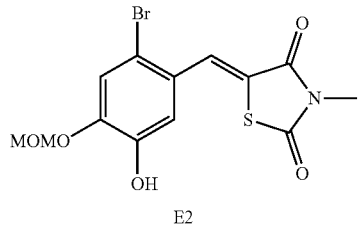 | [M + H]+ 509.0 |
| Ex183 | 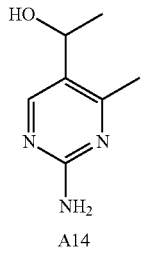 E2 | 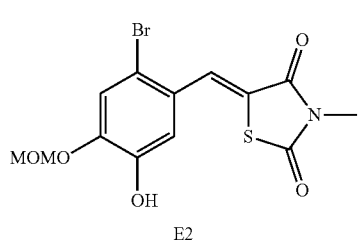 A14 | 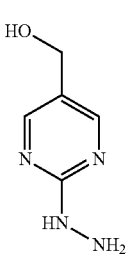 | [M + H]+ 465.0 |
| Ex184 | Br / MOMO / OH (E2) | HO / pyrimidine / HN-NH2 (A10) | Br / HO / O / pyrimidine / HN-NH2 | [M + H]+ 452.0 |

-continued
| Example | Building blocks | | Structure | MS |
|---|---|---|---|---|
| Ex185 | 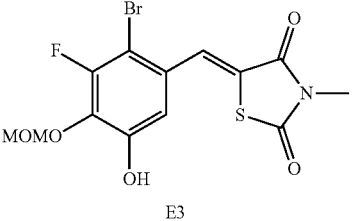 E3 | 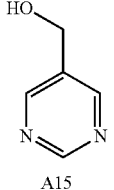 A15 | 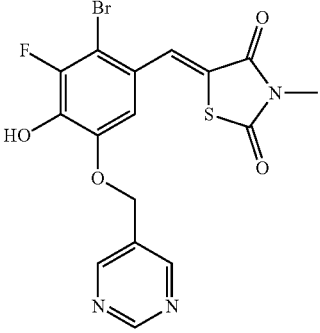 [SMILES: CN1C(=O)S/C(=C\c2cc(OCc3cncnc3)c(O)c(F)c2Br)C1=O] | [M + H]$^+$ 440.0 |
| Ex186 | 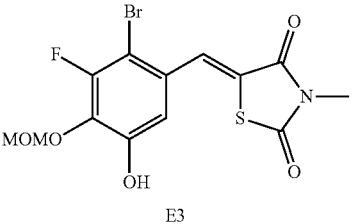 E3 | 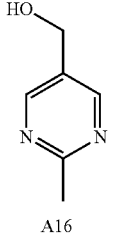 A16 | 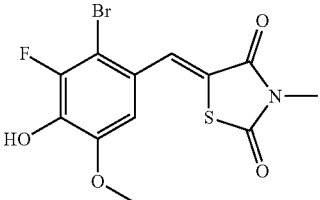 | [M + H]$^+$ 436 |
| Ex187 | 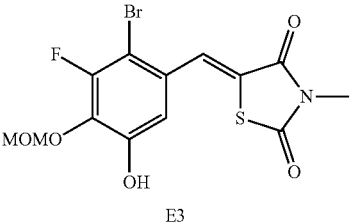 E3 | 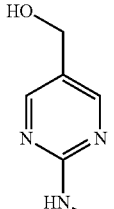 A18 | 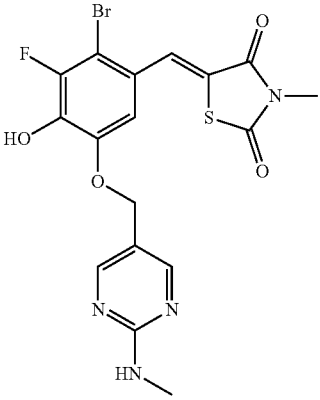 [SMILES: CNc1ncc(COc2cc(/C=C3\SC(=O)N(C)C3=O)c(Br)c(F)c2O)cn1] | [M + H]$^+$ 469.0 |

-continued
| Example | Building blocks | | Structure | MS |
|---|---|---|---|---|
| Ex188 | 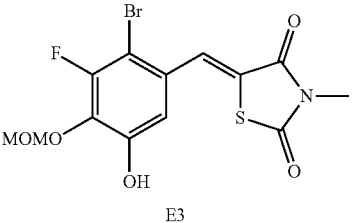 E3 | 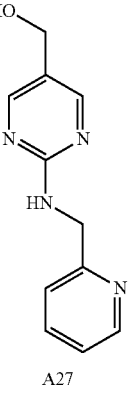 A27 | 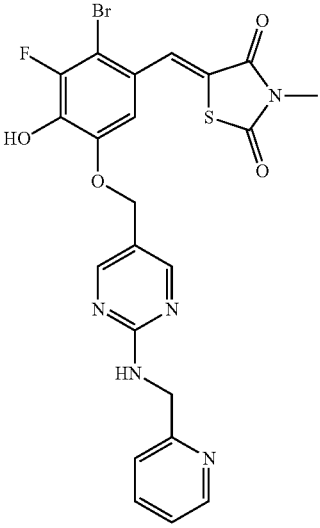 [SMILES: CN1C(=O)S/C(=C\c2cc(OCc3cnc(NCc4ccccn4)nc3)c(O)c(F)c2Br)C1=O] | [M + H]⁺ 546.0 |
| Ex189 | 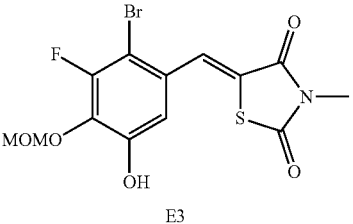 E3 | 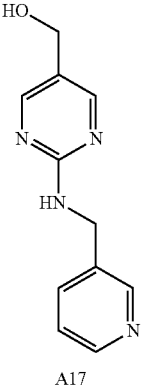 A17 | 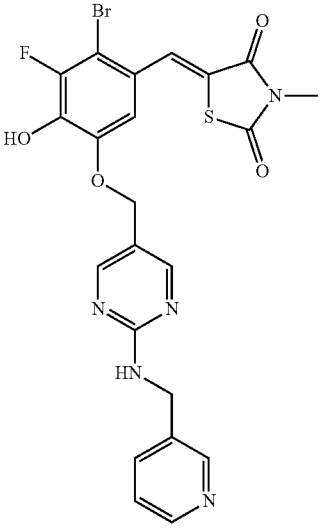 [SMILES: CN1C(=O)S/C(=C\c2cc(OCc3cnc(NCc4cccnc4)nc3)c(O)c(F)c2Br)C1=O] | [M + H]⁺ 546.0 |
| Ex190 | 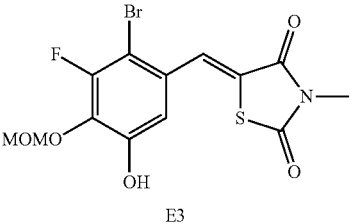 E3 | 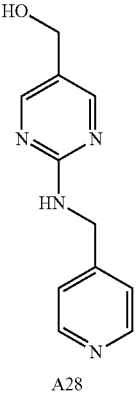 A28 | 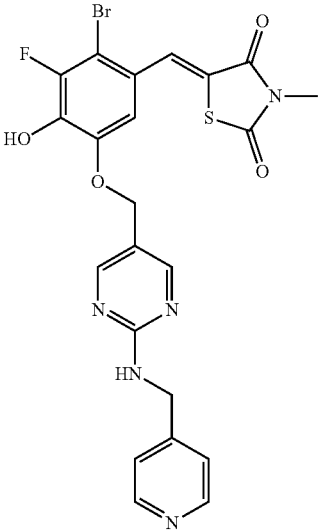 [SMILES: CN1C(=O)S/C(=C\c2cc(OCc3cnc(NCc4ccncc4)nc3)c(O)c(F)c2Br)C1=O] | [M + H]⁺ 546.0 |

-continued
| Example | Building blocks | | Structure | MS |
|---|---|---|---|---|
| Ex191 | 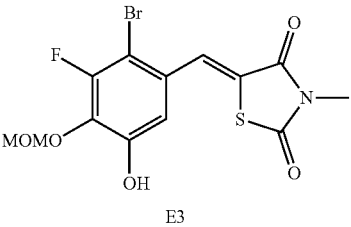<br>E3 | 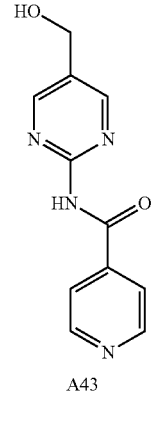<br>A43 | 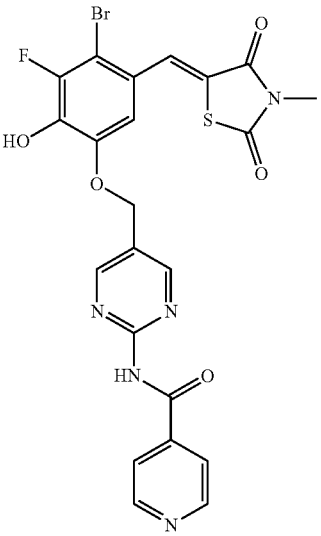 [SMILES: CN1C(=O)S/C(=C\c2cc(OCc3cnc(NC(=O)c4ccncc4)nc3)c(O)c(F)c2Br)C1=O] | [M + H]+ 560.0 |
| Ex192 | 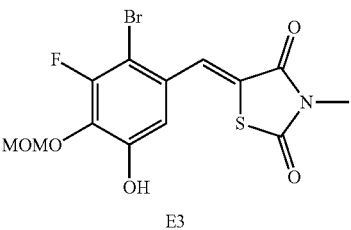<br>E3 | 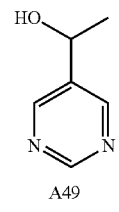<br>A49 | 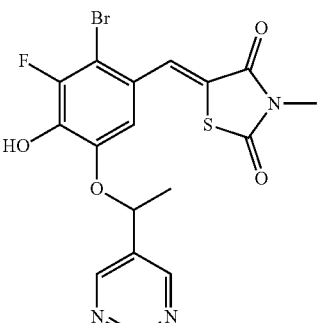 | [M + H]+ 454.0 |
| Ex193 | 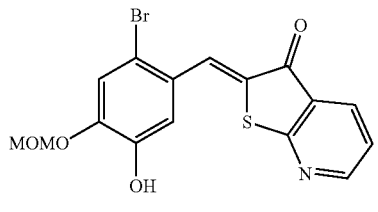<br>E5 | 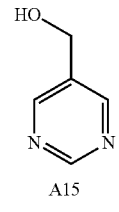<br>A15 | 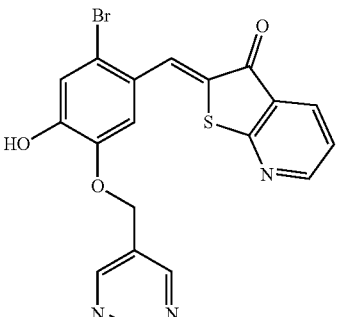 | [M + H]+ 442.0 |
| Ex194 | 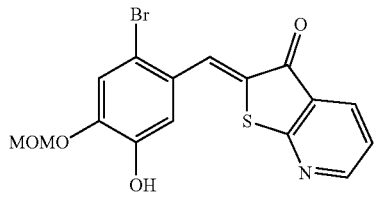<br>E5 | 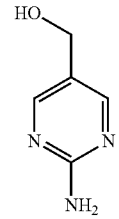<br>A13 | 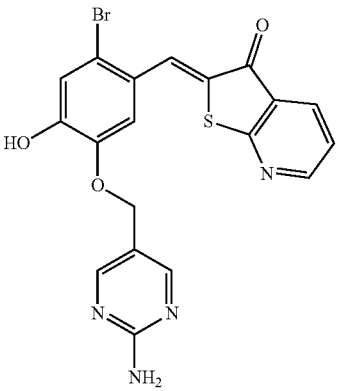 [SMILES: Nc1ncc(COc2cc(/C=C3\Sc4ncccc4C3=O)c(Br)cc2O)cn1] | [M + H]+ 457.0 |

| Example | Building blocks | | Structure | MS |
|---|---|---|---|---|
| Ex195 | 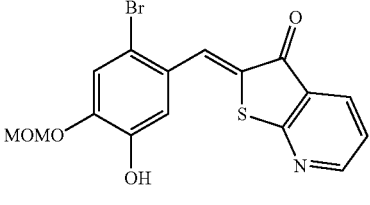 E5 | 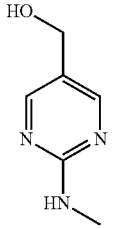 A18 | 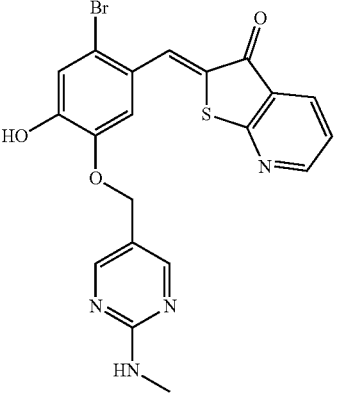 [SMILES: CNc1ncc(COc2cc(/C=C3\Sc4ncccc4C3=O)c(Br)cc2O)cn1] | [M + H]+ 471.0 |
| Ex196 | 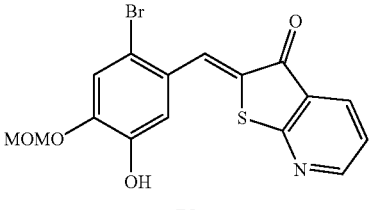 E5 | 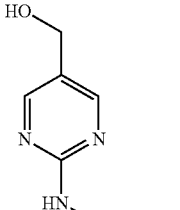 A22 | 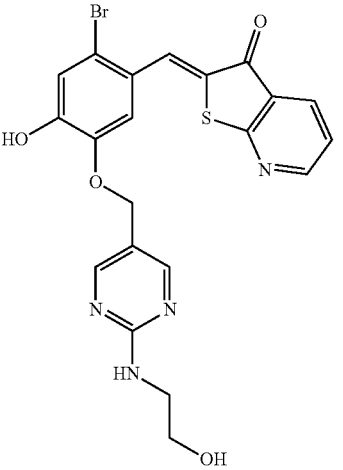 [SMILES: O=C1/C(=C/c2cc(OCc3cnc(NCCO)nc3)c(O)cc2Br)Sc2ncccc21] | [M + H]+ 501.0 |
| Ex197 | 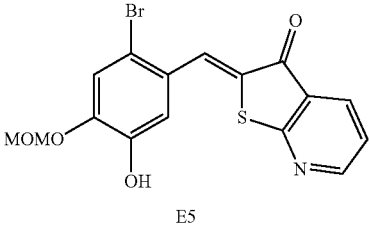 E5 | 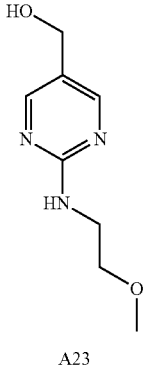 A23 | 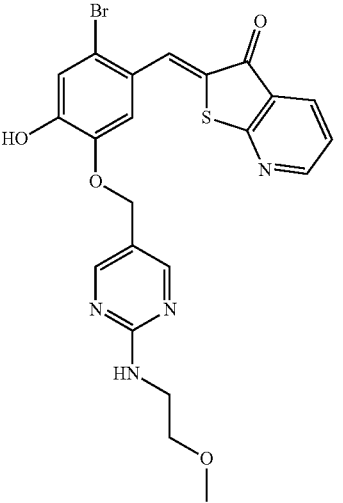 [SMILES: COCCNc1ncc(COc2cc(/C=C3\Sc4ncccc4C3=O)c(Br)cc2O)cn1] | [M + H]+ 515.0 |

-continued
| Example | Building blocks | | Structure | MS |
|---|---|---|---|---|
| Ex198 | 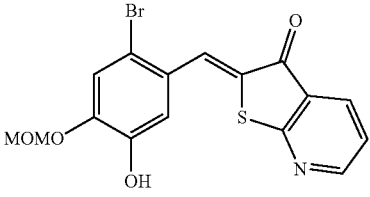 E5 | 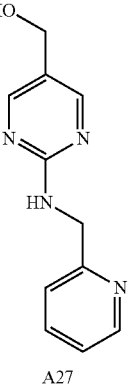 A27 | 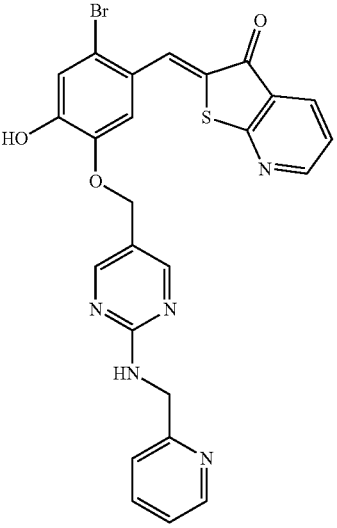 [SMILES: O=C1/C(=C/c2cc(OCc3cnc(NCc4ccccn4)nc3)c(O)cc2Br)Sc2ncccc21] | [M + H]+ 548.0 |
| Ex199 | 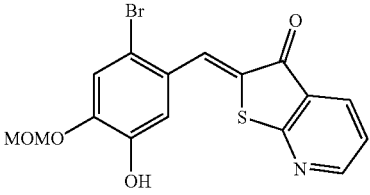 E5 | 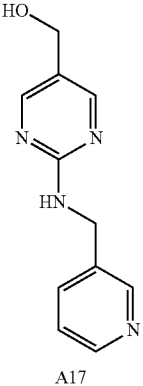 A17 | 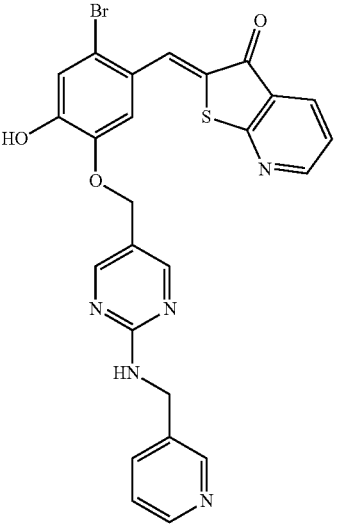 [SMILES: O=C1/C(=C/c2cc(OCc3cnc(NCc4cccnc4)nc3)c(O)cc2Br)Sc2ncccc21] | [M + H]+ 548.0 |
| Ex200 | 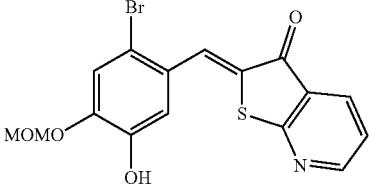 E5 | 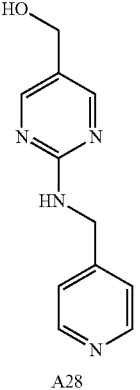 A28 | 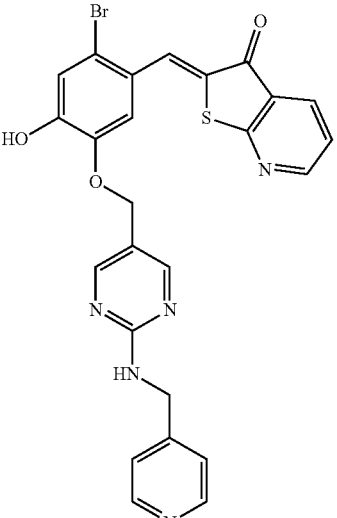 | [M + H]+ 548.0 |

Example 201

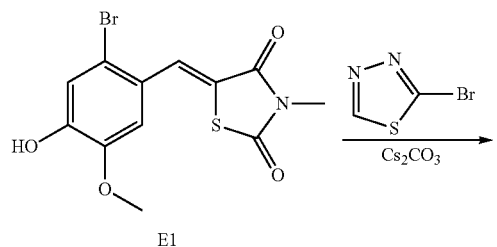

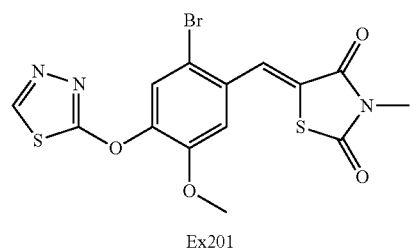

Ex201

To a solution of E1 (200 mg, 0.58 mmol) in DMF (10 mL) is added 2-bromo-1,3,4-thiadiazole (192 mg, 1.16 mmol) and cesium carbonate (568 mg, 1.74 mmol). After stirring at 70° C. for 4 hours, the mixture is concentrated and purified by prep-TLC (EA:PE=1:1) to give Ex201 as a yellow solid (4 mg, 2% yield). (MS: [M+H]$^+$ 428.1)

The following compounds are prepared by essentially the same method as for Ex201.

Example 204

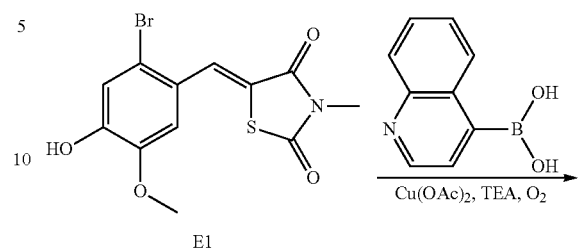

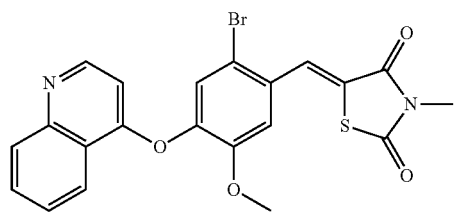

Ex204

Following the procedure for 16 using E1 (200 mg, 0.58 mmol), DCM (10 mL), quinoline-4-boronic acid (301 mg, 1.74 mmol), Cu(OAc)$_2$ (116 mg, 0.64 mmol), and TEA (0.4 mL, 0.9 mmol), purify with prep-TLC (MeOH:DCM=1:20) to give Ex204 as a yellow solid (15 mg, 5% yield). (MS: [M+H]$^+$ 471.1)

| Example | Building blocks | | Structure | MS |
|---|---|---|---|---|
| Ex202 | E1 | (4-chloropyridine) | 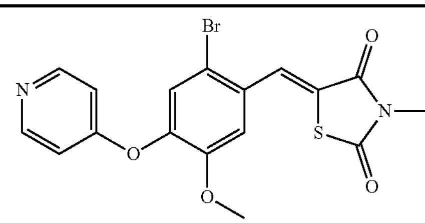 | [M + H]$^+$ 421.0 |

The following compounds are prepared by essentially the same method as for Ex125.

| Example | Building blocks | | Structure | MS |
|---|---|---|---|---|
| Ex203 | E1 | (pyridin-4-ylmethanol) | 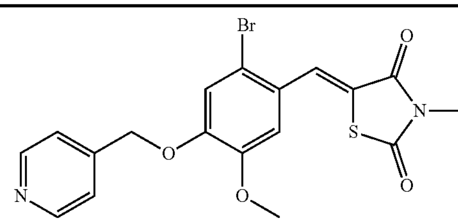 | [M + H]$^+$ 435.0 |

Example 205

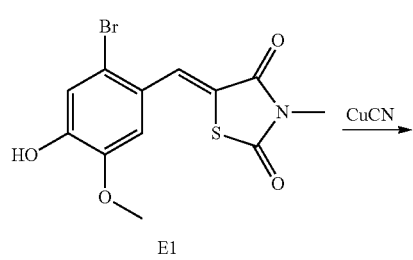

E1

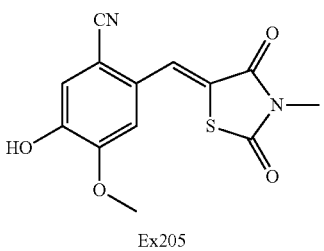

Ex205

A mixture of E1 (86 mg 0.25 mmol) and CuCN (27 mg 0.30 mmol) in DMF (1 mL) is stirred at 150° C. for 4 hours. After cooling to room temperature, the mixture is partitioned between EA/dichloromethane (75 mL, 1:1) and brine (25 mL). The layers are separated and the organic layer is dried over anhydrous sodium sulfate, concentrated, and purified by silica gel column chromatography (EA:hexanes) to give Ex205 as a yellow solid (15 mg, 21% yield).

Example 206

Step 1: amide 261

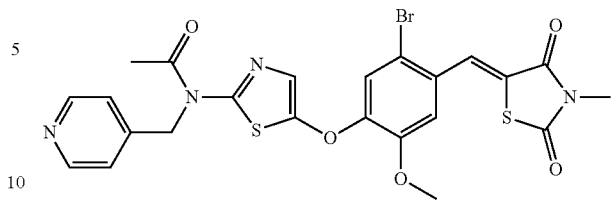

To a solution of E12 (100 mg, 0.21 mmol) in DMF (2 mL) is added 4-(bromomethyl)pyridine hydrobromide (104 mg, 0.42 mmol) and potassium carbonate (171 mg, 1.24 mmol). After stirring at 60° C. for 4 hours, the mixture is concentrated and purified by prep-TLC (MeOH:DCM=1:20) to give 261 as a yellow solid (30 mg, 25% yield). (MS: [M+H]$^+$ 575.1)

Step 2: Ex206

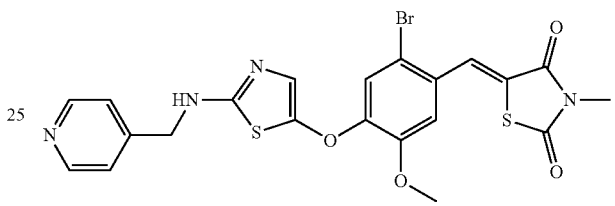

A solution of 261 (30 mg, 0.05 mmol) in methanolic HCl (2M, 5 mL) is stirred at room temperature for 5 hours. The mixture is then concentrated and purified by prep-TLC (MeOH:DCM=1:20) to give Ex206 as a yellow solid (10 mg, 36% yield). (MS: [M+H]$^+$533.1)

The following compound is prepared by essentially the same method as for Ex206.

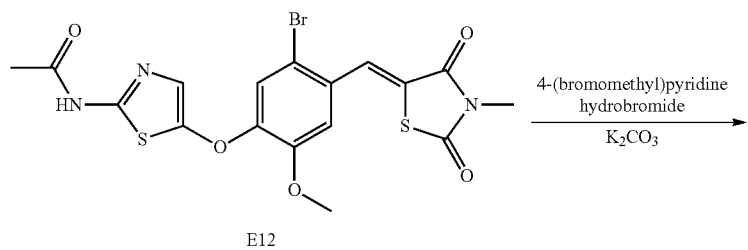

E12

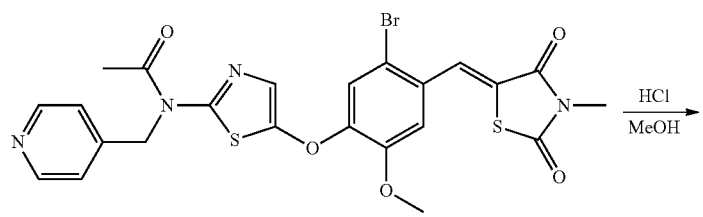

261

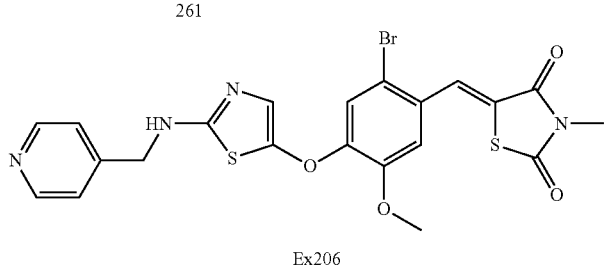

Ex206

US 10,947,206 B2

| Example | Building blocks | Structure | MS |
|---|---|---|---|
| Ex207 | 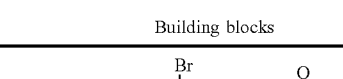 E12 | 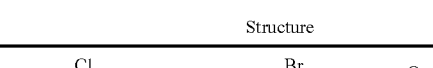 | [M + H]+ 533.0 |

Example 208

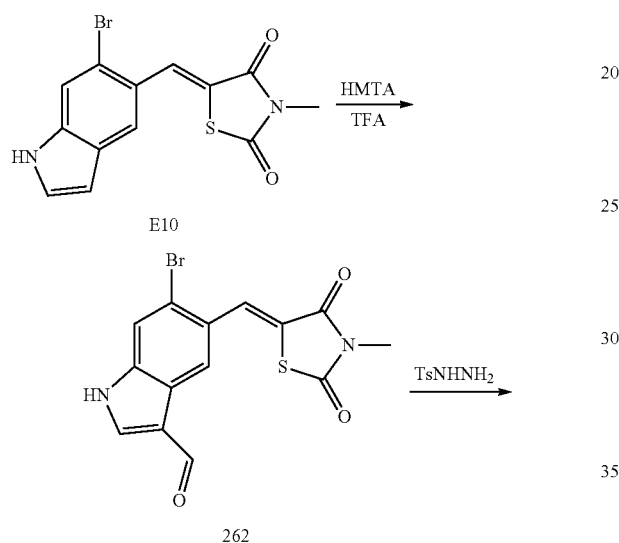

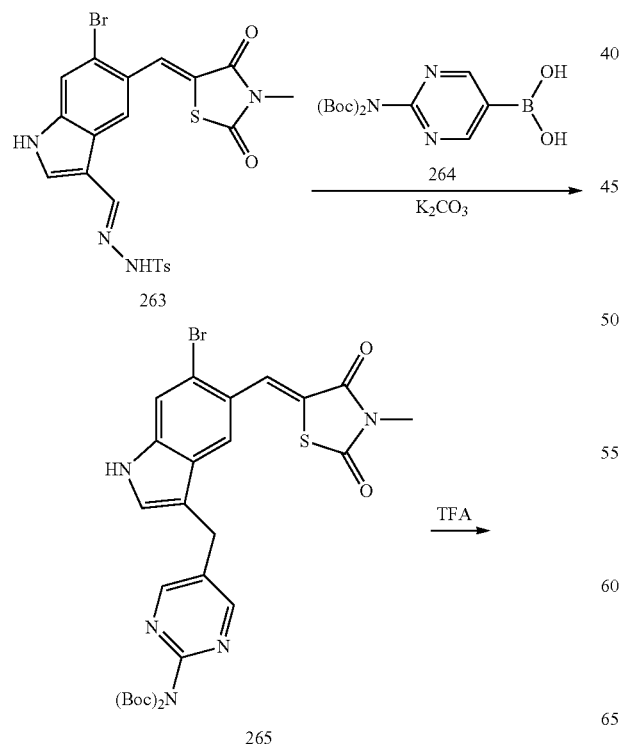

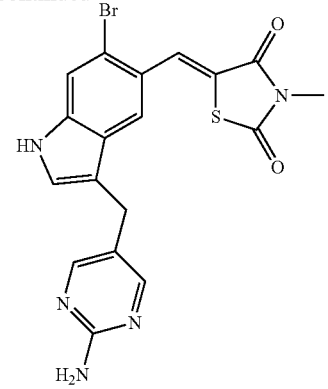

Ex208

Step 1: Aldehyde 262

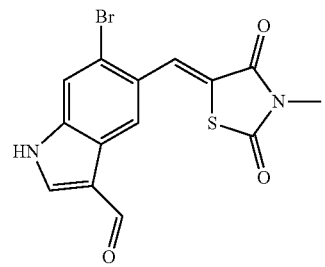 [SMILES: CN1C(=O)S/C(=C\c2cc3c(C=O)c[nH]c3cc2Br)C1=O]

To a solution of E10 (380 mg, 1.1 mmol) in TFA (3 mL) is added HMTA (315 mg, 2.2 mmol) at room temperature. After stirring at 100° C. for 20 minutes under microwave irradiation, the mixture is cooled and concentrated. The residue is partitioned between EA (30 mL) and saturated sodium bicarbonate solution (20 mL). The aqueous layer is extracted with EA (20 mL×2). The combined organic layers are dried over anhydrous sodium sulfate, filtered, concentrated, and purified by silica gel column chromatography (EA:PE=1:5) to give 262 as a yellow solid (210 mg, 51% yield). (MS: [M+H]+ 365.0)

Step 2: Hydrazone 263

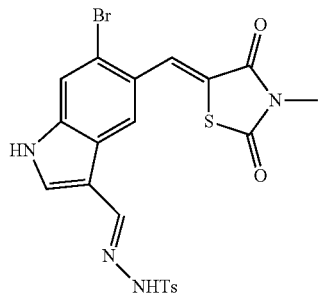

To a mixture of 262 (50 mg, 0.1 mmol) in dioxane (2 mL) is added tosylhydrazide (40 mg, 0.2 mmol) at room temperature. After stirring at 80° C. for 2 hours, the mixture is concentrated and purified by prep-TLC (MeOH:DCM=1:10) to give 263 as a yellow solid (40 mg, 55% yield). (MS: [M+H]$^+$ 533.0)

Step 3: Pyrimidine 265

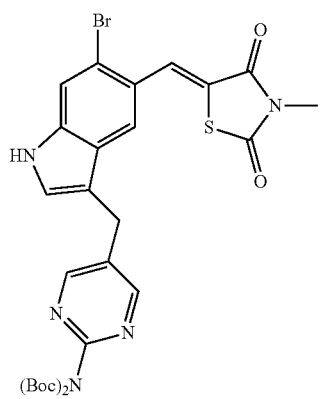

To a mixture of 263 (40 mg, 0.07 mmol) in dioxane (2 mL) is added potassium carbonate (26 mg, 0.2 mmol) and 264 (51 mg, 0.1 mmol). After stirring at 120° C. for 2 hours, the mixture is cooled and filtered. The solid is washed by EA (10 mL×3) and the filtrate is concentrated to give crude 265 as a brown solid (95 mg). (MS: [M+H]$^+$ 644.1)

Step 4: Ex208

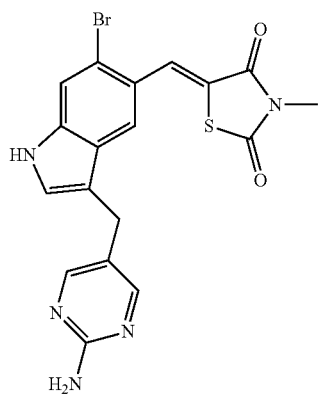 [SMILES: CN1C(=O)S/C(=C\c2cc3c(Cc4cnc(N)nc4)c[nH]c3cc2Br)C1=O]

To a mixture of crude 265 (95 mg) in DCM (2 mL) is added TFA (4 mL) dropwise at room temperature. After stirring for 2 hours, the mixture is concentrated and purified by prep-HPLC to give Ex208 as a yellow solid (5.0 mg, 15% yield). (MS: [M+H]$^+$ 444.0)

Example 209

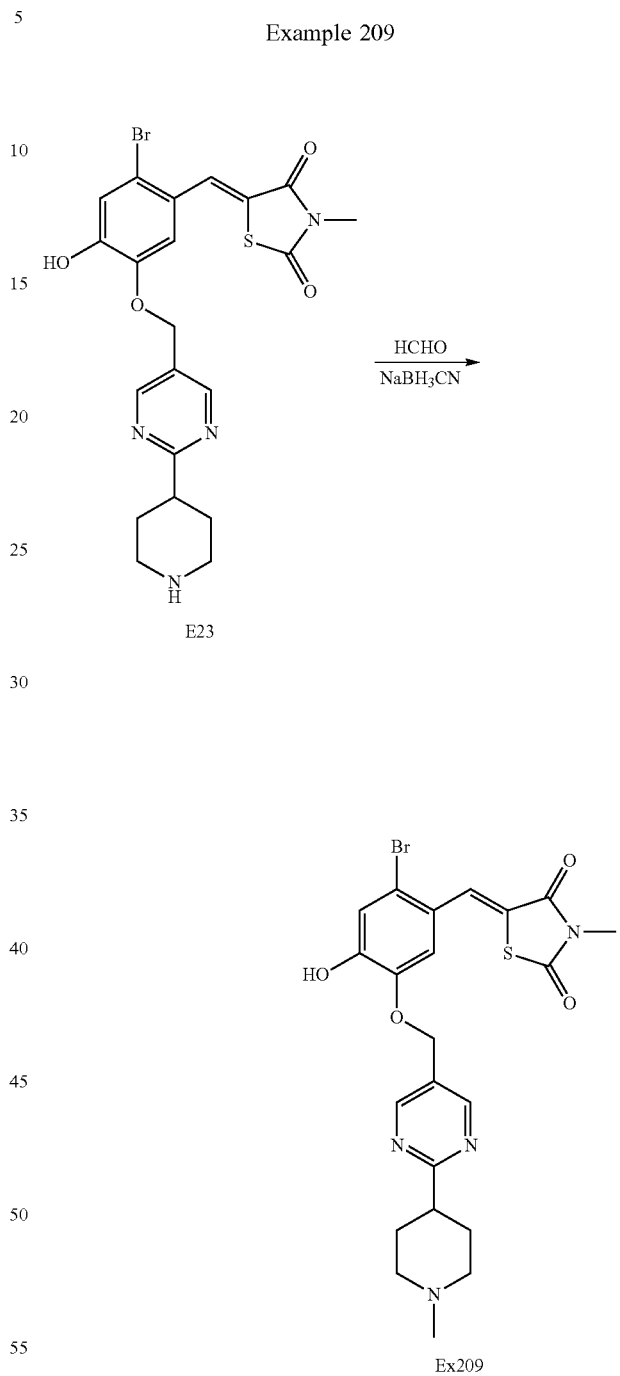

To a solution of E23 (100 mg, 0.2 mmol) in MeOH (20 mL) is added aqueous formaldehyde (37%, 1 mL) at room temperature and stirred for 2 hours before sodium cyanoborohydride (31 mg, 0.5 mmol) is added. After stirring for 2 hours, the mixture is concentrated and triturated with saturated sodium bicarbonate solution (5 mL). The solid is collected by filtration, washed with water (1 mL), and dried to give Ex209 as a yellow solid (33.6 mg, 33% yield). (MS: [M+H]$^+$ 521.1)

Example 210

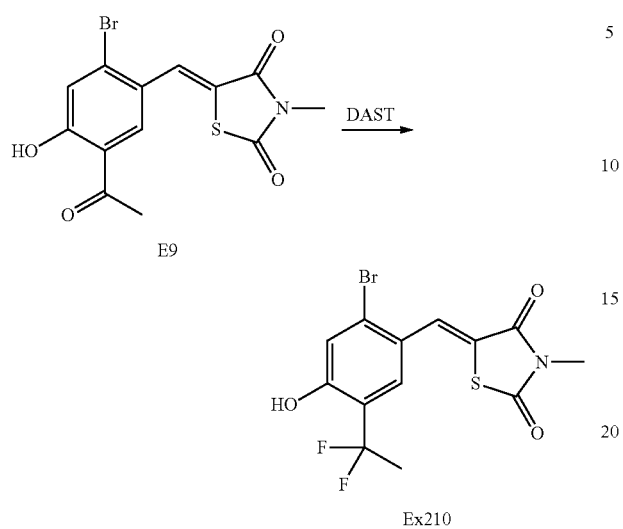

To a solution of E9 (40 mg, 0.1 mmol) in DCM (3 mL) is added DAST (360 mg, 2.2 mmol) dropwise at 0° C. After stirring at room temperature for 1 hour, the mixture is poured into ice water (10 mL) and extracted with DCM (20 mL×3). The combined organic layers are dried over anhydrous sodium sulfate, filtered, concentrated, and triturated with hexane and ethanol (10:1, 22 mL). The solid is collected by filtration, washed with hexane, and dried to give Ex210 as a light yellow solid (30 mg, 71% yield). (MS: [M+H]$^+$ 378.0)

Example 211

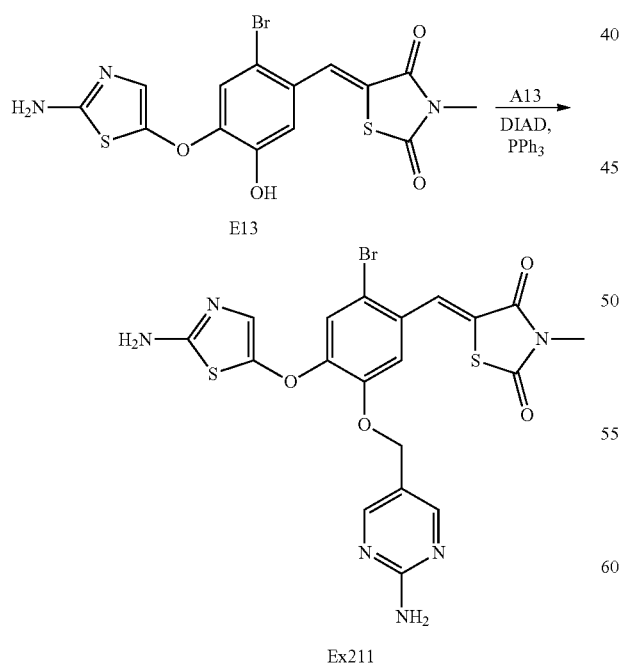

Following the procedure for Ex125 using E13 (80 mg, 0.18 mmol), THF (10 mL) A13 (28 mg, 0.22 mmol), PPh$_3$ (98 mg, 0.37 mmol), and DIAD (57 mg, 0.28 mmol), gives Ex211 as a yellow solid (10 mg, 8% yield). (MS: [M+H]$^+$ 535.1)

Example 212

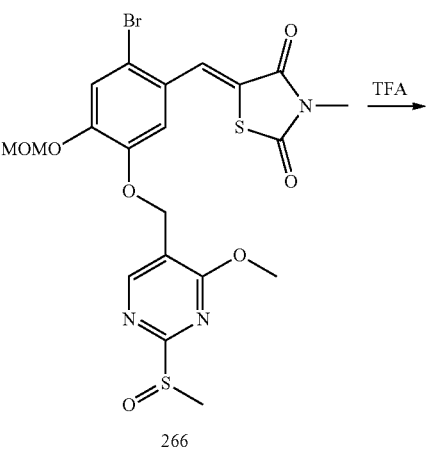

Step 1: Sulfoxide 266

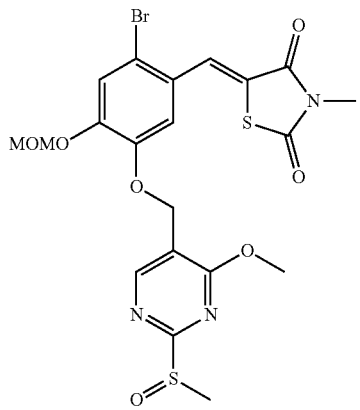

A solution of E16 (27.1 mg, 0.05 mmol) and mCPBA (10.0 mg, 0.06 mmol), in DCM (5 mL) is stirred at 0 to 10° C. for 6 hours. Saturated sodium bicarbonate solution is then added and the mixture is extracted with EA (5 mL×3). The combined organic layers are dried over anhydrous sodium sulfate, filtered, concentrated, and purified by silica gel column chromatography (MeOH:DCM=1:20 to 1:9) to give 266 as a yellow solid (13.8 mg, 50% yield). (MS: [M+H]$^+$ 557.9)

Step 2: Ex212

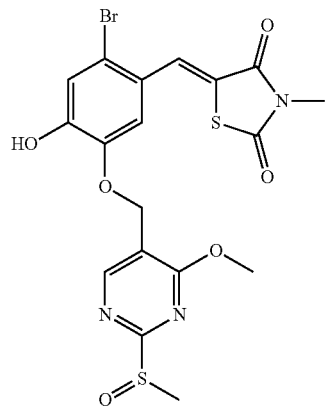 [SMILES: COc1nc(S(C)=O)ncc1COc1cc(/C=C2\SC(=O)N(C)C2=O)c(Br)cc1O]

To a solution of 266 (13.8 mg, 0.025 mmol) in DCM (5 mL) is added TFA (1 mL) dropwise at 0° C. After stirring at room temperature for 1 hour, the mixture is concentrated and triturated with MeOH (1 mL). The solid is collected by filtration and dried to give Ex212 as a yellow solid (6.2 mg, 49% yield). (MS: [M+H]$^+$ 514.0)

The following compounds are prepared by essentially the same method as for Ex212.

| Example | Building block | Structure | MS |
|---|---|---|---|
| Ex213 | (structure) | (structure) | [M + H]$^+$ 484.0 |
| Ex214 | (structure) | (structure) | [M + H]$^+$ 517.9 |

| Example | Building block | Structure | MS |
|---|---|---|---|
| Ex215 | | 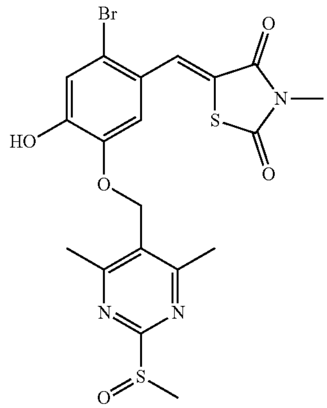 [SMILES: Cc1nc(S(C)=O)nc(C)c1COc1cc(/C=C2\SC(=O)N(C)C2=O)c(Br)cc1O] | [M + H]+ 512.0 |
| Ex216 | | 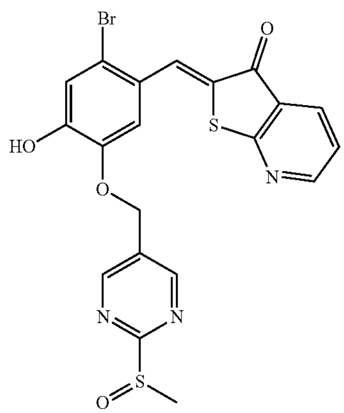 [SMILES: CS(=O)c1ncc(COc2cc(/C=C3\Sc4ncccc4C3=O)c(Br)cc2O)cn1] | [M + H]+ 504.0 |

Example 217

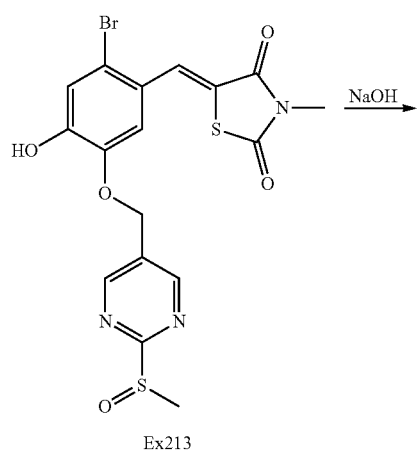

Ex213

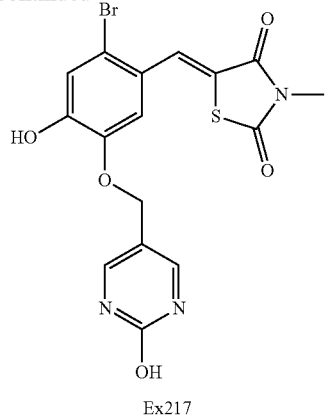

Ex217

To a solution of Ex213 (57 mg, 118 mmol) in THF (5 mL) is added NaOH (9.4 mg, 235 mmol) and water (0.2 ml). After stirring at 0 to 10° C. for 6 hours, the mixture is concentrated to remove THF and 1M HCl is added to reach pH 5. The mixture is then extracted with EA (5 mL×3). The combined organic layers are dried over anhydrous sodium sulfate, concentrated, triturated with MeOH (2 mL), collected by filtration, washed with MeOH (0.5 mL) to give Ex217 as a yellow solid (30 mg, 58% yield). (MS: [M+H]+ 438.0)

The following compound is prepared by essentially the same method as for Ex217.

| Example | Building block | Structure | MS |
|---|---|---|---|
| Ex218 | 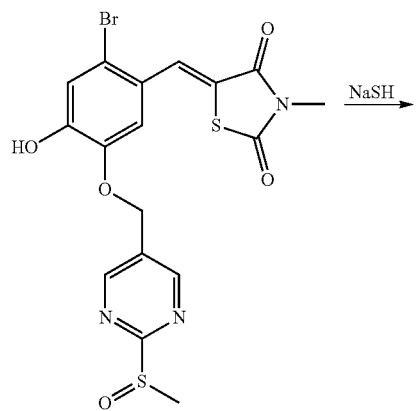 | 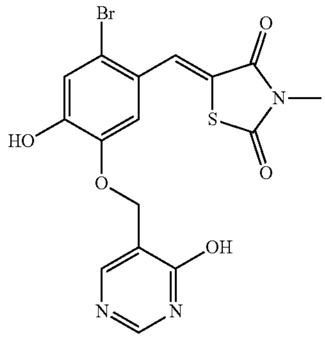 | [M + H]+ 438.0 |

Example 219

Example 220

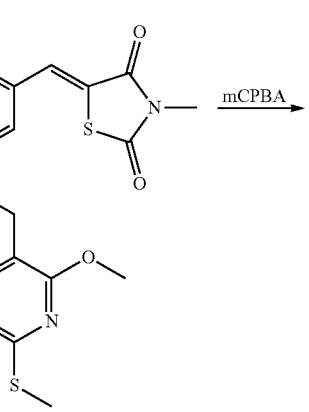

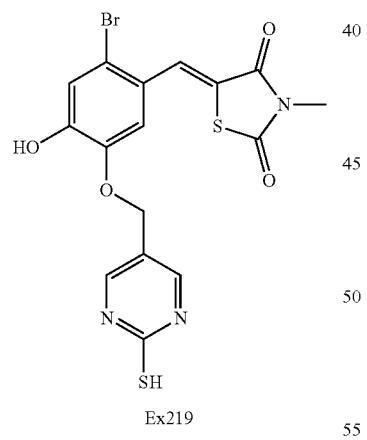

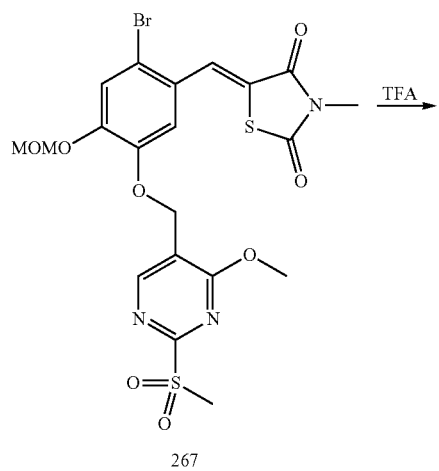

To a solution of Ex213 (50 mg, 103 mmol) in THF (2 mL) is added sodium hydrosulfide (11 mg, 206 mmol) and water (0.5 ml). After stirring at 0 to 10° C. for 6 hours, the mixture is concentrated to remove THF and 1M HCl is added to reach pH 5. The mixture is then extracted with EA (5 mL×3). The combined organic layers are dried over anhydrous sodium sulfate, concentrated, triturated with MeOH (2 mL), collected by filtration, washed with MeOH (0.5 mL) to give Ex219 as a yellow solid (18 mg, 38% yield). (MS: [M+H]+ 454.0)

Step 1: Sulfone 267

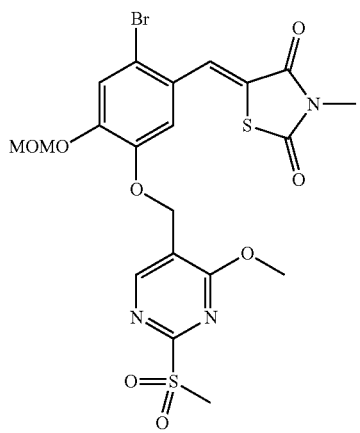

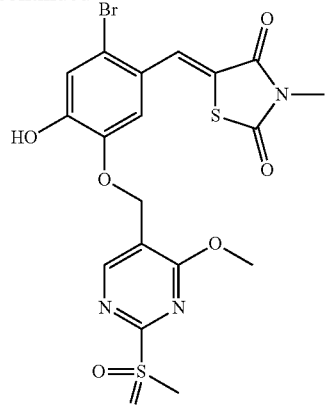

Ex220

To a solution of E16 (27 mg, 0.05 mmol) in DCM (5 mL) is added mCPBA (10 mg, 0.06 mmol). After stirring at 0 to 10° C. for 6 hours, saturated sodium bicarbonate solution is added and the mixture is extracted with EA (5 mL×3). The combined organic layers are dried over anhydrous sodium sulfate, filtered, concentrated, and purified by silica gel column chromatography (MeOH:DCM=1:20 to 1:9) to give 267 as a yellow solid (13.6 mg, 47% yield). (MS: [M+H]$^+$ 574.1)

Step 2: Ex220

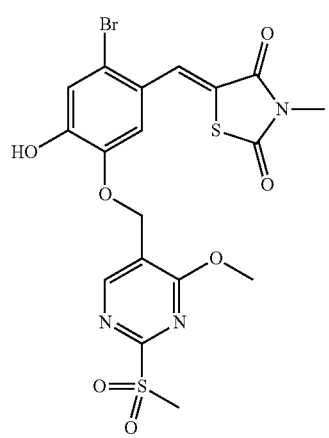 [SMILES: COc1nc(S(C)(=O)=O)ncc1COc1cc(/C=C2\SC(=O)N(C)C2=O)c(Br)cc1O]

To a solution of 267 (13.6 mg 0.024 mmol) in DCM (5 mL) is added TFA (1 mL) dropwise at 0° C. After stirring at room temperature for 1 hour, the mixture is concentrated and triturated with MeOH (1 mL). The solid is collected by filtration and dried to give Ex220 as a yellow solid (6.0 mg 47% yield). (MS: [M+H]$^+$ 530.0)

The following compound is prepared by essentially the same method as for Ex220.

| Example | Building block | Structure | MS |
|---------|----------------|-----------|-----|
| Ex221 | (structure with MOMO, Br, Cl, S-Me pyrimidine) E15 | (structure with HO, Br, Cl, sulfone pyrimidine) | [M + H]$^+$ 533.9 |

Example 222

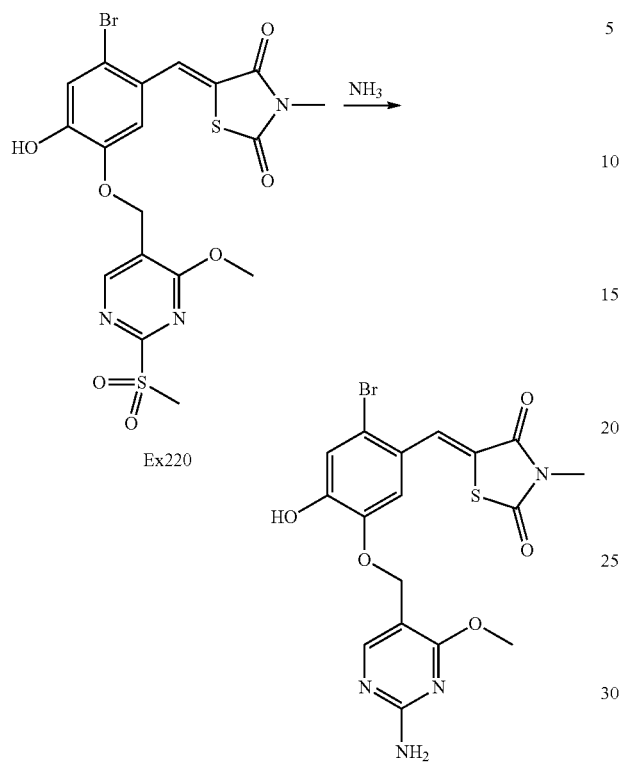

Ammonia is bubbled through a solution of Ex220 (100 mg, 0.19 mmol) in THF at −78° C. for 2 minutes in a sealing tube. After stirring at room temperature overnight, the mixture is concentrated and triturated with MeOH (1 mL). The solid is then collected by filtration and dried to give Ex222 as a yellow solid (13.2 mg, 15% yield). (MS: [M+H]$^+$467.0)

The following compound is prepared by essentially the same method as for Ex222.

| Example | Building block | Structure | MS |
|---|---|---|---|
| Ex223 | Ex215 | 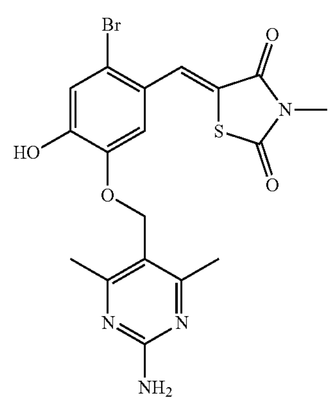 [SMILES: Cc1nc(N)nc(C)c1COc1cc(/C=C2\SC(=O)N(C)C2=O)c(Br)cc1O] | [M + H]$^+$ 465.0 |

Example 268

Step 1: Amide 268

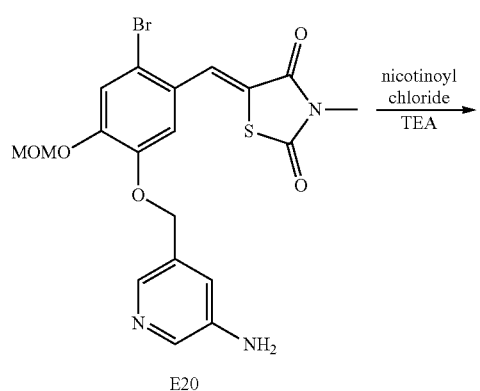

E20

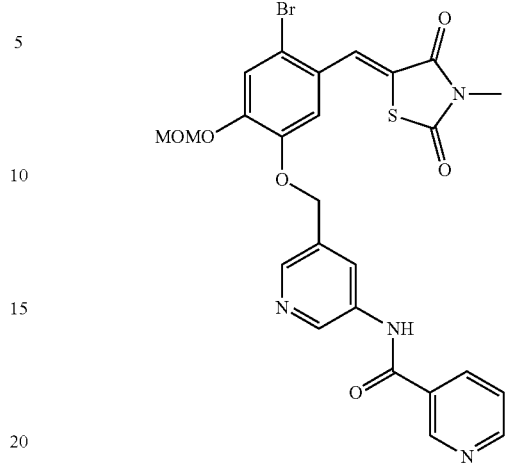

To a solution of E20 (20 mg, 0.04 mmol) in DCM (2 mL) is added nicotinoyl chloride (9 mg, 0.06 mmol) and TEA (9 mg, 0.08 mmol). After stirring at room temperature for 16 hours, the mixture is concentrated and purified by silica gel column chromatography (MeOH:DCM=1:50) to give 268 as an off-white solid (20 mg, 87% yield). (MS: [M+H]585.0)

Step 2: Ex224

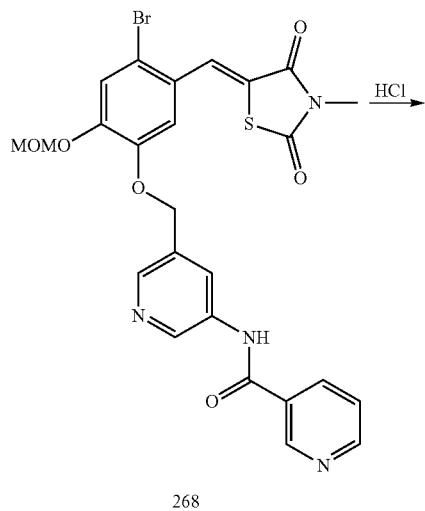

268

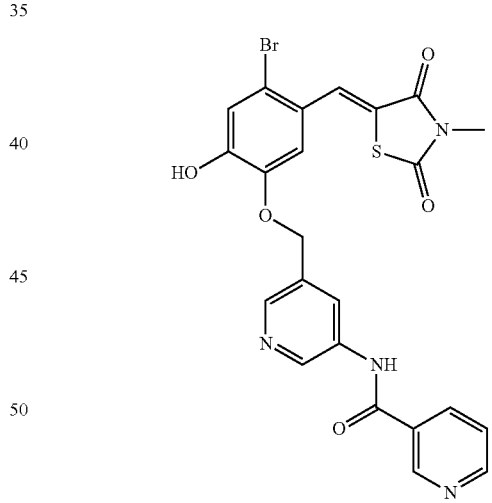

Ex224

A solution of 268 (20 mg, 0.03 mmol) in methanolic HCl (2 M, 5 mL) is stirred at room temperature for 16 hours. The mixture is then filtered and triturated with MeOH (10 mL). The solid is collected by filtration and dried to give Ex224 as a yellow solid (7 mg, 38% yield). (MS: [M+H]$^+$ 541.0)

The following compounds are prepared by essentially the same method as for Ex224.

| Example | Building blocks | Structure | MS |
|---|---|---|---|
| Ex225 | | 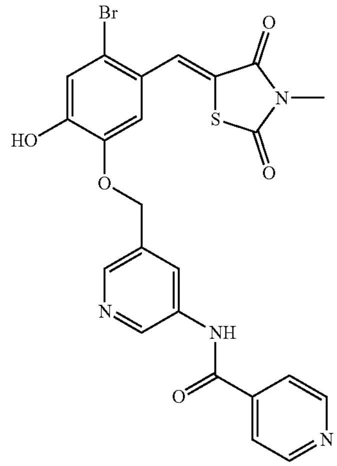 [SMILES: CN1C(=O)S/C(=C\c2cc(OCc3cncc(NC(=O)c4ccncc4)c3)c(O)cc2Br)C1=O] | [M + H]+ 541.0 |
| Ex226 | | 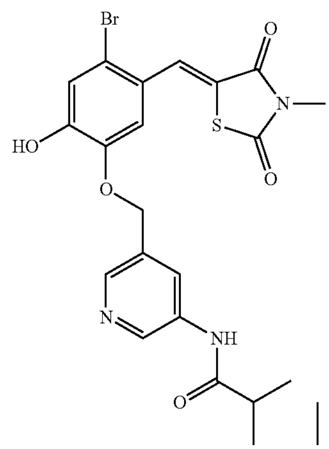 | — |
Example 227
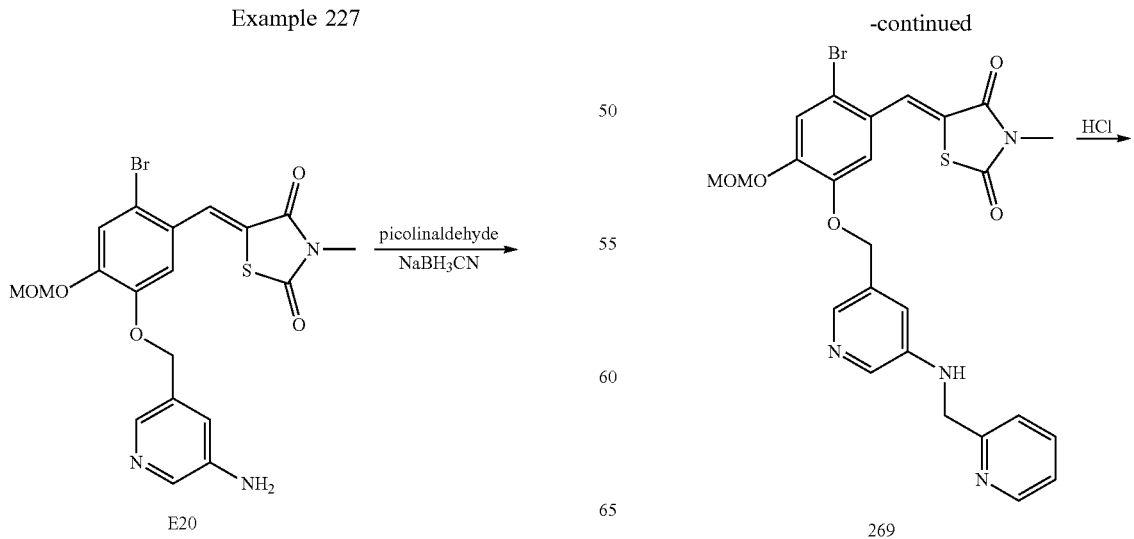

-continued

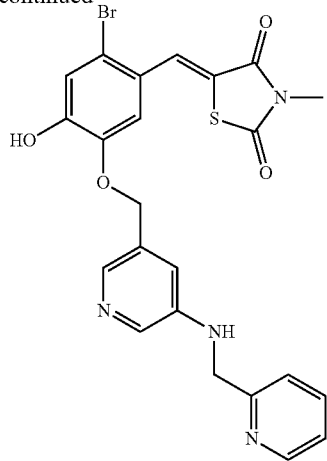

Ex227

Step 1: Amine 269

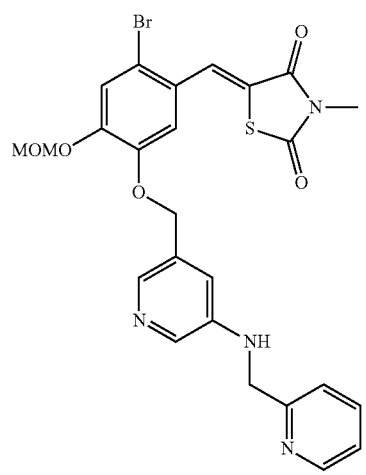

A mixture of E20 (80 mg, 0.2 mmol) in EtOH (3 mL) is added picolinaldehyde (36 mg, 0.3 mmol) at room temperature. After stirring at 90° C. for 16 hours, the mixture is cooled to room temperature and sodium cyanoborohydride (32 mg, 0.5 mmol) is added. The mixture is then stirred at room temperature for 1 hour, concentrated, and purified by silica gel column chromatography (MeOH:DCM=1:50) to give 269 as a yellow solid (60 mg, 63% yield). (MS: [M+H]$^+$ 571.1)

Step 2: Ex227

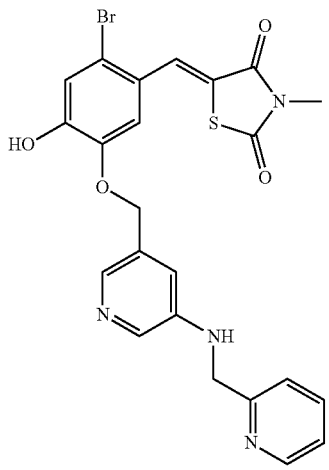 [SMILES: CN1C(=O)S/C(=C\c2cc(OCc3cncc(NCc4ccccn4)c3)c(O)cc2Br)C1=O]

Following the procedure for Ex224 using 269 (60 mg, 0.1 mmol) and HCl (2M in MeOH, 5 mL) gives Ex227 as a yellow solid (25 mg, 45% yield). (MS: [M+H]$^+$ 527.0)

The following compounds are prepared by essentially the same method as for Ex227.

| Example | Building blocks | Structure | MS |
|---|---|---|---|
| Ex228 | 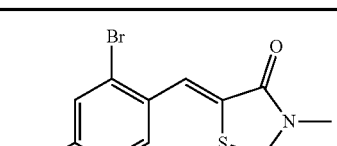 E20 | 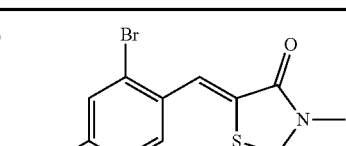 | [M + H]$^+$ 527.0 |

-continued

| Example | Building blocks | Structure | MS |
|---|---|---|---|
| Ex229 | 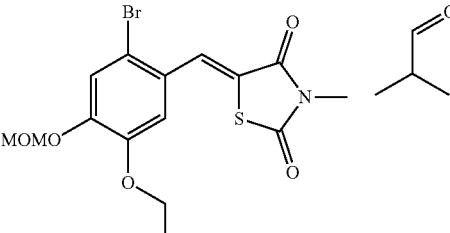 E20 | 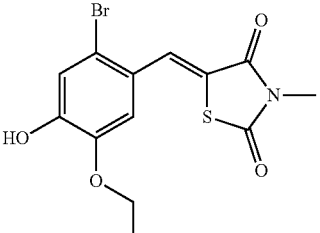 | [M + H]+ 492.0 |

Example 230

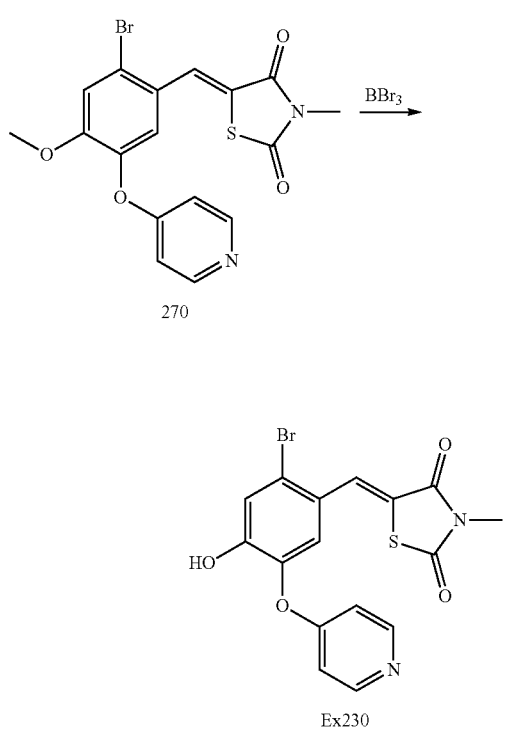

Step 1: Ether 270

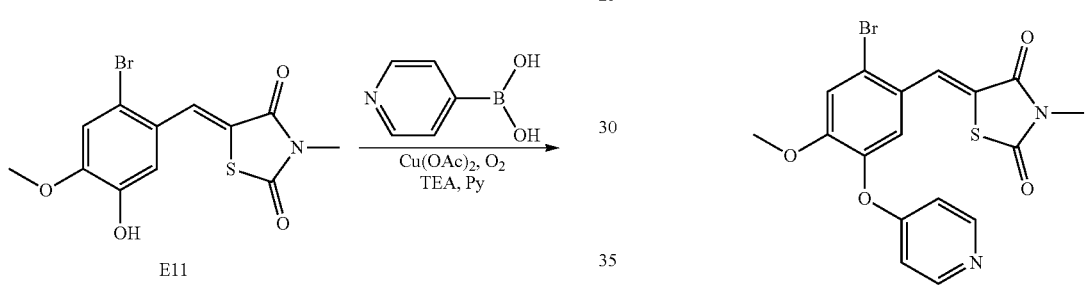

Following the procedure for 16 using E11 (400 mg, 1.16 mmol), DCM (10 mL), 4-pyridineboronic acid (430 mg, 3.49 mmol), Cu(OAc)$_2$ (253 mg, 1.39 mmol), and TEA (588 mg, 5.81 mmol), triturate with EtOH (5 mL) to give 270 as a yellow solid (215 mg, 44% yield). (MS: [M+H]+ 421.0)

Step 2: Ex230

To a solution of 270 (84.3 mg, 0.2 mmol) in DCM (8 mL) is added boron tribromide (100 mg, 0.4 mmol) at −78° C. After stirring at −78° C. for 1 hour and then at room temperature overnight, water is added at −30° C. and the mixture is concentrated and purified by prep-HPLC to give Ex230 as a white solid (32 mg, 40% yield). (MS: [M+H]+ 407.0)

The following compound is prepared by essentially the same method as for Ex230.

| Example | Building blocks | | Structure | MS |
|---|---|---|---|---|
| Ex231 | 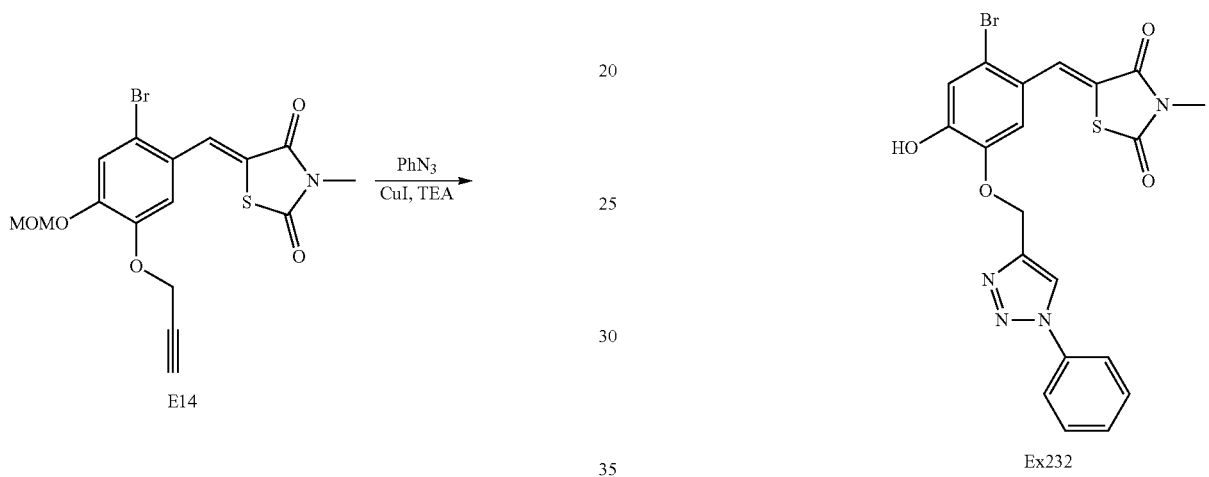 E2 | | 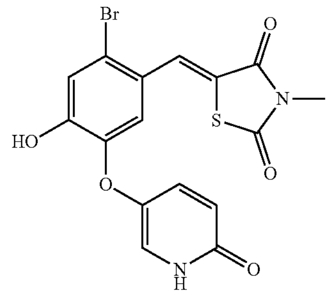 [SMILES: CN1C(=O)S/C(=C\c2cc(Oc3ccc(=O)[nH]c3)c(O)cc2Br)C1=O] | [M + H]+ 423.0 |
Example 232
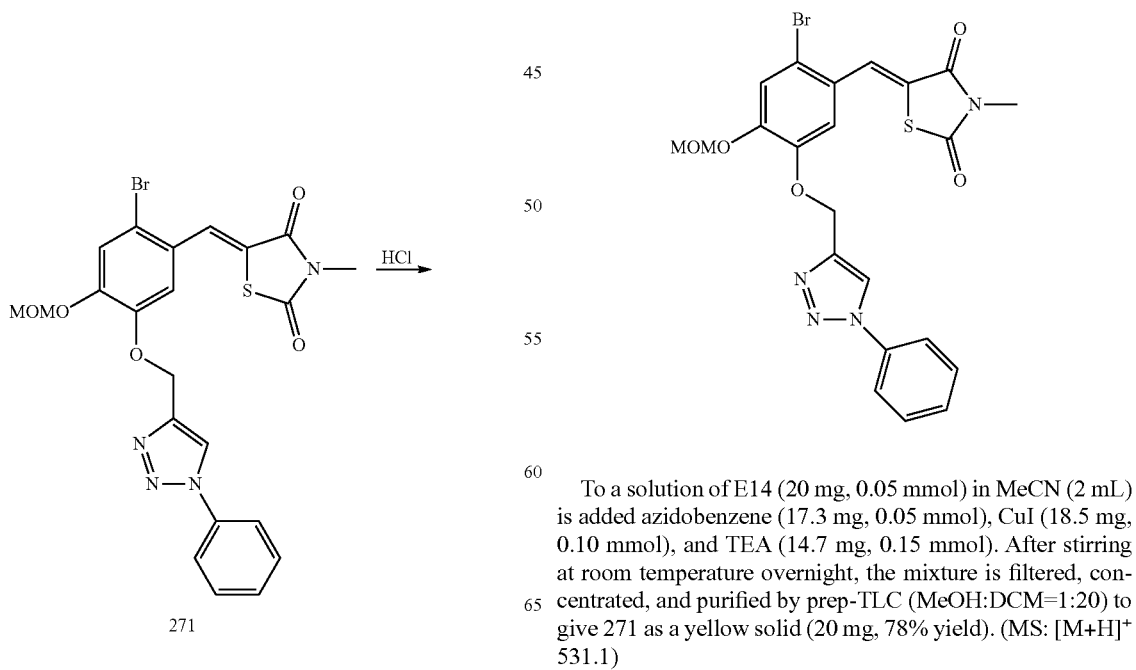
Step 1: Triazole 271
To a solution of E14 (20 mg, 0.05 mmol) in MeCN (2 mL) is added azidobenzene (17.3 mg, 0.05 mmol), CuI (18.5 mg, 0.10 mmol), and TEA (14.7 mg, 0.15 mmol). After stirring at room temperature overnight, the mixture is filtered, concentrated, and purified by prep-TLC (MeOH:DCM=1:20) to give 271 as a yellow solid (20 mg, 78% yield). (MS: [M+H]+ 531.1)

Step 2: Ex232

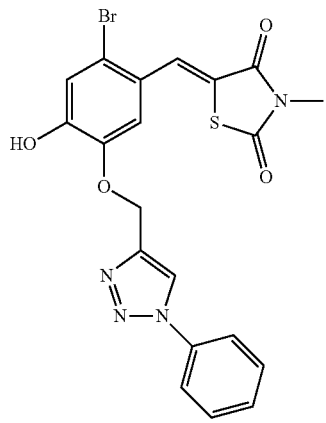 [SMILES: CN1C(=O)S/C(=C\c2cc(OCc3cn(-c4ccccc4)nn3)c(O)cc2Br)C1=O]

A solution of 271 (20 mg, 0.04 mmol) in methanolic HCl (2 M, 5 mL) is stirred at 50° C. for 1 hour. The mixture is then concentrated and purified by prep-TLC (MeOH:DCM=1:20) to give Ex232 as a yellow solid (4 mg, 22% yield). (MS: [M+H]$^+$487.1)

The following compound is prepared by essentially the same method as for Ex232.

| Example | Building blocks | Structure | MS |
|---|---|---|---|
| Ex233 | 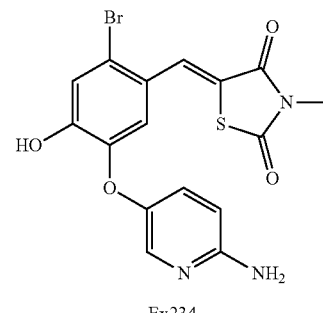 E14 | 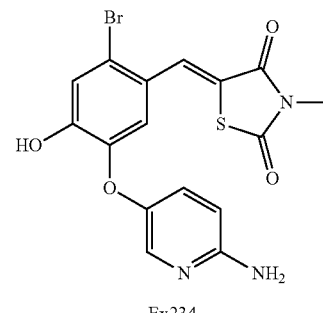 | [M + H]$^+$ 488.0 |

Example 234

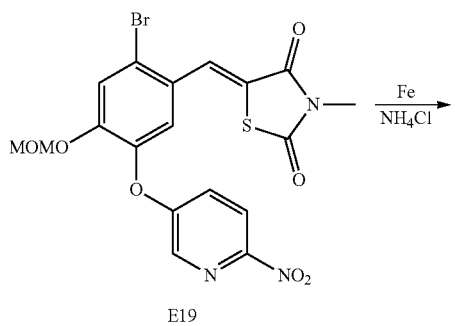

Step 1: Ether 272

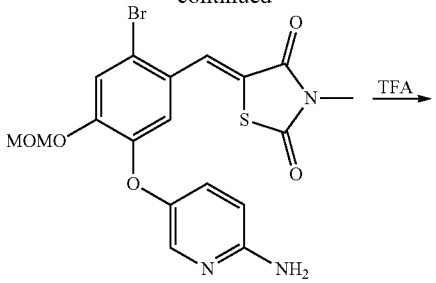

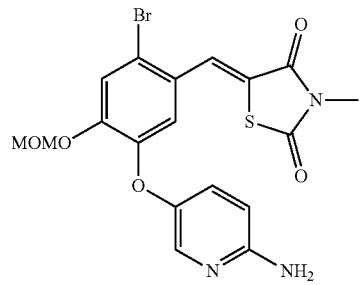

A mixture of E19 (120 mg, 0.24 mmol), iron powder (68 mg, 1.20 mmol), ammonium chloride (65 mg, 1.20 mmol) in EtOH (20 mL) and water (1 mL) is stirred at 90° C.

overnight. After cooling to room temperature, the mixture is filtered, concentrated, and purified by silica gel column chromatography (MeOH:DCM=1:20) to give 272 as a yellow solid (50 mg, 45% yield). (MS: [M+H]+ 466.1)

Step 2: Ex234

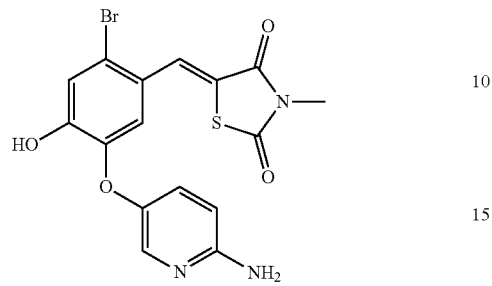

To a solution of 272 (60 mg, 0.13 mmol) in DCM (3 mL) is added TFA (1.5 mL) at 0° C. After stirring at room temperature overnight, the mixture is concentrated and triturated with MeOH (1 mL). The solid is collected by filtration and dried to give Ex234 as a yellow solid (10 mg, 19% yield). (MS: [M+H]+ 422.0)

The following compounds are prepared by essentially the same method as described above.

| Example | Building blocks | | Structure | MS | Reference of preparation |
|---|---|---|---|---|---|
| ExA1 | E6 | A18 | 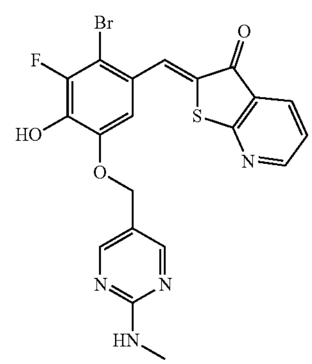 [SMILES: CNc1ncc(COc2cc(/C=C3\Sc4ncccc4C3=O)c(Br)c(F)c2O)cn1] | [M + H]+ 489.0 | Ex125 |
| ExA2 | E6 | A27 | 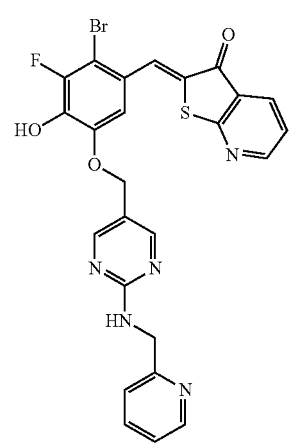 | [M − H]− 566.0 | Ex125 |

-continued

| Example | Building blocks | Structure | MS | Reference of preparation |
|---|---|---|---|---|
| ExA3 | E6, A17 | 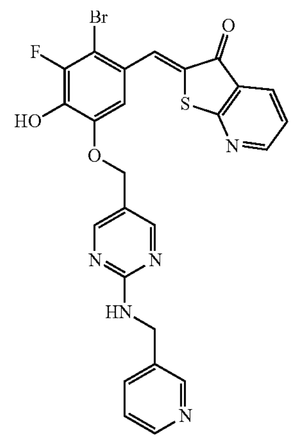 [SMILES: O=C1/C(=C/c2cc(OCc3cnc(NCc4cccnc4)nc3)c(O)c(F)c2Br)Sc2ncccc21] | [M + H]+ 566.0 | Ex125 |
| ExA4 | E6, A16 | 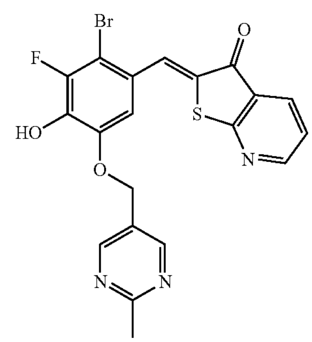 [SMILES: Cc1ncc(COc2cc(/C=C3\Sc4ncccc4C3=O)c(Br)c(F)c2O)cn1] | [M + H]+ 474.0 | Ex125 |
| ExA5 | E3, AA1 | 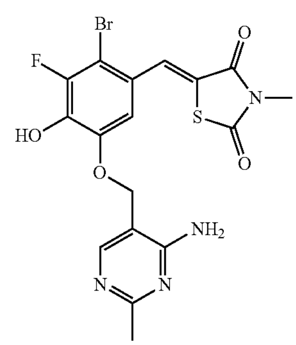 [SMILES: Cc1ncc(COc2cc(/C=C3\SC(=O)N(C)C3=O)c(Br)c(F)c2O)c(N)n1] | [M + H]+ 469.0 | Ex84 |
| ExA6 | E3, B21 | 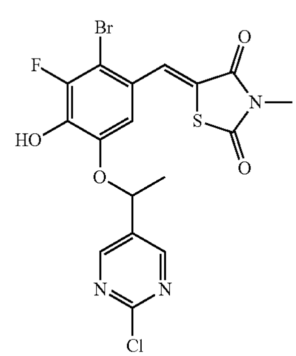 [SMILES: CC(Oc1cc(/C=C2\SC(=O)N(C)C2=O)c(Br)c(F)c1O)c1cnc(Cl)nc1] | [M + H]+ 487.9 | Ex84 |

-continued

| Example | Building blocks | Structure | MS | Reference of preparation |
|---|---|---|---|---|
| ExA7 | E3, BA1 | 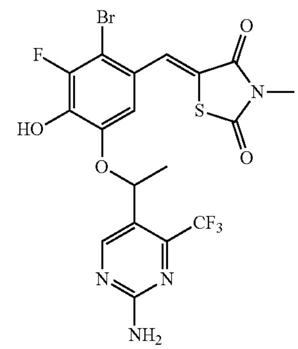 [SMILES: CC(Oc1cc(/C=C2\SC(=O)N(C)C2=O)c(Br)c(F)c1O)c1cnc(N)nc1C(F)(F)F] | [M + H]+ 537.0 | Ex84 |
| ExA8 | E6, B16 | 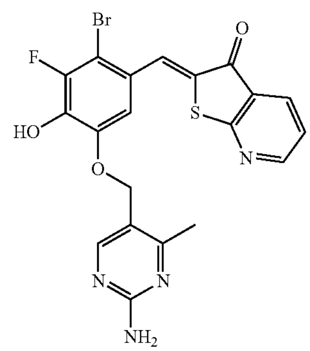 [SMILES: Cc1nc(N)ncc1COc1cc(/C=C2\Sc3ncccc3C2=O)c(Br)c(F)c1O] | [M + H]+ 489.0 | Ex84 |
| ExA9 | E5, BA2 | 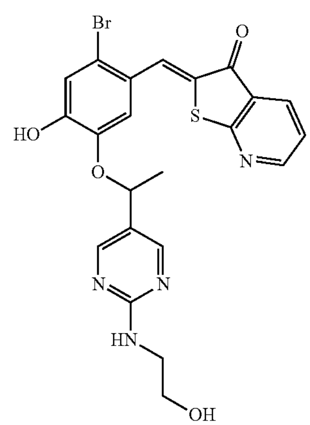 [SMILES: CC(Oc1cc(/C=C2\Sc3ncccc3C2=O)c(Br)cc1O)c1cnc(NCCO)nc1] | [M + H]+ 515.0 | Ex84 |
| ExA10 | E3, BA3 | 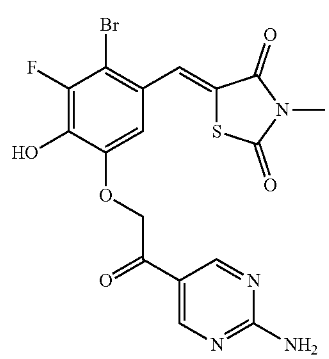 [SMILES: CN1C(=O)S/C(=C\c2cc(OCC(=O)c3cnc(N)nc3)c(O)c(F)c2Br)C1=O] | [M + H]+ 483.0 | Ex84 |

-continued
| Example | Building blocks | | Structure | MS | Reference of preparation |
|---|---|---|---|---|---|
| ExA11 | 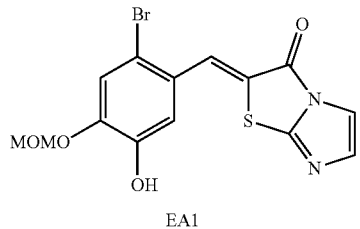<br>EA1 | 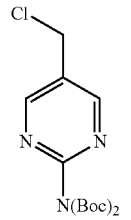<br>B15 | 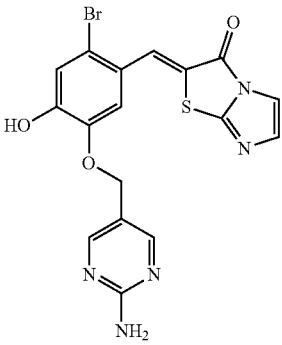 [SMILES: Nc1ncc(COc2cc(/C=c3\sc4nccn4c3=O)c(Br)cc2O)cn1] | [M + H]+ 446.0 | Ex84 |
| ExA12 | 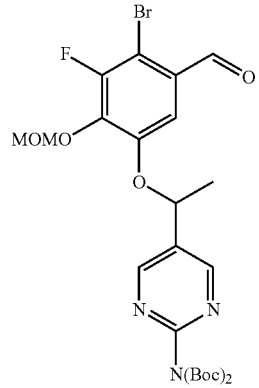<br>CA1 | 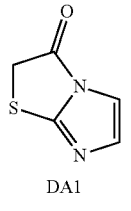<br>DA1 | 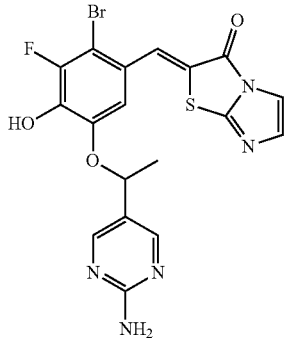 [SMILES: CC(Oc1cc(/C=c2\sc3nccn3c2=O)c(Br)c(F)c1O)c1cnc(N)nc1] | [M + H]+ 478.0 | Ex80 |
| ExA13 | 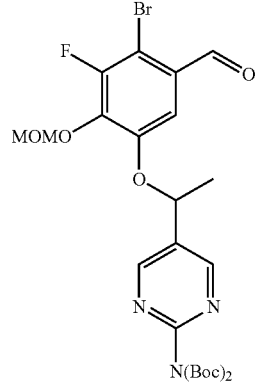<br>CA1 | 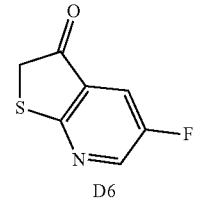<br>D6 | 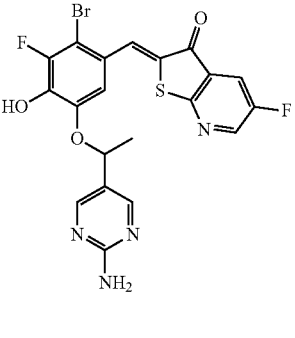 [SMILES: CC(Oc1cc(/C=C2\Sc3ncc(F)cc3C2=O)c(Br)c(F)c1O)c1cnc(N)nc1] | [M + H]+ 507.0 | Ex80 |

| Example | Building blocks | Structure | MS | Reference of preparation |
|---|---|---|---|---|
| ExA14 | EA2 | 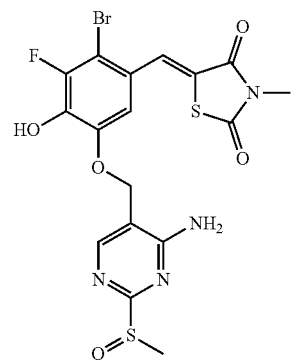 [SMILES: CN1C(=O)S/C(=C\c2cc(OCc3cnc(S(C)=O)nc3N)c(O)c(F)c2Br)C1=O] | [M + H]⁺ 517.0 | Ex212 |
| ExA15 | EA3 | 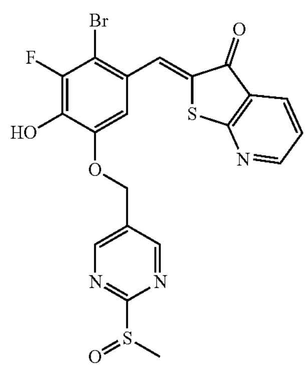 [SMILES: CS(=O)c1ncc(COc2cc(/C=C3\Sc4ncccc4C3=O)c(Br)c(F)c2O)cn1] | [M + H]⁺ 522.0 | Ex212 |
| ExA16 | EA4 | 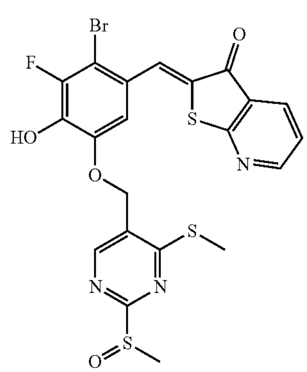 [SMILES: CSc1nc(S(C)=O)ncc1COc1cc(/C=C2\Sc3ncccc3C2=O)c(Br)c(F)c1O] | [M + H]⁺ 567.9.0 | Ex212 |

| Example | Building blocks | Structure | MS | Reference of preparation |
|---|---|---|---|---|
| ExA17 | 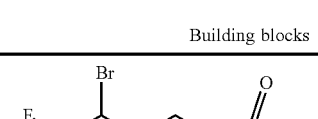<br>EA5 | 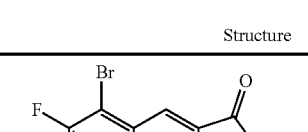 | [M + H]+ 455.0 | Ex217 |

Example A18

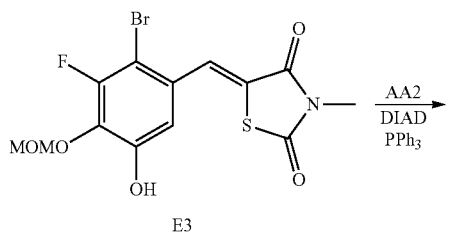
E3

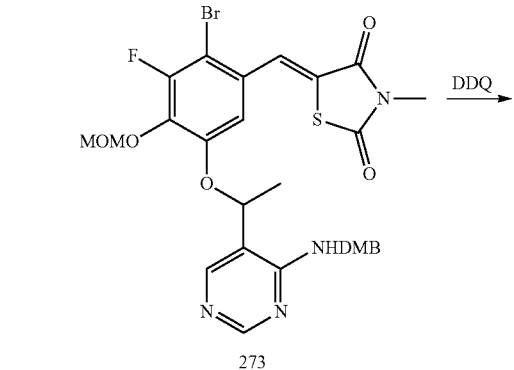
273

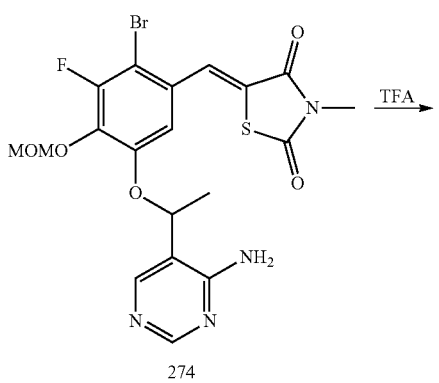
274

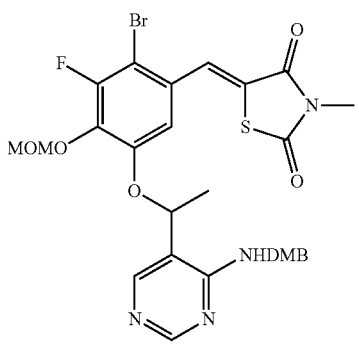
ExA18

Step 1: Ether 273

To a solution of E3 (68 mg, 0.17 mmol) and AA2 (50 mg, 0.17 mmol) in THF (3 mL) is added PPh₃ (90 mg, 0.34 mmol) and DIAD (69 mg, 0.34 mmol). After stirring for at room temperature for 4 hours, the mixture is concentrated and purified by silica gel column chromatography (MeOH: DCM=1:10) to give 273 as a yellow solid (30 mg, 26%). (MS: [M+H]⁺ 683.0)

Step 2: Pyrimidine 274

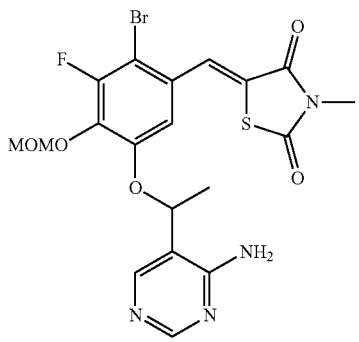

To a solution of 273 (30 mg, 0.04 mmol) in DCM (4 mL) and water (2 mL) is added DDQ (20 mg, 0.08 mmol). After stirring at room temperature for 4 hours, the mixture is diluted with EA (50 mL), washed with water (10 mL), dried over anhydrous sodium sulfate, filtered, concentrated, and purified by silica gel column chromatography (MeOH:DCM=1:10) to give 274 as a yellow solid (15 mg, 65%). (MS: [M+H]$^+$ 512.0)

Step 3: ExA18

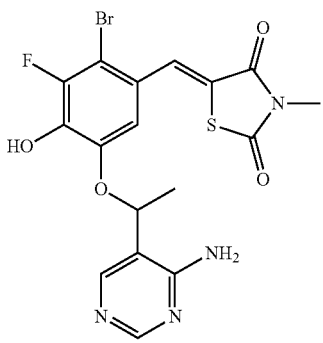 [SMILES: CC(Oc1cc(/C=C2\SC(=O)N(C)C2=O)c(Br)c(F)c1O)c1cncnc1N]

To a solution of 274 (30 mg, 0.04 mmol) in DCM (4 mL) is added TFA (0.4 mL). After stirring at room temperature for 1 hour, the mixture is concentrated and purified by prep-HPLC to give ExA18 as a yellow solid (4 mg, 29%). (MS: [M+H]$^+$ 469.0)

Example A19

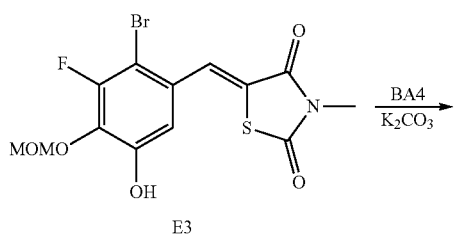

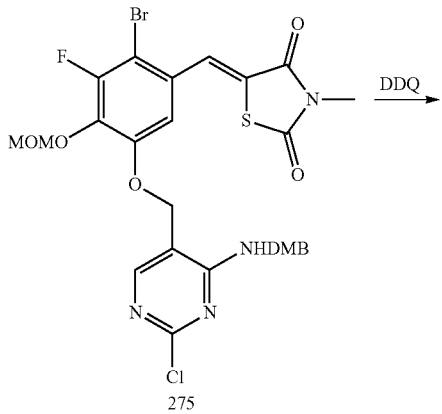

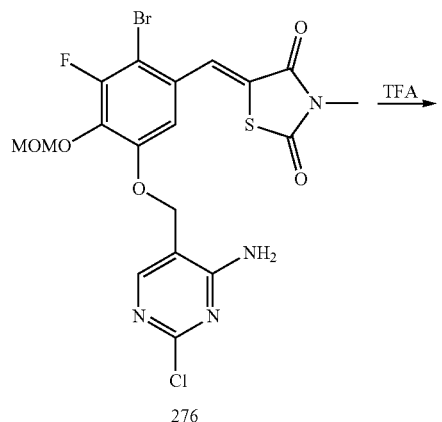

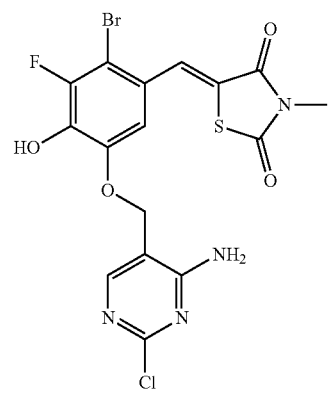

Step 1: Ether 275

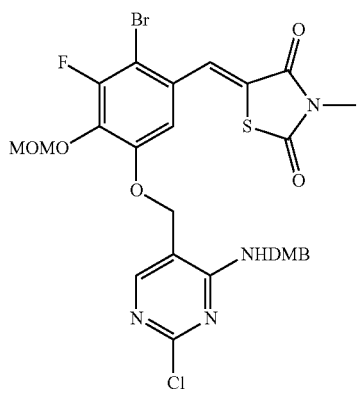

To a solution of BA4 (71 mg 0.2 mmol) in DMF (5 mL) is added E3 (83.5 mg 0.2 mmol) and potassium carbonate (59 mg 0.43 mmol). After stirring at room temperature for 1 hour, the mixture is concentrated and triturated with water (5 mL). The solid is collected by filtration and washed with PE (12 mL) to give 275 as a yellow solid (120 mg 82% yield). (MS: [M+H]$^+$ 683.0)

Step 2: Pyrimidine 276

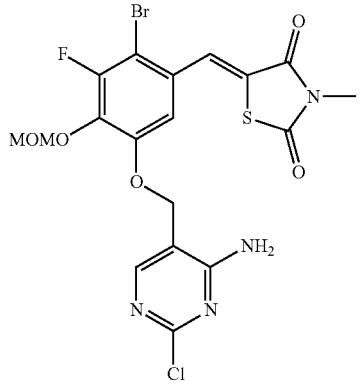

To a solution of 275 (120 mg, 0.18 mmol) in DCM (10 mL) and water (1 mL) is added DDQ (80 mg 0.35 mmol). After stirring at room temperature for 3 hours, the mixture is diluted with water (20 mL) and the aqueous layer is extracted with DCM (20 mL×2). The combined organic layers are concentrated and purified by prep-TLC (EA: PE=1:1) to give 276 as a light yellow solid (45 mg, 48%). (MS: [M+H]$^+$ 533.0)

Step 3: ExA19

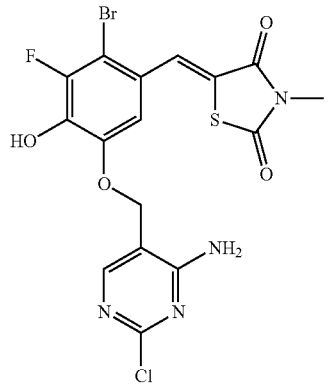

To a solution of 276 (45 mg, 0.08 mmol) in DCM (4 mL) is added TFA (2 mL) dropwise at 0° C. After stirring at room temperature for 30 minutes, the mixture is concentrated and triturated with MeCN (5 mL). The solid is collected by filtration and dried to give ExA19 as a light yellow solid (7 mg, 17% yield). (MS: [M+H]$^+$ 491.0)

Example A20

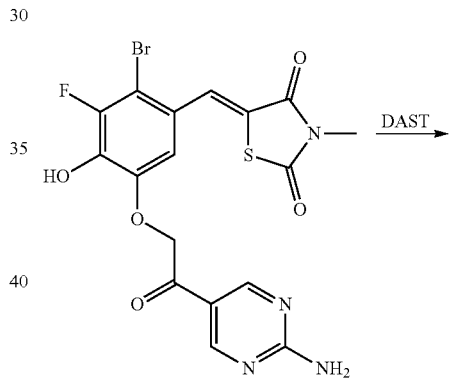

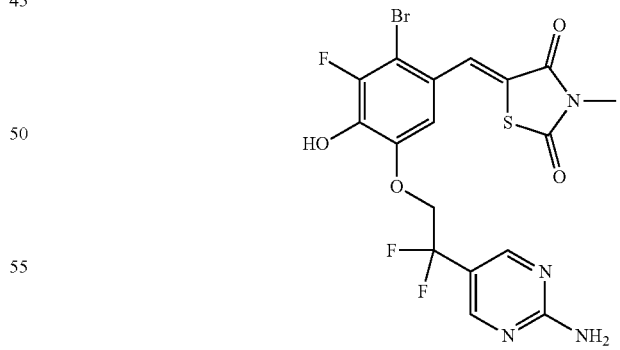

To a solution of ExA10 (45 mg, 0.09 mmol) in DCM is added DAST (145 mg, 0.9 mmol) at 0° C. After stirring at room temperature for 30 minutes, the mixture is concentrated, purified by silica gel column chromatography (MeOH:DCM=1:10), and triturated with MeOH to give ExA20 as a solid (10.8 mg, 24%). (MS: [M+H]$^+$ 505.0)

Example B1

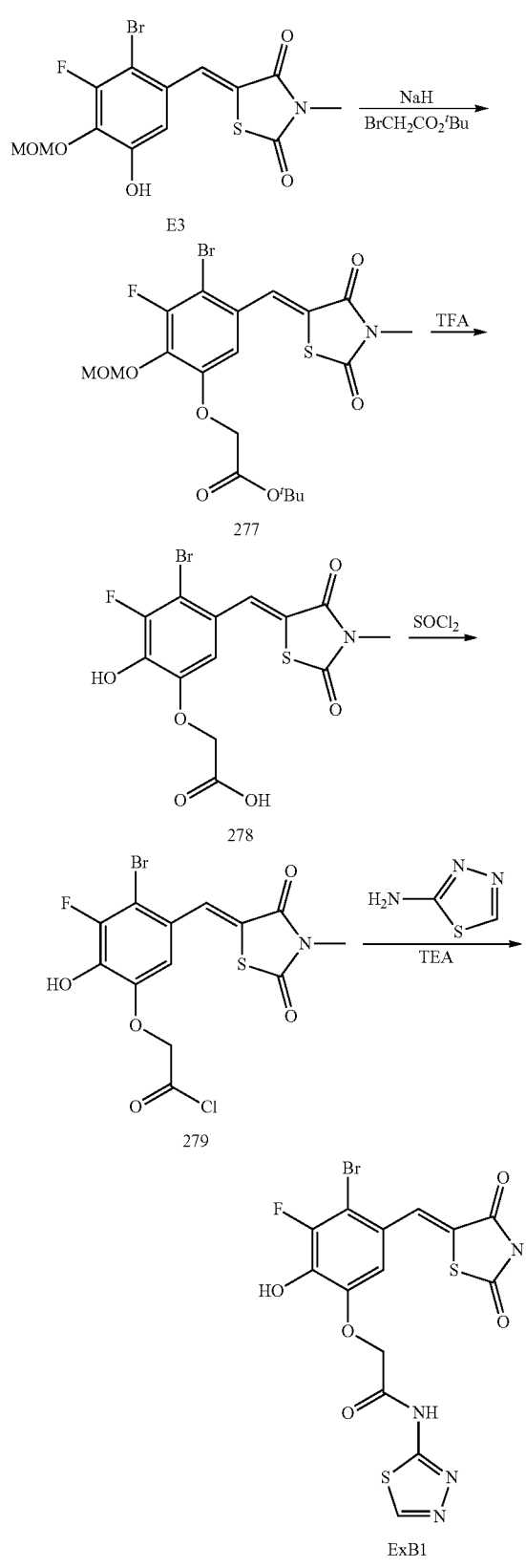

Step 1: Ester 277

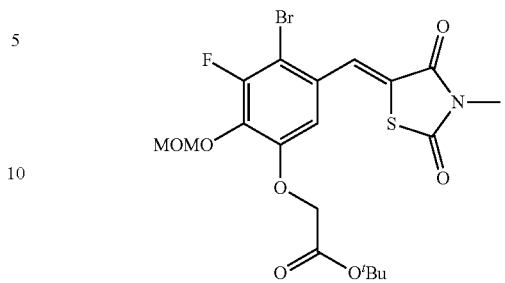

To a solution of E3 (100 mg, 0.25 mmol) in DMF (15 mL) is added NaH (15 mg, 0.38 mmol) at 0° C. and stirred for 30 minutes before tert-butyl 2-bromoacetate (0.074 mL, 0.38 mmol) is added. After stirring at room temperature for 5 hours, water is added and the mixture is extracted with EA (20 mL×3). The combined organic layers are dried over anhydrous sodium sulfate, concentrated, and purified by silica gel column chromatography (EA:PE=1:10) to give 277 as a yellow solid (100 mg, 77%). (MS: [M+H]$^+$ 507.2)

Step 2: Acid 278

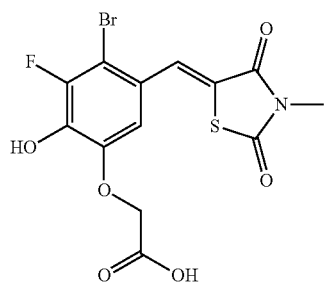

To a solution of 277 (100 mg 0.20 mmol) in DCM (10 mL) is added TFA (2 mL). After stirring at room temperature for 8 hours, the mixture is concentrated and triturated with MeOH (1 mL). The solid is collected by filtration to give 278 (80 mg, 100%). (MS: [M+H]$^+$ 407.2)

Step 3: Acyl Chloride 279

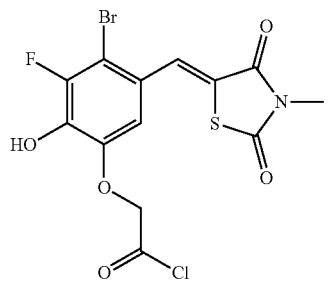 [SMILES: CN1C(=O)S/C(=C\c2cc(OCC(=O)Cl)c(O)c(F)c2Br)C1=O]

To a solution of 278 (80 mg, 0.20 mmol) in MeCN (5 mL) is added thionyl chloride (0.044 mL, 0.60 mmol). After stirring at room temperature for 10 minutes, the mixture is concentrated to give 279 as an oil (80 mg, 96%). (MS: [M+H]$^+$ 425.6).

Step 4: ExB1

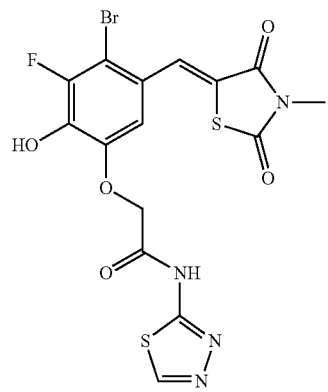 [SMILES: CN1C(=O)S/C(=C\c2cc(OCC(=O)Nc3nncs3)c(O)c(F)c2Br)C1=O]

To a solution of 279 (80 mg, 0.19 mmol), 2-amino-1,3,4-thiadiazole (29 mg, 0.29 mmol) in DCM (10 mL) is added TEA (0.053 mL, 0.38 mmol). After stirring at 25° C. for 5 hours, the mixture is concentrated and purified by pre-HPLC (water:MeOH with 0.1% formic acid=7:1) to give ExB1 as a solid (40 mg, 43%). (MS: [M+H]$^+$ 490.2)

Example B2

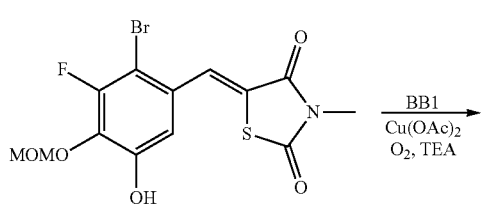

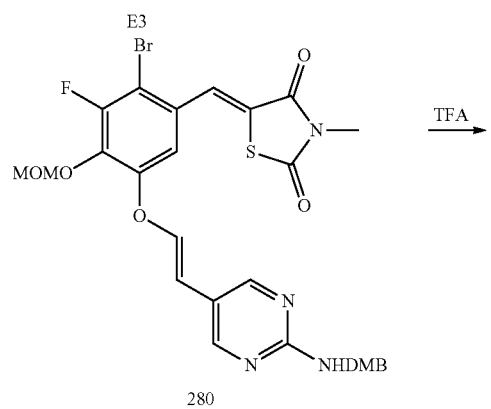

Step 1: Ether 280

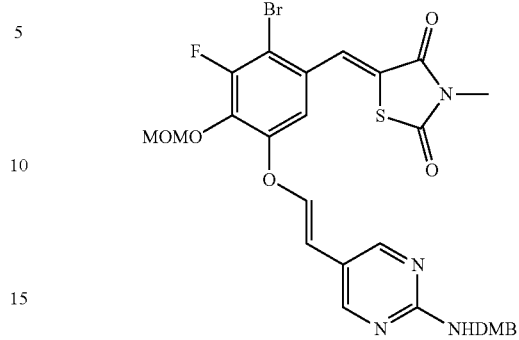

Prepared by essentially the same coupling condition as for CB1. (MS: [M+H]$^+$661.1)

Step 2: ExB2

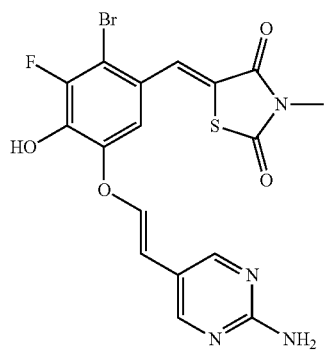 [SMILES: CN1C(=O)S/C(=C\c2cc(O/C=C/c3cnc(N)nc3)c(O)c(F)c2Br)C1=O]

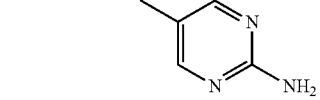

To a solution of 280 (20 mg, 0.03 mmol) in DCM (1 mL) is added TFA (0.1 mL). After stirring at room temperature for 4 hours, the mixture is concentrated and purified by prep-HPLC to give ExB11 as a yellow solid (2.0 mg, 14%). (MS: [M+H]$^+$ 467.0)

Example B3

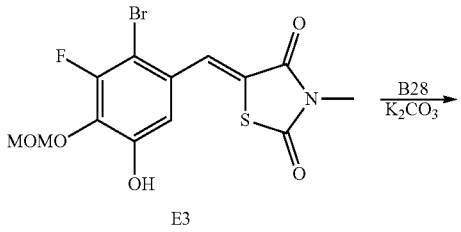

Step 2: ExB3
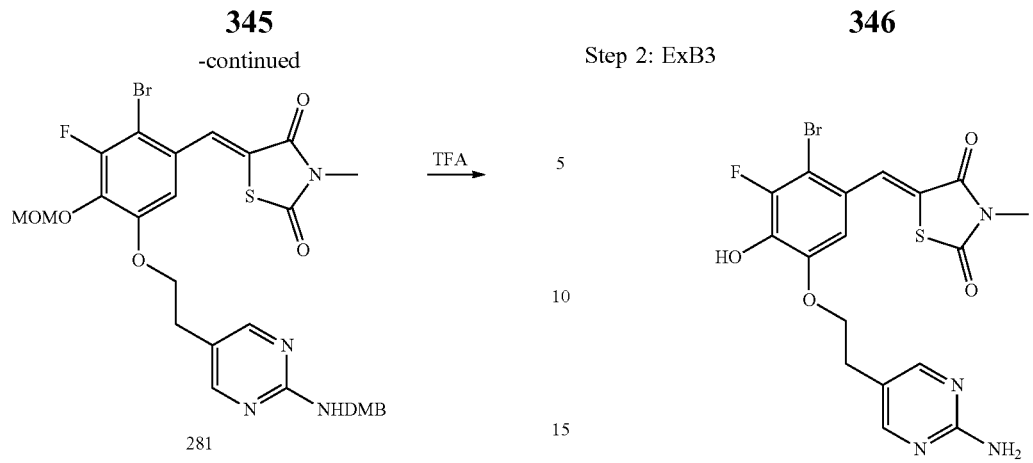
Prepared by essentially the same method as for C8. (MS: [M+H]+ 469.1)
Example B4
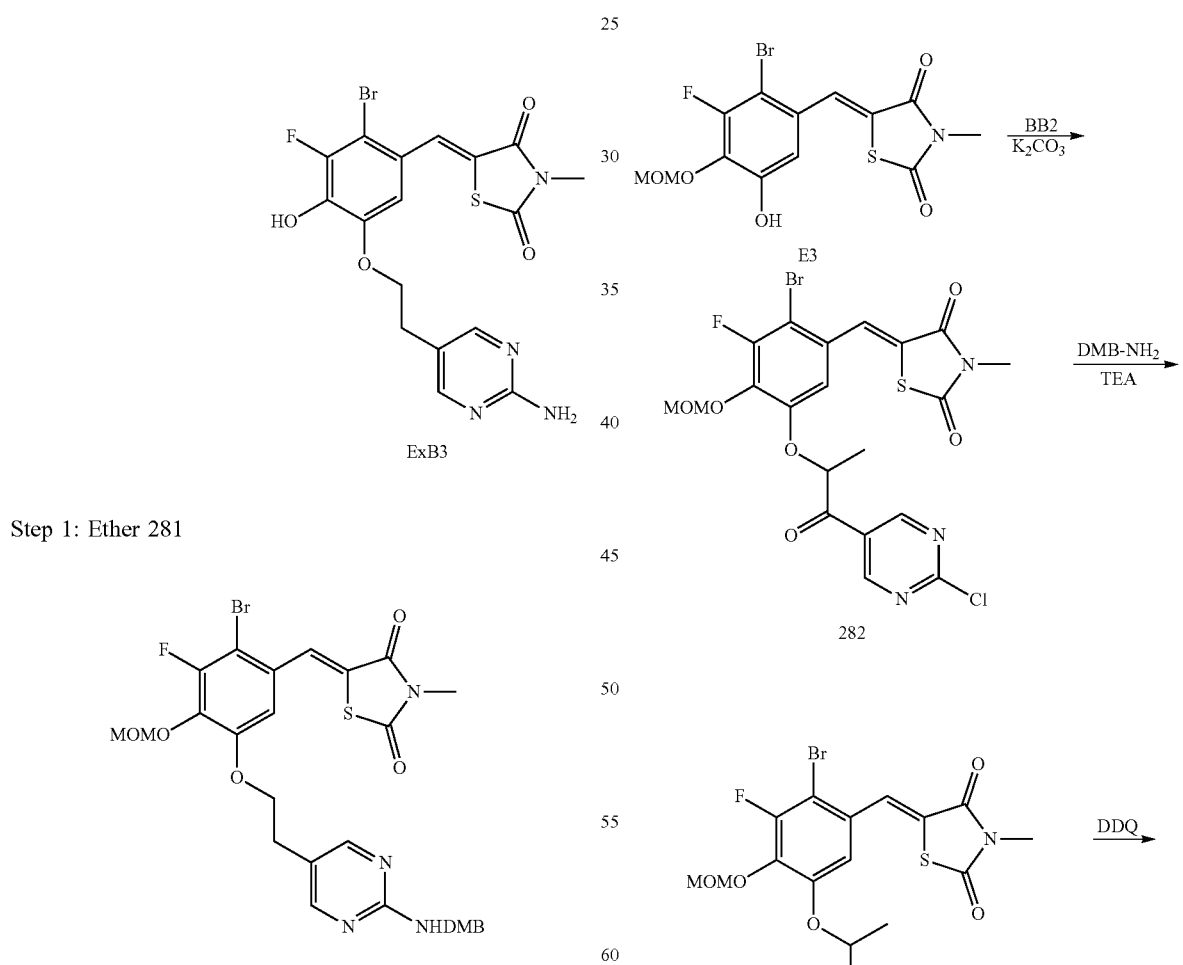
Step 1: Ether 281
Following the procedure for C19 using E3 (44 mg, 0.11 mmol), potassium carbonate (31 mg, 0.22 mmol), DMF (5 mL), and B28 (50 mg, 0.11 mmol), react at 70° C. for 3 hours and purify with silica gel column chromatography (EA:PE=1:2) to give 281 as a yellow solid (25 mg, 35%). (MS: [M+H]+ 663.1)

-continued

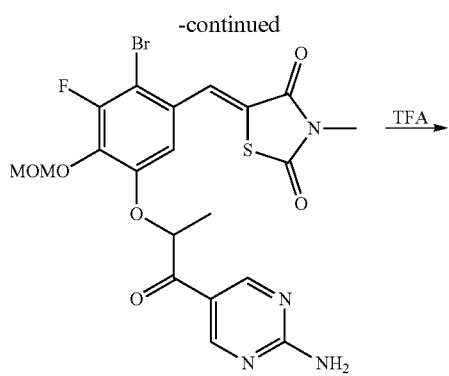
284

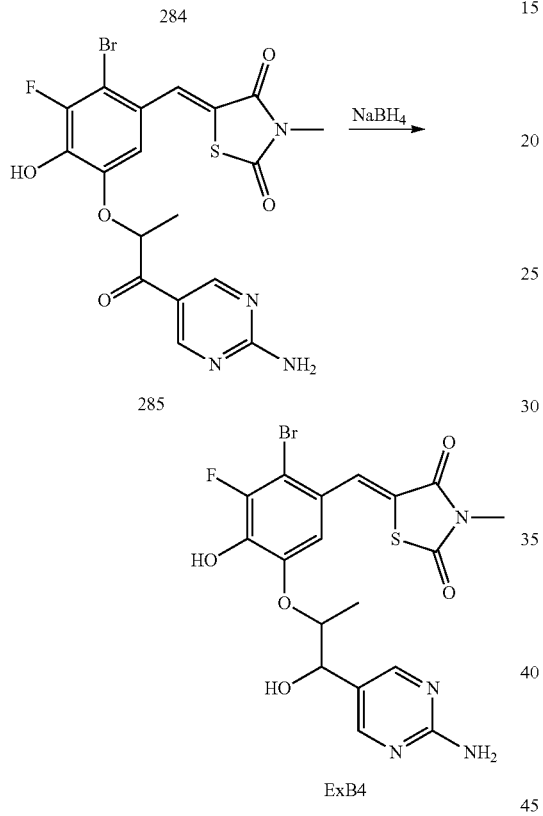
285

ExB4

Step 1: Ether 282

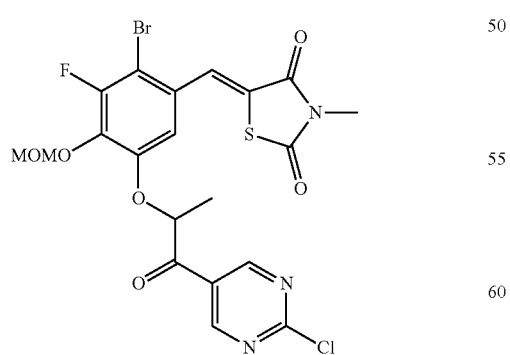

Following the procedure for C19 using E3 (157 mg, 0.4 mmol), potassium carbonate (110 mg, 0.8 mmol), DMF (10 mL), BB2 (100 mg, 0.4 mmol), react at 60° C. for 3 hours and purify with silica gel column chromatography (EA:PE=1:3) to give 282 as a yellow solid (160 mg, 71%). (MS: [M+H]$^+$ 560.1)

Step 2: Pyrimidine 283

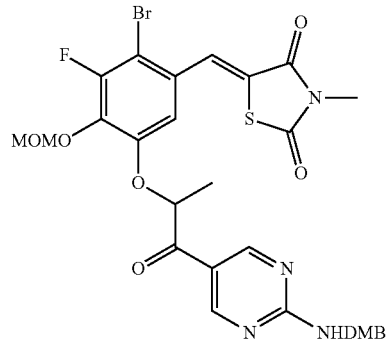

Following the procedure for 57 using 282 (150 mg, 0.27 mmol), TEA (0.07 mL, 0.54 mmol), THF (5 mL), and 2,4-dimethoxybenzylamine (44 mg, 0.27 mmol), react at room temperature overnight and purify with silica gel column chromatography (EA:PE=1:1) to give 283 as a yellow solid (180 mg, 97%). (MS: [M+H]$^+$ 691.1)

Step 3: pyrimidine 284

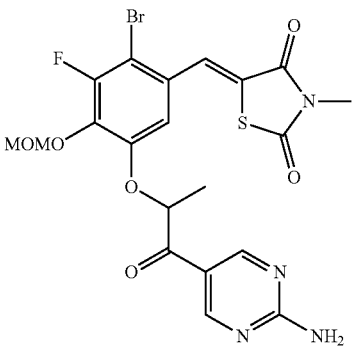

Following the procedure for 276 using 283 (100 mg, 0.14 mmol), DCM (5 mL), water (2 mL), DDQ (65 mg, 0.28 mmol), then purify with silica gel column chromatography (EA:PE=1:1) to give 284 as a yellow solid (70 mg, 92%). (MS: [M+H]$^+$ 541.1)

Step 4: Phenol 285

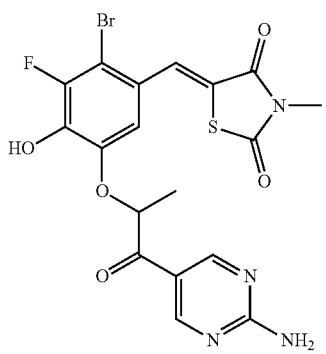

Prepared by essentially the same method as for C8. (MS: [M+H]+ 497.1)

Step 5: ExB4

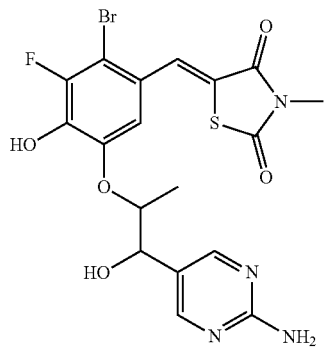 [SMILES: CC(Oc1cc(/C=C2\SC(=O)N(C)C2=O)c(Br)c(F)c1O)C(O)c1cnc(N)nc1]

Following Procedure C using 285 (15 mg, 0.031 mmol), THF (5 mL), and sodium borohydride (1.17 mg, 0.031 mmol), then triturate the crude product with MeCN (5 mL) to give ExB4 as a pale yellow solid (4.5 mg, 30% yield). (MS: [M+H]+ 499.0)

Example B5

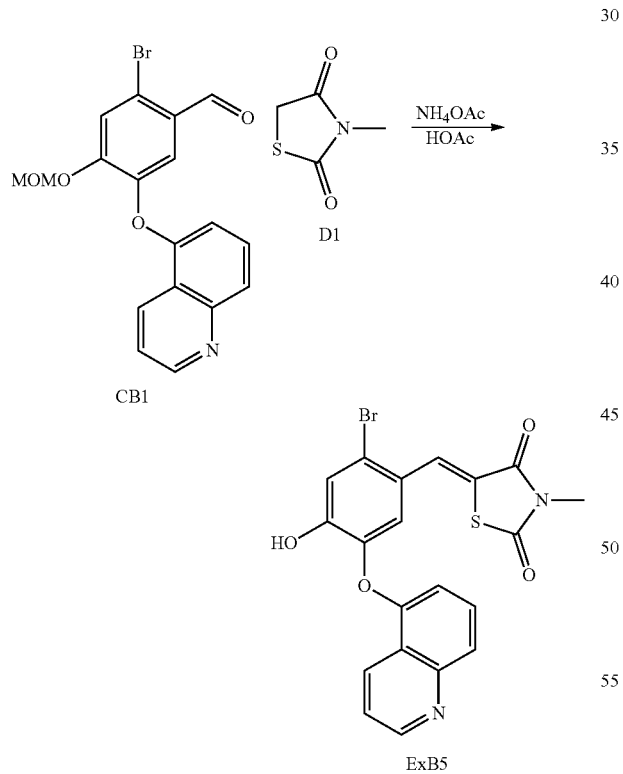

A mixture of CB1 (85 mg, 0.34 mmol), D1 (23 mg, 0.34 mmol) and ammonium acetate (70 mg, 1.54 mmol) in acetic acid (3 mL) is stirred at 130° C. under microwave irradiation for 45 minutes. After cooling to room temperature, the mixture is concentrated and purified by prep-HPLC (water: MeOH with 0.1% formic acid=4:1) to give ExB14 as a yellow solid (30 mg, 30%). (MS: [M+H]+ 459.0)

Example B6

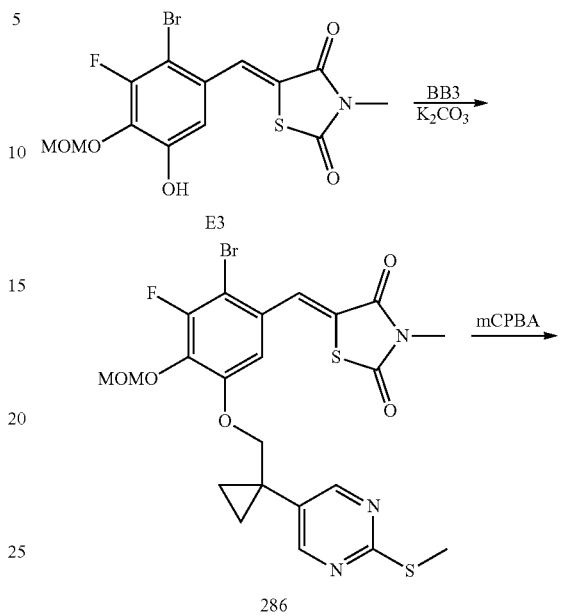

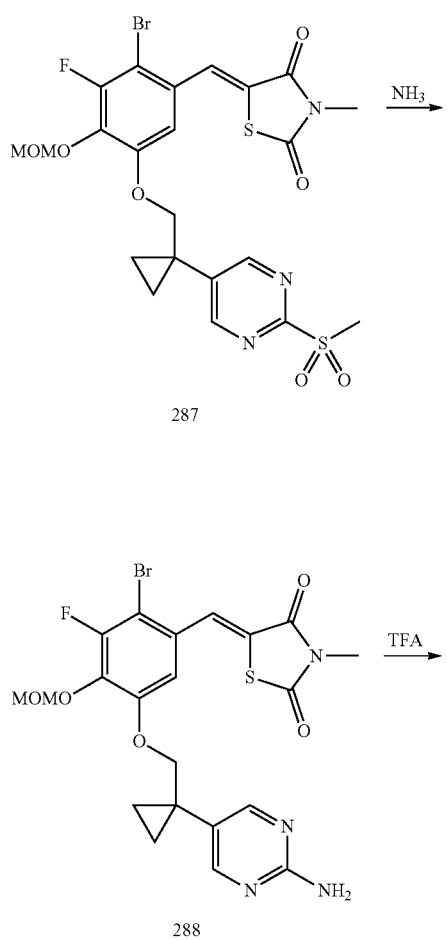

-continued

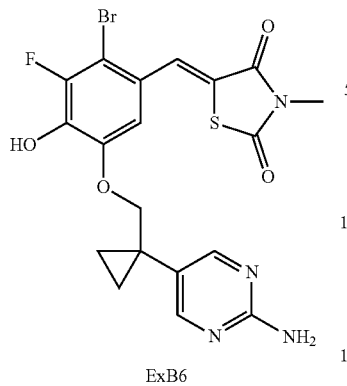

ExB6

Step 2: Ether 286

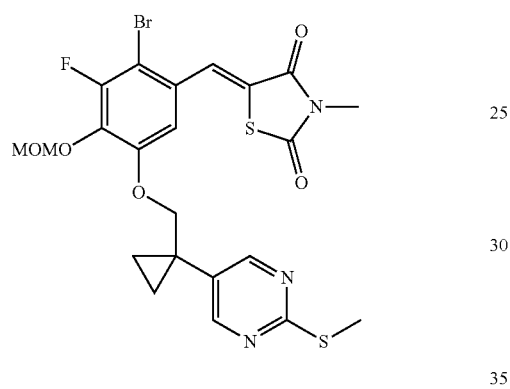

Prepared by essentially the same method as for C19. (MS: [M+H]⁺ 570.0)

Step 2: Sulfone 287

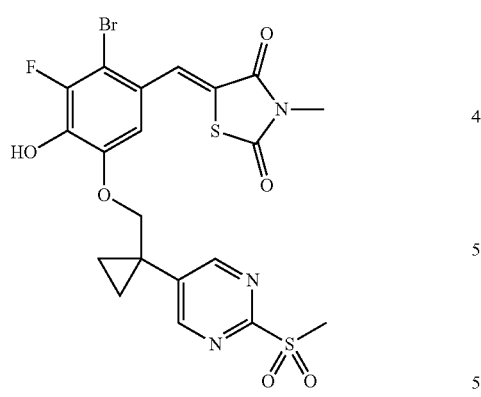

To a solution of 286 (100 mg, 0.18 mmol) in DCM (5 mL) is added mCPBA (60 mg, 0.36 mmol). After stirring at room temperature for 5 hours, the mixture is diluted with EA, washed with saturated sodium thiosulfate aqueous solution, dried over anhydrous anhydrous sodium sulfate, filtered, concentrated, and purified by silica gel column chromatography (EA:PE=1:1) to give 287 as a yellow solid (100 mg, 92%). (MS: [M+H]⁺ 602.1)

Step 3: Pyrimidine 288

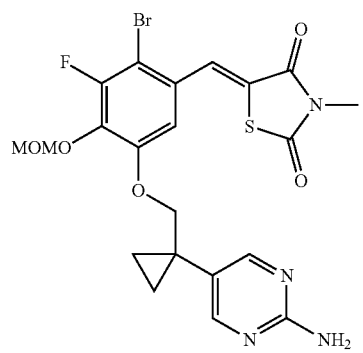

Ammonia is bubbled through to a solution of 287 (100 mg, 0.16 mmol) in THF (5 mL) at −78° C. for 3 minutes in a sealeding tube. After stirring at room temperature for 3 hours, the mixture is concentrated to give 288 as a yellow solid (60 mg, 67%). (MS: [M+H]⁺539.1)

Step 4: ExB6

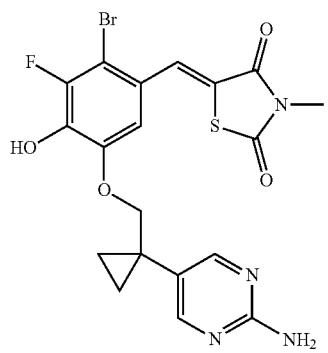 [SMILES: CN1C(=O)S/C(=C\c2cc(OCC3(c4cnc(N)nc4)CC3)c(O)c(F)c2Br)C1=O]

Prepared by essentially the same method as for C8. (MS: [M+H]⁺ 495.1)

Example B7

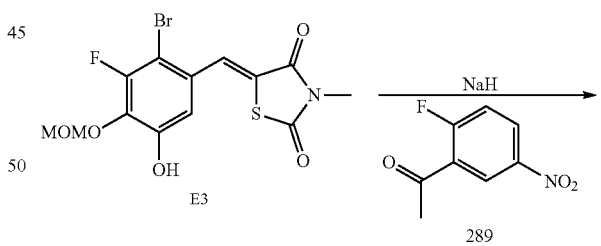

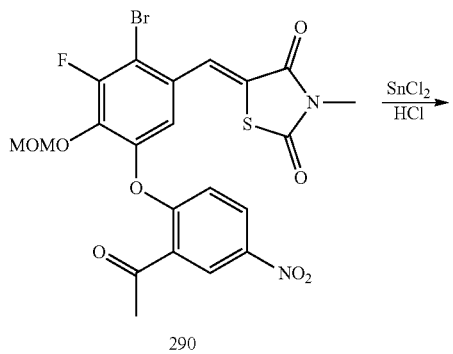

354

Example B8

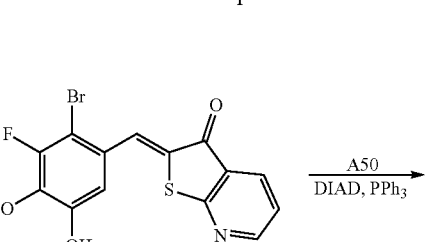

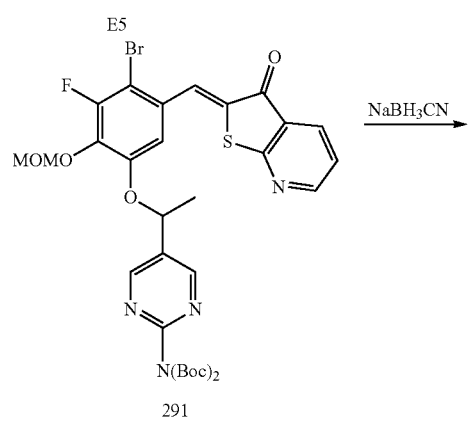

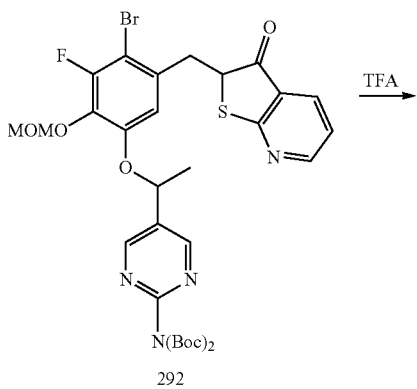

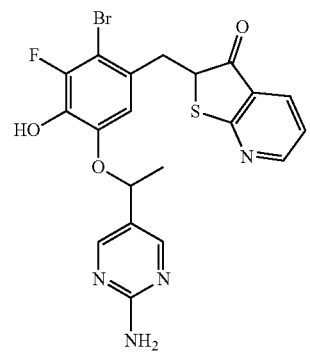

ExB8

353

-continued

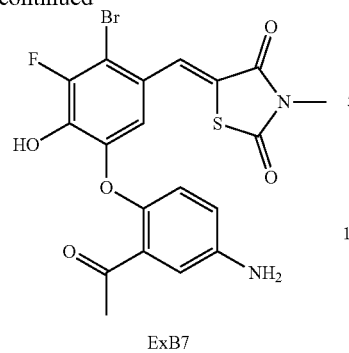

ExB7

Step 1: Ether 290

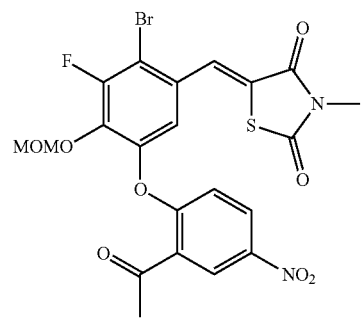

Prepared by essentially the same method as for 277. (MS: [M+H]$^+$ 537.0)

Step 2: ExB7

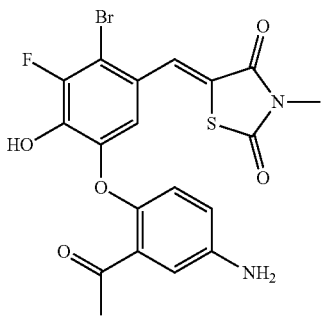 [SMILES: CC(=O)c1cc(N)ccc1Oc1cc(/C=C2\SC(=O)N(C)C2=O)c(Br)c(F)c1O]

To a mixture of 290 (200 mg, 0.37 mmol) in 4 N methanolic HCl (3 mL) is added tin(II) chloride dihydrate (100 mg, 0.44 mmol). After stirring at 60° C. for 5 hours, the mixture is cooled to room temperature and the solid is collected by filtration, dried, washed with MeOH, and purified by prep-HPLC (water:MeCN with 0.1% HCOOH=5:1) to give ExB7 as a yellow solid (10 mg, 6%).

Step 1: Ether 291

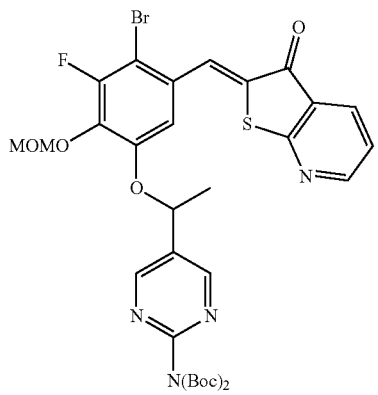

Prepared by essentially the same method as for Example 125. (MS: [M+H]+ 743.1)

Step 2: Pyrimidine 292

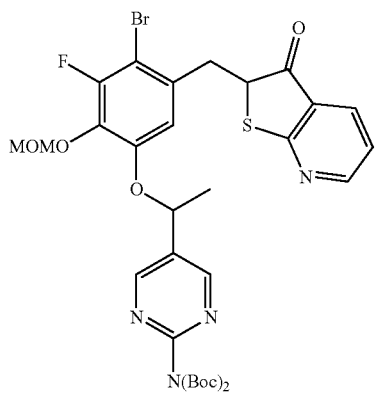

To a mixture of 291 (90 mg, 0.12 mmol) in THF (5 mL) is added sodium cyanoborohydride (38 mg, 0.61 mmol) at 0° C. After stirring at room temperature for 4 hours, water is added and the mixture is extracted with EA (10 mL). The organic layer is washed with water and brine, dried over anhydrous sodium sulfate, filtered, concentrated and purified by silica gel column chromatography (EA:PE=1:3) to give 292 as a yellow solid (30 mg, 33% yield). (MS: [M+H]+ 735.1)

Step 3: ExB8

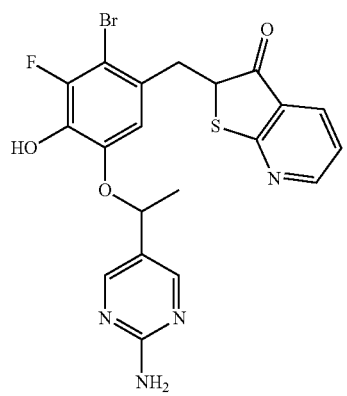 [SMILES: CC(Oc1cc(CC2Sc3ncccc3C2=O)c(Br)c(F)c1O)c1cnc(N)nc1]

Prepared by essentially the same method as for Ex80. (MS: [M+H]+ 510)

Example B9

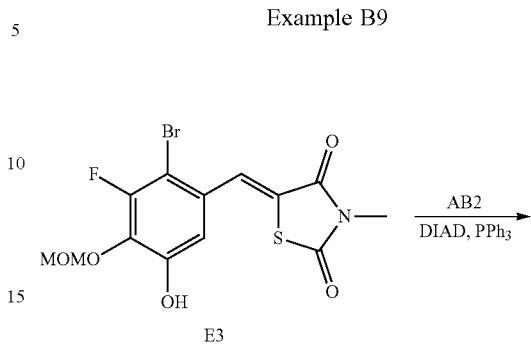

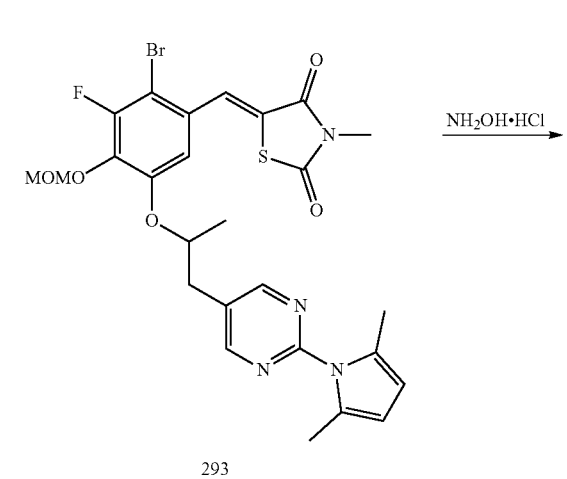

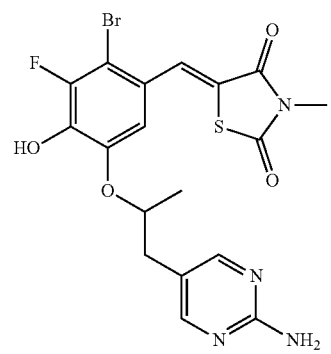

ExB9

Step 1: Ether 293

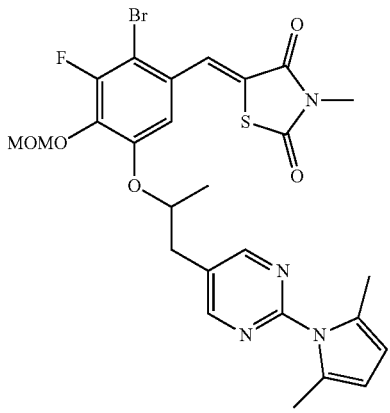

Prepared by essentially the same method as for Ex125. (MS: [M+H]+ 605.1)

Step 2: ExB9

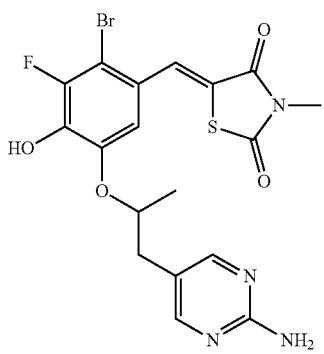

To a solution of 293 (86 mg, 0.14 mmol) in EtOH (15 mL) and water (5 mL) is added hydroxylamine hydrochloride (99 mg, 1.42 mmol). After stirring at 100° C. for 24 hours, the mixture is concentrated and purified by prep-HPLC (water: MeCN with 0.1% HCOOH=6:1) to give ExB9 as a white solid (8 mg 12%). (MS: [M+H]+ 485.0)

Example B10

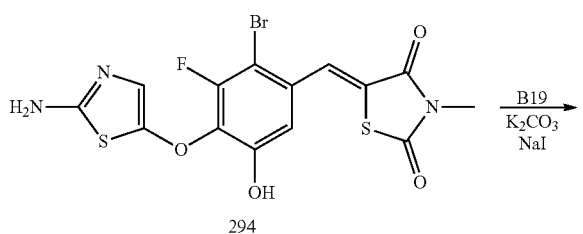

-continued

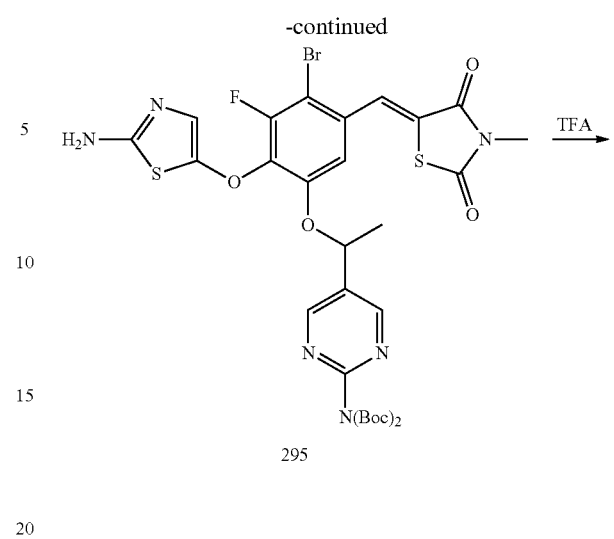

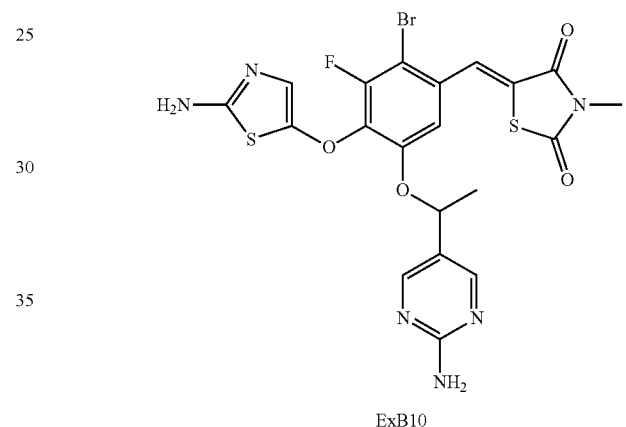

Step 1: Ether 295

To a mixture of 294 (200 mg, 0.45 mmol), B19 (250 mg, 0.6 mmo) and sodium iodide (7 mg, 0.045 mmol) in DMF (5 mL) is added potassium carbonate (124 mg, 0.9 mmol). After stirring at room temperature overnight, water is added and the solid is collected by filtration and dried to give 295. (MS: [M+H]+ 767.1)

Step 2: ExB10
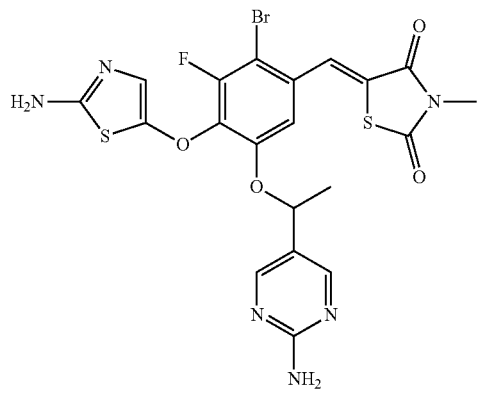 [SMILES: CC(Oc1cc(/C=C2\SC(=O)N(C)C2=O)c(Br)c(F)c1Oc1cnc(N)s1)c1cnc(N)nc1]
A solution of 295 (200 mg, 0.45 mmol) in TFA (5 mL) is stirred at room temperature for 3 hours. The mixture is then concentrated and purified by prep-HPLC (water:MeOH with 0.1% HCOOH=5:1) to give ExB10 (6.4 mg, 3%). (MS: [M+H]$^+$ 567.0)
Example B11
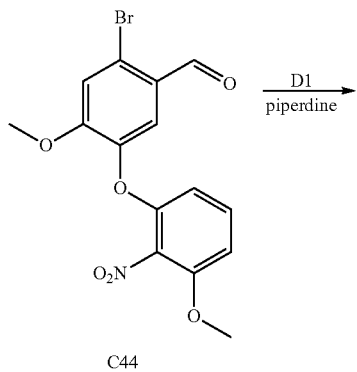
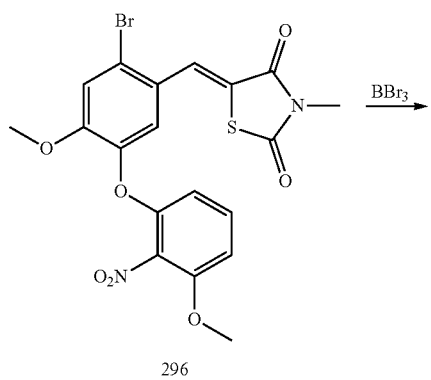
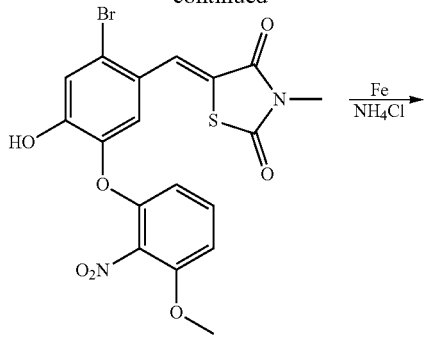
297
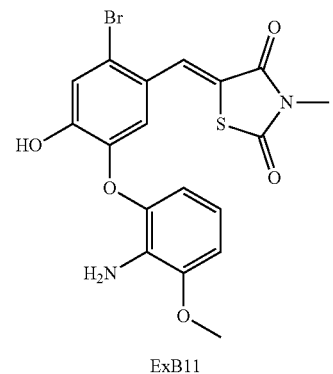
ExB11
Step 1: Thiazolidinone 296
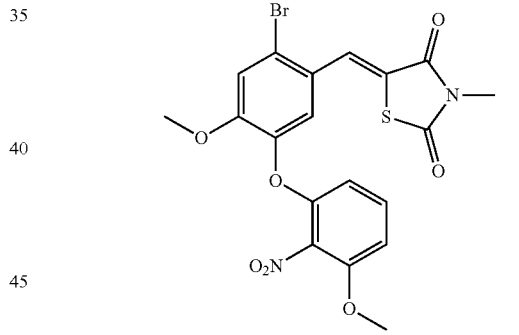
Prepared by essentially the same method as for E1.
Step 2: Phenol 297
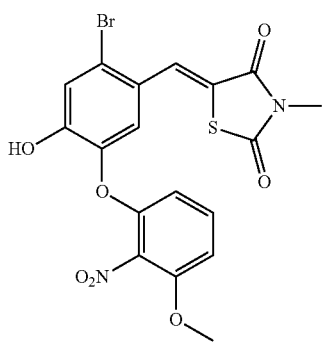 [SMILES: COc1cccc(Oc2cc(/C=C3\SC(=O)N(C)C3=O)c(Br)cc2O)c1[N+](=O)[O-]]

To a solution of 296 in DCM (10 mL) is added boron tribromide (3 mL) at 0° C. After stirring for 3 hours at room temperature, MeOH (10 mL) is added and the mixture is concentrated and purified by silica gel column chromatography (MeOH:DCM 1:9) to give 297 (220 mg, 91%). (MS: [M+H]+ 482.2).

Step 3: ExB11

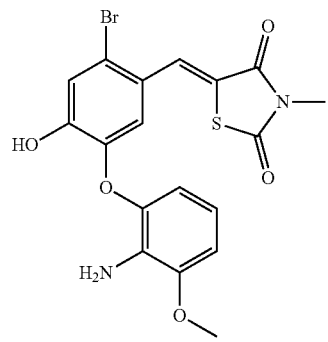 [SMILES: COc1cccc(Oc2cc(/C=C3\SC(=O)N(C)C3=O)c(Br)cc2O)c1N]

To a solution of 297 (220 mg, 0.44 mmol) in EtOH (10 mL) is added saturated ammonium chloride solution (2 mL) and iron powder (246 mg, 4.4 mmol). After stirring at 70° C. for 8 hours, the mixture is concentrated and purified by prep-HPLC (water:MeCN with 0.1% formic acid=6:1) to give ExB11 as a solid (200 mg, 99%).

Example B12

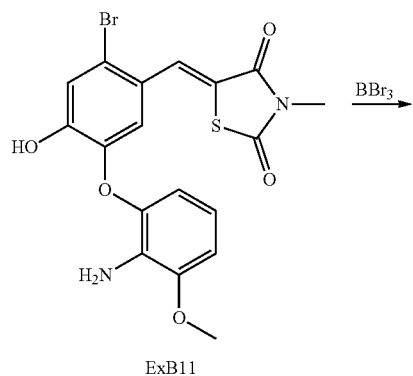

Prepared by essentially the same method as for C3.

Example B13

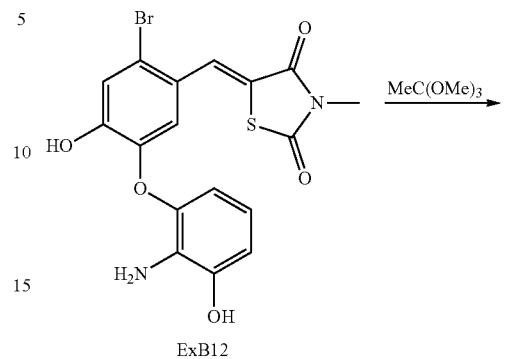

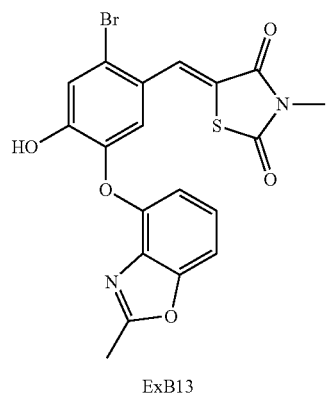

A solution of ExB12 (120 mg, 0.27 mmol) in trimethyl orthoacetate (8 mL) is stirred at 130° C. for 1 hour. After cooling to room temperature, the mixture is concentrated and purified by prep-HPLC (water:MeCN with 0.1% formic acid=5:1) to give ExB13 as a solid (20 mg, 16%). (MS: [M+H]+ 463.3)

Example B14

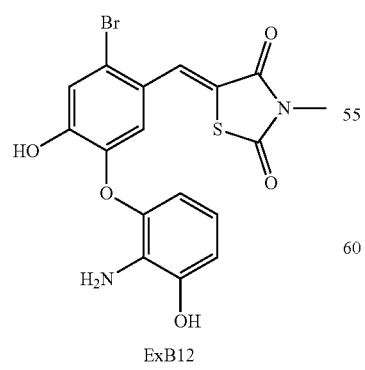

364
Example B15
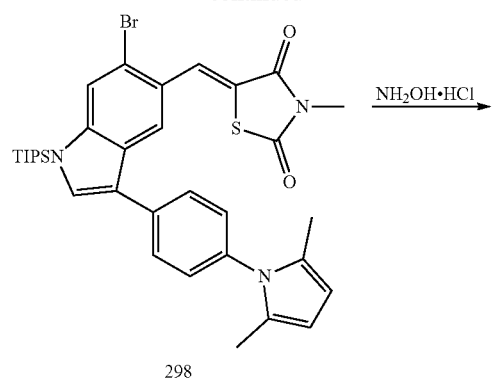
298
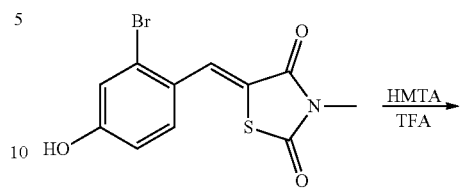
Ex52
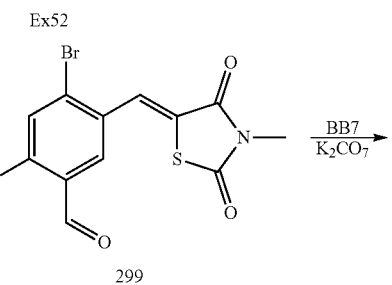
299
Step 1: thiazolidinone 298
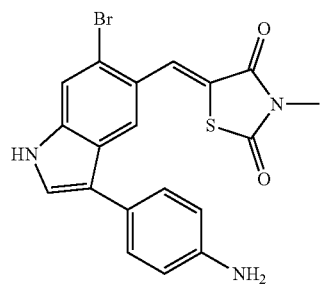
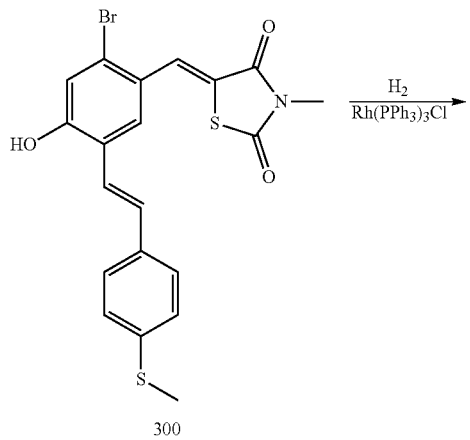
300
Prepared by essentially the same method as for E1.
Step 2: ExB14
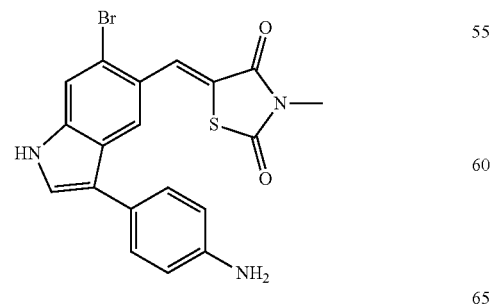
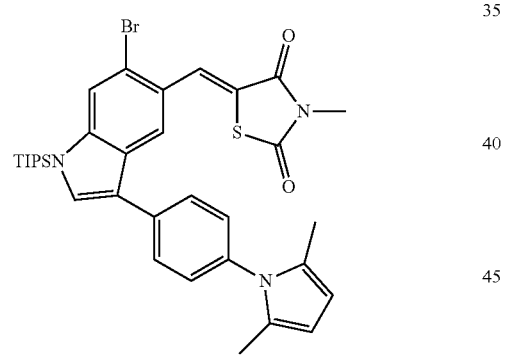
ExB14
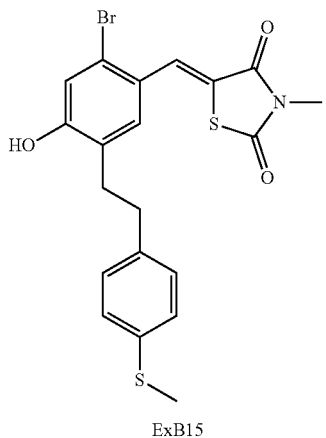
ExB15
Prepared by essentially the same method as for ExB29.

Step 1: Aldehyde 299

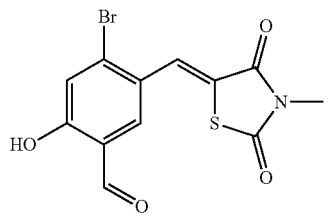 [SMILES: CN1C(=O)S/C(=C\c2cc(C=O)c(O)cc2Br)C1=O]

Prepared by essentially the same method as for C42. (MS: [M+H]+ 342.1)

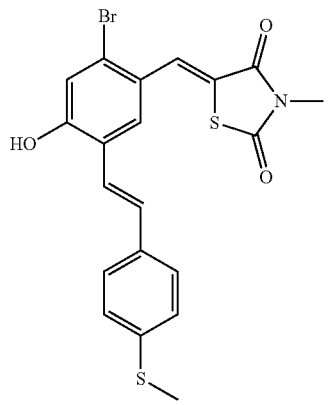 [SMILES: CSc1ccc(/C=C/c2cc(/C=C3\SC(=O)N(C)C3=O)c(Br)cc2O)cc1]

Step 2: Alkene 300

A mixture of 299 (188 mg, 0.55 mmol), BB7 (318 mg, 0.66 mmol) and potassium carbonate (152 mg, 1.1 mmol) in DMSO (5 mL) is stirred at 65° C. for 3 hours. The mixture is then diluted with water, acidified to pH 5, and extracted with EA (10 mL×3). The combined organic layers are dried over anhydrous sodium sulfate, filtered, concentrated, and purified by silica gel column chromatography (EA:PE=1:2) to give 300 as a yellow solid (100 mg, 85%). (MS: [M+H]+ 464.0)

Step 3: ExB15

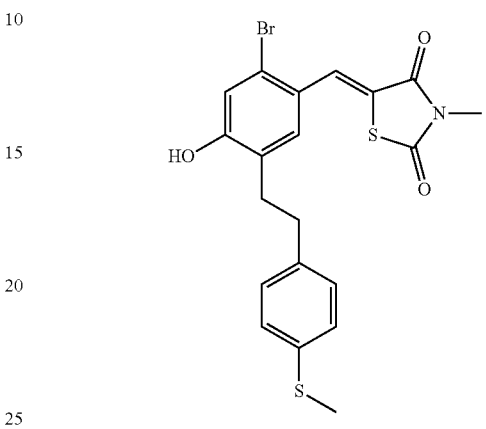

To a solution of 300 (100 mg, 0.22 mmol) in EtOH (5 mL) is added tris(triphenylphosphine)rhodium(I) chloride (20 mg, 0.02 mmol) at room temperature. After stirring under a hydrogen atmosphere at 70° C. for 3 hours, the mixture is filtered, concentrated. The residue is purified by Pre-HPLC (MeCN:H$_2$O=1:4 with 0.1% HCOOH) to give the titled product (33 mg, 33.2%) as a yellow solid. (MS: [M+H]+ 466.1)

The following compounds are prepared by essentially the same method as described above.

| Example | Building blocks | | Structure | MS | Reference of preparation |
|---|---|---|---|---|---|
| ExB16 | CB6 | D1 | 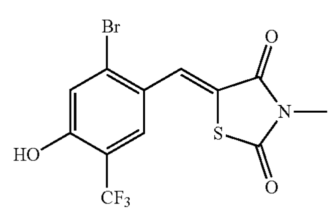 [SMILES: CN1C(=O)S/C(=C\c2cc(C(F)(F)F)c(O)cc2Br)C1=O] | [M + H]+ 381.9 | Ex28 |
| ExB17 | CB6 | D5 | 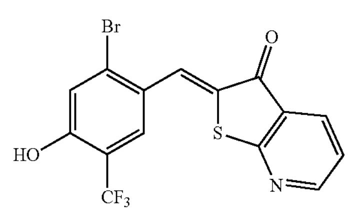 [SMILES: O=C1/C(=C/c2cc(C(F)(F)F)c(O)cc2Br)Sc2ncccc21] | [M + H]+ 403.9 | Ex28 |

-continued

| Example | Building blocks | | Structure | MS | Reference of preparation |
|---|---|---|---|---|---|
| ExB18 | CB7 | D1 | 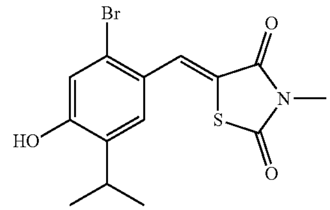 [SMILES: CC(C)c1cc(/C=C2\SC(=O)N(C)C2=O)c(Br)cc1O] | [M + H]+ 358 | Ex28 |
| ExB19 | CB7 | D5 | 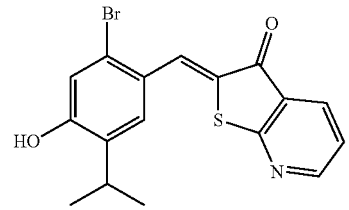 [SMILES: CC(C)c1cc(/C=C2\Sc3ncccc3C2=O)c(Br)cc1O] | [M − H]− 374.0 | Ex28 |
| ExB20 | CB8 | D1 | 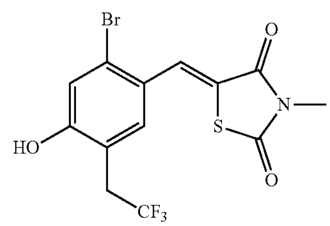 [SMILES: CN1C(=O)S/C(=C\c2cc(CC(F)(F)F)c(O)cc2Br)C1=O] | [M + H]+ 396.2 | Ex28 |
| ExB21 | CB8 | D5 | 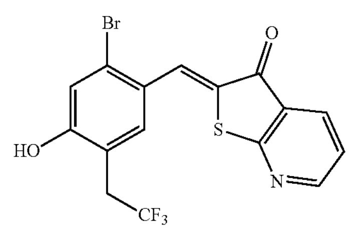 [SMILES: O=C1/C(=C/c2cc(CC(F)(F)F)c(O)cc2Br)Sc2ncccc21] | [M + H]+ 416.0 | Ex28 |
| ExB22 | C1 | DB1 | 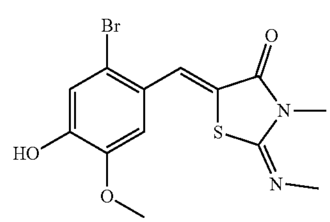 [SMILES: C/N=C1/S/C(=C\c2cc(OC)c(O)cc2Br)C(=O)N1C] | [M − H]− 355.0 | Ex28 |
| ExB23 | C1 | DB2 | 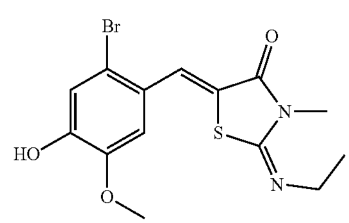 [SMILES: CC/N=C1/S/C(=C\c2cc(OC)c(O)cc2Br)C(=O)N1C] | [M − H]− 369.1 | Ex28 |

-continued

| Example | Building blocks | Structure | MS | Reference of preparation |
|---|---|---|---|---|
| ExB24 | C1, DB3 | 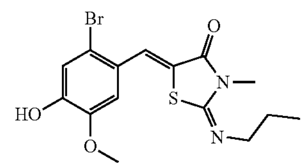 [SMILES: CCC/N=C1/S/C(=C\c2cc(OC)c(O)cc2Br)C(=O)N1C] | [M − H]⁻ 383.3 | Ex28 |
| ExB25 | CB2, D1 | 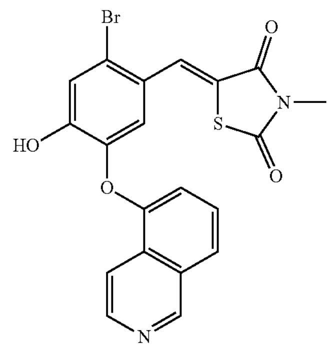 [SMILES: CN1C(=O)S/C(=C\c2cc(Oc3cccc4cnccc34)c(O)cc2Br)C1=O] | [M + H]⁺ 459.0 | ExB5 |
| ExB26 | CB3, D1 | 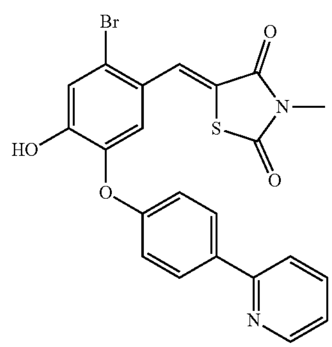 [SMILES: CN1C(=O)S/C(=C\c2cc(Oc3ccc(-c4ccccn4)cc3)c(O)cc2Br)C1=O] | [M + H]⁺ 485.0 | ExB5 |
| ExB27 | CB4, D1 | 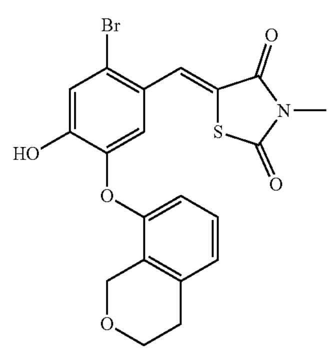 [SMILES: CN1C(=O)S/C(=C\c2cc(Oc3cccc4c3COCC4)c(O)cc2Br)C1=O] | [M + H]⁺ 464.0 | ExB5 |

-continued
| Example | Building blocks | | Structure | MS | Reference of preparation |
|---|---|---|---|---|---|
| ExB28 | 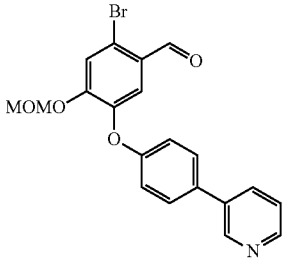 CB5 | 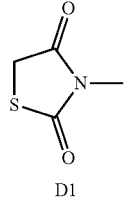 D1 | 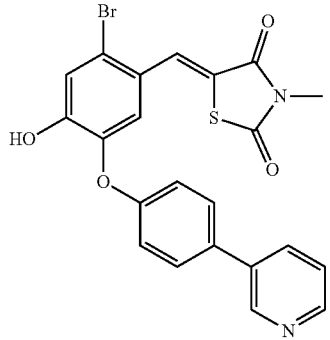 [SMILES: CN1C(=O)S/C(=C\c2cc(Oc3ccc(-c4cccnc4)cc3)c(O)cc2Br)C1=O] | [M + H]+ 485.0 | ExB5 |
| ExB29 | 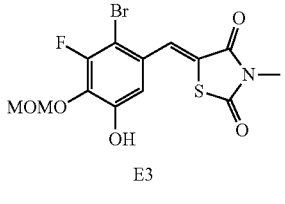 E3 | 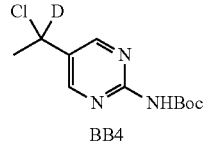 BB4 | 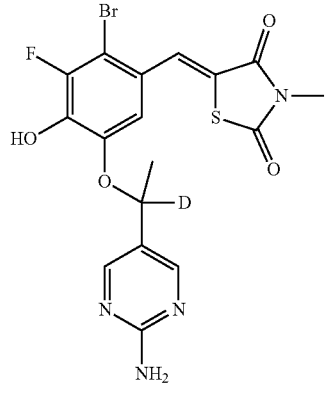 [SMILES: [2H]C(C)(Oc1cc(/C=C2\SC(=O)N(C)C2=O)c(Br)c(F)c1O)c1cnc(N)nc1] | [M + H]+ 472.0 | ExB10 |
| ExB30 | 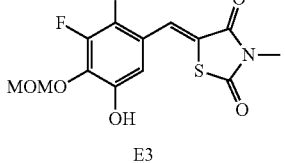 E3 | 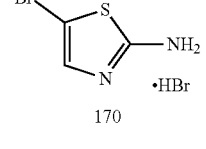 170 | 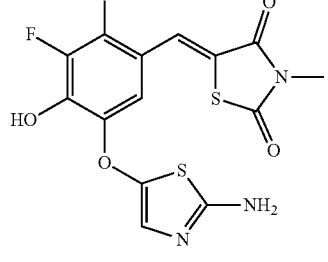 | [M + H]+ 446.0 | ExB3 |
| ExB31 | 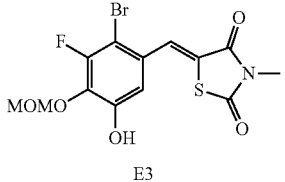 E3 | 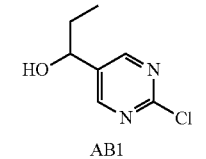 AB1 | 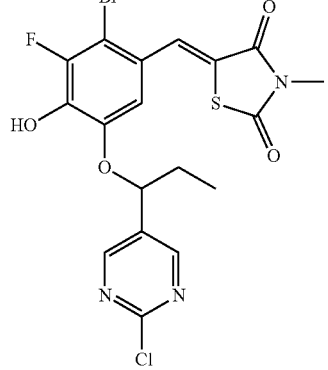 | [M + H]+ 503.7 | Ex125 Ex80 |

-continued

| Example | Building blocks | | Structure | MS | Reference of preparation |
|---|---|---|---|---|---|
| ExB32 | E3 | BB5 | 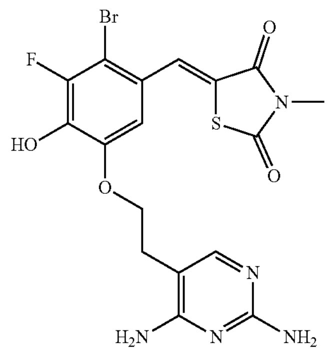 [SMILES: CN1C(=O)S/C(=C\c2cc(OCCc3cnc(N)nc3N)c(O)c(F)c2Br)C1=O] | [M + H]+ 486.0 | ExB3 Ex80 |
| ExB33 | Ex57 | 170 | 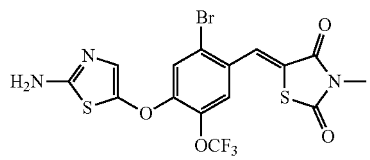 | [M + H]+ 496.1 | C25 |
| ExB34 | Ex59 | 170 | 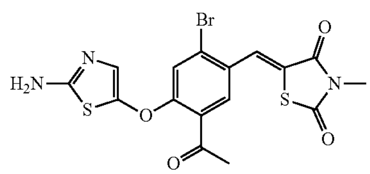 [SMILES: CC(=O)c1cc(/C=C2\SC(=O)N(C)C2=O)c(Br)cc1Oc1cnc(N)s1] | [M + H]+ 454.3 | C25 |
| ExB35 | E2 | BA5-d2 | 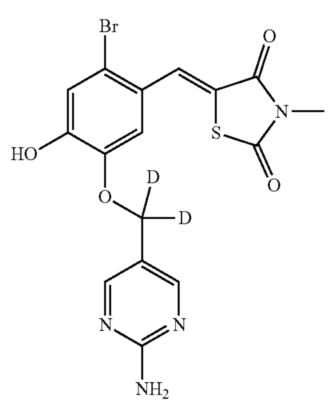 [SMILES: [2H]C([2H])(Oc1cc(/C=C2\SC(=O)N(C)C2=O)c(Br)cc1O)c1cnc(N)nc1] | [M + H]+ 439.1 | Ex14 Ex212 Ex220 |

-continued
| Example | Building blocks | | Structure | MS | Reference of preparation |
|---|---|---|---|---|---|
| ExB36 | 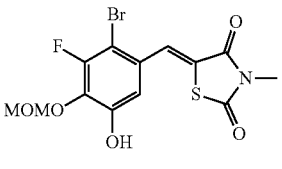 E3 | 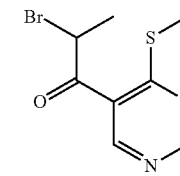 BB6 | 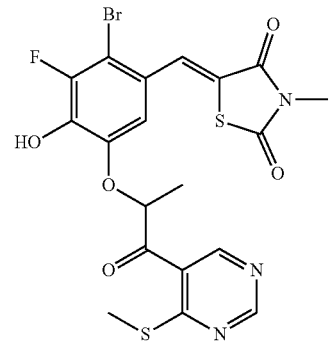 [SMILES: CSc1ncncc1C(=O)C(C)Oc1cc(/C=C2\SC(=O)N(C)C2=O)c(Br)c(F)c1O] | [M + H]+ 528.1 | ExB3 |
| ExB37 | 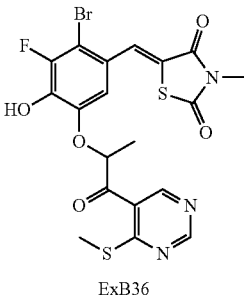 ExB36 | | 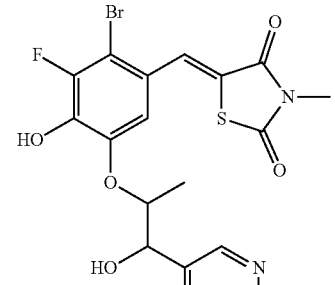 | [M + H]+ 499.0 | Ex212 Ex220 ExB13 |
| ExB38 | 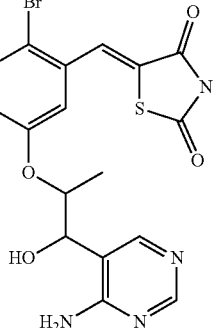 ExB38 | | 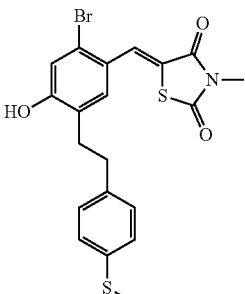 | [M + H]+ 482.1 | Ex212 |
| ExB39 | 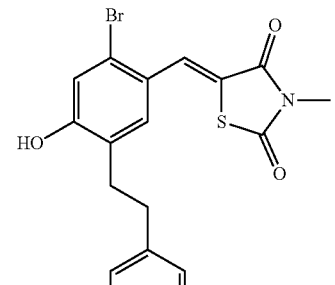 CB11 | 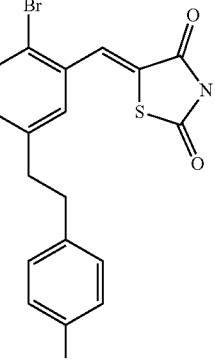 D1 | 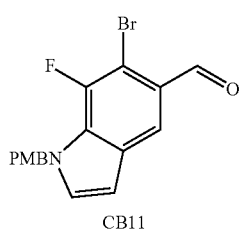 | [M + H]+ 455.0 | Ex80 |

| Example | Building blocks | | Structure | MS | Reference of preparation |
|---|---|---|---|---|---|
| ExB40 | CB12 | D1 | 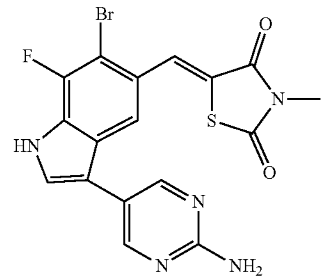 [SMILES: CN1C(=O)S/C(=C\c2cc3c(-c4cnc(N)nc4)c[nH]c3c(F)c2Br)C1=O] | [M − H]⁻ 446.0 | ExB14 |
| ExB41 | 315 | BB8 | 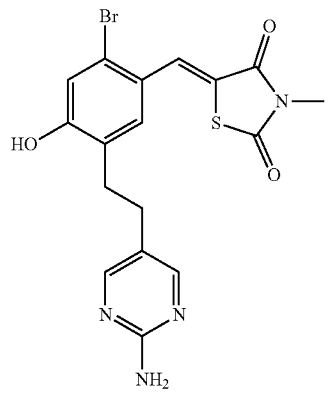 [SMILES: CN1C(=O)S/C(=C\c2cc(CCc3cnc(N)nc3)c(O)cc2Br)C1=O] | [M + H]⁺ 435.1 | ExB15 |
| ExB42 | | BB8 | 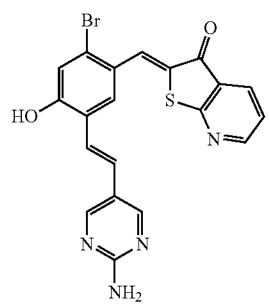 [SMILES: Nc1ncc(/C=C/c2cc(/C=C3\Sc4ncccc4C3=O)c(Br)cc2O)cn1] | [M + H]⁺ 453.2 | ExB15 |
| ExB43 | CB11 | | 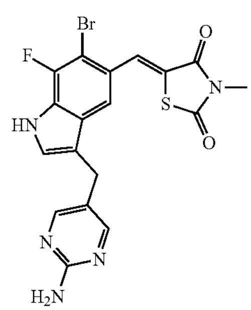 [SMILES: CN1C(=O)S/C(=C\c2cc3c(Cc4cnc(N)nc4)c[nH]c3c(F)c2Br)C1=O] | [M + H]⁺ 464.0 | Ex208 |

Example B44

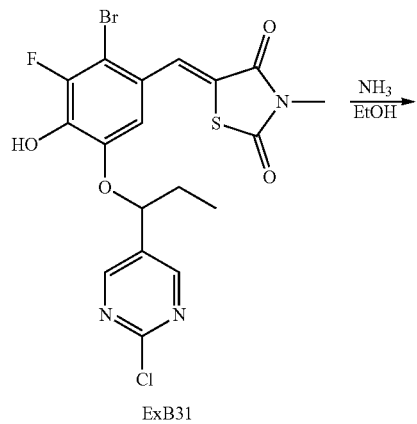

ExB31

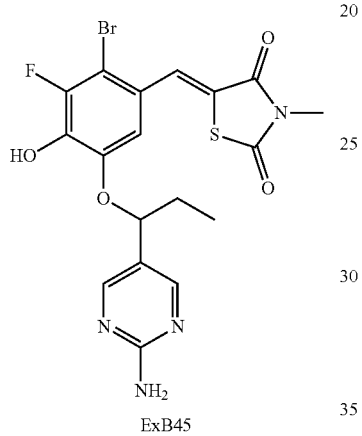

ExB45

A solution of ExB31 (209 mg, 1.59 mmol) in saturated ethanolic ammonia solution (8 mL) is heated at 100° C. under microwave irradiation for 1 hour. After cooling to room temperature, the mixture is concentrated and purified by prep-HPLC (water:MeOH with 0.1% HCOOH=7:1) to give ExB44 as a solid. (20.0 mg, 21%).

Biology

Expression and Purification of Recombinant cGAS Protein cDNA encoding full-length or amino acids 147-520 of human cGAS is inserted into a modified pET28a vector containing an in-frame $His_6$-SUMO tag. The *E. coli* strain BL21/pLys harboring the plasmid is induced with 0.5 mM IPTG at 18° C. overnight. $His_6$-SUMO tag was removed by a SUMO protease following purification of the $His_6$-SUMO-cGAS as described previously (Sun et al, 2013, Science 339, 786).

In Vitro Assay for Inhibition of cGAS Activity by Synthetic Compounds

A 40 μL mixture containing 1.5 ng/μL of recombinant cGAS (aa147-522) and serial dilutions of a test compound or DMSO was added to a 96-well plate and incubated at 37° C. for 20 minutes. At the end of reaction, 20 μL of Kinase Glo (Promega) was added and chemiluminescence measured with a luminometer. Inhibitory effect of a compound is evaluated by plotting percentage of ATP consumption against logarithm of compound concentrations. $IC_{50}$ value was calculated using Graphpad (Sigma).

| Example | Activity |
|---|---|
| Ex1 | A |
| Ex2 | C |
| Ex3 | A |
| Ex4 | C |
| Ex5 | A |
| Ex6 | C |
| Ex7 | C |
| Ex8 | C |
| Ex9 | C |
| Ex10 | C |
| Ex11 | C |
| Ex12 | A |
| Ex13 | C |
| Ex14 | B |
| Ex15 | C |
| Ex16 | A |
| Ex17 | C |
| Ex18 | A |
| Ex19 | C |
| Ex20 | C |
| Ex21 | C |
| Ex22 | C |
| Ex23 | C |
| Ex24 | C |
| Ex25 | B |
| Ex26 | B |
| Ex27 | B |
| Ex28 | A |
| Ex29 | C |
| Ex30 | A |
| Ex31 | B |
| Ex32 | A |
| Ex33 | B |
| Ex34 | B |
| Ex35 | B |
| Ex36 | C |
| Ex37 | B |
| Ex38 | A |
| Ex39 | B |
| Ex40 | B |
| Ex41 | B |
| Ex42 | B |
| Ex43 | B |
| Ex44 | B |
| Ex45 | A |
| Ex46 | A |
| Ex47 | B |
| Ex48 | A |
| Ex49 | A |
| Ex50 | B |
| Ex51 | B |
| Ex52 | B |
| Ex53 | B |
| Ex54 | A |
| Ex55 | B |
| Ex56 | B |
| Ex57 | B |
| Ex58 | B |
| Ex59 | B |
| Ex60 | B |
| Ex61 | B |
| Ex62 | B |
| Ex63 | A |
| Ex64 | B |
| Ex65 | A |
| Ex66 | B |
| Ex67 | B |
| Ex68 | A |
| Ex69 | B |
| Ex70 | B |
| Ex71 | A |
| Ex72 | A |
| Ex73 | A |
| Ex74 | B |
| Ex75 | A |

-continued

Inhibition of cGAS enzyme activity in vitro

| Example | Activity |
| --- | --- |
| Ex76 | B |
| Ex77 | A |
| Ex78 | A |
| Ex79 | A |
| Ex80 | A |
| Ex81 | A |
| Ex82 | A |
| Ex83 | B |
| Ex84 | A |
| Ex85 | B |
| Ex86 | B |
| Ex87 | B |
| Ex88 | B |
| Ex89 | B |
| Ex90 | A |
| Ex91 | B |
| Ex92 | A |
| Ex93 | A |
| Ex94 | B |
| Ex95 | B |
| Ex96 | B |
| Ex97 | B |
| Ex98 | B |
| Ex99 | B |
| Ex100 | C |
| Ex101 | B |
| Ex102 | B |
| Ex103 | B |
| Ex104 | B |
| Ex105 | B |
| Ex106 | A |
| Ex107 | B |
| Ex108 | A |
| Ex109 | B |
| Ex110 | A |
| Ex111 | B |
| Ex112 | A |
| Ex113 | A |
| Ex114 | A |
| Ex115 | A |
| Ex116 | A |
| Ex117 | A |
| Ex118 | A |
| Ex119 | B |
| Ex120 | A |
| Ex121 | A |
| Ex122 | A |
| Ex123 | A |
| Ex124 | A |
| Ex125 | B |
| Ex126 | B |
| Ex127 | B |
| Ex128 | B |
| Ex129 | B |
| Ex130 | B |
| Ex131 | B |
| Ex132 | B |
| Ex133 | B |
| Ex134 | B |
| Ex135 | B |
| Ex136 | B |
| Ex137 | B |
| Ex138 | B |
| Ex139 | B |
| Ex140 | A |
| Ex141 | A |
| Ex142 | A |
| Ex143 | B |
| Ex144 | B |
| Ex145 | B |
| Ex146 | A |
| Ex147 | A |
| Ex148 | A |

-continued

Inhibition of cGAS enzyme activity in vitro

| Example | Activity |
| --- | --- |
| Ex149 | B |
| Ex150 | B |
| Ex151 | B |
| Ex152 | A |
| Ex153 | A |
| Ex154 | B |
| Ex155 | A |
| Ex156 | A |
| Ex157 | A |
| Ex158 | B |
| Ex159 | B |
| Ex160 | A |
| Ex161 | A |
| Ex162 | C |
| Ex163 | C |
| Ex164 | C |
| Ex165 | A |
| Ex166 | C |
| Ex167 | B |
| Ex168 | B |
| Ex169 | B |
| Ex170 | A |
| Ex171 | A |
| Ex172 | A |
| Ex173 | B |
| Ex174 | C |
| Ex175 | B |
| Ex176 | B |
| Ex177 | B |
| Ex178 | B |
| Ex179 | B |
| Ex180 | B |
| Ex181 | B |
| Ex182 | B |
| Ex183 | B |
| Ex184 | A |
| Ex185 | A |
| Ex186 | B |
| Ex187 | A |
| Ex188 | B |
| Ex189 | B |
| Ex190 | A |
| Ex191 | A |
| Ex192 | B |
| Ex193 | A |
| Ex194 | A |
| Ex195 | A |
| Ex196 | A |
| Ex197 | A |
| Ex198 | A |
| Ex199 | A |
| Ex200 | A |
| Ex201 | B |
| Ex202 | B |
| Ex203 | B |
| Ex204 | B |
| Ex205 | B |
| Ex206 | B |
| Ex207 | B |
| Ex208 | B |
| Ex209 | B |
| Ex210 | B |
| Ex211 | B |
| Ex212 | B |
| Ex213 | A |
| Ex214 | B |
| Ex215 | B |
| Ex216 | A |
| Ex217 | B |
| Ex218 | A |
| Ex219 | B |
| Ex220 | B |
| Ex221 | B |

| Example | Activity |
|---|---|
| Ex222 | B |
| Ex223 | B |
| Ex224 | B |
| Ex225 | C |
| Ex226 | C |
| Ex227 | C |
| Ex228 | C |
| Ex229 | C |
| Ex230 | C |
| Ex231 | B |
| Ex232 | C |
| Ex233 | C |
| Ex234 | C |
| ExA1 | A |
| ExA2 | A |
| ExA3 | A |
| ExA4 | A |
| ExA5 | A |
| ExA6 | A |
| ExA7 | A |
| ExA8 | A |
| ExA9 | A |
| ExA10 | B |
| ExA11 | B |
| ExA12 | B |
| ExA13 | A |
| ExA14 | A |
| ExA15 | B |
| ExA16 | A |
| ExA17 | A |
| ExA18 | B |
| ExA19 | A |
| ExA20 | B |
| ExB1 | B |
| ExB2 | A |
| ExB3 | A |
| ExB4 | A |
| ExB5 | C |
| ExB6 | B |
| ExB7 | C |
| ExB8 | C |
| ExB9 | B |
| ExB10 | B |
| ExB11 | C |
| ExB12 | C |
| ExB13 | B |
| ExB14 | B |
| ExB15 | B |
| ExB16 | A |
| ExB17 | A |
| ExB18 | C |
| ExB19 | C |
| ExB20 | B |
| ExB21 | A |
| ExB22 | C |
| ExB23 | C |
| ExB24 | C |
| ExB25 | C |
| ExB26 | C |
| ExB27 | C |
| ExB28 | C |
| ExB29 | A |
| ExB30 | B |
| ExB31 | B |
| ExB32 | A |
| ExB33 | C |
| ExB34 | C |
| ExB35 | A |
| ExB36 | C |
| ExB37 | A |
| ExB38 | C |
| ExB39 | B |
| ExB40 | A |
| ExB41 | B |
| ExB42 | A |
| ExB43 | A |
| ExB44 | A |

Acitivity code: A $IC_{50} \leq 0.5$ μM, B $IC_{50}$ 0.5-10 μM, C $IC_{50} \geq 10$ μM Cellular Assay to Detect Inhibition of cGAS Activity by Synthetic Compounds in a Human Monocyte Cell Line A reporter THP1 cell line harboring a gene encoding *Gaussia* Luciferase under the control of 5 tandem repeats of interferon-stimulated response elements (ISRE) was used to test inhibition of cGAS activity by synthetic compounds in human cells. These cells were plated on 96-well plates at $0.3 \times 10^6$/well and incubated with various concentrations of compounds or DMSO for 5 min, followed by transfection of 2 μg/mL of ISD (Interferon Stimulatory DNA, a 45 bp DNA oligo) or mock transfected using lipofectamine 2000 (Life Technology) method, according to manufacturer's instructions. 16 hours later, 15 μL of the media from each well is transferred to a new plate, 50 μL of solution containing 50 mM Hepes-NaOH, 50 mM NaCl, 10 mM EDTA, 1 μM of coeleanterazine was added to each well and luminescence was measured immediately. Fold increase in luminescence compared to mock transfection is plotted against concentrations of each compound, and $IC_{50}$ is calculated using Graphpad. To evaluate the specificity of a compound, the same procedure was performed except that cells were transfected with 2 μg/mL poly(I:C) or infected with Sendai Virus (SeV) at 50 Unit/mL, which are known to activate the RIG-I-MAVS pathway. A specific inhibitory compound should inhibit interferon induction by DNA but have minimal effect on poly(I:C) or Sendai virus induced interferon reporter gene expression.

| Inhibition of cGAS activity in THP1 cells | | |
|---|---|---|
| Example | THP1-ISD | THP1-SeV |
| Ex11 | B | NT |
| Ex16 | B | NT |
| Ex21 | B | NT |
| Ex28 | A | C |
| Ex30 | A | NT |
| Ex32 | A | NT |
| Ex33 | B | NT |
| Ex38 | B | NT |
| Ex39 | B | NT |
| Ex44 | A | NT |
| Ex45 | B | NT |
| Ex53 | A | NT |
| Ex57 | A | B |
| Ex61 | A | NT |
| Ex63 | B | C |
| Ex65 | B | C |
| Ex67 | B | NT |
| Ex68 | A | C |
| Ex70 | B | C |
| Ex73 | B | C |
| Ex75 | B | C |
| Ex80 | B | C |
| Ex81 | A | C |
| Ex82 | A | NT |
| Ex86 | B | B |
| Ex87 | B | C |

385
-continued

| Inhibition of cGAS activity in THP1 cells | | |
|---|---|---|
| Example | THP1-ISD | THP1-SeV |
| Ex90 | B | NT |
| Ex92 | A | C |
| Ex93 | B | C |
| Ex106 | B | NT |
| Ex107 | B | NT |
| Ex108 | A | C |
| Ex110 | A | NT |
| Ex112 | B | NT |
| Ex113 | B | NT |
| Ex114 | B | NT |
| Ex115 | B | NT |
| Ex116 | A | NT |
| Ex117 | B | NT |
| Ex122 | A | C |
| Ex123 | A | C |
| Ex124 | B | NT |
| Ex131 | B | B |
| Ex135 | B | C |
| Ex137 | B | C |
| Ex139 | B | C |
| Ex140 | A | C |
| Ex141 | A | C |
| Ex147 | A | C |
| Ex148 | A | C |
| Ex149 | A | C |
| Ex152 | A | C |
| Ex153 | B | C |
| Ex155 | B | C |
| Ex156 | B | C |
| Ex157 | B | C |
| Ex165 | B | C |
| Ex170 | A | C |
| Ex171 | B | C |
| Ex177 | B | C |
| Ex184 | A | C |
| Ex185 | B | NT |
| Ex189 | B | NT |
| Ex193 | B | C |
| Ex194 | A | C |
| Ex195 | B | C |
| Ex196 | A | C |
| Ex197 | B | C |
| Ex200 | A | C |
| Ex211 | B | C |
| Ex213 | B | C |
| Ex216 | A | B |
| Ex233 | B | C |
| Ex234 | B | C |
| ExA1 | B | C |
| ExA2 | C | C |
| ExA3 | B | C |
| ExA4 | A | C |
| ExA5 | B | NT |
| ExA6 | B | B |
| ExA7 | B | C |
| ExA9 | B | NT |
| ExA10 | B | NT |
| ExA11 | A | NT |
| ExA12 | C | NT |
| ExA13 | B | NT |
| ExA14 | C | NT |
| ExA15 | B | C |
| ExA17 | C | NT |
| ExA18 | C | NT |
| ExA19 | B | NT |
| ExB21 | B | C |
| ExB2 | A | C |
| ExB3 | A | C |
| ExB4 | C | C |
| ExB35 | A | C |
| ExB40 | B | C |
| ExB43 | C | C |
| ExB44 | B | C |

Acitivity code: A IC$_{50}$ ≤2.5 μM, B IC$_{50}$ 2.5-10 μM, C IC$_{50}$ ≥10 μM NT not tested

386

The invention claimed is:
1. A compound, wherein the compound is one of Formula Ic:

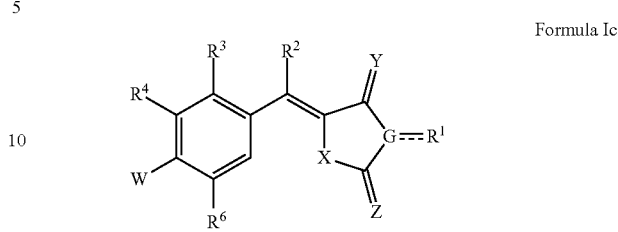

Formula Ic wherein:
X is NH or S;
Y is O or S;
Z is O, S, CHR$^{1a}$ or NR$^{1a}$;
    wherein R$^{1a}$ is hydrogen, C$_{1-6}$alkyl, or C$_{1-6}$alkyl selectively functionalized with one or more halogen, thiol, hydroxyl, carbonyl, carboxyl, carbonyloxyl, C$_{1-6}$alkoxy, C$_{1-6}$hydroxyalkoxy, amino, C$_{1-6}$alkylamino, di(C$_{1-6}$alkyl)amino, or azido groups;
G is N or C;
    if G is N, then R$^1$ is C$_{1-6}$alkyl or C$_{1-6}$alkyl selectively functionalized with one or more halogen, thiol, hydroxyl, carbonyl, carbonyloxyl, C$_{1-6}$alkoxy, C$_{1-6}$hydroxyalkoxy, amino, C$_{1-6}$alkylamino, di(C$_{1-6}$alkyl)amino, or azido groups, or R$^1$-R$^{1a}$ are connected as a —CH$_2$CH$_2$—, —CH$_2$CH$_2$CH$_2$—, —CH=CH—, —C(CH$_3$)=CH— or —CH=C(CH$_3$)— group; and
    if G is C, then Z includes R$^{1a}$ and R$^1$-R$^{1a}$ are connected as a =CH—CH=CH—, =N—CH=CH—, or =CH—N=CH— group;
W is OR$^{10a}$ or NHR$^{10a}$;
    wherein R$^{10a}$ is hydrogen, C$_{1-6}$alkyl, or C$_{1-6}$alkyl selectively functionalized with one or more halogen, thiol, hydroxyl, carbonyl, carboxyl, carbonyloxyl, C$_{1-6}$alkoxy, C$_{1-6}$hydroxyalkoxy, amino, C$_{1-6}$alkylamino, di(C$_{1-6}$alkyl)amino, or azido groups, or R$^{10a}$-R$^6$ are connected as a —CH$_2$—CH$_2$—, —CH=CH—, —N=CH—, or —CH=N— group;
R$^2$ is hydrogen, halogen, C$_{1-6}$alkyl, or C$_{1-6}$alkyl selectively functionalized with one or more halogen, thiol, hydroxyl, carbonyl, carboxyl, carbonyloxyl, C$_{1-6}$alkoxy, C$_{1-6}$hydroxyalkoxy, amino, C$_{1-6}$alkylamino, di(C$_{1-6}$alkyl)amino, or azido groups;
R$^3$ is halogen, —SR$^{3a}$, —S(O)R$^{3a}$, —OR$^{3a}$, —OCH$_2$R$^{3b}$, —OCH(CH$_3$)R$^{3b}$, —OC(O)NHR$^{3a}$, —NR$^{3a}$R$^{4a}$, —NHSO$_2$R$^{3a}$, azido, —CHO, —CO$_2$R$^{3a}$, cyano, C$_{1-6}$alkyl, —CR$^{5a}$R$^{6a}$R$^{7a}$, C$_{2-6}$alkenyl, —C(R$^{5a}$)=C(R$^{8a}$)(R$^{9a}$), C$_{2-6}$alkynyl, —C≡CR$^{8a}$, or R$^2$—R$^3$ are connected as a —CH$_2$CH$_2$— or —CH$_2$CH$_2$CH$_2$— group;
    wherein R$^{3a}$, R$^{3b}$, and R$^{4a}$ are independently hydrogen, phenyl, naphthyl, pyridyl, pyrimidinyl, imidazolyl, 1,2,3-triazolyl, quinolinyl, isoquinolinyl, thiazolyl, tetrazolyl groups, C$_{1-6}$alkyl, cyclic-(C$_{1-8}$alkyl)-, cyclic-(C$_{1-6}$oxaalkyl)-, cyclic-(C$_{1-6}$azaalkyl)-, C$_{2-6}$alkenyl, or C$_{2-6}$alkynyl;
    wherein the phenyl, naphthyl, pyridyl, pyrimidinyl, imidazolyl, 1,2,3-triazolyl, quinolinyl, isoquinolinyl, thiazolyl, or tetrazolyl groups are optionally substituted with 1-3 substituents independently selected from the group consisting of halogen, thiol, C$_{1-6}$alkyl thioether, C$_{1-6}$alkyl sulfoxide, C$_{1-6}$alkyl, C$_{1-6}$alkoxyl, amino, C$_{1-6}$alkylamino, C$_{1-6}$dialkylamino, C$_{1-6}$alkyl sulfonamide, azido, —CHO, —CO$_2$H, C$_{1-6}$alkyl carboxylate, cyano, C2-6alkenyl, and C$_{2-6}$alkynyl group; and the C$_{1-6}$alkyl, cyclic-(C$_{1-8}$alkyl)-, cyclic-(C$_{1-6}$oxaalkyl)-, cyclic-(C$_{1-6}$azaalkyl)-, C$_{2-6}$alkenyl, or C$_{2-6}$alkynyl groups are selectively functionalized with one or more halogen, thiol, hydroxyl, carbonyl, carboxyl, carbonyloxyl, C$_{1-6}$alkoxy, C$_{1-6}$hydroxyalkoxy, amino, C$_{1-6}$alkylamino, di(C$_{1-6}$alkyl)amino, azido, piperidinyl, phenyl, naphthyl, pyridyl, pyrimidinyl, imidazolyl, 1,2,3-triazolyl, quinolinyl, isoquinolinyl, thiazolyl, or tetrazolyl groups;

wherein R$^{5a}$, R$^{6a}$, R$^{7a}$, R$^{8a}$, and R$^{9a}$ are independently hydrogen, phenyl, naphthyl, pyridyl, pyrimidinyl, imidazolyl, 1,2,3-triazolyl, quinolinyl, isoquinolinyl, thiazolyl, tetrazolyl groups, C$_{1-6}$alkyl, cyclic-(C$_{1-8}$alkyl)-, cyclic-(C$_{1-6}$oxaalkyl)-, cyclic-(C$_{1-6}$azaalkyl)-, C$_{2-6}$alkenyl, C$_{2-6}$alkynyl, C$_{1-6}$alkoxyl, cyclic-(C$_{1-8}$alkoxyl)-, cyclic-(C$_{1-6}$oxaalkoxyl)-, or cyclic-(C$_{1-6}$azaalkoxyl)-;

wherein the phenyl, naphthyl, pyridyl, pyrimidinyl, imidazolyl, 1,2,3-triazolyl, quinolinyl, isoquinolinyl, or thiazolyl, tetrazolyl groups are optionally substituted with 1-3 substituents independently selected from the group consisting of halogen, thiol, C$_{1-6}$alkyl thioether, C$_{1-6}$alkyl sulfoxide, C$_{1-6}$alkyl, C$_{1-6}$alkoxyl, amino, C$_{1-6}$alkylamino, C$_{1-6}$dialkylamino, C$_{1-6}$alkyl sulfonamide, azido, —CHO, —CO$_2$H, C$_{1-6}$alkyl carboxylate, cyano, C$_{2-6}$alkenyl, and C$_{2-6}$alkynyl groups; and the C$_{1-6}$alkyl, cyclic-(C$_{1-8}$alkyl)-, cyclic-(C$_{1-6}$oxaalkyl)-, cyclic-(C$_{1-6}$azaalkyl)-, C$_{2-6}$alkenyl, or C$_{2-6}$alkynyl groups are selectively functionalized with one or more halogen, thiol, hydroxyl, carbonyl, carboxyl, carbonyloxyl, C$_{1-6}$alkoxy, C$_{1-6}$hydroxyalkoxy, amino, C$_{1-6}$alkylamino, di(C$_{1-6}$alkyl)amino, azido, piperidinyl, phenyl, naphthyl, pyridyl, pyrimidinyl, imidazolyl, 1,2,3-triazolyl, quinolinyl, isoquinolinyl, thiazolyl, or tetrazolyl groups;

R$^6$ is hydrogen, halogen, —SR$^{3a}$, —S(O)R$^{3a}$, —OR$^{3a}$, —OCH$_2$R$^{3b}$, —OCH(CH$_3$)R$^{3b}$, —OC(O)NHR$^{3a}$, —NR$^{3a}$R$^{4a}$, —NHSO$_2$R$^{3a}$, azido, —CHO, CO$_2$R$^{3a}$, cyano, C$_{1-6}$alkyl, —CR$^{5a}$R$^{6a}$R$^{7a}$, C$_{2-6}$alkenyl, —C(R$^{5a}$)=C(R$^{8a}$)(R$^{9a}$), C$_{2-6}$alkynyl, or —C≡CR$^{8a}$;

wherein R$^{3a}$, R$^{3b}$, and R$^{4a}$ are independently hydrogen, phenyl, naphthyl, pyridyl, pyrimidinyl, imidazolyl, 1,2,3-triazolyl, quinolinyl, isoquinolinyl, thiazolyl, tetrazolyl groups, C$_{1-6}$alkyl, cyclic—(C$_{1-8}$alkyl)—, cyclic—(C$_{1-6}$oxaalkyl)—, cyclic—(C$_{1-6}$azaalkyl)—, C$_{2-6}$alkenyl, or C$_{2-6}$alkynyl;

wherein the phenyl, naphthyl, pyridyl, pyrimidinyl, imidazolyl, 1,2,3—triazolyl, quinolinyl, isoquinolinyl, thiazolyl, or tetrazolyl groups are optionally substituted with 1-3 substituents independently selected from the group consisting of halogen, thiol, C$_{1-6}$alkyl thioether, C$_{1-6}$alkyl sulfoxide, C$_{1-6}$alkyl, C$_{1-6}$alkoxyl, amino, C$_{1-6}$alkylamino, C$_{1-6}$dialkylamino, C$_{1-6}$alkyl sulfonamide, azido, —CHO, —CO$_2$H, C$_{1-6}$alkyl carboxylate, cyano, C$_{2-6}$alkenyl, and C$_{2-6}$alkynyl group; and the C$_{1-6}$alkyl, cyclic—(C$_{1-8}$alkyl)—, cyclic—(C$_{1-6}$oxaalkyl)—, cyclic—(C$_{1-6}$azaalkyl)—, C$_{2-6}$alkenyl, or C$_{2-6}$alkynyl groups are selectively functionalized with one or more halogen, thiol, hydroxyl, carbonyl, carboxyl, carbonyloxyl, C$_{1-6}$alkoxy, C$_{1-6}$hydroxyalkoxy, amino, C$_{1-6}$alkylamino, di(C$_{1-6}$alkyl)amino, azido, piperidinyl, phenyl, naphthyl, pyridyl, pyrimidinyl, imidazolyl, 1,2,3—triazolyl, quinolinyl, quinolinyl, isoquinolinyl, thiazolyl, or tetrazolyl groups;

wherein R$^{5a}$, R$^{6a}$, R$^{7a}$, R$^{8a}$, and R$^{9a}$ are independently hydrogen, phenyl, naphthyl, pyridyl, pyrimidinyl, imidazolyl, 1,2,3—triazolyl, quinolinyl, isoquinolinyl, thiazolyl, tetrazolyl groups, C$_{1-6}$alkyl, cyclic—(C$_{1-8}$alkyl)—, cyclic—(C$_{1-6}$oxaalkyl)—, cyclic—(C$_{1-6}$azaalkyl)—, C$_{2-6}$alkenyl, C$_{2-6}$alkynyl, C$_{2-6}$alkynyl, C$_{1-6}$alkoxyl, cyclic—(C$_{1-8}$alkoxyl)—, cyclic—(C$_{1-6}$oxaalkoxyl)—, or cyclic—(C$_{1-6}$azaalkoxyl)—;

wherein the phenyl, naphthyl, pyridyl, pyrimidinyl, imidazolyl, 1,2,3—triazolyl, quinolinyl, isoquinolinyl, or thiazolyl, tetrazolyl groups are optionally substituted with 1-3 substituents independently selected from the group consisting of halogen, thiol, C$_{1-6}$alkyl thioether, C$_{1-6}$alkyl sulfoxide, C$_{1-6}$alkyl, C$_{1-6}$alkoxyl, amino, C$_{1-6}$alkylamino, C$_{1-6}$diakylamino, C$_{1-6}$alkyl sulfonamide, azido, —CHO, —CO$_2$H, C$_{1-6}$alkyl carboxylate, cyano, C$_{2-6}$alkenyl, and C$_{2-6}$alkynyl groups; and the C$_{1-6}$alkyl, cyclic—(C$_{1-8}$alkyl)—, cyclic—(C$_{1-6}$oxaalkyl)—, cyclic—(C$_{1-6}$azaalkyl)—, C$_{2-6}$alkenyl, or C$_{2-6}$alkynyl groups are selectively functionalized with one or more halogen, thiol, hydroxyl, carbonyl, carboxyl, carbonyloxyl, C$_{1-6}$alkoxy, C$_{1-6}$hydroxyalkoxy, amino, C$_{1-6}$alkylamino, di(C$_{1-6}$alkyl)amino, azido, piperidinyl, phenyl, naphthyl, pyridyl, pyrimidinyl, imidazolyl, 1,2,3—triazolyl, quinolinyl, isoquinolinyl, thiazolyl, or tetrazolyl groups;

R$^4$ is hydrogen or halogen;

or a pharmaceutically acceptable salt thereof.

2. The compound of claim 1, wherein X is S; Z is O or S; and

G is N; and R$^1$ is C$_{1-6}$alkyl or C$_{1-6}$alkyl selectively functionalized with one or more halogen, thiol, hydroxyl, carbonyl, carbonyloxyl, C$_{1-6}$alkoxy, C$_{1-6}$hydroxyalkoxy, amino, C$_{1-6}$alkylamino, di(C$_{1-6}$alkyl)amino, or azido groups; or G is N; Z is NR$^{1a}$; and R$^1$-R$^{1a}$ are connected as a —CH$_2$CH$_2$—, —CH$_2$CH$_2$CH$_2$—, —CH=CH—, —C(CH$_3$)=CH—, or —CH=C(CH$_3$)— group; or G is C; Z is NR$^{1a}$; and R$^1$-R$^{1a}$ are connected as a =CH—CH=CH—, =N—CH=CH—, or =CH—N=CH— group.

3. The compound of claim 1, wherein the compound is one of Formula Id:

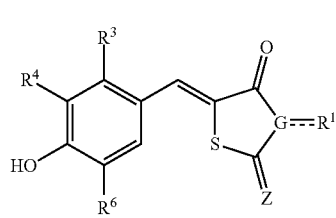

Formula Id wherein:

R$^3$ is halogen.

4. The compound of claim 3, wherein Z is O or S; and G is N; and $R^1$ is $C_{1-6}$alkyl or $C_{1-6}$alkyl selectively functionalized with one or more halogen, thiol, hydroxyl, carbonyl, carboxyl, carbonyloxyl, $C_{1-6}$alkoxy, $C_{1-6}$hydroxyalkoxy, amino, $C_{1-6}$alkylamino, di($C_{1-6}$alkyl)amino, or azido groups; or G is N; Z is $NR^{1a}$; and $R^1$-$R^{1a}$ are connected as a —$CH_2CH_2$—, —$CH_2CH_2CH_2$—, —CH=CH—, —C($CH_3$)=CH—, or —CH=C($CH_3$)— group; or G is C; Z is $NR^{1a}$; and $R^1$-$R^{1a}$ are connected as a =CH—CH=CH—, =N—CH=CH—, or =CH—N=CH— group.

5. A compound selected from the group consisting of:

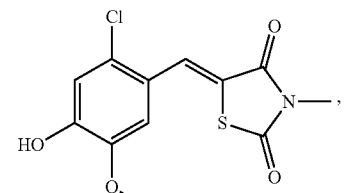

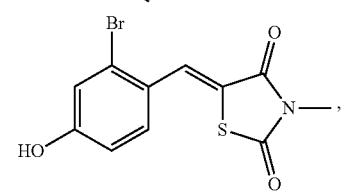

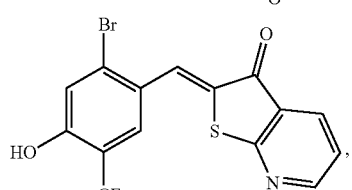

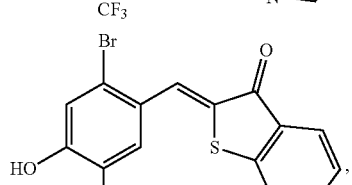

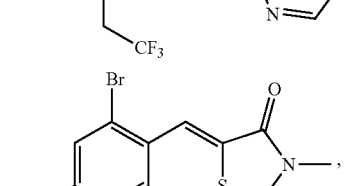

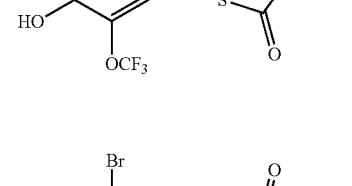

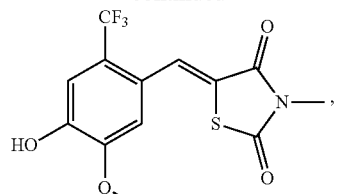

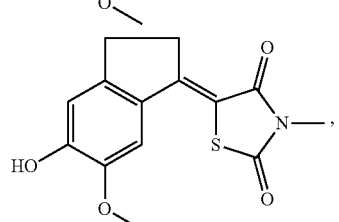

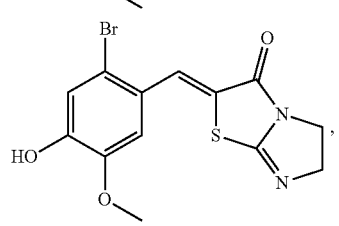

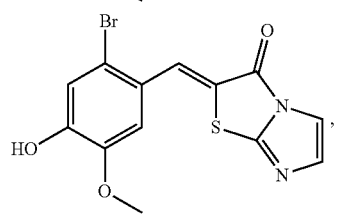

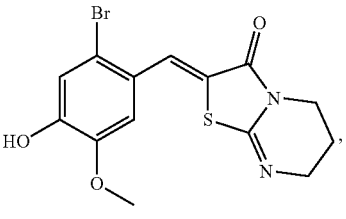

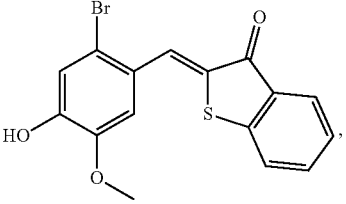

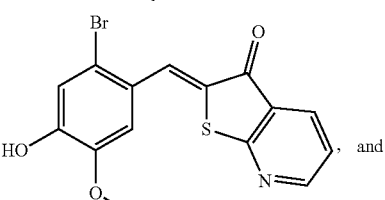

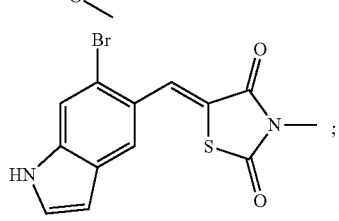, and

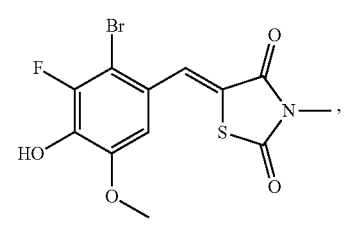;

or a pharmaceutically acceptable salt thereof.

6. A compound is selected from the group consisting of:
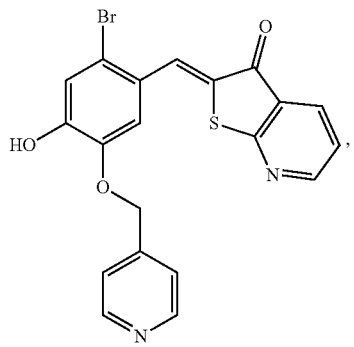
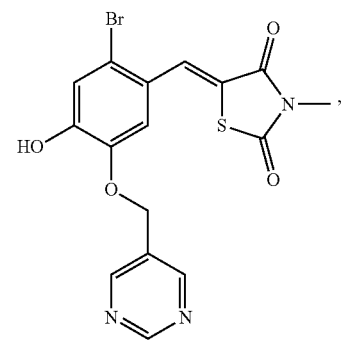
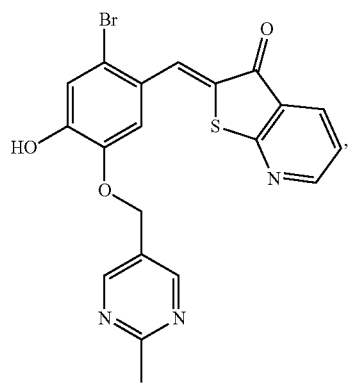
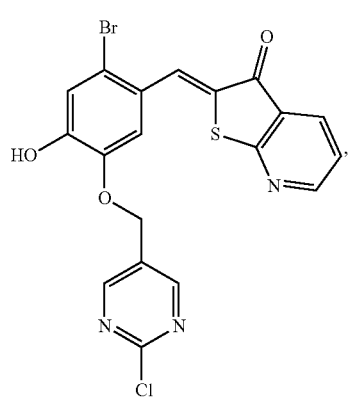
-continued
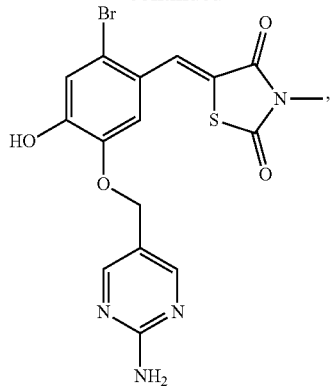
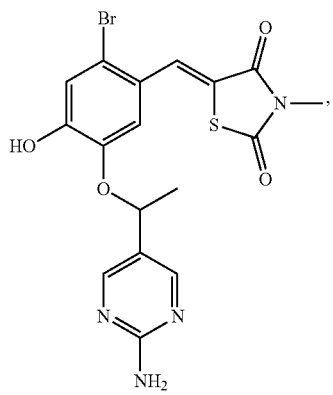
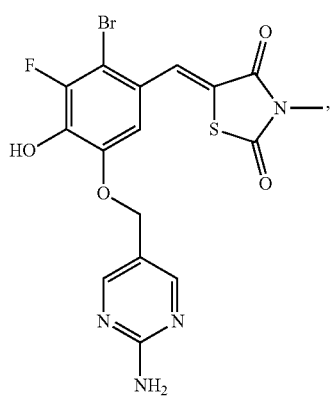
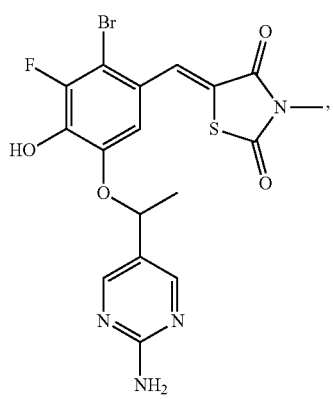

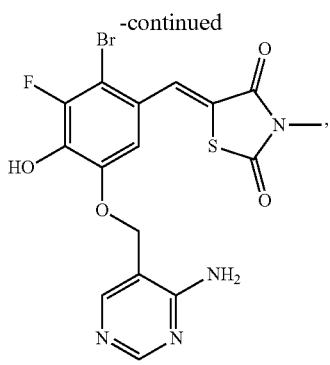

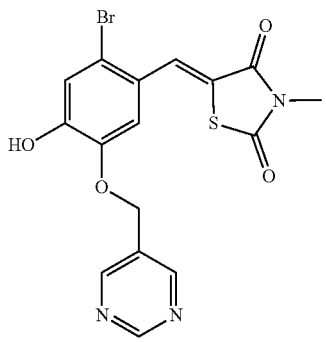 [SMILES: CN1C(=O)S/C(=C\c2cc(OCc3cncnc3)c(O)cc2Br)C1=O]

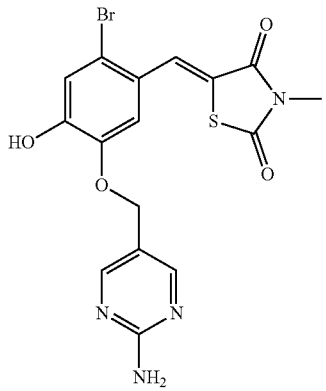

or a pharmaceutically acceptable salt thereof.

7. A pharmaceutical composition comprising a compound of claim 1, and a pharmaceutically acceptable carrier.

8. The compound of claim 1, wherein X is S; Y is O; and Z is O.

9. The compound of claim 8, wherein G is N.

10. The compound of claim 9, wherein $R^1$ is $C_{1-6}$alkyl.

11. The compound of claim 10, wherein $R^1$ is methyl.

12. The compound of claim 9, wherein $R^1$ is $C_{1-6}$alkyl functionalized with one or more halogen, thiol, hydroxyl, carboxyl, carbonyloxyl, $C_{1-6}$alkoxy, $C_{1-6}$hydroxyalkoxy, amino, $C_{1-6}$alkylamino, di($C_{1-6}$alkyl)amino, or azido groups.

13. The compound of claim 9, wherein $R^3$ is halogen.

14. The compound of claim 13, wherein $R^4$ is hydrogen.

15. The compound of claim 1, wherein X is S; Y is O or S; G is N; Z is $NR^{1a}$; and $R^1$-$R^{1a}$ are connected as a —$CH_2CH_2$—, —$CH_2CH_2CH_2$—, —CH=CH—, —C(CH$_3$)=CH—, or —CH=C(CH$_3$)— group.

16. The compound of claim 15, wherein Y is O.

17. The compound of claim 1, wherein X is S; Y is O or S; G is C; Z is $NR^{1a}$; and $R^1$-$R^{1a}$ are connected as a=CH—CH=CH—, =N—CH=CH—, or =CH—N=CH— group.

18. The compound of claim 17, wherein Y is O.

19. The compound of claim 1, wherein $R^2$ is hydrogen, Cl, Br, or methyl.

20. The compound of claim 19, wherein $R^2$ is hydrogen.

21. The compound of claim 6, wherein the compound is or a pharmaceutically acceptable salt thereof.

22. The compound of claim 6, wherein the compound is or a pharmaceutically acceptable salt thereof.

23. The compound of claim 6, wherein the compound is

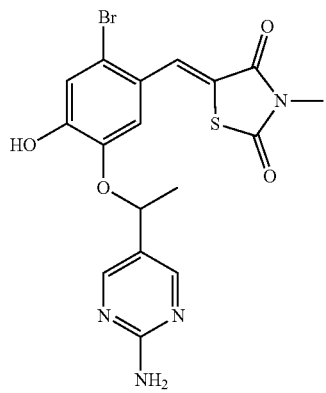 [SMILES: CC(Oc1cc(/C=C2\SC(=O)N(C)C2=O)c(Br)cc1O)c1cnc(N)nc1]

or a pharmaceutically acceptable salt thereof.

24. The compound of claim 6, wherein the compound is

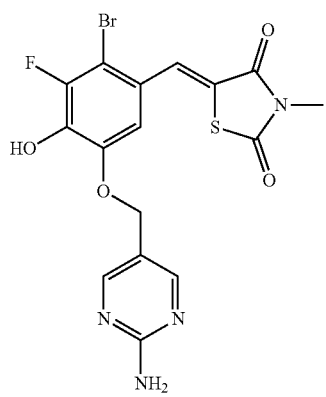 [SMILES: CN1C(=O)S/C(=C\c2cc(OCc3cnc(N)nc3)c(O)c(F)c2Br)C1=O]

or a pharmaceutically acceptable salt thereof.

25. The compound of claim 6, wherein the compound is

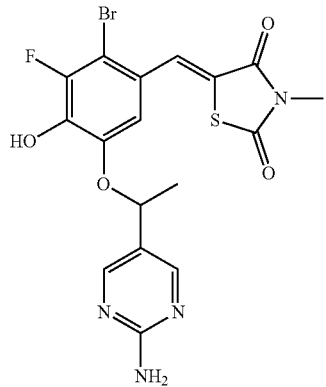

or a pharmaceutically acceptable salt thereof.

26. The compound of claim 6, wherein the compound is

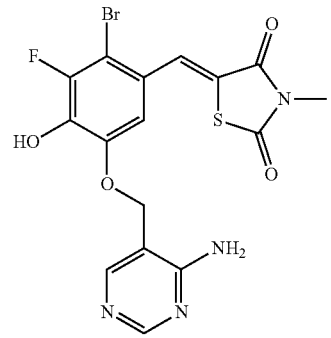 [SMILES: CN1C(=O)S/C(=C\c2cc(OCc3cncnc3N)c(O)c(F)c2Br)C1=O]

or a pharmaceutically acceptable salt thereof.

27. The compound of claim 6, wherein the compound is

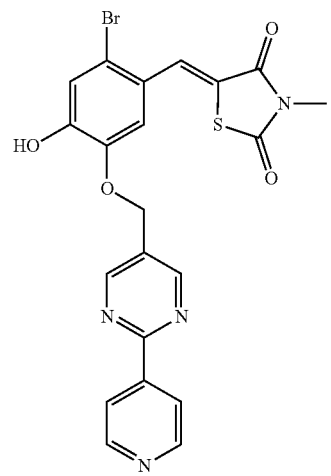 [SMILES: CN1C(=O)S/C(=C\c2cc(OCc3cnc(-c4ccncc4)nc3)c(O)cc2Br)C1=O]

or a pharmaceutically acceptable salt thereof.

28. The compound of claim 1, wherein $R^3$ is halogen.
29. The compound of claim 1, wherein $R^3$ is Br.
30. The compound of claim 1, wherein $R^4$ is hydrogen.
31. The compound of claim 1, wherein $R^4$ is halogen.
32. The compound of claim 1, wherein $R^4$ is F.
33. The compound of claim 3, wherein $R^3$ is Br.
34. The compound of claim 3, wherein $R^4$ is hydrogen.
35. The compound of claim 3, wherein $R^4$ is halogen.
36. The compound of claim 3, wherein Z is O.
37. The compound of claim 1, wherein Z is O, $CHR^{1a}$ or $NR^{1a}$.
38. The compound of claim 1, wherein Z is O.
39. The compound of claim 1, wherein X is S.
40. The compound of claim 1, wherein Y is O.
41. The compound of claim 1, wherein Y is O, and Z is O.
42. The compound of claim 1, wherein $R^6$ is —$OR^{3a}$.
43. The compound of claim 42, wherein $R^{3a}$ is $C_{1-6}$alkyl.
44. The compound of claim 42, wherein $R^{3a}$ is $C_{1-6}$alkyl selectively functionalized with one or more halogen, thiol, hydroxyl, carbonyl, carboxyl, carbonyloxyl, $C_{1-6}$alkoxy, $C_{1-6}$hydroxyalkkoxy, amino, $C_{1-6}$alkylamino, di($C_{1-6}$alkyl)amino, azido, piperidinyl, phenyl, naphthyl, pyridyl, pyrimidinyl, imidazolyl, 1,2,3—triazolyl, quinolinyl, isoquinolinyl, thiazolyl, or tetrazolyl groups.
45. The compound of claim 44, wherein $R^{3a}$ is $C_{1-6}$alkyl selectively functionalized with a pyrimidinyl group.

46. The compound of claim 44, wherein $R^{3a}$ is $C_{1-6}$alkyl selectively functionalized with a pyridyl group.

* * * * *